US009408615B2

(12) United States Patent
Fitz et al.

(10) Patent No.: US 9,408,615 B2
(45) Date of Patent: *Aug. 9, 2016

(54) PATIENT SELECTABLE JOINT ARTHROPLASTY DEVICES AND SURGICAL TOOLS

(75) Inventors: Wolfgang Fitz, Sherborn, MA (US); Philipp Lang, Lexington, MA (US)

(73) Assignee: ConforMIS, Inc., Bedford, MA (US)

( * ) Notice: Subject to any disclaimer, the term of this patent is extended or adjusted under 35 U.S.C. 154(b) by 1035 days.

This patent is subject to a terminal disclaimer.

(21) Appl. No.: 13/013,265

(22) Filed: Jan. 25, 2011

(65) Prior Publication Data

US 2011/0213427 A1 Sep. 1, 2011

Related U.S. Application Data

(63) Continuation of application No. 11/671,745, filed on Feb. 6, 2007, now Pat. No. 8,066,708, which is a continuation-in-part of application No. 11/002,573, filed on Dec. 2, 2004, now Pat. No. 7,534,263, which
(Continued)

(51) Int. Cl.
*A61B 17/56* (2006.01)
*A61B 17/17* (2006.01)
(Continued)

(52) U.S. Cl.
CPC ............ *A61B 17/1739* (2013.01); *A61B 17/15* (2013.01); *A61B 17/154* (2013.01);
(Continued)

(58) Field of Classification Search
CPC .. A61B 17/154; A61B 17/155; A61B 17/157; A61B 5/4504; A61B 5/4523; A61B 5/4528; A61B 5/4533; A61B 5/4514; A61B 17/158; A61B 17/1666; A61B 17/167; A61F 2/38; A61F 2/30756; A61F 2/30942
USPC ........... 606/87, 86 R, 102, 91, 80, 96, 88, 89; 600/407, 587; 623/22.16, 22.15, 22.12, 623/22.11, 22.28, 23.26, 20.28, 20.31, 623/17.12; 701/1, 11, 7; 29/592
See application file for complete search history.

(56) References Cited

U.S. PATENT DOCUMENTS 3,808,606 A   5/1974  Tronzo ................................. 3/1
3,843,975 A  10/1974  Tronzo ................................. 3/1
(Continued)

FOREIGN PATENT DOCUMENTS

DE   2306552     8/1974  ................ A61F 1/00
DE   44 34 539   4/1996  ................ A61F 2/38
(Continued)

OTHER PUBLICATIONS

Cohen et al., "Computer-Aided Planning of Patellofemoral Joint OA Surgery: Developing Physical Models from Patient MRI", MICCAI, Oct. 11-13, 1998, 13 pages.
(Continued)

*Primary Examiner* — Pedro Philogene
(74) *Attorney, Agent, or Firm* — Sunstein Kann Murphy & Timbers LLP

(57) ABSTRACT

Disclosed herein are methods, compositions and tools for repairing articular surfaces repair materials and for repairing an articular surface. The articular surface repairs are customizable or highly selectable by patient and geared toward providing optimal fit and function. The surgical tools are designed to be customizable or highly selectable by patient to increase the speed, accuracy and simplicity of performing total or partial arthroplasty.

21 Claims, 62 Drawing Sheets

Related U.S. Application Data is a continuation-in-part of application No. 10/724,010, filed on Nov. 25, 2003, now Pat. No. 7,618,451.

(60) Provisional application No. 60/765,592, filed on Feb. 6, 2006, provisional application No. 60/785,168, filed on Mar. 23, 2006, provisional application No. 60/788,339, filed on Mar. 31, 2006.

(51) Int. Cl.
*A61B 17/15* (2006.01)
*A61B 17/16* (2006.01)
*A61F 2/30* (2006.01)
*A61F 2/38* (2006.01)
*G06F 17/50* (2006.01)
*A61B 5/00* (2006.01)

(52) U.S. Cl.
CPC ............ *A61B17/155* (2013.01); *A61B 17/157* (2013.01); *A61B 17/1666* (2013.01); *A61B 17/1677* (2013.01); *A61B 17/1682* (2013.01); *A61B 17/1703* (2013.01); *A61B 17/1746* (2013.01); *A61B 17/1767* (2013.01); *A61F 2/30756* (2013.01); *A61F 2/30942* (2013.01); *A61F 2/38* (2013.01); *G06F 17/50* (2013.01); A61B 5/4504 (2013.01); A61B 5/4514 (2013.01); A61B 5/4523 (2013.01); A61B 5/4528 (2013.01); A61B 5/4533 (2013.01); A61B 17/158 (2013.01); A61B 17/1675 (2013.01); A61B 2017/568 (2013.01); A61B 2034/105 (2016.02); Y10T 29/49 (2015.01)

(56) References Cited

U.S. PATENT DOCUMENTS

| | | | |
|---|---|---|---|
| 3,938,198 A | 2/1976 | Kahn et al. | 3/1.912 |
| 3,982,281 A | 9/1976 | Giliberty | 3/1.913 |
| 3,987,499 A | 10/1976 | Scharbach et al. | 3/1.91 |
| 4,203,444 A | 5/1980 | Bonnell et al. | 128/276 |
| 4,340,978 A | 7/1982 | Buechel et al. | 3/1.911 |
| 4,368,040 A | 1/1983 | Weissman | 433/36 |
| 4,501,266 A | 2/1985 | McDaniel | 128/69 |
| 4,601,290 A | 7/1986 | Effron et al. | 128/305 |
| 4,627,853 A | 12/1986 | Campbell et al. | 623/16 |
| 4,715,860 A | 12/1987 | Amstutz et al. | 623/22 |
| 4,721,104 A | 1/1988 | Kaufman et al. | 128/92 |
| 4,759,350 A | 7/1988 | Dunn et al. | 128/92 VW |
| 4,841,975 A | 6/1989 | Woolson | 128/653 |
| 4,886,258 A | 12/1989 | Scott | 269/328 |
| 4,936,862 A | 6/1990 | Walker et al. | 623/23 |
| 4,979,949 A | 12/1990 | Matsen, III et al. | 606/53 |
| 5,002,547 A | 3/1991 | Poggie et al. | 606/88 |
| 5,007,936 A * | 4/1991 | Woolson | 128/898 |
| 5,053,039 A | 10/1991 | Hofmann et al. | 606/87 |
| 5,108,452 A | 4/1992 | Fallin | 623/23 |
| 5,122,144 A | 6/1992 | Bert et al. | 606/88 |
| 5,129,908 A | 7/1992 | Peterson | 606/88 |
| 5,154,717 A | 10/1992 | Matsen, III et al. | 606/53 |
| 5,234,433 A | 8/1993 | Bert et al. | 606/88 |
| 5,250,050 A | 10/1993 | Poggie et al. | 606/79 |
| 5,258,032 A | 11/1993 | Bertin | 623/20 |
| 5,299,288 A * | 3/1994 | Glassman et al. | 700/245 |
| 5,303,148 A | 4/1994 | Mattson et al. | 364/413.01 |
| 5,314,482 A | 5/1994 | Goodfellow et al. | 623/20 |
| 5,360,446 A | 11/1994 | Kennedy | 623/16 |
| 5,380,332 A | 1/1995 | Ferrante | 606/79 |
| 5,387,216 A | 2/1995 | Thornhill et al. | 606/88 |
| 5,403,319 A | 4/1995 | Matsen, III et al. | 606/88 |
| 5,437,676 A | 8/1995 | Bouraly et al. | 606/88 |
| 5,474,559 A | 12/1995 | Bertin et al. | 606/89 |
| 5,486,180 A | 1/1996 | Dietz et al. | 606/87 |
| 5,501,687 A | 3/1996 | Willert et al. | 606/94 |
| 5,503,162 A | 4/1996 | Athanasiou et al. | 128/774 |
| 5,540,696 A | 7/1996 | Booth, Jr. et al. | 606/88 |
| 5,542,947 A | 8/1996 | Treacy | 606/88 |
| 5,571,205 A | 11/1996 | James | 623/24 |
| 5,575,793 A | 11/1996 | Carls et al. | 606/80 |
| 5,578,037 A | 11/1996 | Sanders et al. | 606/80 |
| 5,597,379 A | 1/1997 | Haines et al. | 606/80 |
| 5,601,563 A | 2/1997 | Burke et al. | 606/86 |
| 5,613,970 A | 3/1997 | Houston et al. | 606/88 |
| 5,616,146 A | 4/1997 | Murray | 606/80 |
| 5,630,820 A | 5/1997 | Todd | 606/90 |
| 5,658,290 A | 8/1997 | Techiera | 606/80 |
| 5,681,316 A | 10/1997 | DeOrio et al. | 606/88 |
| 5,681,354 A | 10/1997 | Eckhoff | 623/20 |
| 5,682,886 A | 11/1997 | Delp et al. | 128/653.1 |
| 5,688,282 A | 11/1997 | Baron et al. | 606/90 |
| 5,690,635 A | 11/1997 | Matsen, III et al. | 606/88 |
| 5,735,277 A | 4/1998 | Schuster | 128/653.1 |
| 5,749,876 A | 5/1998 | Duvillier et al. | 606/88 |
| 5,766,259 A | 6/1998 | Sammarco | 623/21 |
| 5,768,134 A | 6/1998 | Swaelens et al. | 364/468.28 |
| 5,769,092 A | 6/1998 | Williamson, Jr. | 128/898 |
| 5,776,137 A | 7/1998 | Katz | 606/88 |
| 5,788,701 A | 8/1998 | McCue | 606/88 |
| 5,795,353 A | 8/1998 | Felt | 623/18 |
| 5,800,438 A | 9/1998 | Tuke et al. | 606/90 |
| 5,830,216 A | 11/1998 | Insall et al. | 606/88 |
| 5,860,981 A | 1/1999 | Bertin et al. | 606/89 |
| 5,871,018 A | 2/1999 | Delp et al. | 128/898 |
| 5,880,976 A | 3/1999 | DiGioia, III et al. | 364/578 |
| 5,885,296 A | 3/1999 | Masini | 606/86 |
| 5,885,297 A * | 3/1999 | Matsen, III | 606/87 |
| 5,885,298 A | 3/1999 | Herrington et al. | 606/88 |
| 5,897,559 A | 4/1999 | Masini | 606/86 |
| 5,911,723 A | 6/1999 | Ashby et al. | 606/88 |
| 5,916,220 A | 6/1999 | Masini | 606/88 |
| 5,961,523 A | 10/1999 | Masini | 606/86 |
| 5,968,051 A | 10/1999 | Luckman et al. | 606/88 |
| 5,995,738 A | 11/1999 | DiGioia, III et al. | 395/500.32 |
| 6,002,859 A | 12/1999 | DiGioia, III et al. | 395/500.32 |
| 6,007,537 A | 12/1999 | Burkinshaw et al. | 606/66 |
| 6,010,509 A | 1/2000 | Delgado et al. | 606/88 |
| 6,046,379 A | 4/2000 | Stone et al. | 623/11 |
| 6,056,754 A | 5/2000 | Haines et al. | 606/80 |
| 6,056,756 A | 5/2000 | Eng et al. | 606/87 |
| 6,077,270 A | 6/2000 | Katz | 606/88 |
| 6,096,043 A | 8/2000 | Techiera et al. | 606/88 |
| 6,102,916 A | 8/2000 | Masini | 606/88 |
| 6,106,529 A | 8/2000 | Techiera | 606/88 |
| 6,110,209 A | 8/2000 | Stone | 623/16.11 |
| 6,126,690 A | 10/2000 | Ateshian et al. | 623/18 |
| 6,156,069 A | 12/2000 | Amstutz | 623/22.11 |
| 6,161,080 A | 12/2000 | Aouni-Ateshian et al. | 703/11 |
| 6,187,010 B1 | 2/2001 | Masini | 606/86 |
| 6,197,064 B1 | 3/2001 | Haines et al. | 623/20.31 |
| 6,203,546 B1 | 3/2001 | MacMahon | 606/87 |
| 6,205,411 B1 * | 3/2001 | DiGioia et al. | 703/11 |
| 6,235,060 B1 | 5/2001 | Kubein-Meesenburg et al. | 623/20.31 |
| 6,296,646 B1 | 10/2001 | Williamson | 606/90 |
| 6,344,043 B1 | 2/2002 | Pappas | 606/96 |
| 6,358,253 B1 | 3/2002 | Torrie et al. | 606/96 |
| 6,375,658 B1 | 4/2002 | Hangody et al. | 606/80 |
| 6,379,367 B1 | 4/2002 | Vibe-Hansen et al. | 606/151 |
| 6,383,228 B1 | 5/2002 | Schmotzer | 623/23.35 |
| 6,443,988 B2 | 9/2002 | Felt et al. | 623/17.12 |
| 6,459,948 B1 | 10/2002 | Ateshian et al. | 700/117 |
| 6,478,799 B1 | 11/2002 | Williamson | 606/90 |
| 6,510,334 B1 | 1/2003 | Schuster et al. | 600/407 |
| 6,575,980 B1 | 6/2003 | Robie et al. | 606/88 |
| 6,620,168 B1 | 9/2003 | Lombardo et al. | 606/88 |
| 6,626,948 B2 | 9/2003 | Storer et al. | 623/23.14 |
| 6,632,225 B2 | 10/2003 | Sanford et al. | 606/87 |
| 6,673,077 B1 | 1/2004 | Katz | 606/88 |
| 6,673,116 B2 | 1/2004 | Reiley | 623/21.18 |
| 6,679,917 B2 | 1/2004 | Ek | 623/20.14 |
| 6,702,821 B2 | 3/2004 | Bonutti | 606/88 |
| 6,712,856 B1 | 3/2004 | Carignan et al. | 623/20.35 |
| 6,875,218 B2 | 4/2005 | Dye et al. | 606/91 |

(56) References Cited

U.S. PATENT DOCUMENTS

| | | | |
|---|---|---|---|
| 6,905,514 B2 | 6/2005 | Carignan et al. | 623/20.35 |
| 6,928,742 B2 | 8/2005 | Broers et al. | 33/512 |
| 6,969,393 B2 | 11/2005 | Pinczewski et al. | 606/88 |
| 6,984,249 B2 | 1/2006 | Keller | 623/20.24 |
| 7,008,430 B2 | 3/2006 | Dong et al. | 606/80 |
| 7,060,074 B2 | 6/2006 | Rosa et al. | 606/88 |
| 7,104,997 B2 | 9/2006 | Lionberger et al. | 606/88 |
| 7,115,131 B2 | 10/2006 | Engh et al. | 606/79 |
| 7,117,027 B2 | 10/2006 | Zheng et al. | 600/426 |
| 7,141,053 B2 | 11/2006 | Rosa et al. | 606/86 |
| 7,184,814 B2 | 2/2007 | Lang et al. | 600/416 |
| 7,239,908 B1 | 7/2007 | Alexander et al. | 600/427 |
| 7,282,054 B2 | 10/2007 | Steffensmeier et al. | 606/96 |
| 7,427,200 B2 * | 9/2008 | Noble et al. | 434/274 |
| 7,442,196 B2 | 10/2008 | Fisher et al. | 606/88 |
| 7,468,075 B2 | 12/2008 | Lang et al. | 623/16.11 |
| 7,534,263 B2 | 5/2009 | Burdulis, Jr. et al. | |
| 7,603,192 B2 | 10/2009 | Martin et al. | 700/98 |
| 7,615,054 B1 | 11/2009 | Bonutti | 606/88 |
| 7,618,451 B2 | 11/2009 | Berez et al. | |
| 7,695,477 B2 | 4/2010 | Creger et al. | 606/87 |
| 7,747,305 B2 | 6/2010 | Dean et al. | 600/424 |
| 7,806,896 B1 | 10/2010 | Bonutti | 606/86 R |
| 7,833,275 B2 * | 11/2010 | Mears et al. | 623/22.11 |
| 7,881,768 B2 | 2/2011 | Lang et al. | 600/407 |
| 7,981,158 B2 | 7/2011 | Fitz et al. | |
| 7,983,777 B2 | 7/2011 | Melton et al. | 700/98 |
| 8,036,729 B2 | 10/2011 | Lang et al. | 600/407 |
| 8,062,302 B2 | 11/2011 | Lang et al. | |
| 8,066,708 B2 | 11/2011 | Lang et al. | |
| 8,070,752 B2 | 12/2011 | Metzger et al. | 606/88 |
| 8,083,745 B2 | 12/2011 | Lang et al. | |
| 8,092,462 B2 | 1/2012 | Pinczewski et al. | 606/88 |
| 8,105,330 B2 | 1/2012 | Fitz et al. | |
| 8,109,942 B2 | 2/2012 | Carson | 606/130 |
| 8,112,142 B2 | 2/2012 | Alexander et al. | 600/407 |
| 8,122,582 B2 | 2/2012 | Burdulis, Jr. et al. | |
| 8,123,753 B2 | 2/2012 | Poncet | 606/87 |
| RE43,282 E | 3/2012 | Alexander et al. | 600/427 |
| 8,160,345 B2 | 4/2012 | Pavlovskaia et al. | 382/131 |
| 8,167,888 B2 | 5/2012 | Steffensmeier | 606/88 |
| 8,175,683 B2 * | 5/2012 | Roose | 600/427 |
| 8,221,430 B2 | 7/2012 | Park et al. | 606/88 |
| 8,234,097 B2 | 7/2012 | Steines et al. | 703/1 |
| 8,257,360 B2 | 9/2012 | Richard et al. | 606/86 |
| 8,265,730 B2 | 9/2012 | Alexander et al. | 600/410 |
| 8,282,646 B2 | 10/2012 | Schoenefeld et al. | 606/88 |
| 8,306,601 B2 | 11/2012 | Lang et al. | 600/407 |
| 8,311,306 B2 | 11/2012 | Pavlovskaia et al. | 382/131 |
| 8,337,501 B2 | 12/2012 | Fitz et al. | |
| 8,337,503 B2 | 12/2012 | Lian | 606/87 |
| 8,337,507 B2 | 12/2012 | Lang et al. | 606/102 |
| 8,343,218 B2 | 1/2013 | Lang et al. | 623/16.11 |
| 8,357,166 B2 | 1/2013 | Aram et al. | 606/88 |
| 8,361,076 B2 | 1/2013 | Roose et al. | 606/88 |
| 8,366,771 B2 | 2/2013 | Burdulis, Jr. et al. | |
| 8,369,926 B2 | 2/2013 | Lang et al. | 600/407 |
| 8,377,066 B2 | 2/2013 | Katrana et al. | 606/86 R |
| 8,377,068 B2 | 2/2013 | Aker et al. | 606/87 |
| 8,377,129 B2 | 2/2013 | Fitz et al. | |
| 8,380,471 B2 | 2/2013 | Iannotti et al. | 703/6 |
| 8,398,646 B2 | 3/2013 | Metzger et al. | 606/88 |
| 8,407,067 B2 | 3/2013 | Uthgenannt et al. | 705/2 |
| 8,419,740 B2 | 4/2013 | Aram et al. | 606/88 |
| 8,425,524 B2 | 4/2013 | Aker et al. | 606/88 |
| 8,439,926 B2 | 5/2013 | Borjarski et al. | |
| 8,460,304 B2 | 6/2013 | Fitz et al. | |
| 8,480,754 B2 | 7/2013 | Bojarski et al. | 623/20.35 |
| 8,500,740 B2 | 8/2013 | Borjarski et al. | |
| 8,529,568 B2 | 9/2013 | Bouadi | 606/84 |
| 8,529,630 B2 | 9/2013 | Borjarski et al. | |
| 8,545,569 B2 | 10/2013 | Fitz et al. | 623/20.14 |
| 8,551,099 B2 | 10/2013 | Lang et al. | |
| 8,551,102 B2 | 10/2013 | Fitz et al. | |
| 8,551,103 B2 | 10/2013 | Fitz et al. | |
| 8,551,169 B2 | 10/2013 | Fitz et al. | |
| 8,556,906 B2 | 10/2013 | Fitz et al. | |
| 8,556,907 B2 | 10/2013 | Fitz et al. | |
| 8,556,971 B2 | 10/2013 | Lang | 623/14.12 |
| 8,556,983 B2 | 10/2013 | Bojarski et al. | 623/20.35 |
| 8,561,278 B2 | 10/2013 | Fitz et al. | |
| 8,562,611 B2 | 10/2013 | Fitz et al. | |
| 8,562,618 B2 | 10/2013 | Fitz et al. | |
| 8,568,479 B2 | 10/2013 | Fitz et al. | |
| 8,568,480 B2 | 10/2013 | Fitz et al. | |
| 8,585,708 B2 | 11/2013 | Fitz et al. | |
| 8,617,172 B2 | 12/2013 | Fitz et al. | |
| 8,617,242 B2 | 12/2013 | Philipp | 623/16.11 |
| 8,623,026 B2 | 1/2014 | Wong et al. | |
| 8,634,617 B2 | 1/2014 | Tsougarakis et al. | 382/128 |
| 8,638,998 B2 | 1/2014 | Steines et al. | 382/128 |
| 8,641,716 B2 | 2/2014 | Fitz et al. | |
| 8,657,827 B2 | 2/2014 | Fitz et al. | |
| 8,682,052 B2 | 3/2014 | Fitz et al. | 382/131 |
| 8,690,945 B2 | 4/2014 | Fitz et al. | 623/16.11 |
| 8,709,089 B2 | 4/2014 | Lang et al. | 623/18.11 |
| 8,735,773 B2 | 5/2014 | Lang | 219/121.72 |
| 8,768,028 B2 | 7/2014 | Lang et al. | 382/131 |
| 8,771,365 B2 | 7/2014 | Bojarski et al. | 623/20.32 |
| 8,801,720 B2 | 8/2014 | Park et al. | 606/88 |
| 8,951,259 B2 | 2/2015 | Fitz et al. | |
| 8,951,260 B2 | 2/2015 | Lang et al. | |
| 8,998,915 B2 | 4/2015 | Fitz et al. | |
| 9,023,050 B2 | 5/2015 | Lang et al. | |
| 9,055,953 B2 | 6/2015 | Lang et al. | |
| 9,066,728 B2 | 6/2015 | Burdulis, Jr. et al. | |
| 9,072,531 B2 | 7/2015 | Fitz et al. | |
| 9,084,617 B2 | 7/2015 | Lang et al. | |
| 9,107,679 B2 | 8/2015 | Lang et al. | |
| 9,107,680 B2 | 8/2015 | Fitz et al. | |
| 9,113,921 B2 | 8/2015 | Lang et al. | 606/79 |
| 9,125,672 B2 | 9/2015 | Fitz et al. | |
| 9,125,673 B2 | 9/2015 | Fitz et al. | |
| 9,186,161 B2 | 11/2015 | Lang et al. | |
| 2001/0001120 A1 | 5/2001 | Masini | 606/86 |
| 2001/0051830 A1 | 12/2001 | Tuke et al. | 623/22.12 |
| 2001/0051831 A1 | 12/2001 | Rao et al. | 623/22.42 |
| 2002/0029038 A1 | 3/2002 | Haines | 606/54 |
| 2002/0059049 A1 | 5/2002 | Bradbury et al. | 703/11 |
| 2002/0068979 A1 | 6/2002 | Brown et al. | 623/20.3 |
| 2002/0072821 A1 | 6/2002 | Baker | 700/98 |
| 2002/0087274 A1 | 7/2002 | Alexander et al. | 702/19 |
| 2002/0127264 A1 | 9/2002 | Felt et al. | 424/423 |
| 2002/0133230 A1 | 9/2002 | Repicci | 623/14.12 |
| 2002/0143402 A1 | 10/2002 | Steinberg | 623/22.16 |
| 2002/0151986 A1 | 10/2002 | Asculai et al. | 424/484 |
| 2002/0173852 A1 | 11/2002 | Felt et al. | 623/20.32 |
| 2002/0177770 A1 | 11/2002 | Lang et al. | 600/410 |
| 2002/0183850 A1 | 12/2002 | Felt et al. | 623/20.16 |
| 2003/0028196 A1 | 2/2003 | Bonutti | 606/87 |
| 2003/0069591 A1 | 4/2003 | Carson et al. | 606/130 |
| 2003/0100907 A1 | 5/2003 | Rosa et al. | 606/86 |
| 2003/0120347 A1 | 6/2003 | Steinberg | 623/22.17 |
| 2003/0158558 A1 | 8/2003 | Horn | 606/87 |
| 2003/0163137 A1 | 8/2003 | Smucker et al. | 606/87 |
| 2003/0216669 A1 | 11/2003 | Lang et al. | 600/587 |
| 2003/0236521 A1 | 12/2003 | Brown et al. | 606/80 |
| 2004/0098133 A1 | 5/2004 | Carignan et al. | 623/20.35 |
| 2004/0102866 A1 | 5/2004 | Harris et al. | 700/117 |
| 2004/0117015 A1 | 6/2004 | Biscup | 623/16.11 |
| 2004/0153162 A1 | 8/2004 | Sanford et al. | 623/20.3 |
| 2004/0167390 A1 | 8/2004 | Alexander et al. | 600/410 |
| 2004/0167630 A1 | 8/2004 | Rolston | 623/20.14 |
| 2004/0204760 A1 | 10/2004 | Fitz et al. | 623/14.12 |
| 2004/0236424 A1 | 11/2004 | Berez et al. | 623/14.12 |
| 2004/0249386 A1 | 12/2004 | Faoro | 606/88 |
| 2005/0015153 A1 | 1/2005 | Goble et al. | 623/23.46 |
| 2005/0021039 A1 | 1/2005 | Cusick et al. | 606/88 |
| 2005/0021042 A1 | 1/2005 | Marnay et al. | 606/99 |
| 2005/0055028 A1 | 3/2005 | Haines | 606/79 |
| 2005/0085920 A1 | 4/2005 | Williamson | 623/20.14 |
| 2005/0107886 A1 | 5/2005 | Crabtree et al. | 623/20.24 |
| 2005/0119664 A1 | 6/2005 | Carignan et al. | 606/96 |
| 2005/0143745 A1 | 6/2005 | Hodorek et al. | 606/87 |

(56) References Cited

U.S. PATENT DOCUMENTS

| | | | | |
|---|---|---|---|---|
| 2005/0148843 A1 | 7/2005 | Roose | | 600/407 |
| 2005/0171545 A1 | 8/2005 | Walsh et al. | | 606/72 |
| 2005/0171612 A1 | 8/2005 | Rolston | | 623/20.19 |
| 2005/0192588 A1 | 9/2005 | Garcia | | 606/88 |
| 2005/0216305 A1 | 9/2005 | Funderud | | 705/2 |
| 2005/0234461 A1 | 10/2005 | Burdulis, Jr. et al. | | 606/79 |
| 2005/0267584 A1 | 12/2005 | Burdulis et al. | | 623/20.19 |
| 2005/0278034 A1 | 12/2005 | Johnson et al. | | 623/20.15 |
| 2006/0052795 A1 | 3/2006 | White | | 606/102 |
| 2006/0074432 A1 | 4/2006 | Stad et al. | | 606/90 |
| 2006/0122616 A1 | 6/2006 | Bennett et al. | | 606/87 |
| 2006/0149283 A1 | 7/2006 | May et al. | | 606/96 |
| 2006/0200162 A1 | 9/2006 | Farling et al. | | 606/88 |
| 2006/0235421 A1 | 10/2006 | Rosa et al. | | 606/88 |
| 2007/0015995 A1 | 1/2007 | Lang | | 600/407 |
| 2007/0073305 A1 | 3/2007 | Lionberger et al. | | 606/87 |
| 2007/0118141 A1 | 5/2007 | Marchyn et al. | | 606/88 |
| 2007/0198022 A1 | 8/2007 | Lang et al. | | 606/88 |
| 2007/0203430 A1 | 8/2007 | Lang et al. | | 600/587 |
| 2007/0226986 A1 | 10/2007 | Park et al. | | 29/592 |
| 2007/0233141 A1 | 10/2007 | Park et al. | | 606/88 |
| 2007/0233151 A1 | 10/2007 | Chudik | | 606/96 |
| 2007/0233156 A1 | 10/2007 | Metzger | | 606/130 |
| 2007/0276224 A1 | 11/2007 | Lang et al. | | 600/410 |
| 2007/0276501 A1 | 11/2007 | Betz et al. | | 623/17.16 |
| 2007/0282451 A1 | 12/2007 | Metzger et al. | | 623/20.28 |
| 2007/0288030 A1 | 12/2007 | Metzger et al. | | 606/87 |
| 2007/0293868 A1 | 12/2007 | Delfosse et al. | | 606/88 |
| 2008/0015433 A1 | 1/2008 | Alexander et al. | | 600/427 |
| 2008/0021566 A1 | 1/2008 | Peters et al. | | 623/20.16 |
| 2008/0058945 A1 | 3/2008 | Hajaj et al. | | 623/20.14 |
| 2008/0114370 A1 | 5/2008 | Schoenefeld | | 606/96 |
| 2008/0140212 A1 | 6/2008 | Metzger et al. | | 623/20.31 |
| 2008/0147072 A1 | 6/2008 | Park et al. | | 606/87 |
| 2008/0215059 A1 | 9/2008 | Carignan et al. | | 606/96 |
| 2008/0243127 A1 | 10/2008 | Lang et al. | | 606/87 |
| 2008/0257363 A1 | 10/2008 | Schoenefeld et al. | | 128/897 |
| 2008/0262624 A1 | 10/2008 | White et al. | | 623/20.32 |
| 2008/0275452 A1 | 11/2008 | Lang et al. | | 606/88 |
| 2008/0281328 A1 | 11/2008 | Lang et al. | | 606/87 |
| 2008/0281329 A1 | 11/2008 | Lang et al. | | 606/87 |
| 2008/0281426 A1 | 11/2008 | Fitz et al. | | 623/17.16 |
| 2008/0319448 A1 | 12/2008 | Lavallee et al. | | 606/102 |
| 2009/0024131 A1 | 1/2009 | Metzger et al. | | 606/88 |
| 2009/0076371 A1 | 3/2009 | Lang et al. | | 600/424 |
| 2009/0087276 A1 | 4/2009 | Rose | | 409/79 |
| 2009/0088753 A1 | 4/2009 | Aram et al. | | 606/79 |
| 2009/0088758 A1 | 4/2009 | Bennett | | 606/82 |
| 2009/0099567 A1 | 4/2009 | Zajac | | 606/79 |
| 2009/0110498 A1 | 4/2009 | Park | | 408/1 R |
| 2009/0131941 A1* | 5/2009 | Park et al. | | 606/87 |
| 2009/0131942 A1 | 5/2009 | Aker et al. | | 606/88 |
| 2009/0138020 A1 | 5/2009 | Park et al. | | 606/88 |
| 2009/0151736 A1 | 6/2009 | Belcher et al. | | 128/898 |
| 2009/0163922 A1 | 6/2009 | Meridew et al. | | 606/88 |
| 2009/0222014 A1 | 9/2009 | Bojarski et al. | | 606/88 |
| 2009/0226068 A1 | 9/2009 | Fitz et al. | | 382/131 |
| 2009/0254093 A1 | 10/2009 | White et al. | | 606/89 |
| 2009/0307893 A1 | 12/2009 | Burdulis, Jr. et al. | | 29/527.1 |
| 2009/0326666 A1 | 12/2009 | Wyss et al. | | 623/20.29 |
| 2010/0049195 A1 | 2/2010 | Park et al. | | 606/87 |
| 2010/0082035 A1 | 4/2010 | Keefer | | 606/97 |
| 2010/0087829 A1 | 4/2010 | Metzger et al. | | 606/96 |
| 2010/0152741 A1 | 6/2010 | Park et al. | | 606/89 |
| 2010/0160917 A1 | 6/2010 | Fitz et al. | | 606/88 |
| 2010/0168754 A1 | 7/2010 | Fitz et al. | | 606/88 |
| 2010/0256479 A1 | 10/2010 | Park et al. | | 600/410 |
| 2010/0274534 A1 | 10/2010 | Steines et al. | | 703/1 |
| 2010/0281678 A1 | 11/2010 | Burdulis, Jr. et al. | | 29/592 |
| 2010/0298894 A1 | 11/2010 | Bojarski et al. | | 606/86 |
| 2010/0303313 A1 | 12/2010 | Lang et al. | | 382/128 |
| 2010/0305573 A1 | 12/2010 | Fitz et al. | | 606/87 |
| 2010/0305574 A1 | 12/2010 | Fitz et al. | | 606/88 |
| 2010/0331991 A1 | 12/2010 | Wilkinson et al. | | 623/20.32 |
| 2010/0332194 A1 | 12/2010 | McGuan et al. | | 703/1 |
| 2011/0029093 A1 | 2/2011 | Bojarski et al. | | 623/20.35 |
| 2011/0040387 A1 | 2/2011 | Ries et al. | | 623/20.27 |
| 2011/0046735 A1 | 2/2011 | Metzger et al. | | 623/14.12 |
| 2011/0066193 A1 | 3/2011 | Lang et al. | | 606/86 |
| 2011/0071533 A1 | 3/2011 | Metzger et al. | | 606/88 |
| 2011/0071581 A1 | 3/2011 | Lang et al. | | 606/86 |
| 2011/0092804 A1 | 4/2011 | Schoenefeld et al. | | 600/416 |
| 2011/0125009 A1 | 5/2011 | Lang et al. | | 600/425 |
| 2011/0166578 A1 | 7/2011 | Stone et al. | | 606/88 |
| 2011/0213368 A1 | 9/2011 | Fitz et al. | | 606/80 |
| 2011/0213373 A1 | 9/2011 | Fitz et al. | | 606/87 |
| 2011/0213374 A1 | 9/2011 | Fitz et al. | | 606/87 |
| 2011/0213377 A1 | 9/2011 | Lang et al. | | 606/89 |
| 2011/0213428 A1 | 9/2011 | Fitz et al. | | 606/86 R |
| 2011/0213429 A1 | 9/2011 | Lang et al. | | 606/86 R |
| 2011/0213430 A1 | 9/2011 | Lang et al. | | 606/86 R |
| 2011/0218539 A1 | 9/2011 | Fitz et al. | | 606/87 |
| 2011/0218542 A1 | 9/2011 | Lian | | 606/88 |
| 2011/0218545 A1 | 9/2011 | Catanzarite et al. | | 606/96 |
| 2011/0218584 A1 | 9/2011 | Fitz et al. | | 606/86 R |
| 2011/0230888 A1 | 9/2011 | Lang et al. | | 606/87 |
| 2011/0238073 A1 | 9/2011 | Lang et al. | | 606/89 |
| 2011/0295329 A1 | 12/2011 | Fitz et al. | | 606/86 R |
| 2011/0313423 A1 | 12/2011 | Lang et al. | | 606/87 |
| 2011/0319897 A1 | 12/2011 | Lang et al. | | 606/79 |
| 2011/0319900 A1 | 12/2011 | Lang et al. | | 606/87 |
| 2012/0029520 A1 | 2/2012 | Lang et al. | | 606/89 |
| 2012/0041446 A1 | 2/2012 | Wong et al. | | 606/96 |
| 2012/0066892 A1 | 3/2012 | Lang et al. | | 29/592 |
| 2012/0071881 A1 | 3/2012 | Lang et al. | | 606/87 |
| 2012/0071882 A1 | 3/2012 | Lang et al. | | 606/88 |
| 2012/0071883 A1 | 3/2012 | Lang et al. | | 606/88 |
| 2012/0072185 A1 | 3/2012 | Lang et al. | | 703/1 |
| 2012/0078598 A1 | 3/2012 | McDaniel | | 703/6 |
| 2012/0101503 A1 | 4/2012 | Lang et al. | | 606/87 |
| 2012/0123422 A1 | 5/2012 | Agnihotri et al. | | 606/89 |
| 2012/0141034 A1 | 6/2012 | Iannotti et al. | | 382/199 |
| 2012/0143197 A1 | 6/2012 | Lang et al. | | 606/87 |
| 2012/0151730 A1 | 6/2012 | Fitz et al. | | 29/407.01 |
| 2012/0158001 A1 | 6/2012 | Burdulis, Jr. et al. | | 606/88 |
| 2012/0197260 A1 | 8/2012 | Fitz et al. | | 606/88 |
| 2012/0209394 A1 | 8/2012 | Bojarski et al. | | 623/20.32 |
| 2012/0239045 A1 | 9/2012 | Li | | 606/88 |
| 2012/0265496 A1 | 10/2012 | Mahfouz | | 703/1 |
| 2012/0276509 A1 | 11/2012 | Iannotti et al. | | 434/267 |
| 2012/0289966 A1 | 11/2012 | Fitz et al. | | 606/88 |
| 2012/0296337 A1 | 11/2012 | Fitz et al. | | 606/80 |
| 2012/0310364 A1 | 12/2012 | Li et al. | | 623/23.55 |
| 2012/0316564 A1 | 12/2012 | Serbousek et al. | | 606/80 |
| 2012/0323246 A1 | 12/2012 | Catanzarite et al. | | 606/88 |
| 2013/0006250 A1 | 1/2013 | Metzger et al. | | 606/87 |
| 2013/0018379 A1 | 1/2013 | Fitz et al. | | 606/88 |
| 2013/0018380 A1 | 1/2013 | Fitz et al. | | 623/14.12 |
| 2013/0018464 A1 | 1/2013 | Fitz et al. | | 606/88 |
| 2013/0023884 A1 | 1/2013 | Bojarski et al. | | 623/20.14 |
| 2013/0024000 A1 | 1/2013 | Bojarski et al. | | 623/20.14 |
| 2013/0030419 A1 | 1/2013 | Fitz et al. | | 606/1 |
| 2013/0030441 A1 | 1/2013 | Fitz et al. | | 606/88 |
| 2013/0035766 A1 | 2/2013 | Meridew | | 623/22.21 |
| 2013/0066321 A1 | 3/2013 | Mannss et al. | | 606/88 |
| 2013/0079781 A1 | 3/2013 | Fitz et al. | | 606/80 |
| 2013/0079876 A1 | 3/2013 | Fitz et al. | | 623/14.12 |
| 2013/0081247 A1 | 4/2013 | Fitz et al. | | 29/407.09 |
| 2013/0096562 A1 | 4/2013 | Fitz et al. | | 606/88 |
| 2013/0103363 A1 | 4/2013 | Lang et al. | | 703/1 |
| 2013/0119579 A1 | 5/2013 | Iannotti et al. | | 264/256 |
| 2013/0123792 A1 | 5/2013 | Fitz et al. | | 606/96 |
| 2013/0184713 A1 | 7/2013 | Bojarski et al. | | 606/88 |
| 2013/0184764 A1 | 7/2013 | Stone et al. | | 606/280 |
| 2013/0211409 A1 | 8/2013 | Burdulis, Jr. et al. | | 606/88 |
| 2013/0253522 A1 | 9/2013 | Bojarski et al. | | 606/88 |
| 2013/0289570 A1 | 10/2013 | Chao | | 606/88 |
| 2013/0296874 A1 | 11/2013 | Chao | | 606/88 |
| 2013/0317511 A1 | 11/2013 | Bojarski et al. | | 606/102 |
| 2013/0331850 A1 | 12/2013 | Bojarski et al. | | 606/102 |
| 2014/0031826 A1 | 1/2014 | Bojarski et al. | | 606/87 |
| 2014/0058396 A1 | 2/2014 | Fitz et al. | | 606/87 |
| 2014/0058397 A1 | 2/2014 | Fitz et al. | | 606/88 |
| 2014/0066935 A1 | 3/2014 | Fitz et al. | | 606/87 |

(56) References Cited

U.S. PATENT DOCUMENTS

| | | | |
|---|---|---|---|
| 2014/0066936 A1 | 3/2014 | Fitz et al. | 606/87 |
| 2014/0074441 A1 | 3/2014 | Fitz et al. | 703/1 |
| 2014/0163568 A1 | 6/2014 | Wong et al. | 606/96 |
| 2014/0188240 A1 | 7/2014 | Lang et al. | 623/22.12 |
| 2014/0213431 A1 | 7/2014 | Choo et al. | 606/86 R |
| 2014/0324205 A1 | 10/2014 | Park et al. | 700/98 |

FOREIGN PATENT DOCUMENTS

| | | | | |
|---|---|---|---|---|
| DE | 20303498 | 8/2003 | | A61B 17/15 |
| EP | 0337901 | 10/1989 | | A61B 17/14 |
| EP | 0 704 193 | 4/1996 | | A61F 2/30 |
| EP | 0908836 | 4/1999 | | G06F 19/00 |
| EP | 0993807 | 4/2000 | | A61B 17/17 |
| EP | 1074229 | 2/2001 | | A61F 2/38 |
| FR | 2819714 | 7/2002 | | A61F 2/44 |
| FR | 2918554 | 1/2009 | | A61B 17/17 |
| GB | 1451283 | 9/1976 | | A61F 1/24 |
| JP | 2002-102236 | 9/2002 | | A61B 17/16 |
| WO | WO 93/25157 | 12/1993 | | A61F 2/38 |
| WO | WO 95/28688 | 10/1995 | | G06T 15/00 |
| WO | WO 95/30390 | 11/1995 | | A61F 2/38 |
| WO | WO 98/12994 | 4/1998 | | A61F 2/28 |
| WO | WO 98/20816 | 5/1998 | | A61F 2/38 |
| WO | WO 98/32384 | 7/1998 | | A61B 17/58 |
| WO | WO 99/40864 | 8/1999 | | A61B 17/56 |
| WO | WO 99/56674 | 11/1999 | | A61F 2/36 |
| WO | WO 00/09179 | 2/2000 | | A61L 25/00 |
| WO | WO 00/19911 | 4/2000 | | A61B 17/02 |
| WO | WO 00/35346 | 6/2000 | | A61B 5/11 |
| WO | WO 00/68749 | 11/2000 | | G05B 19/4099 |
| WO | WO 01/10356 | 2/2001 | | A61F 2/46 |
| WO | WO 01/66021 | 9/2001 | | A61B 17/14 |
| WO | WO 01/70142 | 9/2001 | | A61F 2/38 |
| WO | WO 01/77988 | 10/2001 | | G06F 19/00 |
| WO | WO 02/22013 | 3/2002 | | A61B 5/55 |
| WO | WO 02/22014 | 3/2002 | | A61B 5/55 |
| WO | WO 02/23483 | 3/2002 | | A61B 5/55 |
| WO | WO 02/061688 | 8/2002 | | G06T 17/00 |
| WO | WO 02/096268 | 12/2002 | | |
| WO | WO 03/037192 | 5/2003 | | A61B 17/15 |
| WO | WO 03/047470 | 6/2003 | | A61F 2/34 |
| WO | WO 03/055400 | 7/2003 | | A61B 17/74 |
| WO | WO 2004/006811 | 1/2004 | | A61F 2/46 |
| WO | WO 2004/032806 | 4/2004 | | A61F 2/30 |
| WO | WO 2004/049981 | 6/2004 | | A61F 2/46 |
| WO | WO 2005/051239 | 6/2005 | | A61F 2/08 |
| WO | WO 2005/051240 | 6/2005 | | A61F 2/08 |
| WO | WO 2005/067521 | 7/2005 | | |
| WO | WO 2006/060795 | 6/2006 | | A61B 17/17 |
| WO | WO 2006/127283 | 11/2006 | | A61B 17/17 |
| WO | WO 2007/092841 | 8/2007 | | A61B 17/15 |
| WO | WO 2007/109641 | 9/2007 | | A61F 2/30 |
| WO | WO 2008/021494 | 2/2008 | | G06F 19/00 |
| WO | WO 2008/112996 | 9/2008 | | A61B 17/15 |
| WO | WO 2008/117028 | 10/2008 | | A61B 17/15 |
| WO | WO 2008/157412 | 12/2008 | | A61B 17/17 |
| WO | WO 2009/001083 | 12/2008 | | A61B 17/15 |
| WO | WO 2009/009660 | 1/2009 | | A61F 2/30 |
| WO | WO 2009/106366 | 9/2009 | | A61B 17/15 |
| WO | WO 2009/106816 | 9/2009 | | A61B 19/00 |
| WO | WO 2009/111639 | 9/2009 | | A61B 17/58 |
| WO | WO 2010/099231 | 9/2010 | | A61B 2/38 |
| WO | WO 2010/121147 | 10/2010 | | A61B 17/90 |
| WO | WO 2010/148103 | 12/2010 | | A61B 17/17 |
| WO | WO 2011/059641 | 5/2011 | | A61B 17/15 |
| WO | WO 2011/130421 | 10/2011 | | A61B 17/56 |
| WO | WO 2012/021241 | 2/2012 | | A61B 17/88 |
| WO | WO 2012/021846 | 2/2012 | | A61B 17/90 |
| WO | WO 2012/021894 | 2/2012 | | A61F 2/46 |
| WO | WO 2012/021895 | 2/2012 | | A61F 2/46 |
| WO | WO 2012/027150 | 3/2012 | | G06F 19/00 |
| WO | WO 2012/051542 | 4/2012 | | A61B 17/16 |
| WO | WO 2012/112694 | 8/2012 | | A61B 6/00 |
| WO | WO 2012/112698 | 8/2012 | | A61F 2/30 |
| WO | WO 2012/112701 | 8/2012 | | A61F 2/30 |
| WO | WO 2012/112702 | 8/2012 | | A61F 2/30 |
| WO | WO 2013/119865 | 8/2013 | | A61B 17/90 |
| WO | WO 2014/145281 | 9/2014 | | A61B 17/56 |

OTHER PUBLICATIONS

Cohen et al., "Knee Cartilage Topography Thickness and Contact Areas From MRI: In-Vitro Calibration and In-Vivo Measurements", Osteoarthritis and Cartilage vol. 7, No. 1, pp. 95-109 (1999).

Tsai et al., "Accurate Surface Voxelization for Manipulating Volumetric Surfaces and Solids with Application in Simulating Musculoskeletal Surgery", Inst. of Information and Computer Engineering, pp. 234-243, 2001.

International Searching Authority, International Search Report—International Application No. PCT/US2012/025269 dated Aug. 31, 2012, together with the Written Opinion of the International Searching Authority, 14 pages.

International Searching Authority, International Search Report—International Application No. PCT/US2012/025274 dated Oct. 25, 2012, together with the Written Opinion of the International Searching Authority, 12 pages.

International Searching Authority, International Search Report—International Application No. PCT/US2012/025277 dated Oct. 25, 2012, together with the Written Opinion of the International Searching Authority, 12 pages.

International Searching Authority, International Search Report—International Application No. PCT/US2012/025280 dated Oct. 25, 2012, together with the Written Opinion of the International Searching Authority, 11 pages.

European Patent Office, Extended European Search Report—Application No. 13164557.4-1659 dated Nov. 25, 2013, 8 pages.

European Patent Office, Extended European Search Report—Application No. 13167237.0-1659 dated Nov. 25, 2013, 8 pages.

European Patent Office, Extended European Search Report—Application No. 13167246.1-1659 dated Nov. 25, 2013, 8 pages.

European Patent Office, Extended European Search Report—Application No. 13167257.8-1659 dated Nov. 25, 2013, 8 pages.

United States Patent and Trademark Office, Office Action pertaining to U.S. Appl. No. 13/405,843 dated Dec. 10, 2013, 9 pages.

Brandt et al., In German: "CRIGOS—Development of a Compact Robot System for Image-Guided Orthopedic Surgery," *Der Orthopäde*, Springer-Verlag, vol. 29, No. 7, pp. 645-649 (Jul. 2000).

Brandt et al., English Translation with Certification: "CRIGOS—Development of a Compact Robot System for Image-Guided Orthopedic Surgery," *Der Orthopäde*, Springer-Verlag, vol. 29, No. 7, pp. 645-649 (Jul. 2000).

CAOS, "MIS meets CAOS Spring 2005 Symposium Schedule", *CAOS Spring 2005 Symposium*, pp. 1-9, May 19, 2005.

Chelule et al., "Patient-Specific Template to Preserve Bone Stock in Total Knee Replacement: Preliminary Results", *15th Annual ISTA Symposium*, Sep. 2002, 1 page.

Hafez et al., "Computer Assisted Total Knee Replacement: Could a Two-Piece Custom Template Replace the Complex Conventional Instrumentations?" Session 6: Novel Instruments; *Computer Aided Surgery*, Session 6, vol. 9, No. 3, pp. 93-94 (Jun. 2004).

Hafez et al., "Computer-assisted Total Knee Arthroplasty Using Patient-specific Templating," *Clinical Orthopaedics and Related Research*, No. 444, pp. 184-192 (Mar. 2006).

Radermacher et al., "Computer Assisted Orthopedic Surgery by Means of Individual Templates • Aspects and Analysis of Potential Applications •" *Proceedings of the First International Symposium on Medical Robotics and Computer Assisted Surgery*, vol. 1: Sessions I-III, MRCAS '94, Pittsburgh, PA, pp. 42-48 (Sep. 22-24, 1994).

Schiffers et al., In German: "Planning and execution of orthopedic surgery using individualized templates," *Der Orthopäde*, Springer-Verlag, vol. 29, No. 7, pp. 636-640, (Jul. 2000).

Schiffers et al., English Translation with Certification: "Planning and execution of orthopedic surgery using individualized templates," *Der Orthopäde*, Springer-Verlag, vol. 29, No. 7, pp. 636-640, (Jul. 2000).

(56) References Cited

OTHER PUBLICATIONS

Thoma et al., In German: "Use of a New Subtraction Procedure Based on Three-Dimensional CT Scans for the Individual Treatment of Bone Defects in the Hip and Knee," *Journal DGPW*, No. 17, pp. 27-28 (May 1999).

Thoma et al., English Translation with Certification: "Use of a New Subtraction Procedure Based on Three-Dimensional CT Scans for the Individual Treatment of Bone Defects in the Hip and Knee," *Journal DGPW*, No. 17, pp. 27-28 (May 1999).

Thoma et al., In German: "Custom-made knee endoprosthetics using subtraction data of three-dimensional CT scans—A new approach," *Der Orthopäde*, Springer-Verlag, vol. 29, No. 7, pp. 641-644, (Jul. 2000).

Thoma et al., English Translation with Certification: "Custom-made knee endoprosthetics using subtraction data of three-dimensional CT scans—A new approach," *Der Orthopäde*, Springer-Verlag, vol. 29, No. 7, pp. 641-644, (Jul. 2000).

United States Patent and Trademark Office, Office Action dated Oct. 23, 2009, pertaining to U.S. Appl. No. 10/764,010, 13 pages.

United States Patent and Trademark Office, Office Action dated Jan. 9, 2009, pertaining to U.S. Appl. No. 10/764,010 11 pages.

Bromberg & Sunstein LLP, Response to Office Action dated Jan. 9, 2009, pertaining to U.S. Appl. No. 10/764,010, 25 pages.

United States Patent and Trademark Office, Office Action dated May 17, 2010, pertaining to U.S. Appl. No. 10/764,010, 12 pages.

Sunstein Kann Murphy & Timbers LLP, Response to Office Action dated May 17, 2010, pertaining to U.S. Appl. No. 10,764,010, 21 pages.

United States Patent and Trademark Office, Notice of Allowance dated Dec. 16, 2010, pertaining to U.S. Appl. No. 10/764,010, 11 pages.

United States Patent and Trademark Office, Notice of Allowance dated Aug. 5, 2011, pertaining to U.S. Appl. No. 10/764,010, 14 pages.

Sunstein Kann Murphy & Timbers LLP, Amendment dated Jun. 28, 2010 pertaining to U.S. Appl. No. 11/410,515, 16 pages.

United States Patent and Trademark Office, Office Action dated Oct. 6, 2010 pertaining to U.S. Appl. No. 11/410,515, 20 pages.

Sunstein Kann Murphy & Timbers LLP, Amendment dated Apr. 6, 2011 pertaining to U.S. Appl. No. 11/410,515, 12 pages.

Sunstein Kann Murphy & Timbers LLP, Preliminary Amendment dated Jul. 31, 2009, pertaining to U.S. Appl. No. 11/739,326, 19 pages.

United States Patent and Trademark Office, Office Action dated Apr. 20, 2010, pertaining to U.S. Appl. No. 11/739,326, 13 pages.

Sunstein Kann Murphy & Timbers LLP, Response to Office Action dated Apr. 20, 2010, pertaining to U.S. Appl. No. 11/739,326, 22 pages.

United States Patent and Trademark Office, Notice of Allowance dated Nov. 24, 2010, pertaining to U.S. Appl. No. 11/739,326, 8 pages.

Sunstein Kann Murphy & Timbers LLP, Preliminary Amendment dated Jul. 31, 2009 pertaining to U.S. Appl. No. 11/769,434, 44 pages.

United States Patent and Trademark Office, Office Action dated Aug. 2, 2010 pertaining to U.S. Appl. No. 11/769,434, 83 pages.

Sunstein Kann Murphy & Timbers LLP, Amendment dated Feb. 2, 2011 pertaining to U.S. Appl. No. 11/769,434, 44 pages.

Sunstein Kann Murphy & Timbers LLP, Preliminary Amendment dated Aug. 12, 2011, pertaining to U.S. Appl. No. 13/017,886, 13 pages.

United States Patent and Trademark Office, Office Action dated Jun. 23, 2011 pertaining to U.S. Appl. No. 11/410,515, 13 pages.

United States Patent and Trademark Office, Office Action dated Jan. 13, 2012 pertaining to U.S. Appl. No. 12/776,840, 10 pages.

Portheine et al., In German: "Computer-Assisted Total Knee Endoprosthetics with Planning-Specific Treatement Templates", Biomed. Tech., vol. 46, Supp. vol. 1, Jan. 2001.

Portheine et al., English Translation with Certification: "Computer-Assisted Total Knee Endoprosthetics with Planning-Specific Treatement Templates", Biomed. Tech., vol. 46, Supp. vol. 1, Jan. 2001.

European Patent Office, Extended European Search Report—Application No. 10765271.1-2310, dated Dec. 19, 2012, 6 pages.

European Patent Office, European Search Report—Application No. 12170854.9-1526 dated Oct. 9, 2012, 6 pages.

European Patent Office, European Search Report—Application No. 09716738.1, dated Feb. 6, 2012, 10 pages.

Clarke et al., "Human Hip Joint Geometry and Hemiarthroplasty Selection," The Hip. C.V. Mosby, St. Louis 63-89 (1975).

Conaty, et al., "Surgery of the Hip and Knee in Patients with Rheumatoid Arthritis," J. Bone Joint Surg. Am. 55(2):301-314 (1973).

Iida et al., "Socket Location in Total Hip Replacement: Preoperative Computed Tomography and Computer Simulation" Acta Orthop Scand; 59(1): 1-5 (1988).

Kidder et al., "3D Model Acquisition, Design, Planning and Manufacturing of Orthopaedic Devices: A Framework," Proceedings of the SPIE—Advanced Sensor and Control-System Interface, Boston, MA, vol. 2911, pp. 9-22, 21 (Nov. 1996).

Kshirsagar et al., "Measurement of Localized Cartilage Volume and Thickness of Human Knee Joints by Computer Analysis of Three-Dimensional Magnetic Resonance Images," Invest Radiol. 33(5): 289-299 (May 1998).

Mahaisavariya et al., "Morphological Study of the Proximal Femur: A New Method of Geometrical Assessment Using 3 Dimensional Reverse Engineering," Med. Eng. and Phys., vol. 24, pp. 617-622, 2002.

Matsen, III et al., "Robotic Assistance in Orthopaedic Surgery: A Proof of Principle Using Distal Femoral Arthroplasty", Clinical Ortho. and Related Research, 296:178-186 (1993).

Portheine et al., "CT-Based Planning and Individual Template Navigation in TKA", Navigation and Robotics in Total Joint and Spine Surgery, Springer, 48:336-342 (2004).

Portheine et al., "Development of a Clinical Demonstrator for Computer Assisted Orthopedic Surgery with CT Image Based Individual Templates." in Lemke HU, Vannier MW, Inamura K (eds). Computer Assisted Radiology and Surgery. Amsterdam, Elsevier 944-949, 1997.

Radermacher, English Translation : Helmholtz Institute of Biomedical Technology, "Computer-Assisted Planning and Execution of Orthopedic Surgery Using Individual Surgical Templates", May 18, 1999.

Radermacher, German Version: Helmholtz Institute of Biomedical Technology, "Computer-Assisted Planning and Execution of Orthopedic Surgery Using Individual Surgical Templates", May 18, 1999.

Radermacher, "Computer Assisted Orthopaedic Surgery With Image Based Individual Templates" Clinical Orthopaedics, Sep. 1998, vol. 354, pp. 28-38.

Radermacher et al., "Image Guided Orthopedic Surgery Using Individual Templates—Experimental Results and Aspects of the Development of a Demonstrator for Pelvis Surgery." In Troccaz J. Grimson E., Mosges R (eds). Computer Vision, Virtual Reality and Robotics in Medicine and Medical Robotics and Computer Assisted Surgery, Lecture Notes in Computer Science. Berlin, Springer-Verlag 606-616, 1997.

Radermacher et al., "Computer Integrated Orthopedic Surgery—Connection of Planning and Execution in Surgical Inventions." In Taylor, R., Lavallee, S., Burdea G. Mosges, R. (eds). Computer Integrated Surgery. Cambridge, MIT press 451-463, 1996.

Radermacher et al.,"Technique for Better Execution of CT Scan Planned Orthopedic Surgery on Bone Structures." in Lemke HW, Inamura, K., Jaffe, CC, Vannier, MW (eds). Computer Assisted Radiology, Berlin, Springer 933-938, 1995.

Radermacher et al., "CT Image Based Planning and Execution of Interventions in Orthopedic Surgery Using Individual Templates—Experimental Results and Aspects of Clinical Applications." In Nolte LP, Ganz, R. (eds). CAOS—Computer Assisted Orthopaedic Surgery. Bern, Hans Huber (In Press) 1998.

Testi et al.,"Border Tracing Algorithm Implementation for the Femoral Geometry Reconstruction," Comp. Meth. and Programs in Biomed., vol. 65, pp. 175-182, 2001.

(56) References Cited

OTHER PUBLICATIONS

Zimmer, Inc., "There's a New Addition to the Flex Family! The Zimmer® Unicompartmental Knee System", pp. 1-8 (2004).
European Patent Office, European Search Report—Application No. EP 03790194, dated Jul. 13, 2006, 7 pages.
International Searching Authority, International Search Report—International Application No. PCT/US2005/044008, dated Mar. 30, 2006, together with the Written Opinion of the International Searching Authority, 12 pages.
International Searching Authority, International Search Report—International Application No. PCT/US2007/061681, dated Sep. 7, 2007, together with the Written Opinion of the International Searching Authority, 12 pages.
International Searching Authority, International Preliminary Report on Patentability—International Application No. PCT/US2005/044008, dated Jun. 14, 2007, together with the Written Opinion of the International Searching Authority, 8 pages.
International Searching Authority, International Search Report—International Application No. PCT/US2008/057045, dated Jul. 15, 2008, together with the Written Opinion of the International Searching Authority, 9 pages.
International Searching Authority, Invitation to Pay Additional Fees, and Where Applicable, Protest Fee—International Application No. PCT/US2008/066994, dated Oct. 21, 2008, 5 pages.
International Searching Authority, International Search Report—International Application No. PCT/US2008/066994, dated Feb. 19, 2009, together with the Written Opinion of the International Searching Authority, 16 pages.
Bromberg & Sunstein LLP, Amendment dated Sep. 22, 2008, pertaining to U.S. Appl. No. 09/882,363, 15 pages.
United States Patent and Trademark, Office Office Action dated Jan. 6, 2009, pertaining to U.S. Appl. No. 09/882,363, 9 pages.
Bromberg & Sunstein LLP, Request for Continued Examination dated Jul. 6, 2009, pertaining to U.S. Appl. No. 09/882,363, 16 pages.
International Searching Authority, International Search Report—International Application No. PCT/US2009/036189, dated Jul. 13, 2009, together with the Written Opinion of the International Searching Authority, 11 pages.
Sunstein Kann Murphy & Timbers LLP, Supplemental Amendment dated Sep. 18, 2009, pertaining to U.S. Appl. No. 09/882,363, 11 pages.
United States Patent and Trademark Office, Office Action dated May 5, 2008, pertaining to U.S. Appl. No. 10/724,010, 13 pages.
Bromberg & Sunstein LLP, Request for Continued Examination and Response dated Nov. 4, 2008, pertaining to U.S. Appl. No. 10/724,010, 15 pages.
United States Patent and Trademark Office, Office Action dated Jan. 29, 2009, pertaining to U.S. Appl. No. 10/724,010, 9 pages.
Bromberg & Sunstein LLP, Response to Office Action dated Jan. 29, 2009, pertaining to U.S. Appl. No. 10/724,010, 16 pages.
United States Patent and Trademark Office, Office Action dated Nov. 26, 2007, pertaining to U.S. Appl. No. 11/002,573, 15 pages.
Bromberg & Sunstein LLP, Request for Continued Examination and Response dated Feb. 27, 2008, pertaining to U.S. Appl. No. 11/002,573, 19 pages.
United States Patent and Trademark Office, Office Action dated May 9, 2008, pertaining to U.S. Appl. No. 11/002,573, 17 pages.
Bromberg & Sunstein LLP, Amendment dated Aug. 12, 2008, pertaining to U.S. Appl. No. 11/002,573, 25 pages.
Bromberg & Sunstein LLP, Preliminary Amendment dated Aug. 22, 2006, pertaining to U.S. Appl. No. 11/410,515, 10 pages.
United States Patent and Trademark Office, Office Action dated Dec. 30, 2008, pertaining to U.S. Appl. No. 11/410,515, 32 pages.
Bromberg & Sunstein LLP, Amendment dated Jun. 30, 2009, pertaining to U.S. Appl. No. 11/410,515, 18 pages.
Sunstein Kann Murphy & Timbers LLP, Supplemental Amendment dated Aug. 26, 2009, pertaining to U.S. Appl. No. 11/410,515, 11 pages.
Sunstein Kann Murphy & Timbers LLP, Supplemental Amendment dated Sep. 21, 2009, pertaining to U.S. Appl. No. 11/410,515, 11 pages.
United States Patent and Trademark Office, Office Action dated Dec. 28, 2009, pertaining to U.S. Appl. No. 11/410,515, 43 pages.
United States Patent and Trademark Office, Office action dated Jan. 26, 2010, pertaining to U.S. Appl. No. 11/671,745, 9 pages.
International Searching Authority, International Search Report—International Application No. PCT/US10/31415, dated Jun. 29, 2010, together with the Written Opinion of the International Searching Authority, 9 pages.
United States Patent and Trademark Office, Office Action dated Oct. 20, 2010, pertaining to U.S. Appl. No. 12/135,719, 10 pages.
Sunstein Kann Murphy & Timbers LLP, Response to Office Action dated Aug. 26, 2010, pertaining to U.S. Appl. No. 12/361,213, 22 pages.
United States Patent and Trademark Office, Office Action dated Feb. 28, 2011, pertaining to U.S. Appl. No. 12/048,764, 12 pages.
European Patent Office, Extended European Search Report—European Application No. 10181743.5-2310, dated Mar. 11, 2011, 6 pages.
United States Patent and Trademark Office, Office Action dated Apr. 20, 2011, pertaining to U.S. Appl. No. 12/135,612, 13 pages.
Birnbaum et al., "Computer-Assisted Orthopedic Surgery With Individual Templates and Comparison to Conventional Operation Method", Spine, vol. 26, No. 4, pp. 365-369, Feb. 2001.
Chelule et al., "Computer Aided Design of Personalized Jigs in Total Knee Replacement", $3^{rd}$ Annual Meeting of CAOS Int'l Proc., Spain, Jun. 18, 21, 2003, pp. 58-59.
Froemel et al., "Computer Assisted Template Based Navigation for Total Knee Replacement", Documents presented at CAOS on Jun. 17, 2001, 4 pages.
Hafez et al., "Computer Assisted Total Knee Replacement: Could a Two-Piece Custom Template Replace the Complex Conventional Instrumentations?", $4^{th}$ Annual Meeting of CAOS Int'l Proc., Chicago, Jun. 16-19, 2004, pp. 63-64.
Hafez et al., "Computer-Assisted Total Hip Arthroplasty: The Present and the Future", Future Rheumatol., vol. 1, pp. 121-131, 2006.
Portheine et al., In German: "Potentials of CT-based Planning and Template-based Procedure in Hip and Knee Surgery", Orth. Prac., vol. 36, pp. 786-791, 2000.
Portheine et al., English Translation with Certification: "Potentials of CT-based Planning and Template-based Procedure in Hip and Knee Surgery", Orth. Prac., vol. 36, pp. 786-791, 2000.
Portheine, In German: "Model-Based Operation Planning in Orthopedic Surgery", Thesis, RWTH Aachen University, Apr. 22, 2004, 90 pages.
Portheine, English Translation with Certification: "Model-Based Operation Planning in Orthopedic Surgery", Thesis, RWTH Aachen University, Apr. 22, 2004, 170 pages.
Radermacher et al., "Computer Integrated Surgery—Connecting Planning and Execution of Surgical Intervention in Orthopedics", Surgical Therapy Technology, Helmholtz-Institut Aachen Research Report, 1991-1992, pp. 187, 196-202.
Radermacher et al., "Computer Assisted Matching of Planning and Execution in Orthopedic Surgery", IEEE, EMBS, San Diego, 1993, pp. 946-947.
Radermacher, "Computer Assisted Matching of Planning and Execution in Orthopedic Surgery", Slide Presentation, San Diego, Nov. 29, 1993, 22 pages.
Radermacher et al., "Computer Integrated Advanced Orthopedics (CIAO)", $2^{nd}$ European Conference on Eng. and Med., presented Apr. 26, 1993, 12 pages.
Radermacher et al., "Surgical Therapy Technology", Helmholtz-Institut Aachen Research Report, 1993-1994, pp. 189-219.
Radermacher, "Image Guided Orthopedic Surgery with Individual Templates", Helmhotz-Institute for Biomed. Eng., 2 pages, 1997.
Radermacher et al., In German: "Computer-assisted operative interventions in orthopedics—are there prospects for endoprosthetics as well?", Prac. Ortho., vol. 27, pp. 149-164, 1997.

(56) References Cited

OTHER PUBLICATIONS

Radermacher et al., English Translation with Certification: "Computer-assisted operative interventions in orthopedics—are there prospects for endoprosthetics as well?", Prac. Ortho., vol. 27, pp. 1-17, 1997.
Radermacher et al., "Computer Based Decision Support for the Planning of Contact Faces for Manual Registration with Individual Templates", Helmholtz-Institute for Biomed. Eng., 7 pages, 1997-98.
Radermacher, In German: "Computer-Based Decision Support in the Selection and Evaluation of Contact Surfaces for Manual Referencing", Lecture presented at Helmholtz Meeting '98 and OSS '98, 7 pages.
Radermacher, English Translation with Certification: "Computer-Based Decision Support in the Selection and Evaluation of Contact Surfaces for Manual Referencing", Lecture presented at Helmholtz Meeting '98 and OSS '98, 8 pages.
Radermacher et al,. In German: "Computer-Assisted Planning and Operation in Orthopedics", Orth. Prac. $36^{th}$ year, pp. 731-737, Dec. 2000.
Radermacher et al., English Translation with Certification: "Computer-Assisted Planning and Operation in Orthopedics", Orth. Prac. $36^{th}$ year, pp. 731-737, Dec. 2000.
Radermacher, "Template Based Navigation—An Efficient Technique for Hip and Knee Surgery", CAOS First Asian Meet, India, Mar. 27-28, 2004, pp. 44-50.
Rau et al., "Small and Neat", Medical Tech. Int'l, pp. 65, 67 and 69, 1993-94.
Schkommadau et al., "Clinical Application of Individual Templates for Pedicle Screw Placement in Comparison to Computer Navigation", Poster presented at CAOS, Feb. 18, 2000, 1 page.
Schkommadau et al., In German: "Clinical Experience With the Individual Template Technique", Orth. Prac., vol. 37, No. 1, pp. 19-22, 2001.
Schkommadau et al., English Translation with Certification: "Clinical Experience With the Individual Template Technique", Orth. Prac., vol. 37, No. 1, pp. 19-22, 2001.
Seel et al., "Three-Dimensional Planning and Virtual Radiographs in Revision Total Hip Arthroplasty for Instability", Clinical Orthopaedics and Related Research, No. 442, pp. 35-38, Jan. 2006.
Staudte et al., In German: "Computer-Assisted Operation Planning and Technique in Orthopedics", North Rhine-Westphalia Acad. for Sciences, Lecture N.444, ISSN 0944-8799, 2000, 17 pages.
Staudte et al., English Translation with Certification: "Computer-Assisted Operation Planning and Technique in Orthopedics", North Rhine-Westphalia Acad. for Sciences, Lecture N.444, ISSN 0944-8799, 2000, 34 pages.
European Patent Office, Extended European Search Report—Application No. 10181149.5-1526 dated Apr. 19, 2012, 9 pages.
European Patent Office, Extended European Search Report—Application No. 10181198.2-1526 dated Apr. 19, 2012, 9 pages.
United States Patent and Trademark Office, Office Action dated Jan. 26, 2012, pertaining to U.S. Appl. No. 12/139,324, 14 pages.
United States Patent and Trademark Office, Office Action dated Jun. 5, 2012, pertaining to U.S. Appl. No. 12/776,984, 7 pages.
United States Patent and Trademark Office, Office Action dated May 31, 2012, pertaining to U.S. Appl. No. 12/398,753, 7 pages.
Macdonald et al., "Inaccuracy of Acetabular Reaming Under Surgical Conditions", Journ. of Arthro., vol. 14, No. 6, pp. 730-737, 1999.
Müller-Wittig et al., "A Computer-Assisted Planning System for Total Knee Replacement", CG Topics, pp. 17-19, Jun. 2000.
International Searching Authority, International Search Report—International Application No. PCT/US2013/025216 dated May 30, 2013, together with the Written Opinion of the International Searching Authority, 12 pages.
United States Patent and Trademark Office, Office Action dated Feb. 13, 2014, pertaining to U.S. Appl. No. 13/306,501, 25 pages.
Delp et al., "Computer Assisted Knee Replacement", Clinical Orthopaedics, pp. 49-56, Sep. 1998.
Duane Morris LLP et al., Counsel for Wright Medical Technology, Inc. et al., United States District Court of Massachusetts, Civil Action No. 13-12312- Document No. 55—Defendants' Preliminary Invalidity and Non-Infringement Disclosures—Wright Medical Technology, Inc. et al. 22 pages, 2014.
International Searching Authority, International Search Report—International Application No. PCT/US2015/012203 dated May 4, 2015, together with the Written Opinion of the International Searching Authority, 12 pages.
International Searching Authority, International Search Report—International Application No. PCT/US2014/030015 dated Aug. 27, 2014, together with the Written Opinion of the International Searching Authority, 9 pages.
United States Patent & Trademark Office, Office Action dated May 19, 2015, pertaining to U.S. Appl. No. 13/013,195, 8 pages.
Sunstein Kann Murphy & Timbers LLP, Amendment to Office Action dated May 19, 2015, pertaining to U.S. Appl. No. 13/013,195, 16 pages.
United States Patent & Trademark Office, Notice of Allowance dated Sep. 18, 2015, pertaining to U.S. Appl. No. 13/013,195, 7 pages.
United States Patent & Trademark Office, Office Action dated Jun. 17, 2015, pertaining to U.S. Appl. No. 13/013,354, 11 pages.
Sunstein Kann Murphy & Timbers LLP, Response to Office Action dated Jun. 17, 2015, pertaining to U.S. Appl. No. 13/013,354, 8 pages.
United States Patent & Trademark Office, Office Action dated Jun. 23, 2015, pertaining to U.S. Appl. No. 13/013,383, 13 pages.
Sunstein Kann Murphy & Timbers LLP, Request for Continued Examination and Response filed Sep. 22, 2015, pertaining to U.S. Appl. No. 13/013,383, 33 pages.
Sunstein Kann Murphy & Timbers LLP, Request for Continued Examination and Response filed Apr. 28, 2015, pertaining to U.S. Appl. No. 13/013,418, 12 pages.
United States Patent & Trademark Office, Office Action dated Jun. 1, 2015, pertaining to U.S. Appl. No. 13/013,418, 12 pages.
United States Patent & Trademark Office, Office Action dated May 18, 2015, pertaining to U.S. Appl. No. 13/013,446, 6 pages.
Sunstein Kann Murphy & Timbers LLP, Amendment to Office Action dated May 18, 2015, pertaining to U.S. Appl. No. 13/013,446, 10 pages.
United States Patent & Trademark Office, Notice of Allowance dated Sep. 18, 2015, pertaining to U.S. Appl. No. 13/013,446, 5 pages.
United States Patent & Trademark Office, Office Action dated Jun. 23, 2015, pertaining to U.S. Appl. No. 13/013,461, 13 pages.
Sunstein Kann Murphy & Timbers LLP, Request for Continued Examination and Response filed Sep. 22, 2015, pertaining to U.S. Appl. No. 13/013,461, 19 pages.
United States Patent & Trademark Office, Office Action dated Nov. 12, 2014, pertaining to U.S. Appl. No. 13/013,470, 12 pages.
Sunstein Kann Murphy & Timbers LLP, Response to Office Action dated Nov. 12, 2014, pertaining to U.S. Appl. No. 13/013,470, 11 pages.
United States Patent & Trademark Office, Notice of Allowance dated Jun. 17, 2015, pertaining to U.S. Appl. No. 13/013,470, 5 pages.
Sunstein Kann Murphy & Timbers LLP, Request for Continued Examination and Response filed May 22, 2015, pertaining to U.S. Appl. No. 13/014,448, 19 pages.
United States Patent & Trademark Office, Office Action dated Jun. 23, 2015, pertaining to U.S. Appl. No. 13/014,448, 14 pages.
Sunstein Kann Murphy & Timbers LLP, Amendment to Office Action dated Nov. 26, 2014, pertaining to U.S. Appl. No. 13/014,457, 11 pages.
United States Patent & Trademark Office, Office Action dated Jun. 23, 2015, pertaining to U.S. Appl. No. 13/014,457, 14 pages.
Sunstein Kann Murphy & Timbers LLP, Request for Continued Examination and Response filed May 26, 2015, pertaining to U.S. Appl. No. 13/014,466, 15 pages.
United States Patent & Trademark Office, Office Action dated Jul. 15, 2015, pertaining to U.S. Appl. No. 13/014,466, 13 pages.
United States Patent & Trademark Office, Notice of Allowance dated Nov. 30, 2015, pertaining to U.S. Appl. No. 13/014,466, 5 pages.
United States Patent & Trademark Office, Office Action dated Jun. 23, 2015, pertaining to U.S. Appl. No. 13/014,474, 14 pages.

(56) References Cited

OTHER PUBLICATIONS

Sunstein Kann Murphy & Timbers LLP, Request for Continued Examination and Response filed Sep. 23, 2015, pertaining to U.S. Appl. No. 13/014,474, 14 pages.
United States Patent & Trademark Office, Office Action dated May 18, 2015, pertaining to U.S. Appl. No. 13/013,435, 7 pages.
Sunstein Kann Murphy & Timbers LLP, Response to Office Action dated May 18, 2015, pertaining to U.S. Appl. No. 13/013,435, 13 pages.
United States Patent & Trademark Office, Notice of Allowance dated Sep. 23, 2015, pertaining to U.S. Appl. No. 13/013,435, 7 pages.
Sunstein Kann Murphy & Timbers LLP, Request for Continued Examination and Response filed May 22, 2015, pertaining to U.S. Appl. No. 13/013,288, 11 pages.
United States Patent & Trademark Office, Office Action dated Jul. 15, 2015, pertaining to U.S. Appl. No. 13/013,288, 11 pages.
United States Patent & Trademark Office, Notice of Allowance Nov. 20, 2015, pertaining to U.S. Appl. No. 13/013,288, 5 pages.
U.S. Appl. No. 10/681,750, filed Oct. 7, 2003.
U.S. Appl. No. 10/724,010, filed Nov. 25, 2003.
U.S. Appl. No. 11/002,573, filed Dec. 2, 2004.
U.S. Appl. No. 11/671,745, filed Feb. 6, 2007.
U.S. Appl. No. 12/048,764, filed Mar. 14, 2008.
U.S. Appl. No. 12/135,603, filed Jun. 9, 2008.
U.S. Appl. No. 12/135,612, filed Jun. 9, 2008.
U.S. Appl. No. 12/135,719, filed Jun. 9, 2008.
U.S. Appl. No. 12/139,324, filed Jun. 13, 2008.
U.S. Appl. No. 12/361,213, filed Jan. 28, 2009.
U.S. Appl. No. 12/398,753, filed Mar. 5, 2009.
U.S. Appl. No. 12/606,830, filed Oct. 27, 2009.
U.S. Appl. No. 12/606,844, filed Oct. 27, 2009.
U.S. Appl. No. 12/761,865, filed Apr. 16, 2010.
U.S. Appl. No. 12/776,701, filed May 10, 2010.
U.S. Appl. No. 12/776,984, filed May 10, 2010.
U.S. Appl. No. 12/776,840, filed May 10, 2010.
U.S. Appl. No. 12/777,756, filed May 11, 2010.
U.S. Appl. No. 12/777,809, filed May 11, 2010.
U.S. Appl. No. 12/777,852, filed May 11, 2010.
U.S. Appl. No. 13/010,279, filed Jan. 20, 2011.
U.S. Appl. No. 13/010,299, filed Jan. 20, 2011.
U.S. Appl. No. 13/010,312, filed Jan. 20, 2011.
U.S. Appl. No. 13/013,195, filed Jan. 25, 2011.
U.S. Appl. No. 13/013,288, filed Jan. 25, 2011.
U.S. Appl. No. 13/013,354, filed Jan. 25, 2011.
U.S. Appl. No. 13/013,383, filed Jan. 25, 2011.
U.S. Appl. No. 13/013,418, filed Jan. 25, 2011.
U.S. Appl. No. 13/013,435, filed Jan. 25, 2011.
U.S. Appl. No. 13/013,446, filed Jan. 25, 2011.
U.S. Appl. No. 13/013,461, filed Jan. 25, 2011.
U.S. Appl. No. 13/013,470, filed Jan. 25, 2011.
U.S. Appl. No. 13/014,448, filed Jan. 26, 2011.
U.S. Appl. No. 13/014,457, filed Jan. 26, 2011.
U.S. Appl. No. 13/014,466, filed Jan. 26, 2011.
U.S. Appl. No. 13/014,474, filed Jan. 26, 2011.
U.S. Appl. No. 13/163,121, filed Jun. 17, 2011.
U.S. Appl. No. 13/207,396, filed Aug. 10, 2011.
U.S. Appl. No. 13/294,617, filed Nov. 11, 2011.
U.S. Appl. No. 13/305,622, filed Nov. 28, 2011.
U.S. Appl. No. 13/305,634, filed Nov. 28, 2011.
U.S. Appl. No. 13/305,636, filed Nov. 28, 2011.
U.S. Appl. No. 13/306,501, filed Nov. 29, 2011.
U.S. Appl. No. 13/306,509, filed Nov. 29, 2011.
U.S. Appl. No. 13/302,833, filed Nov. 22, 2011.
U.S. Appl. No. 13/336,543, filed Dec. 23, 2011.
U.S. Appl. No. 13/405,797, filed Feb. 27, 2012.
U.S. Appl. No. 13/405,826, filed Feb. 27, 2012.
U.S. Appl. No. 13/405,843, filed Feb. 27, 2012.
U.S. Appl. No. 13/553,057, filed Jul. 19, 2012.
U.S. Appl. No. 13/554,453, filed Jul. 20, 2012.
U.S. Appl. No. 13/625,748, filed Sep. 24, 2012.
U.S. Appl. No. 13/625,686, filed Sep. 24, 2012.
U.S. Appl. No. 13/625,694, filed Sep. 24, 2012.
U.S. Appl. No. 13/625,702, filed Sep. 24, 2012.
U.S. Appl. No. 13/625,710, filed Sep. 24, 2012.
U.S. Appl. No. 13/625,714, filed Sep. 24, 2012.
U.S. Appl. No. 13/625,720, filed Sep. 24, 2012.
U.S. Appl. No. 13/625,728, filed Sep. 24, 2012.
U.S. Appl. No. 13/625,732, filed Sep. 24, 2012.
U.S. Appl. No. 13/625,738, filed Sep. 24, 2012.
U.S. Appl. No. 13/625,742, filed Sep. 24, 2012.
U.S. Appl. No. 13/718,699, filed Dec. 18, 2012.
U.S. Appl. No. 13/718,717, filed Dec. 18, 2012.
U.S. Appl. No. 13/754,133, filed Jan. 30, 2013.
U.S. Appl. No. 13/835,863, filed Mar. 15, 2013.
U.S. Appl. No. 13/865,958, filed Apr. 18, 2013.
U.S. Appl. No. 13/872,017, filed Apr. 26, 2013.
U.S. Appl. No. 13/892,547, filed May 13, 2013.
U.S. Appl. No. 13/913,990, filed Jun. 10, 2013.
U.S. Appl. No. 13/915,609, filed Jun. 11, 2013.
U.S. Appl. No. 13/935,446, filed Jul. 3, 2013.
U.S. Appl. No. 13/954,090, filed Jul. 30, 2013.
U.S. Appl. No. 14/021,595, filed Sep. 9, 2013.
U.S. Appl. No. 14/072,751, filed Nov. 5, 2013.
U.S. Appl. No. 14/072,754, filed Nov. 5, 2013.
U.S. Appl. No. 14/072,766, filed Nov. 5, 2013.
U.S. Appl. No. 14/072,771, filed Nov. 5, 2013.
U.S. Appl. No. 14/148,067, filed Jan. 6, 2014.
U.S. Appl. No. 14/148,511, filed Jan. 6, 2014.
U.S. Appl. No. 14/308,070, filed Jun. 18, 2014.
U.S. Appl. No. 14/390,835, filed Oct. 6, 2014.
U.S. Appl. No. 14/615,906, filed Feb. 6, 2015.
U.S. Appl. No. 14/791,672, filed Jul. 6, 2015.

* cited by examiner

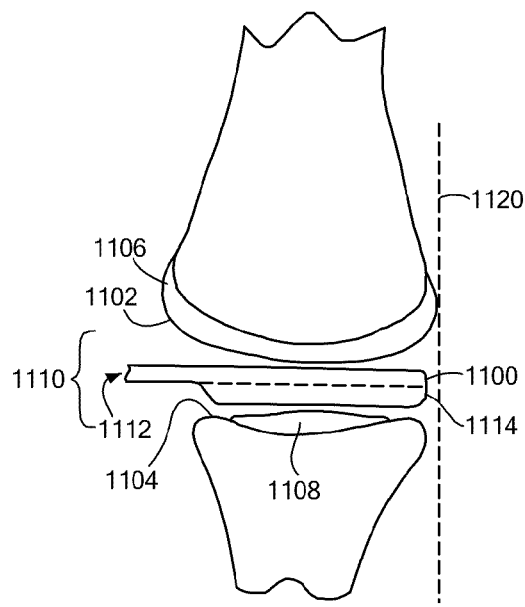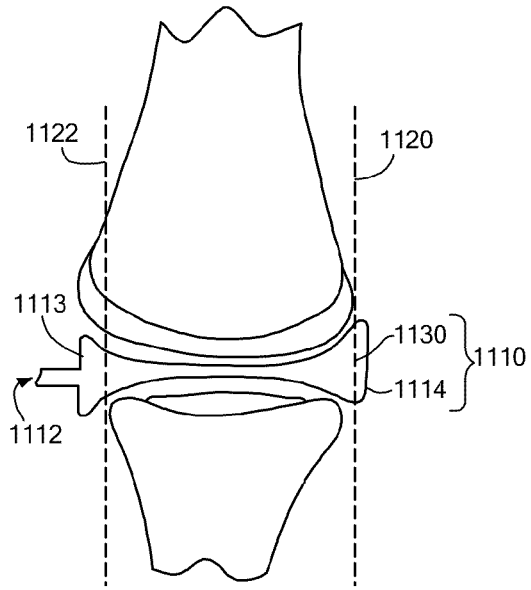
FIG. 11A  FIG. 11B
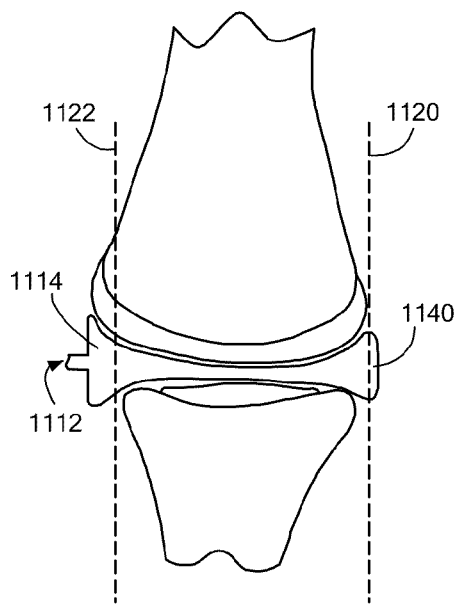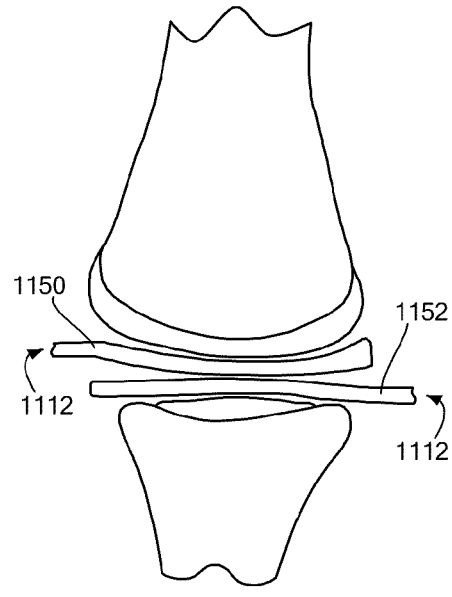
FIG. 11C  FIG. 11D

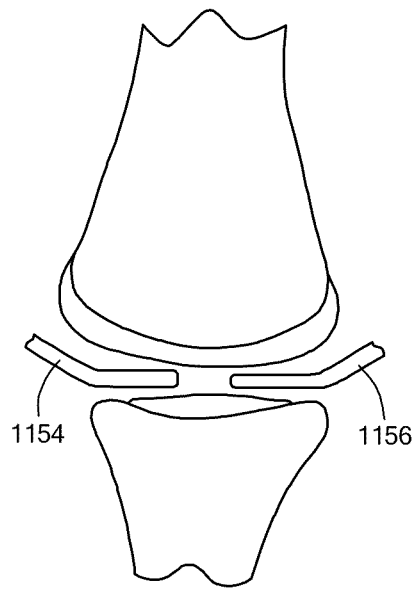
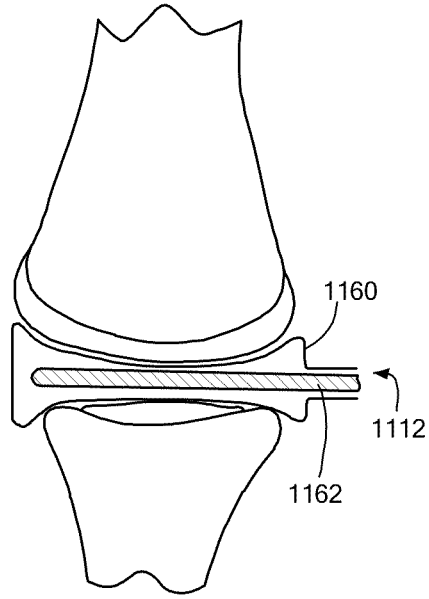
FIG. 11E                    FIG. 11F
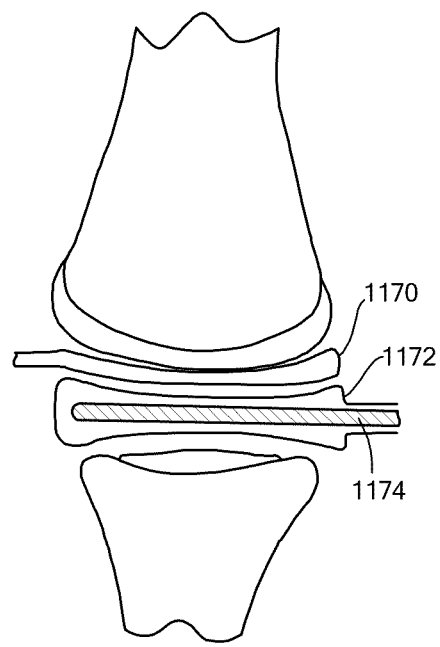
FIG. 11G

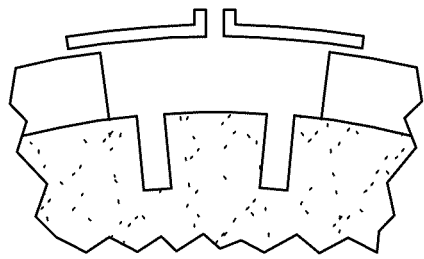
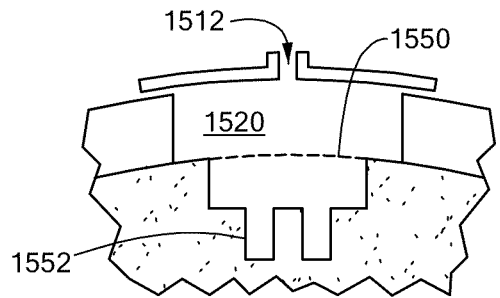
FIG. 14G(1)          FIG. 14G(2)
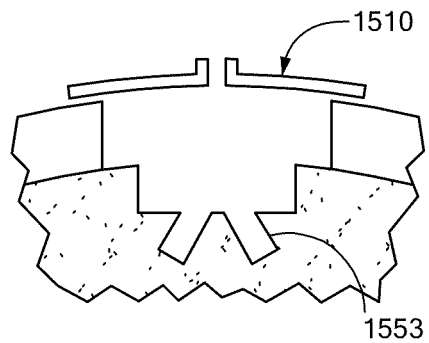
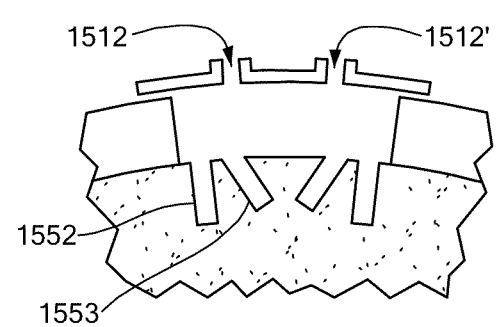
FIG. 14G(3)          FIG. 14G(4)
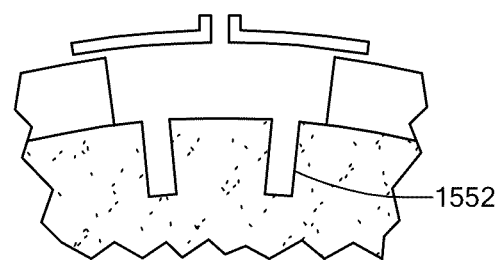
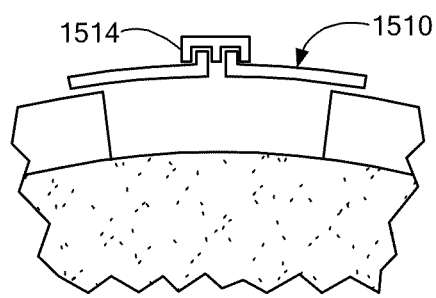
FIG. 14G(5)          FIG. 14G(6)
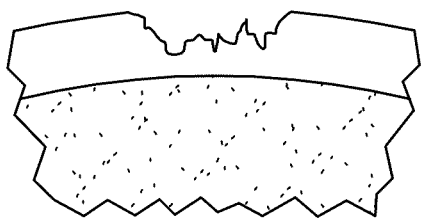
FIG. 14G(7)

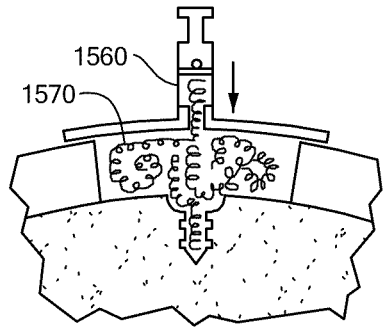
*FIG. 14G(8)*
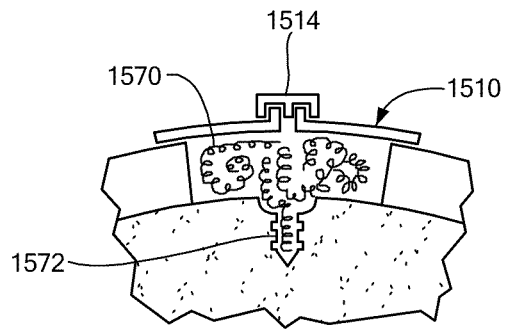
*FIG. 14G(9)*
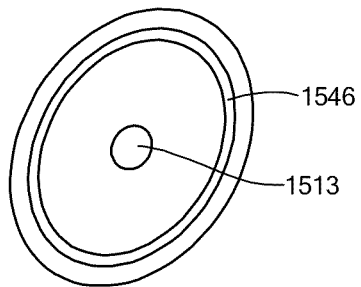
*FIG. 14H*
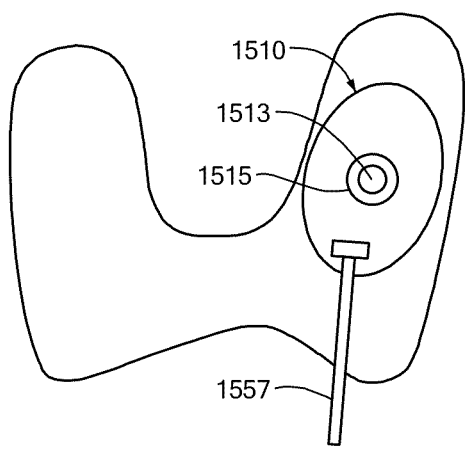
*FIG. 14I*
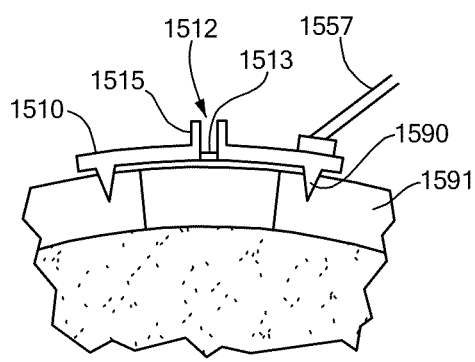
*FIG. 14J*

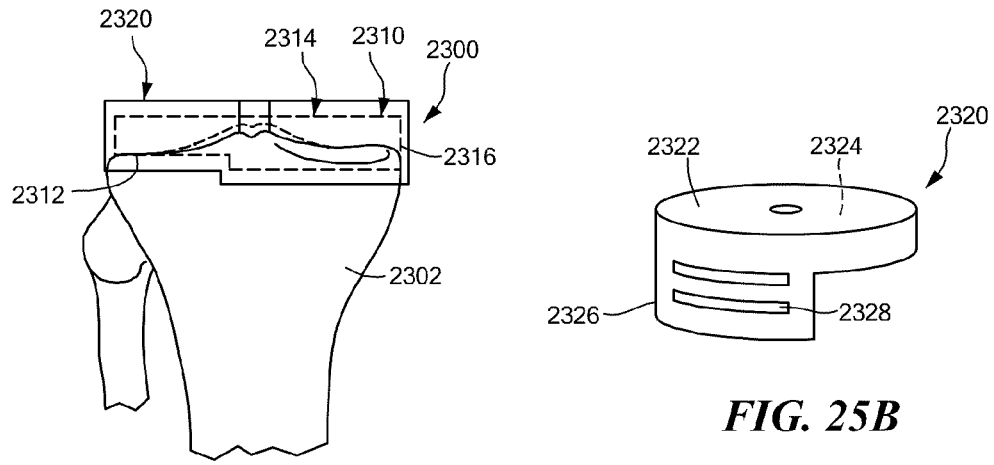
FIG. 25A
FIG. 25B
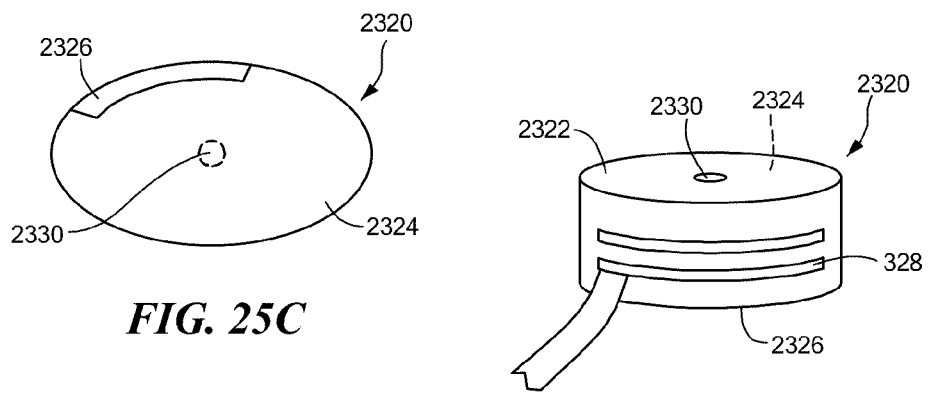
FIG. 25C
FIG. 25D
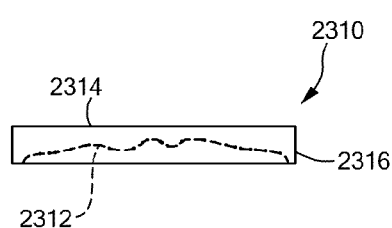
FIG. 25E
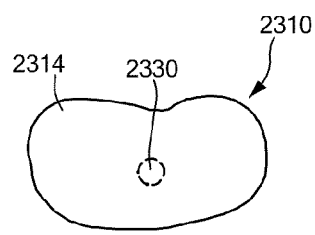
FIG. 25F

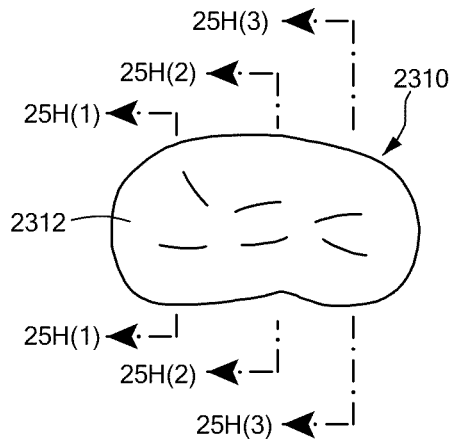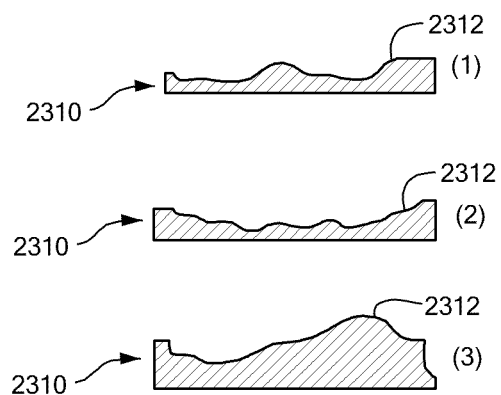
*FIG. 25G*    *FIG. 25H*
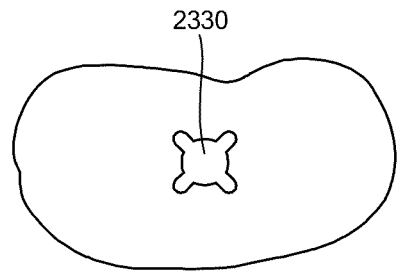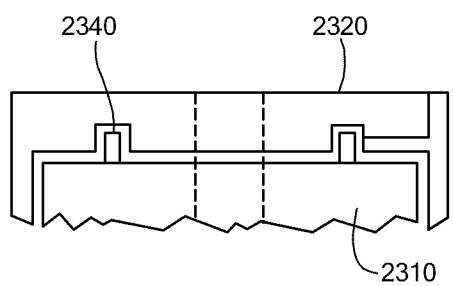
*FIG. 25I*    *FIG. 25J*
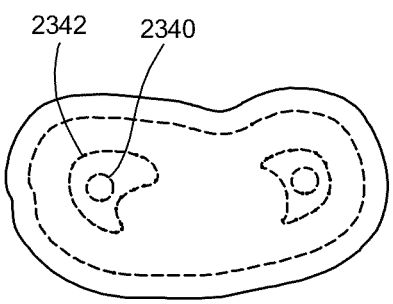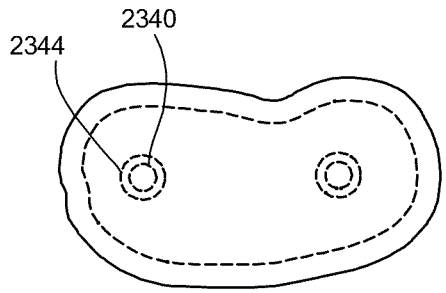
*FIG. 25K*    *FIG. 25L*

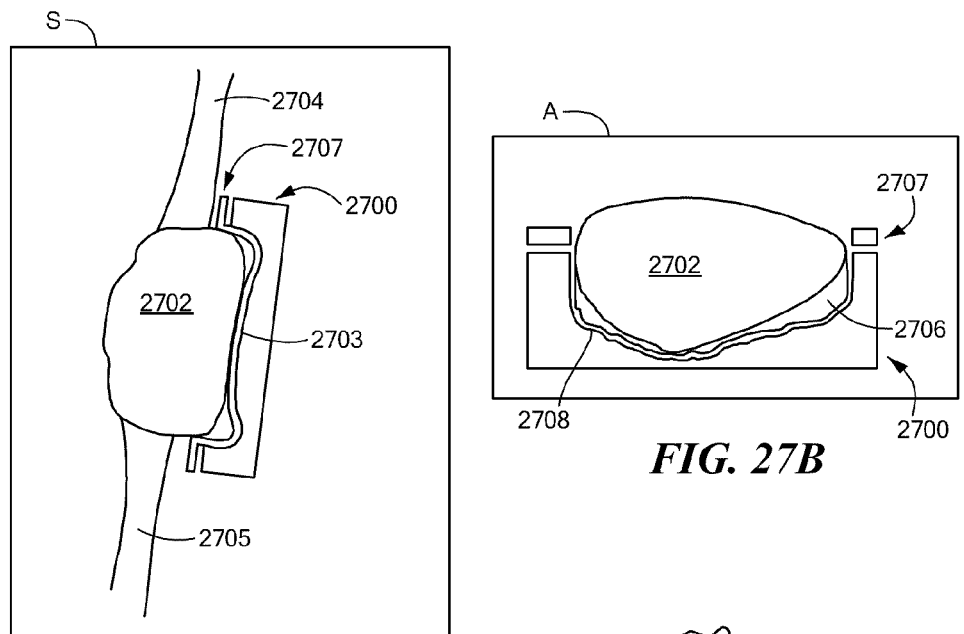
FIG. 27A
FIG. 27B
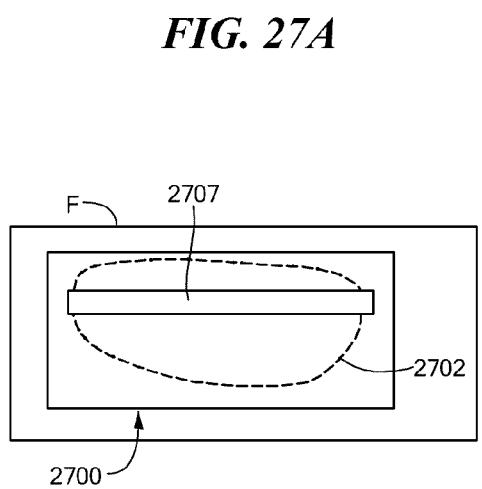
FIG. 27C
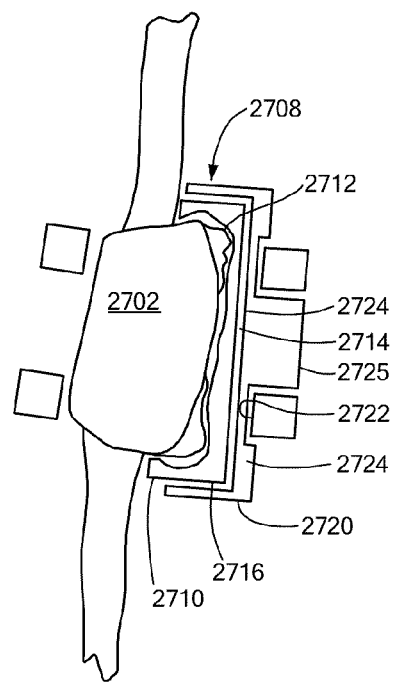
FIG. 27D

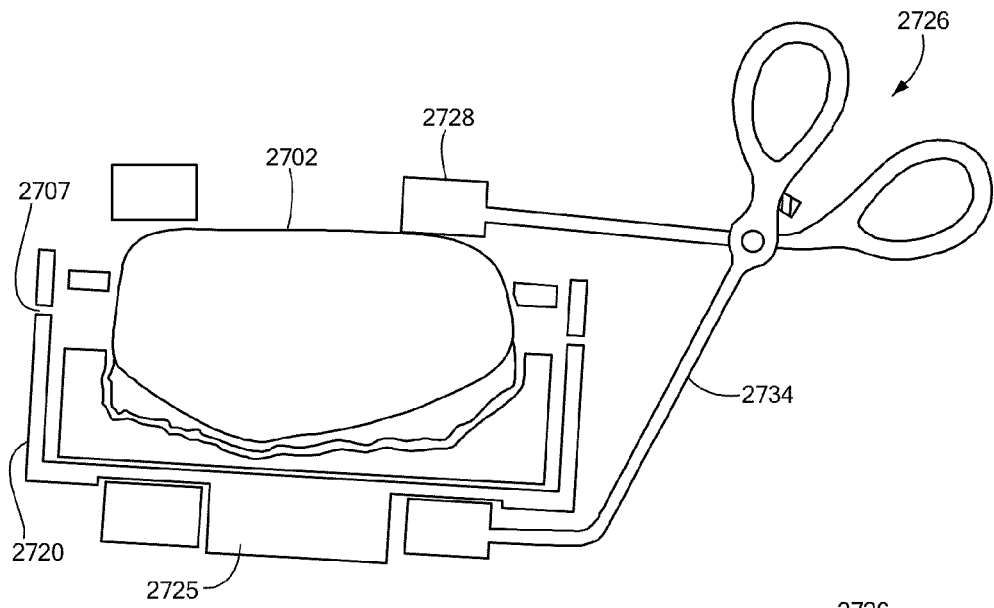
FIG. 27E
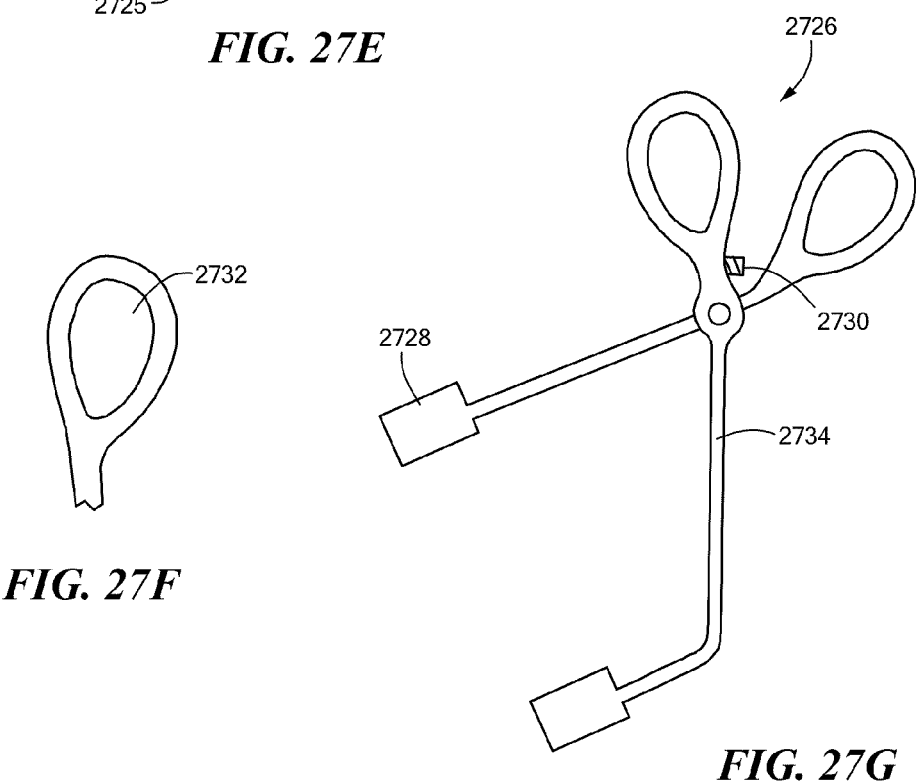
FIG. 27F
FIG. 27G

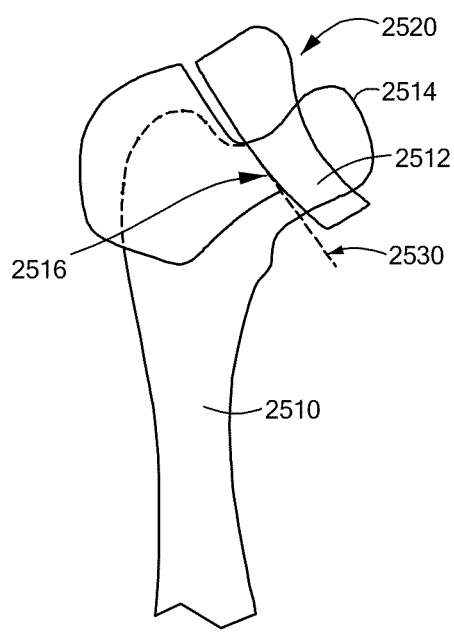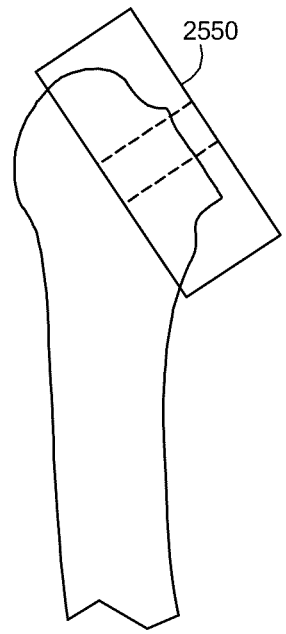
*FIG. 28A*  *FIG. 28C*
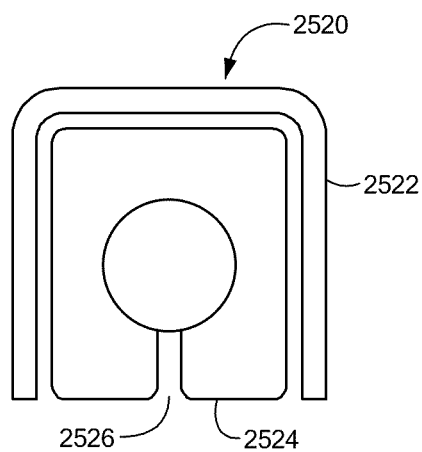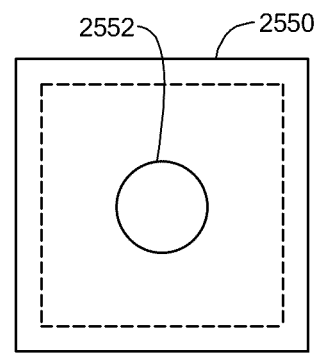
*FIG. 28B*  *FIG. 28D*

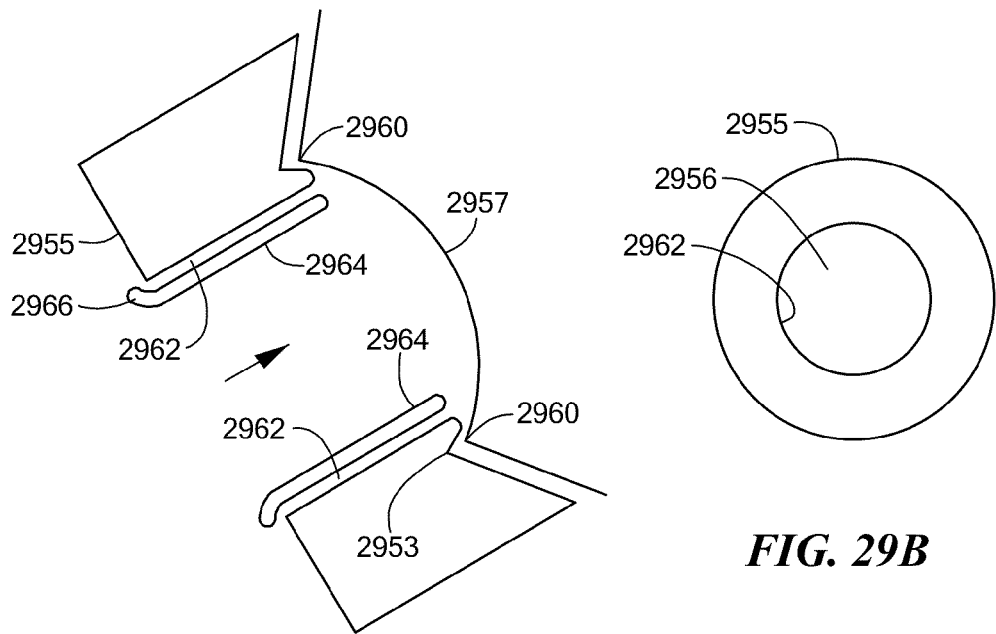
FIG. 29A
FIG. 29B
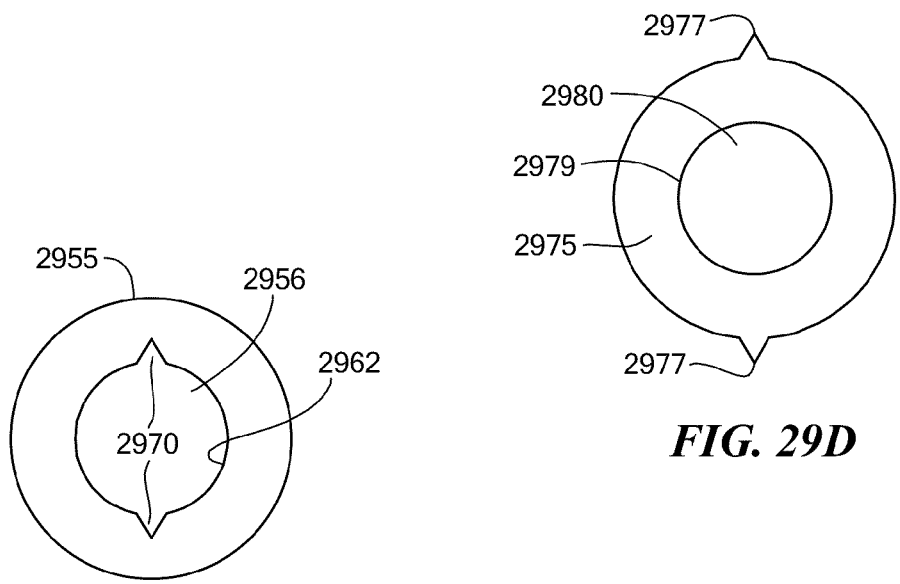
FIG. 29C
FIG. 29D

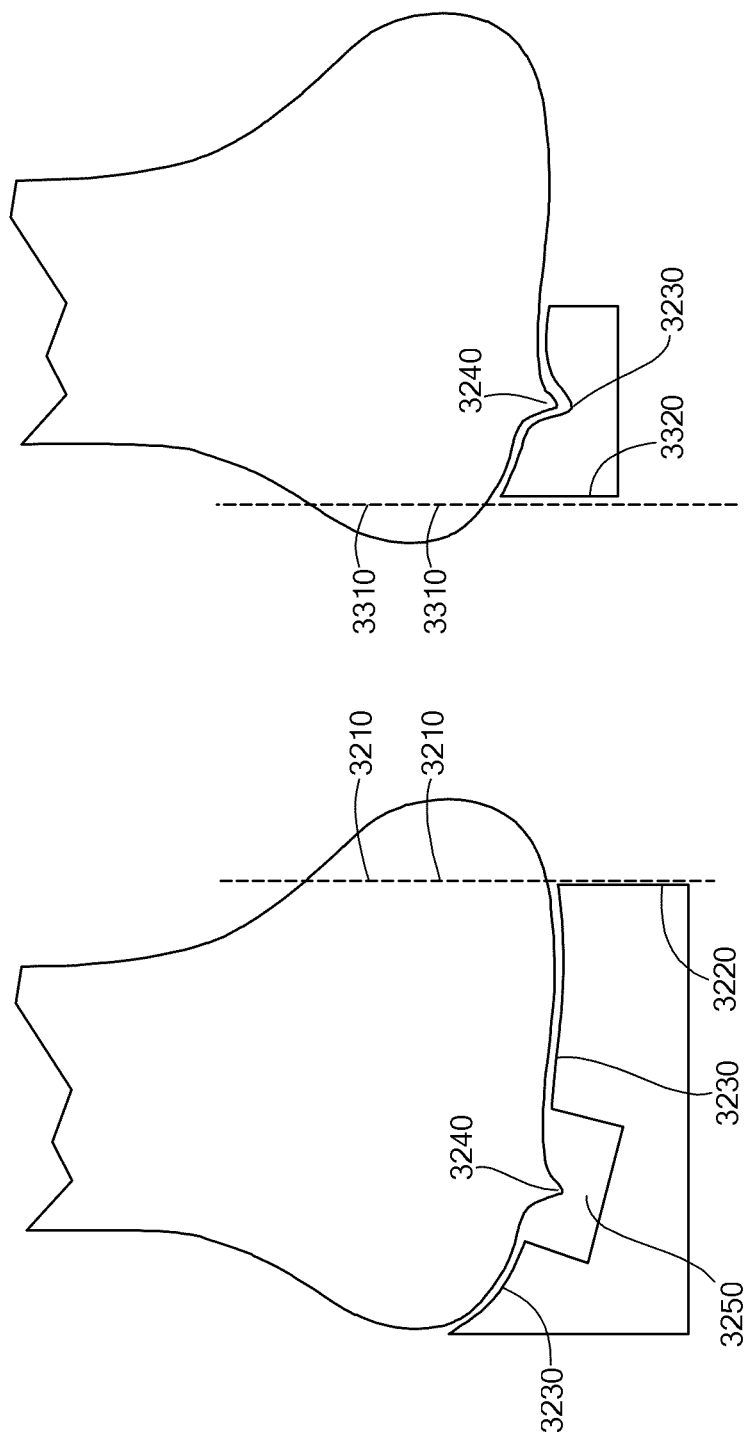

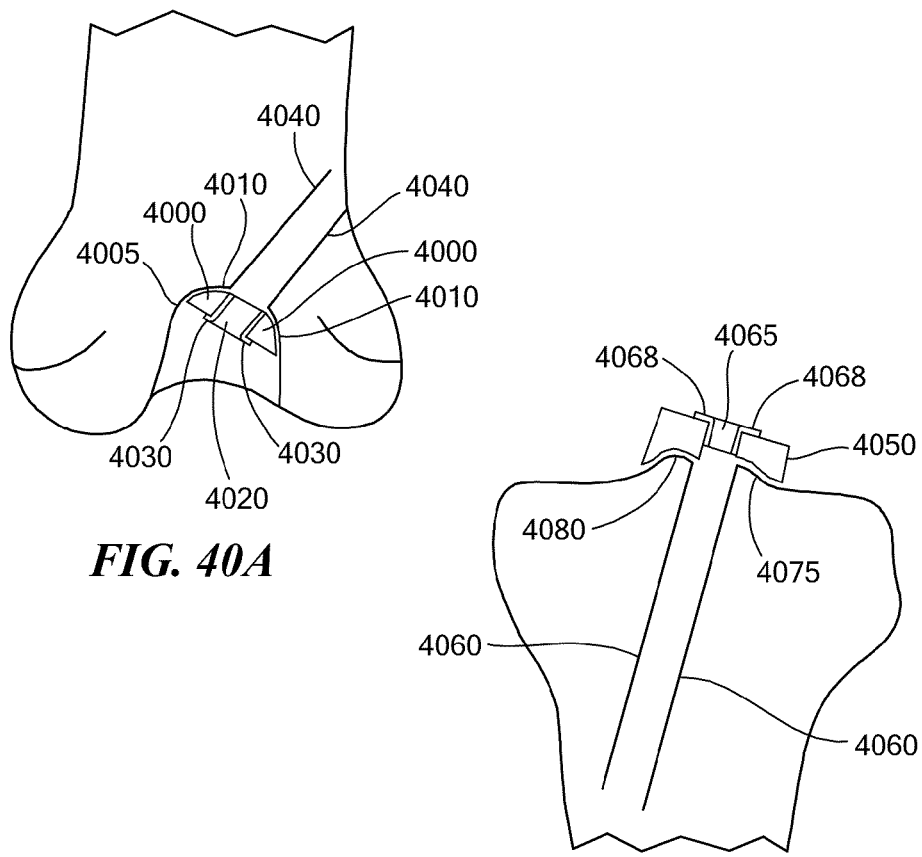
FIG. 40A
FIG. 40B
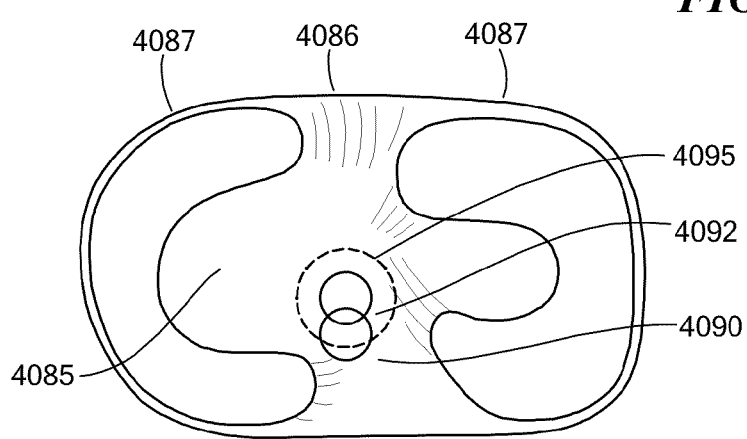
FIG. 40C

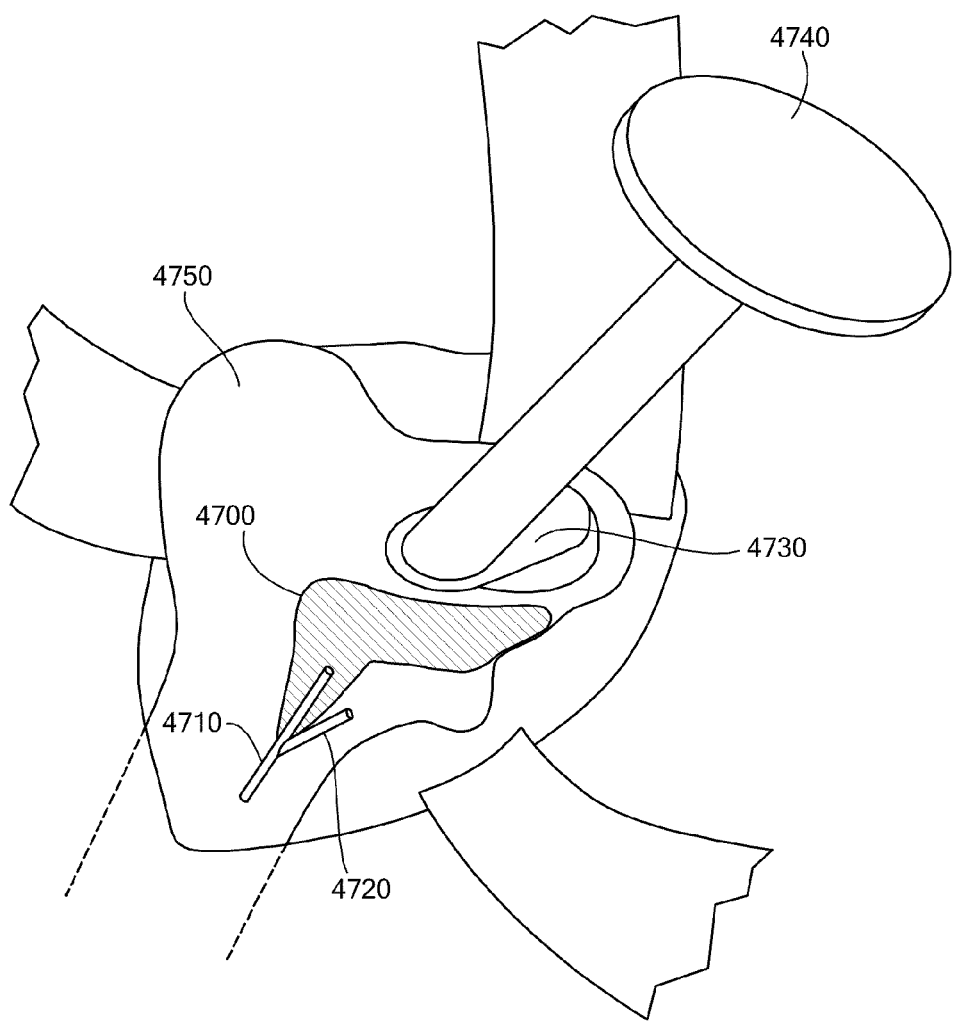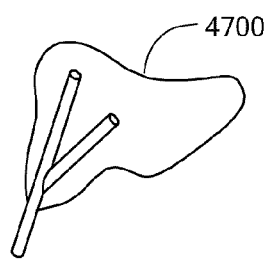
*FIG. 47*

PATIENT SELECTABLE JOINT ARTHROPLASTY DEVICES AND SURGICAL TOOLS

CROSS-REFERENCE TO RELATED APPLICATIONS

This application is a continuation of U.S. Ser. No. 11/671,745 entitled "Patient Selectable Joint Arthroplasty Devices and Surgical Tools" filed Feb. 6, 2007, which in turn claims the benefit of: U.S. Ser. No. 60/765,592 entitled "SURGICAL TOOLS FOR PERFORMING JOINT ARTHROPLASTY" filed Feb. 6, 2006; U.S. Ser. No. 60/785,168, entitled "SURGICAL TOOLS FOR PERFORMING JOINT ARTHROPLASTY" filed Mar. 23, 2006; and U.S. Ser. No. 60/788,339, entitled "SURGICAL TOOLS FOR PERFORMING JOINT ARTHROPLASTY" filed Mar. 31, 2006.

U.S. Ser. No. 11/671,745 is also a continuation-in-part of U.S. Ser. No. 11/002,573 for "SURGICAL TOOLS FACILITATING INCREASED ACCURACY, SPEED AND SIMPLICITY IN PERFORMING JOINT ARTHROPLASTY" filed Dec. 2, 2004, which in turn is a continuation-in-part of U.S. Ser. No. 10/724,010 for "PATIENT SELECTABLE JOINT ARTHROPLASTY DEVICES AND SURGICAL TOOLS FACILITATING INCREASED ACCURACY, SPEED AND SIMPLICITY IN PERFORMING TOTAL AND PARTIAL JOINT ARTHROPLASTY" filed Nov. 25, 2003.

Each of the above-described applications are hereby incorporated by reference in their entireties.

FIELD OF THE INVENTION

The present invention relates to orthopedic methods, systems and prosthetic devices and more particularly relates to methods, systems and devices for articular resurfacing. The present invention also includes surgical molds designed to achieve optimal cut planes in a joint in preparation for installation of a joint implant.

BACKGROUND OF THE INVENTION

There are various types of cartilage, e.g., hyaline cartilage and fibrocartilage. Hyaline cartilage is found at the articular surfaces of bones, e.g., in the joints, and is responsible for providing the smooth gliding motion characteristic of moveable joints. Articular cartilage is firmly attached to the underlying bones and measures typically less than 5 mm in thickness in human joints, with considerable variation depending on joint and site within the joint. In addition, articular cartilage is aneural, avascular, and alymphatic. In adult humans, this cartilage derives its nutrition by a double diffusion system through the synovial membrane and through the dense matrix of the cartilage to reach the chondrocyte, the cells that are found in the connective tissue of cartilage.

Adult cartilage has a limited ability of repair; thus, damage to cartilage produced by disease, such as rheumatoid and/or osteoarthritis, or trauma can lead to serious physical deformity and debilitation. Furthermore, as human articular cartilage ages, its tensile properties change. The superficial zone of the knee articular cartilage exhibits an increase in tensile strength up to the third decade of life, after which it decreases markedly with age as detectable damage to type II collagen occurs at the articular surface. The deep zone cartilage also exhibits a progressive decrease in tensile strength with increasing age, although collagen content does not appear to decrease. These observations indicate that there are changes in mechanical and, hence, structural organization of cartilage with aging that, if sufficiently developed, can predispose cartilage to traumatic damage.

For example, the superficial zone of the knee articular cartilage exhibits an increase in tensile strength up to the third decade of life, after which it decreases markedly with age as detectable damage to type II collagen occurs at the articular surface. The deep zone cartilage also exhibits a progressive decrease in tensile strength with increasing age, although collagen content does not appear to decrease. These observations indicate that there are changes in mechanical and, hence, structural organization of cartilage with aging that, if sufficiently developed, can predispose cartilage to traumatic damage.

Once damage occurs, joint repair can be addressed through a number of approaches. One approach includes the use of matrices, tissue scaffolds or other carriers implanted with cells (e.g., chondrocytes, chondrocyte progenitors, stromal cells, mesenchymal stem cells, etc.). These solutions have been described as a potential treatment for cartilage and meniscal repair or replacement. See, also, International Publications WO 99/51719 to Fofonoff, published Oct. 14, 1999; WO01/91672 to Simon et al., published Dec. 6, 2001; and WO01/17463 to Mannsmann, published Mar. 15, 2001; U.S. Pat. No. 6,283,980 B1 to Vibe-Hansen et al., issued Sep. 4, 2001, U.S. Pat. No. 5,842,477 to Naughton issued Dec. 1, 1998, U.S. Pat. No. 5,769,899 to Schwartz et al. issued Jun. 23, 1998, U.S. Pat. No. 4,609,551 to Caplan et al. issued Sep. 2, 1986, U.S. Pat. No. 5,041,138 to Vacanti et al. issued Aug. 29, 1991, U.S. Pat. No. 5,197,985 to Caplan et al. issued Mar. 30, 1993, U.S. Pat. No. 5,226,914 to Caplan et al. issued Jul. 13, 1993, U.S. Pat. No. 6,328,765 to Hardwick et al. issued Dec. 11, 2001, U.S. Pat. No. 6,281,195 to Rueger et al. issued Aug. 28, 2001, and U.S. Pat. No. 4,846,835 to Grande issued Jul. 11, 1989. However, clinical outcomes with biologic replacement materials such as allograft and autograft systems and tissue scaffolds have been uncertain since most of these materials cannot achieve a morphologic arrangement or structure similar to or identical to that of normal, disease-free human tissue it is intended to replace. Moreover, the mechanical durability of these biologic replacement materials remains uncertain.

Usually, severe damage or loss of cartilage is treated by replacement of the joint with a prosthetic material, for example, silicone, e.g. for cosmetic repairs, or metal alloys. See, e.g., U.S. Pat. No. 6,383,228 to Schmotzer, issued May 7, 2002; U.S. Pat. No. 6,203,576 to Afriat et al., issued Mar. 20, 2001; U.S. Pat. No. 6,126,690 to Ateshian, et al., issued Oct. 3, 2000. Implantation of these prosthetic devices is usually associated with loss of underlying tissue and bone without recovery of the full function allowed by the original cartilage and, with some devices, serious long-term complications associated with the loss of significant amount of tissue and bone can include infection, osteolysis and also loosening of the implant.

Further, joint arthroplasties are highly invasive and require surgical resection of the entire or the majority of the articular surface of one or more bones. With these procedures, the marrow space is reamed in order to fit the stem of the prosthesis. The reaming results in a loss of the patient's bone stock. U.S. Pat. No. 5,593,450 to Scott et al. issued Jan. 14, 1997 discloses an oval domed shaped patella prosthesis. The prosthesis has a femoral component that includes two condyles as articulating surfaces. The two condyles meet to form a second trochlear groove and ride on a tibial component that articulates with respect to the femoral component. A patella component is provided to engage the trochlear groove. U.S. Pat. No. 6,090,144 to Letot et al. issued Jul. 18, 2000 discloses a knee prosthesis that includes a tibial component and a meniscal component that is adapted to be engaged with the tibial component through an asymmetrical engagement.

Another joint subject to invasive joint procedures is the hip. U.S. Pat. No. 6,262,948 to Storer et al. issued Sep. 30, 2003 discloses a femoral hip prosthesis that replaces the natural femoral head. U.S. Patent Publications 2002/0143402 A1 and 2003/0120347 to Steinberg published Oct. 3, 2002 and Jun. 26, 2003, respectively, also disclose a hip prosthesis that replaces the femoral head and provides a member for communicating with the ball portion of the socket within the hip joint.

A variety of materials can be used in replacing a joint with a prosthetic, for example, silicone, e.g. for cosmetic repairs, or suitable metal alloys are appropriate. See, e.g., U.S. Pat. No. 6,443,991 B1 to Running issued Sep. 3, 2002, U.S. Pat. No. 6,387,131 B1 to Miehlke et al. issued May 14, 2002; U.S. Pat. No. 6,383,228 to Schmotzer issued May 7, 2002; U.S. Pat. No. 6,344,059 B1 to Krakovits et al. issued Feb. 5, 1002; U.S. Pat. No. 6,203,576 to Afriat et al. issued Mar. 20, 2001; U.S. Pat. No. 6,126,690 to Ateshian et al. issued Oct. 3, 2000; U.S. Pat. No. 6,013,103 to Kaufman et al. issued Jan. 11, 2000. Implantation of these prosthetic devices is usually associated with loss of underlying tissue and bone without recovery of the full function allowed by the original cartilage and, with some devices, serious long-term complications associated with the loss of significant amounts of tissue and bone can cause loosening of the implant. One such complication is osteolysis. Once the prosthesis becomes loosened from the joint, regardless of the cause, the prosthesis will then need to be replaced. Since the patient's bone stock is limited, the number of possible replacement surgeries is also limited for joint arthroplasty.

As can be appreciated, joint arthroplasties are highly invasive and require surgical resection of the entire, or a majority of the, articular surface of one or more bones involved in the repair. Typically with these procedures, the marrow space is fairly extensively reamed in order to fit the stem of the prosthesis within the bone. Reaming results in a loss of the patient's bone stock and over time subsequent osteolysis will frequently lead to loosening of the prosthesis. Further, the area where the implant and the bone mate degrades over time requiring the prosthesis to eventually be replaced. Since the patient's bone stock is limited, the number of possible replacement surgeries is also limited for joint arthroplasty. In short, over the course of 15 to 20 years, and in some cases even shorter time periods, the patient can run out of therapeutic options ultimately resulting in a painful, non-functional joint.

A variety of tools are available to assist surgeons in performing joint surgery. In the knee, for example, U.S. Pat. No. 4,501,266 to McDaniel issued Feb. 26, 1985 discloses a knee distraction device that facilitates knee arthroplasty. The device has an adjustable force calibration mechanism that enables the device to accommodate controlled selection of the ligament-tensioning force to be applied to the respective, opposing sides of the knee. U.S. Pat. No. 5,002,547 to Poggie et al. issued Mar. 26, 1991 discloses a modular apparatus for use in preparing the bone surface for implantation of a modular total knee prosthesis. The apparatus has cutting guides, templates, alignment devices along with a distractor and clamping instruments that provide modularity and facilitate bone resection and prosthesis implantation. U.S. Pat. No. 5,250,050 to Poggie et al. issued Oct. 5, 1993 is also directed to a modular apparatus for use in preparing a bone surface for the implantation of a modular total knee prosthesis. U.S. Pat. No. 5,387,216 to Thornhill et al. issued Feb. 7, 1995 discloses instrumentation for use in knee revision surgery. A bearing sleeve is provided that is inserted into the damaged canal in order to take up additional volume. The rod passes through the sleeve and is positioned to meet the natural canal of the bone. The rod is then held in a fixed position by the bearing sleeve. A cutting guide can then be mounted on the rod for cutting the bone and to provide a mounting surface for the implant. U.S. Pat. No. 6,056,756 to Eng et al. issued May 2, 2000 discloses a tool for preparing the distal femoral end for a prosthetic implant. The tool lays out the resection for prosthetic replacement and includes a jack for pivotally supporting an opposing bone such that the jack raises the opposing bone in flexion to the spacing of the intended prosthesis. U.S. Pat. No. 6,106,529 to Techiera issued Aug. 22, 2000 discloses an epicondylar axis referencing drill guide for use in resection to prepare a bone end for prosthetic joint replacement. U.S. Pat. No. 6,296,646 to Williamson issued Oct. 2, 2001 discloses a system that allows a practitioner to position the leg in the alignment that is directed at the end of the implant procedure and to cut both the femur and tibia while the leg is fixed in alignment. U.S. Pat. No. 6,620,168 to Lombardi et al. issued Sep. 16, 2003 discloses a tool for intermedullary revision surgery along with tibial components.

U.S. Pat. No. 5,578,037 to Sanders et al. issued Nov. 26, 1996 discloses a surgical guide for femoral resection. The guide enables a surgeon to resect a femoral neck during a hip arthroplasty procedure so that the femoral prosthesis can be implanted to preserve or closely approximate the anatomic center of rotation of the hip.

U.S. Pat. No. 6,206,927 to Fell, et al., issued Mar. 27, 2001, and U.S. Pat. No. 6,558,421 to Fell, et al., issued May 6, 2003, disclose a surgically implantable knee prosthesis that does not require bone resection. This prosthesis is described as substantially elliptical in shape with one or more straight edges. Accordingly, these devices are not designed to substantially conform to the actual shape (contour) of the remaining cartilage in vivo and/or the underlying bone. Thus, integration of the implant can be extremely difficult due to differences in thickness and curvature between the patient's surrounding cartilage and/or the underlying subchondral bone and the prosthesis.

Interpositional knee devices that are not attached to both the tibia and femur have been described. For example, Platt et al. (1969) "Mould Arthroplasty of the Knee," Journal of Bone and Joint Surgery 51B(1):76-87, describes a hemi-arthroplasty with a convex undersurface that was not rigidly attached to the tibia. Devices that are attached to the bone have also been described. Two attachment designs are commonly used. The McKeever design is a cross-bar member, shaped like a "t" from a top perspective view, that extends from the bone mating surface of the device such that the "t" portion penetrates the bone surface while the surrounding surface from which the "t" extends abuts the bone surface. See McKeever, "Tibial Plateau Prosthesis," Chapter 7, p. 86. An alternative attachment design is the Macintosh design, which replaces the "t" shaped fin for a series of multiple flat serrations or teeth. See Potter, "Arthroplasty of the Knee with Tibial Metallic Implants of the McKeever and Macintosh Design," Surg. Clins. Of North Am. 49(4): 903-915 (1969).

U.S. Pat. No. 4,502,161 to Wall issued Mar. 5, 1985, describes a prosthetic meniscus constructed from materials such as silicone rubber or Teflon with reinforcing materials of stainless steel or nylon strands. U.S. Pat. No. 4,085,466 to Goodfellow et al. issued Mar. 25, 1978, describes a meniscal component made from plastic materials. Reconstruction of meniscal lesions has also been attempted with carbon-fiber-polyurethane-poly (L-lactide). Leeslag, et al., Biological and Biomechanical Performance of Biomaterials (Christel et al., eds.) Elsevier Science Publishers B.V., Amsterdam. 1986. pp. 347-352. Reconstruction of meniscal lesions is also possible with bioresorbable materials and tissue scaffolds.

However, currently available devices do not always provide ideal alignment with the articular surfaces and the resultant joint congruity. Poor alignment and poor joint congruity can, for example, lead to instability of the joint. In the knee joint, instability typically manifests as a lateral instability of the joint.

Thus, there remains a need for compositions for joint repair, including methods and compositions that facilitate the integration between the cartilage replacement system and the surrounding cartilage. There is also a need for tools that increase the accuracy of cuts made to the bone in a joint in preparation for surgical implantation of, for example, an artificial joint.

SUMMARY OF THE INVENTION

The present invention provides novel devices and methods for replacing a portion (e.g., diseased area and/or area slightly larger than the diseased area) of a joint (e.g., cartilage and/or bone) with a non-pliable, non-liquid (e.g., hard) implant material, where the implant achieves a near anatomic fit with the surrounding structures and tissues. In cases where the devices and/or methods include an element associated with the underlying articular bone, the invention also provides that the bone-associated element achieves a near anatomic alignment with the subchondral bone. The invention also provides for the preparation of an implantation site with a single cut, or a few relatively small cuts.

In one aspect, the invention includes a method for providing articular replacement material, the method comprising the step of producing articular replacement (e.g., cartilage replacement material) of selected dimensions (e.g., size, thickness and/or curvature).

In another aspect, the invention includes a method of making cartilage repair material, the method comprising the steps of (a) measuring the dimensions (e.g., thickness, curvature and/or size) of the intended implantation site or the dimensions of the area surrounding the intended implantation site; and (b) providing cartilage replacement material that conforms to the measurements obtained in step (a). In certain aspects, step (a) comprises measuring the thickness of the cartilage surrounding the intended implantation site and measuring the curvature of the cartilage surrounding the intended implantation site. In other embodiments, step (a) comprises measuring the size of the intended implantation site and measuring the curvature of the cartilage surrounding the intended implantation site. In other embodiments, step (a) comprises measuring the thickness of the cartilage surrounding the intended implantation site, measuring the size of the intended implantation site, and measuring the curvature of the cartilage surrounding the intended implantation site. In other embodiments, step (a) comprises reconstructing the shape of healthy cartilage surface at the intended implantation site.

In any of the methods described herein, one or more components of the articular replacement material (e.g., the cartilage replacement material) can be non-pliable, non-liquid, solid or hard. The dimensions of the replacement material can be selected following intraoperative measurements. Measurements can also be made using imaging techniques such as ultrasound, MRI, CT scan, x-ray imaging obtained with x-ray dye and fluoroscopic imaging. A mechanical probe (with or without imaging capabilities) can also be used to select dimensions, for example an ultrasound probe, a laser, an optical probe and a deformable material or device.

In any of the methods described herein, the replacement material can be selected (for example, from a pre-existing library of repair systems), grown from cells and/or hardened from various materials. Thus, the material can be produced pre- or post-operatively. Furthermore, in any of the methods described herein the repair material can also be shaped (e.g., manually, automatically or by machine), for example using mechanical abrasion, laser ablation, radiofrequency ablation, cryoablation and/or enzymatic digestion.

In any of the methods described herein, the articular replacement material can comprise synthetic materials (e.g., metals, liquid metals, polymers, alloys or combinations thereof) or biological materials such as stem cells, fetal cells or chondrocyte cells.

In another aspect, the invention includes a method of repairing a cartilage in a subject, the method of comprising the step of implanting cartilage repair material prepared according to any of the methods described herein.

In yet another aspect, the invention provides a method of determining the curvature of an articular surface, the method comprising the step of intraoperatively measuring the curvature of the articular surface using a mechanical probe. The articular surface can comprise cartilage and/or subchondral bone. The mechanical probe (with or without imaging capabilities) can include, for example an ultrasound probe, a laser, an optical probe and/or a deformable material.

In a still further aspect, the invention provides a method of producing an articular replacement material comprising the step of providing an articular replacement material that conforms to the measurements obtained by any of the methods of described herein.

In a still further aspect, the invention includes a partial or full articular prosthesis comprising a first component comprising a cartilage replacement material; and an optional second component comprising one or more metals, wherein said second component can have a curvature similar to subchondral bone, wherein said prosthesis comprises less than about 80% of the articular surface. In certain embodiments, the first and/or second component comprises a non-pliable material (e.g., a metal, a polymer, a metal alloy, a solid biological material). Other materials that can be included in the first and/or second components include polymers, biological materials, metals, metal alloys or combinations thereof. Furthermore, one or both components can be smooth or porous (or porous coated) using any methods or mechanisms to achieve in-growth of bone known in the art. In certain embodiments, the first component exhibits biomechanical properties (e.g., elasticity, resistance to axial loading or shear forces) similar to articular cartilage. The first and/or second component can be bioresorbable and, in addition, the first or second components can be adapted to receive injections.

In another aspect, an articular prosthesis comprising an external surface located in the load bearing area of an articular surface, wherein the dimensions of said external surface achieve a near anatomic fit with the adjacent, underlying or opposing cartilage is provided. The prosthesis can comprise one or more metals or metal alloys.

In yet another aspect, an articular repair system comprising (a) cartilage replacement material, wherein said cartilage replacement material has a curvature similar to surrounding, adjacent, underlying or opposing cartilage; and (b) at least one non-biologic material, wherein said articular surface repair system comprises a portion of the articular surface equal to, smaller than, or greater than, the weight-bearing surface that is provided. In certain embodiments, the cartilage replacement material is non-pliable (e.g., hard hydroxyapatite, etc.). In certain embodiments, the system exhibits biomechanical (e.g., elasticity, resistance to axial loading or shear forces) and/or biochemical properties similar to articular cartilage. The first and/or second component can be bioresorbable and, in addition, the first or second components can be adapted to receive injections.

In a still further aspect of the invention, an articular surface repair system comprising a first component comprising a cartilage replacement material, wherein said first component has dimensions similar to that of adjacent, surrounding, underlying or opposing cartilage; and a second component, wherein said second component has a curvature similar to subchondral bone, wherein said articular surface repair system comprises less than about 80% of the articular surface (e.g., a single femoral condyle, tibia, etc.) is provided. In certain embodiments, the first component is non-pliable (e.g., hard hydroxyapatite, etc.). In certain embodiments, the system exhibits biomechanical (e.g., elasticity, resistance to axial loading or shear forces) and/or biochemical properties similar to articular cartilage. The first and/or second component can be bioresorbable and, in addition, the first or second components can be adapted to receive injections. In certain embodiments, the first component has a curvature and thickness similar to that of adjacent, underlying, opposing or surrounding cartilage. The thickness and/or curvature can vary across the implant material.

In a still further embodiment, a partial articular prosthesis comprising (a) a metal or metal alloy; and (b) an external surface located in the load bearing area of an articular surface, wherein the external surface designed to achieve a near anatomic fit with the adjacent surrounding, underlying or opposing cartilage is provided.

Any of the repair systems or prostheses described herein (e.g., the external surface) can comprise a polymeric material, for example attached to said metal or metal alloy. Any of the repair systems can be entirely composed of polymer. Further, any of the systems or prostheses described herein can be adapted to receive injections, for example, through an opening in the external surface of said cartilage replacement material (e.g., an opening in the external surface terminates in a plurality of openings on the bone surface). Bone cement, polymers, Liquid Metal, therapeutics, and/or other bioactive substances can be injected through the opening(s). In certain embodiments, bone cement is injected under pressure in order to achieve permeation of portions of the marrow space with bone cement. In addition, any of the repair systems or prostheses described herein can be anchored in bone marrow or in the subchondral bone itself. One or more anchoring extensions (e.g., pegs, pins, etc.) can extend through the bone and/or bone marrow.

In any of the embodiments and aspects described herein, the joint can be a knee, shoulder, hip, vertebrae, elbow, ankle, wrist etc.

In another aspect, a method of designing an articular implant comprising the steps of obtaining an image of a joint, wherein the image includes both normal cartilage and diseased cartilage; reconstructing dimensions of the diseased cartilage surface to correspond to normal cartilage; and designing the articular implant to match the dimensions of the reconstructed diseased cartilage surface or to match an area slightly greater than the diseased cartilage surface is provided. The image can be, for example, an intraoperative image including a surface detection method using any techniques known in the art, e.g., mechanical, optical, ultrasound, and known devices such as MRI, CT, ultrasound, digital tomosynthesis and/or optical coherence tomography images. In certain embodiments, reconstruction is performed by obtaining a surface that follows the contour of the normal cartilage. The surface can be parametric and include control points that extend the contour of the normal cartilage to the diseased cartilage and/or a B-spline surface. In other embodiments, the reconstruction is performed by obtaining a binary image of cartilage by extracting cartilage from the image, wherein diseased cartilage appears as indentations in the binary image; and performing, for example, a morphological closing operation (e.g., performed in two or three dimensions using a structuring element and/or a dilation operation followed by an erosion operation) to determine the shape of an implant to fill the areas of diseased cartilage.

In yet another aspect, described herein are systems for evaluating the fit of an articular repair system into a joint, the systems comprising one or more computing means capable of superimposing a three-dimensional (e.g., three-dimensional representations of at least one articular structure and of the articular repair system) or a two-dimensional cross-sectional image (e.g., cross-sectional images reconstructed in multiple planes) of a joint and an image of an articular repair system to determine the fit of the articular repair system. The computing means can be: capable of merging the images of the joint and the articular repair system into a common coordinate system; capable of selecting an articular repair system having the best fit; capable of rotating or moving the images with respect to each other; and/or capable of highlighting areas of poor alignment between the articular repair system and the surrounding articular surfaces. The three-dimensional representations can be generated using a parametric surface representation.

In yet another aspect, surgical tools for preparing a joint to receive an implant are described, for example a tool comprising one or more surfaces or members that conform at least partially to the shape of the articular surfaces of the joint (e.g., a femoral condyle and/or tibial plateau of a knee joint). In certain embodiments, the tool comprises Lucite silastic and/or other polymers or suitable materials. The tool can be reuseable or single-use. The tool can be comprised of a single component or multiple components. In certain embodiments, the tool comprises an array of adjustable, closely spaced pins. In any embodiments described herein, the surgical tool can be designed to further comprise an aperture therein, for example one or more apertures having dimensions (e.g., diameter, depth, etc.) smaller or equal to one or more dimensions of the implant and/or one or more apertures adapted to receive one or more injectables. Any of the tools described herein can further include one or more curable (hardening) materials or compositions, for example that are injected through one or more apertures in the tool and which solidify to form an impression of the articular surface.

In still another aspect, a method of evaluating the fit of an articular repair system into a joint is described herein, the method comprising obtaining one or more three-dimensional images (e.g., three-dimensional representations of at least one articular structure and of the articular repair system) or two-dimensional cross-sectional images (e.g., cross-sectional images reconstructed in multiple planes) of a joint, wherein the joint includes at least one defect or diseased area; obtaining one or more images of one or more articular repair systems designed to repair the defect or diseased area; and evaluating the images to determine the articular repair system that best fits the defect (e.g., by superimposing the images to determine the fit of the articular repair system into the joint). In certain embodiments, the images of the joint and the articular repair system are merged into a common coordinate system. The three-dimensional representations can be generated using a parametric surface representation. In any of these methods, the evaluation can be performed by manual visual inspection and/or by computer (e.g., automated). The images can be obtained, for example, using a C-arm system and/or radiographic contrast.

In yet another aspect, described herein is a method of placing an implant into an articular surface having a defect or diseased area, the method comprising the step of imaging the joint using a C-arm system during placement of the implant, thereby accurately placing the implant into a defect or diseased area.

Also disclosed is a customizable, or patient specific, implant configured for placement between joint surfaces formed by inserting a hollow device having an aperture and a lumen into a target joint, and injecting material into the hollow device to form an implant.

A customizable, or patient specific, implant configured for placement between joint surfaces is also disclosed wherein the implant is formed by inserting a retaining device that engages at least a portion of one joint surface in a joint and injecting material into an aperture of the retaining device to form an implant.

The invention is also directed to tools. In accordance with another embodiment of the invention, a surgical tool includes a template. The template has at least one contact surface for engaging a surface associated with a joint. The at least one contact surface substantially conforms with the surface. The template further includes at least one guide aperture for directing movement of a surgical instrument.

In accordance with related embodiments of the invention, the surface may be an articular surface, a non-articular surface, a cartilage surface, a weight bearing surface, a non-weight surface and/or a bone surface. The joint has a joint space, with the surface either within the joint space or external to the joint space. The template may include a mold. The template may include at least two pieces, the at least two pieces including a first piece that includes one or more of the at least one contact surfaces, the second piece including one or more of the at least one guide apertures or guide surfaces. The at least one contact surface may include a plurality of discrete contact surfaces.

In accordance with further related embodiments of the invention, the contact surface may be made of a biocompatible material, such as acylonitrile butadiene styrene, polyphenylsulfone, and polycarbonate. The contact surface may be capable of heat sterilization without deforming. For example, the contact surface may be capable of heat sterilization without deforming at temperatures lower than 207 degrees Celsius, such as a contact surface made of polyphenylsulfone. The contact surface may be substantially transparent or semi-transparent, such as a contact surface made of Somos 11120.

In still further embodiments of the invention, the template may include a reference element, such as a pin or aiming device, for establishing a reference plane relative to at least one of a biomechanical axis and an anatomical axis of a limb. In other embodiments, the reference element may be used for establishing an axis to assist in correcting an axis deformity.

In accordance with another embodiment of the invention, a method of joint arthroplasty is provided. The method includes obtaining an image of a joint, wherein the image includes a surface associated with a joint. A template is created having at least one contact surface that conforms with the surface. The template includes at least one guide aperture or guide surface or element for directing movement of a surgical instrument. The template is positioned such that the contact surface abuts the surface in a predefined orientation.

In related embodiments of the invention, the joint surface is at least one of an articular surface, a non-articular surface, a cartilage surface, a weight bearing surface, a non-weight bearing surface, and a bone surface. The joint has a joint space, wherein the surface may be within the joint space or external to the joint space. The at least one contact surface may include a plurality of discrete contact surfaces. Creating the template may include rapid prototyping, milling and/or creating a mold, the template furthermore may be sterilizable and/or biocompatible. The rapid prototyping may include laying down successive layers of plastic. The template may be a multi-piece template. The multi-piece template may include a first piece that includes one or more of the at least one contact surfaces, and a second piece that includes one or more of the at least one guide apertures or guide surface or element. Obtaining the image may include determining dimensions of bone underlying the cartilage, and adding a predefined thickness to the bone dimensions, the predefined thickness representing the cartilage thickness. Adding the predefined thickness may be a function of at least one of an anatomic reference database, an age, a gender, and race matching. Obtaining the imaging may include performing an optical imaging technique, an ultrasound, a CT, a spiral CT, and/or an MRI.

In further related embodiments of the invention, the method may further include anchoring the contact surface to the cartilage. The anchoring may include using at least one of k-wire and adhesive. The anchoring may include drilling a bit through the cartilage, and leaving the bit in place. The anchoring may include forming the template to normal joint surface, arthritic joint surface or the interface between normal and arthritic joint surface or combinations thereof.

In still further related embodiments of the invention, the template may include a reference element. The method may include establishing, via the reference element, a reference plane relative to at least one of an axis and a anatomical axis of a limb. The biomechanical axis may extend from a center of a hip to a center of an ankle. Alternatively, an axis may be established via the reference element that is used to align surgical tools in correcting an axis deformity.

In further related embodiments of the invention, the method further includes performing at least one of a muscle sparing technique and a bone sparing technique. An incision for inserting the template may be equal to or less than one of 15 cm, 13 cm, 10 cm, 8 cm, and 6 cm. At least a portion of the template may be sterilized. Sterilizing may include heat sterilization and/or sterilization using gas. The sterilized portion may includes a mold.

In accordance with another embodiment of the invention, a surgical tool includes a template. The template has at least one contact surface for engaging a surface associated with a joint, the at least one contact surface substantially conforming with the surface. The contact surface is optionally substantially transparent or semi-transparent. The template further includes at least one guide aperture for directing movement of a surgical instrument.

In accordance with another embodiment of the invention, a method of joint arthroplasty is presented. The method includes obtaining an image associated with a joint. A template is created having at least one contact surface that conforms with a surface associated with the joint, the template including a reference element and at least one guide aperture or guide surface or element for directing movement of a surgical instrument. The template is aligned in an orientation on the joint such that the reference element establishes a reference plane relative to a biomechanical axis of a limb. The template is anchored to the joint such that the contact surface abuts the joint in said orientation. The biomechanical axis may extend, for example, from a center of a hip to a center of an ankle.

In accordance with another embodiment of the invention, a method of joint arthroplasty includes obtaining an image of a joint. A template is created having at least one contact surface that conforms with a surface associated with the joint, the template including a reference element and at least one guide aperture or guide surface or element for directing movement of a surgical instrument, the template including a reference element. The template is aligned in an orientation on the surface such that the reference element establishes an axis. The template may be anchored to the surface. A surgical tool is aligned using the reference element to correct an axis deformity.

In accordance with another embodiment of the invention, a surgical tool includes a template. The template includes a mold having at least one contact surface for engaging a surface associated with a joint. The at least one contact surface substantially conforms with the surface. The mold is made of a biocompatible material. The template further includes at least one guide aperture or guide surface or guide element for directing movement of a surgical instrument. The mold may be sterilizable and/or substantially transparent or semi-transparent.

In accordance with still another embodiment of the invention, a surgical tool includes a template. The template includes a mold having at least one contact surface for engaging a joint surface. The at least one contact surface substantially conforms with the joint surface. The mold is made of a biocompatible material. Furthermore, the mold is capable of heat sterilization without deforming. The template includes at least one guide aperture or guide surface or guide element for directing movement of a surgical instrument.

In accordance with related embodiments of the invention, the mold may be capable of heat sterilization without deformation. The contact surface may be made of polyphenylsulfone.

In accordance with another embodiment of the invention, a method of using a surgical tool is presented. The surgical tool includes a first template removably attached to a second template. The method includes anchoring the first template to a femoral joint surface, the first template having a first contact surface for engaging the femoral joint surface. The second template is anchored to a tibial joint surface, the second template having a second contact surface for engaging a tibial joint surface. After anchoring the first template and the second template, the second template is released from the first template, such that the second template is capable of moving independent of the first template.

In accordance with related embodiments of the invention, the method may further include using the second template to direct a surgical cut on the tibia. Anchoring the second template may occur subsequent or prior to anchoring the first template. At least one of the first and second templates may include a mold. The first contact surface may substantially conform with the femoral joint surface. The second contact surface may substantially conform with the tibial joint surface.

In accordance with another embodiment of the invention, a method of performing joint arthroplasty includes obtaining a first image associated with a first joint, obtaining a second image of a second joint, and optionally obtaining a third image of a third joint. A biomechanical axis associated with the first joint and the second joint and optionally the third joint is determined. A template is provided for enabling surgery to correct an anatomic abnormality associated with at least one of the first, second and/or third joint.

In another embodiment, gait, loading and other physical activities as well as static positions of a joint may be simulated using a computer workstation. The template and the resultant surgical procedures, e.g. cuts, drilling, rasping, can be optimized using this information to achieve an optimal functional result. For example, the template and the resultant implant position may be optimized for different degrees of flexion and extension, internal or external rotation, abduction or adduction. Thus, the templates may be used to achieve motion that is optimized in one, two or more directions.

In accordance with related embodiments of the invention, the template may include at least one contact surface for engaging a surface associated with the first joint, the second joint and/or the third joint, the at least one contact surface substantially conforming with the surface. The template may include at least one guide aperture or guide surface or guide element for directing movement of a surgical instrument.

In further related embodiments of the invention, obtaining the first image may include imaging one of at least 5 cm, at least 10 cm, at least 15 cm, at least 20 cm, at least 25 cm, at least 30 cm, and at least 35 cm beyond the first joint. Obtaining the first image/and or second image and/or the third image may include performing a CT or an MRI. Performing the MRI may include obtaining a plurality of MRI scans. Optionally, two or more imaging modalities can be used and information obtained from the imaging modalities can be combined.

In accordance with another embodiment of the invention, a method of performing joint arthroplasty includes obtaining a computer image of a surface associated with a first joint. At least one deformity seen in the computer image is removed pertaining to the surface, so as to form an improved anatomic or functional result. The at least one deformity is removed from the surface to create a modified surface. A template is provided based, at least in part, on the removal of the deformity. The template includes at least one contact surface for engaging the modified surface, the at least one contact surface substantially conforming with the modified surface.

In accordance with another embodiment of the invention, a method of performing joint arthroplasty includes obtaining a computer image of a surface associated with a first joint. At least one deformity seen in the computer image is removed such as a biomechanical or anatomical axis deformity, so as to form an improved anatomic or functional result. The at least one deformity is removed in the surgical planning by modifying the shape or position of a template including the shape and/or position of guide apertures, guide surface or guide elements. A template is provided based, at least in part, on the removal of the deformity. The template includes at least one contact surface for engaging the joint surface. The shape and/or position of guide apertures, guide surface or guide elements is selected or designed to achieve a correction of the deformity.

In accordance with related embodiments of the invention, the template may be used in a surgical procedure. The template may include at least one guide aperture, guide surface or guide elements, the method further including using the at least one guide aperture, guide surface or guide elements to direct movement of a surgical instrument. The at least one deformity may include a osteophyte, a subchondral cyst, and/or an arthritic deformation.

In accordance with another embodiment of the invention, a method of performing joint arthroplasty includes obtaining an image of a surface associated with a first joint, the image including at least one deformity. A template is provided, based at least in part on the image, the template having at least one contact surface for engaging portions of the surface free of the deformity. The at least one contact surface substantially conforms with the portions of the surface. The template is used in a surgical procedure.

In accordance with related embodiments of the invention, the template may include at least one guide aperture, guide surface or guide elements, the method further including using the at least one guide aperture, guide surface or guide elements to direct movement of a surgical instrument. The at least one deformity may include a osteophyte, a subchondral cyst, and/or an arthritic deformation.

In accordance with another embodiment of the invention, a method of performing joint arthroplasty includes obtaining an image of a surface associated with a joint, the image including at least subchondral bone. A template is provided, based at least in part on the image. The template includes at least one contact surface substantially conforming with the subchondral bone. Residual cartilage is removed from the surface in areas where the at least one contact surface is to contact the subchondral bone. The template is positioned such that the at least one contact surface abuts the subchondral bone in a predefined orientation.

In accordance with another embodiment of the invention, a method of performing joint arthroplasty includes providing a template. The template is fixated to bone associated with a joint without performing any cuts to the joint. The template may be used in a surgical procedure.

In accordance with related embodiments of the invention, fixating may include drilling into the bone and leaving a drill bit in the bone. An image of a surface associated with a joint may be obtained, the template having at least one contact surface that conforms with the surface.

Another tool is disclosed that is formed at least partially in situ and comprises: a mold formed in situ using at least one of an inflatable hollow device or a retaining device to conform to the joint surface on at least one surface having a surface for engaging a joint surface; a block that communicates with the mold; and at least one guide aperture in the block.

A method of placing an implant into a joint is also provided. The method comprises the steps of imaging the joint using a C-arm system, obtaining a cross-sectional image with the C-arm system, and utilizing the image for placing the implant into a joint.

In accordance with another embodiment of the invention, a system for joint arthroplasty includes a first template. The first template includes at least one surface for engaging a first surface of a joint, the surface being a mirror image of portions or all of the first surface. The first template further includes at least one guide for directing movement of a surgical instrument. A linkage cross-references at least one surgical tool relative to said guide and relative to one of an anatomical and a biomechanical axis.

In accordance with related embodiments of the invention, the surgical tool may be a second template, the second template including at least one guide for directing movement of a surgical instrument. The second template may include a surface that is a mirror image of a second surface of the joint. The second joint surface may oppose the first joint surface. At least one guide of the second template may direct the surgical instrument in at least one of a cut, a milling, and a drilling oriented in a predefined location relative to said first template and adapted in shape, size or orientation to an implant shape. The shape and/or position of the at least one guide of the first template may be based, at least in part, on one or more axis related to said joint. The linkage may be an attachment mechanism, which may cause the first template to directly contact the at least one surgical tool, or alternatively, attaches the first template and the at least one surgical tool such that the first template and the at least one surgical tool do not directly contact each other. The linkage may allow for rotation relative to one of an anatomical and a biomechanical axis. The first template may include a removably attached block, the block including the at least one guide of the first template.

In accordance with another embodiment of the invention, a system for joint arthroplasty is presented that includes a first template. The first template includes at least one surface for engaging a first surface of a joint, the surface being a mirror image of portions or all of the first surface. The first template further includes at least one guide for directing movement of a surgical instrument. A linkage cross-references at least one surgical tool on a second surface of the joint opposing the first surface.

In accordance with another embodiment of the invention, a system for joint arthroplasty is presented that includes a first template. The first template includes at least one first template surface for engaging a first surface of a joint, the first template surface being a mirror image of portions or all of the first surface. The first template further includes at least one guide for directing movement of a surgical instrument. A second template includes at least one second template surface for engaging a second surface of a joint, the second template being a mirror image of portions or all of the second surface. The second template further includes at least one guide for directing movement of a surgical instrument. A linkage cross-references the first template and the second template.

In accordance with another embodiment of the invention, a system for joint arthroplasty includes a first template. The first template includes at least one surface for engaging a first surface of a joint, the surface being a mirror image of portions or all of the first surface. The first template further includes at least one guide for directing movement of a surgical instrument. A linkage cross-references at least one surgical tool, wherein the linkage allows for rotation relative to one of an anatomical and a biomechanical axis.

In accordance with another embodiment of the invention, a method of joint arthroplasty includes positioning at least one contact surface of a first template onto a first surface of a joint. A second template is cross-referenced to the first template to align position of the second template on a second surface of the joint, the second template including at least one guide. Movement of the surgical instrument is directed using the at least one guide of the second template relative to said guide and relative to one of an anatomical and a biomechanical axis.

In accordance with related embodiments of the invention, the at least one contact surface of the first template is substantially a mirror image of the first surface. The method may further include obtaining electronic image data of the joint, and determining a shape of the at least one contact surface of the first template based, at least in part, on electronic image data.

In accordance with other related embodiments of the invention, the method may further include, prior to directing movement of the surgical instrument, positioning at least one contact surface of the second template to the second joint surface. The at least one contact surface of the second template may be substantially a mirror image of the second surface. The method may further include obtaining electronic image data of the joint, and determining a shape of the at least one contact surface of the second template based, at least in part, on electronic image data.

In accordance with yet further related embodiments of the invention, cross-referencing the second template to the first template may includes attaching the second template to the first template. Attaching the second template to the first template may include performing intraoperative adjustments. The second template is attached to the first template via a pin, and wherein performing intraoperative adjustments includes rotating the second template around the pin. The method may further include performing an intraoperative adjustment on the position of the second template on the second surface of the joint, wherein performing the intraoperative adjustment includes using one of spacers, ratchets, and telescoping devices. The method may further include performing an intraoperative adjustment on the position of the second template on the second surface of the joint, wherein performing the intraoperative adjustment includes adjusting for at least one of joint flexion, joint extension, joint abduction, and joint rotation. Directing movement of the surgical instrument using the at least one guide of the second template may include making one or more cuts or drill holes, the method further comprising implanting a joint prosthesis as a function of the one or more cuts or drill holes. The first template may include at least one guide, the method further comprising directing movement of a surgical instrument using the at least one guide of the first template. Directing movement of the surgical instrument using the at least one guide of the first template may include making one or more cuts or drill holes, the method further comprising implanting a joint prosthesis as a function of the one or more cuts or drill holes. Directing movement of the surgical instrument using the at least one guide of the second template may include making at least one of a cut, a drill hole, and a reaming, the method further comprising implanting a joint prosthesis.

In still further related embodiments of the invention, the first surface of the joint may be a femoral surface, and the second surface of the joint may be a tibial surface. The method may further include obtaining electronic image data of a joint, determining the at least one of a biomechanical axis and an anatomical axis of the joint based, at least in part, on the electronic image data, wherein the shape and/or position of the guide of the second template is based, at least in part, on the at least one of the biomechanical axis and the anatomical axis. The electronic image data may be obtained pre-operatively, intraoperatively, optically, an MRI, a CT, and/or a spiral CT. The first template may include a thickness based, at least in part, on at least one of a thickness of an implant to be attached to the first surface of the joint and a desired space between two opposing surfaces of the joint.

In accordance with another embodiment of the invention, a method of joint arthroplasty includes positioning at least one contact surface of a first template onto a first surface of a joint. A second template is cross-referenced to the first template to align position of the second template on a second surface of the joint, the second surface opposing the first surface. The second template includes at least one guide. Movement of the surgical instrument is directed using the at least one guide of the second template.

In accordance with another embodiment of the invention, a method of joint arthroplasty includes positioning at least one contact surface of a first template onto a first surface of a joint, wherein the at least one contact surface of the first template is substantially a mirror image of the first surface. A second template is cross-referenced to the first template to align position of the second template onto a second surface of the joint, the at least one contact surface of the second template substantially a mirror image of the second surface of the joint. The second template includes at least one guide. Movement of the surgical instrument is directed using the at least one guide of the second template.

In accordance with another embodiment of the invention, a method of joint arthroplasty includes positioning at least one contact surface of a first template onto a first surface of a joint. A second template is cross-referenced to the first template to align position of the second template on a second surface of the joint, the second template including at least one guide. Cross-referencing allows rotation of the second template relative to one of a biomechanical and an anatomical axis. Movement of the surgical instrument is directed using the at least one guide of the second template.

In accordance with another embodiment of the invention, a method of joint arthroplasty includes obtaining electronic image data of a joint, and determining width space of the joint based, at least in part, on the electronic image data. A template is provided that includes at least one guide for directing movement of a surgical instrument, wherein at least one of the shape and position of the guide is based, at least in part, on the width space of the joint.

In accordance with related embodiment of the invention, the template may include at least one surface for engaging a surface of a joint, the surface being a mirror image of portions or all of the surface. Obtaining electronic image data may include at least one of a CT scan, MRI scan, optical scan, and a ultrasound imaging. Obtaining electronic image data may include obtaining image data of a medial space, a lateral space, anterior space, and/or posterior space of the joint. At least two of the lateral space, anterior space, and posterior space of the joint may be compared. Obtaining image data may be performed in two dimensions or three dimensions. Determining width of the joint may include measuring the distance from the subchondral bone plate of one articular surface to the subchondral bone plate of the opposing articular surface. Alternatively, determining width of the joint may include measuring the distance from the subchondral bone plate of one articular surface to the subchondral bone plate of the opposing articular surface. Obtaining the image data of the joint may be performed in at least one of joint flexion, joint extension, and joint rotation. At least one of the shape and position of the guide may be further based, at least in part, on the anatomical or biomechanical axis alignment of the joint.

In accordance with another embodiment of the invention, a method of joint arthroplasty includes obtaining electronic image data of a joint, and determining cartilage loss associated with the joint based, at least in part, on the electronic image data. A template may be provided that includes at least one guide for directing movement of a surgical instrument so as to correct an axis alignment of the joint, wherein at least one of the shape and position of the guide is based, at least in part, on the cartilage loss.

In accordance with related embodiments of the invention, the method may further include measuring at least one axis associated with the joint. Measuring may include a standing x-ray, a weight bearing x-ray, a CT scout scan, a MRI localizer scan, a CT scan, and/or a MRI scan. Obtaining image data may include a spiral CT, spiral CT arthography, MRI, optical imaging, optical coherence tomography, and/or ultrasound. The template may include at least one contact surface for engaging a surface of the joint, the contact surface being a mirror image of portions or all of the joint surface.

In accordance with another embodiment of the invention, a method for joint arthroplasty includes obtaining electronic image data of a joint, and determining a plurality of measurements based, at least in part, on the image data. The measurements may be selected from at least one of an axis associated with the joint and a plane associated with the joint. A template is provided that includes at least one guide for directing movement of a surgical instrument, wherein at least one of the shape and position of the guide is based, at least in part, on the plurality of measurements.

In accordance with related embodiments of the invention, obtaining image data of the joint may include an x-ray, a standing x-ray, a CT scan, an MRI scan, CT scout scans, and/or MRI localizer scans. The plurality of measurements may include a plurality of axis, a plurality of planes, or a combination of an axis and a plane. The template may include at least one contact surface for engaging a surface of a joint, the contact surface being a mirror image of portions or all of the joint surface.

In accordance with another embodiment of the invention, a surgical tool includes a template having a surface for engaging a joint surface, the surface being a mirror image of a portion or all of the joint surface. The template further includes two or more guides for directing movement of a surgical instrument, wherein the shape and/or position of at least one of the guides is based, at least in part, on at least one axis related to said joint.

In accordance with related embodiments of the invention, the template further includes a block removably attached to the surface, the block including the two or more guides. The two or more guides may include at least one guide for a cut, a milling, and a drilling. A second surgical tool may be attached to the template, the second tool including at least one guide aperture for guiding a surgical instrument. At least one guide of the second surgical tool may guide a surgical instrument to make cuts that are parallel, non-parallel, perpendicular, or non-perpendicular to cuts guided by the first template.

In accordance with another embodiment of the invention, a method of joint arthroplasty includes performing an extended scan of a joint to obtain electronic image data that includes the joint and at least 15 cm or greater beyond the joint. At least one of an anatomical and a biomechanical axis associated with the joint is determined based, at least in part, on the electronic image data. A template is provided that includes at least one guide for directing movement of a surgical instrument, wherein at least one of the shape and position of the guide is based, at least in part, on the at least one of the anatomical and the biomechanical axis.

In accordance with related embodiments of the invention, the joint may be a knee joint, and performing the extended scan of a joint to obtain electronic image data includes obtaining electronic image data at least 15 cm, 20 cm, or 25 cm beyond the tibiofemoral joint space.

In accordance with another embodiment of the invention, a method of joint arthroplasty includes performing an imaging scan acquisition that obtains electronic image data through more than one joint. At least one of an anatomical axis and a biomechanical axis associated with the joint is determined based, at least in part, on the electronic image data. A template is provided that includes at least one guide for directing movement of a surgical instrument, wherein at least one of the shape and position of the guide is based, at least in part, on the at least one of the anatomical and the biomechanical axis.

In accordance with related embodiments of the invention, performing the imaging acquisition includes performing a CT, MRI, an X-ray, and/or a two-plane x-ray, wherein the CT and the MRI includes a slice, spiral, and/or volume acquisition. The guide may direct the movement of a surgical instrument to correct a varus deformity and/or a valgus deformity.

In accordance with another embodiment of the invention, a method of joint arthroplasty includes obtaining a first image of a joint in a first plane, wherein the first image generates a first image volume. A second image of a joint in a second plane is obtained, wherein the second image generates a second image data volume. The first and second image data volumes is combined to form a resultant image data volume, wherein the resultant image data volume is substantially isotropic. A template is provided based on the resultant image data volume, the template including at least one surface for engaging a first surface of a joint, the surface being a mirror image of portions or all of the first surface. The template further includes at least one guide for directing movement of a surgical instrument.

In accordance with related embodiments of the invention, obtaining the first image and the second image may includes a spiral CT, volumetric CT, and/or an MRI scan.

In accordance with another embodiment of the invention, a method for joint arthroplasty includes performing a first cut on a joint to create a first cut joint surface. Performing the first cut includes positioning at least one contact surface of a first template onto a first surface of a joint, the at least one contact surface being a mirror image of the first surface of the joint. The first template includes a guide for directing movement of a surgical instrument to perform the first cut. The first cut is cross-referenced to perform a second cut associated with an opposing surface of the joint.

In accordance with related embodiments of the invention, cross-referencing the first cut to make the second cut may include attaching a second template to the first template so as to assist positioning at least one contact surface of the second template onto a second surface of the joint. The second template includes a guide for directing movement of a surgical instrument to perform the second cut. The second template may include at least one contact surface being a mirror image of the second surface of the joint. Cross-referencing the first cut to make the second cut may include positioning at least one contact surface of a third template onto at least a portion of the first cut surface, and attaching a second template to the third template so as to position at least one contact surface of the second template onto a second surface of the joint. The at least one contact surface of the third template may be a mirror image of the first cut surface. The first cut may be a horizontal femoral cut, with the second cut being a vertical femoral cut. The first cut may be femoral cut with the second cut being a tibial cut. The first cut may be a femoral cut, and the second cut is a patellar cut. The first cut may be an acetabular reaming and the second cut is a femoral cut.

In accordance with another embodiment of the invention, a method for joint arthroplasty includes positioning at least one contact surface of a template onto a surface of a joint, the at least one contact surface being a mirror image of at least a portion of the surface of the joint. The template includes a guide for directing movement of a surgical instrument. The first template is stabilized onto the first surface.

In accordance with related embodiments of the invention, the method may further include obtaining electronic image data of the joint, and determining a shape of the at least one contact surface of the first template based, at least in part, on electronic image data. Stabilizing may include using k-wires, a screw, an anchor, and/or a drill bit left in place on the joint. Stabilizing may includes positioning the contact surface on at least one or more concavities and convexities on the joint. Stabilizing may include positioning the contact surface on at least one concavity and at least convexity on the joint. Stabilizing may include positioning the contact surface, at least partially, on an arthritic portion of the joint. Stabilizing may include positioning the contact surface, at least partially, on an interface between a normal and an arthritic portion of the joint. Stabilizing may include positioning the contact surface, at least partially, against an anatomic feature. The anatomic feature may be a trochlea, an intercondylar notch, a medial condyle and a lateral condyle, a medial trochlea and a lateral trochlea, a medial tibial plateau and a lateral tibial plateau, a fovea capities, an acetabular fossa, a tri-radiate cartilage, an acetabular wall, or an acetabular rim. Positioning the contact surface on the surface of the joint may include positioning the contact surface on, at least partially, a normal portion of the joint. Determining the position of the guide on the template may be based, at least in part, on ligament balancing and/or to optimize at least one of flexion and extension gap. The method may further include adjusting the position of the guide relative to the joint intraoperatively, using for example, a spacer, a ratchet device, and a pin that allows rotation.

In accordance with another embodiment of the invention, a method for joint arthroplasty includes positioning at least one contact surface of a template onto a surface of a joint, such that the contact surface, at least partially, rests on, and is a mirror image of, an interface between an arthritic and a normal portion of the joint surface. The template includes a guide for directing movement of a surgical instrument. A surgical intervention is made on the joint with the surgical instrument based, at least in part, on the guide.

In accordance with another embodiment of the invention, a template includes at least one contact surface for positioning onto a surface of a joint, the contact surface at least partially being a mirror image of an interface between an arthritic and a normal portion of the joint surface. A guide directs movement of a surgical instrument.

In accordance with another embodiment of the invention, a method for joint arthroplasty includes positioning at least one contact surface of a template onto a surface of a joint, such that the contact surface, at least partially, rests on, and is a mirror image of, an arthritic portion of the joint surface. The template includes a guide for directing movement of a surgical instrument. A surgical intervention is made on the joint with the surgical instrument based, at least in part, on the guide.

In accordance with another embodiment of the invention, a template includes at least one contact surface for positioning onto a surface of a joint, the contact surface at least partially being a mirror image of a normal portion of the joint surface. The template includes a guide for directing movement of a surgical instrument.

In accordance with another embodiment of the invention, a method for joint arthroplasty includes performing a phantom scan of one of a MRI and CT instrument. Using the one of the an MRI and CT instrument, a scan on a joint is performed. A shape of the at least one contact surface of the first template is determined, based, at least in part, on the phantom scan and the scan of the joint, the at least one contact surface being a mirror image of at least a portion of the surface of the joint. The template includes a guide for directing movement of a surgical instrument.

In accordance with related embodiments of the invention, the phantom scan may be performed prior to the scan of the joint, the method further comprising adjusting the one of the MRI and the CT instrument. The phantom scan may be performed after performing the scan of the joint, wherein the scan of the joint is optimized based on the phantom scan.

In accordance with another embodiment of the invention, a method for joint arthroplasty includes determining a desired femoral component rotation for one of a uni-compartmental or total knee replacement. A template is provided that includes at least one guide for directing movement of a surgical instrument, attached linkage, and/or tool. At least one of the shape and position of the guide is based, at least in part, on the desired femoral component rotation.

In accordance with related embodiments of the invention, determining the desired femoral component rotation may include measuring one or more anatomic axis and/or planes relevant to femoral component rotation. The one or more anatomic axis and/or planes may be a transepicondylar axis, the Whiteside line, and/or the posterior condylar axis. The guide may direct a femoral cut, the method further comprising rotating the template so that the femoral cut is parallel to a tibial cut with substantially equal tension medially and laterally applied from medial and lateral ligaments and soft tissue.

In accordance with another embodiment of the invention, a method for joint arthroplasty includes determining a desired tibial component rotation for one of a uni-compartmental or total knee replacement. A tibial template is provided that includes at least one guide for directing movement of a surgical instrument, attached linkage, and/or tool. At least one of the shape and position of the guide is based, at least in part, on the desired tibial component rotation.

In accordance with related embodiments of the invention, determining the desired tibial component rotation may include measuring one or more anatomic axis and/or planes relevant to tibial component rotation. The one or more anatomic axis and/or planes may be at an anteroposterior axis of the tibia, and/or the medial one-third of the tibial tuberosity. The guide may direct a femoral cut, the method further comprising rotating the template so that the femoral cut is parallel to a tibial cut with substantially equal tension medially and laterally applied from medial and lateral ligaments and soft tissue.

In accordance with another embodiment of the invention, a method of hip arthroplasty includes determining leg length discrepancy and obtaining electronic image data of the hip joint. A template is provided that includes at least one guide for directing movement of a surgical instrument, attached linkage, and/or tool. The template includes at least one contact surface that is a mirror image of the femoral neck, wherein at least one of the shape and position of the template and/or guide is based, at least in part, on the electronic image data.

In accordance with related embodiments of the invention, determining leg length discrepancy may include a standing x-ray of the leg, a CT scout scan, a CT, and/or an MRI. The guide may assist a surgical instrument in cutting the femoral neck.

In accordance with another embodiment of the invention, a method for joint arthroplasty includes determining a desired femoral component rotation for a hip. A template is provided that includes at least one guide for directing movement of a surgical instrument, attached linkage, and/or tool. At least one of the shape and position of the guide is based, at least in part, on the desired femoral component rotation.

In accordance with another embodiment of the invention, a method for joint arthroplasty includes determining a desired acetabular component rotation for a hip. An acetabular template is provided that includes at least one guide for directing movement of a surgical instrument, attached linkage, and/or tool. At least one of the shape and position of the guide is based, at least in part, on the desired acetabular component rotation.

In accordance with another embodiment of the invention, a method for joint arthroplasty includes determining a desired humerus component rotation for a shoulder. A template is provided that includes at least one guide for directing movement of a surgical instrument, attached linkage, and/or a tool. At least one of the shape and position of the guide is based, at least in part, on the desired humerus component rotation.

In accordance with another embodiment of the invention, a method for joint arthroplasty includes providing a template that includes at least one surface for engaging a surface of a joint based, at least in part, on substantially isotropic input data. The surface is a mirror image of portions or all of the joint surface. The template includes at least one guide for directing movement of a surgical instrument.

In related embodiments of the invention, said input data is acquired using fusion of image planes, or substantially isotropic MRI and spiral CT.

In accordance with another embodiment of the invention, a method for ligament repair includes obtaining electronic image data of at least one surface associated with a ligament. A first template is created based, at least in part, on the image data. The first template has at least one contact surface that conforms with at least a portion of the surface. The first template includes at least one guide for directing movement of a surgical instrument involved with the ligament repair.

In related embodiments of the invention, the ligament may be an anterior cruciate ligament or a posterior cruciate ligament. The method may further include determining a tunnel site for a ligament graft. Determining the tunnel site may include identifying an origin of the ligament on a first articular surface, and an insertion position onto a second articular surface opposing the first articular surface. Determining the tunnel site may include identifying at least one of a bony landmark and a remainder of a ligament based on the image data. The surface may be adjacent to the tunnel site, or a non-weight bearing surface. The first template may includes a drill guide aperture, the method further including positioning the template such that the at least one contact surface contacts the at least a portion of the surface, and drilling a ligament tunnel, wherein the drilling is guided by the drill guide aperture. At least one of the shape, position and orientation of the drill guide aperture on the first template may be based, at least in part, on a distance of the tunnel to adjacent cortical bone. The drill guide aperture may includes a stop, such that a desired drill depth is obtained. The image data may be obtained preoperatively. The image data may be obtained by a CT scan or an MRI scan. The image data may be obtained in joint flexion, joint extension, joint abduction, joint adduction, and/or joint rotation. The method may further include identifying a graft harvest site based on the image data, and using the first template to guide harvesting of at least one of ligament and bone form the graft harvest site. The method may further include cross-referencing a second template to the first template to align position of the second template on a second surface associated with the ligament, the second template including at least one guide, and directing movement of the instrument using the at least one guide of the second template relative to said guide. The first and second surfaces may be opposing articular surfaces. The first surface may be a femoral surface and the second surface may be a tibial surface. The first template may include a tissue retractor. The tissue retractor may be a flange or an extender on the template. The template may be used for single bundle or a double bundle ligament reconstruction.

In any of the embodiments and aspects described herein, the joint can be, without limitation, a knee, shoulder, hip, vertebrae, elbow, ankle, foot, toe, hand, wrist or finger.

BRIEF DESCRIPTION OF THE DRAWINGS

The foregoing features of the invention will be more readily understood by reference to the following detailed description, taken with reference to the accompanying drawings, in which:

FIG. 7A shows an example of normal thickness cartilage and a cartilage defect. FIG. 7B shows an imaging technique or a mechanical, optical, laser or ultrasound device measuring the thickness and detecting a sudden change in thickness indicating the margins of a cartilage defect. FIG. 7C shows a weight-bearing surface mapped onto the articular cartilage. FIG. 7D shows an intended implantation site and cartilage defect. FIG. 7E depicts placement of an exemplary single component articular surface repair system. FIG. 7F shows an exemplary multi-component articular surface repair system. FIG. 7G shows an exemplary single component articular surface repair system. FIG. 7H shows an exemplary multi-component articular surface repair system.

FIG. 8A shows a magnified view of an area of diseased cartilage. FIG. 8B shows a measurement of cartilage thickness adjacent to the defect. FIG. 8C depicts placement of a multi-component mini-prosthesis for articular resurfacing. FIG. 8D is a schematic depicting placement of a single component mini-prosthesis utilizing stems or pegs. FIG. 8E depicts placement of a single component mini-prosthesis utilizing stems and an opening for injection of bone cement.

FIG. 9A depicts normal thickness cartilage in the anterior and central and posterior portion of a femoral condyle and a large area of diseased cartilage in the posterior portion of the femoral condyle. FIG. 9B depicts placement of a single component articular surface repair system. FIG. 9C depicts a multi-component articular surface repair system.

FIGS. 11A-G illustrate, in cross-section, the use of an inflation device to form an implant, in accordance with various embodiments of the invention. FIG. 11A illustrates a single lumen balloon inserted between two joint surfaces where the inflation occurs within the bounds of the joint. FIG. 11B illustrates another single lumen balloon inserted between two joint surfaces where the inflatable surfaces extend beyond a first and second edge of a joint. FIG. 11C illustrates another single lumen balloon between two joint surfaces. FIG. 11D illustrates a multi-balloon solution using two balloons where the balloons are adjacent to each other within the joint. FIG. 11E illustrates an alternative multi-balloon solution wherein a first balloon is comprised within a second balloon. FIG. 11F illustrates another multi-balloon solution where a first balloon lies within the lumen of a second balloon and further wherein the second balloon is adjacent a third balloon. FIG. 11G illustrates a 3 balloon configuration wherein a first balloon lies adjacent a second balloon and a third balloon fits within the lumen of one of the first or second balloon.

In FIG. 12A the inflation device enables the implant to achieve a surface conforming to the irregularities of the joint surface. In FIG. 12B the inflation device enables the implant to achieve a surface that sits above the irregular joint surface; FIG. 12C illustrates a device formed where a central portion of the device sits above the joint surface irregularities while the proximal and distal ends illustrated form a lateral abutting surface to the joint defects. FIG. 12D illustrates a device formed using a first inflation device within a second inflation device, with an exterior configuration similar to that shown in FIG. 12A; while FIG. 12E illustrates an alternative device formed using at least two different inflation devices having an exterior shape similar to the device shown in FIG. 12C.

FIGS. 14A-J illustrate the use of a retaining device to form an implant in situ, in accordance with various embodiments of the invention.

FIG. 15A shows an exemplary single component articular surface repair system with varying curvature and radii. FIG. 15B depicts a multi-component articular surface repair system with a second component that mirrors the shape of the subchondral bone and a first component closely matches the shape and curvature of the surrounding normal cartilage.

FIG. 18B-D show various cross-sectional representations of the pegs: FIG. 18B shows a peg having a groove; FIG. 18C shows a peg with radially-extending arms that help anchor the device in the underlying bone; and FIG. 18D shows a peg with multiple grooves or flanges.

FIGS. 20B-E are overhead views of the implant showing that the shape of the peg need not be conical.

FIG. 26Y shows a tibial implant and femoral implant inserted onto the tibia and femur, respectively, in accordance with an embodiment of the invention.

FIG. 27A-G illustrate patellar cutting blocks and molds used to prepare the patella for receiving a portion of a knee implant, in accordance with various embodiments of the invention.

FIG. 28A-H illustrate femoral head cutting blocks and molds used to create a surface for receiving the femoral portion of a knee implant, in accordance with various embodiments of the invention.

FIG. 29A-D illustrate acetabulum cutting blocks and molds used to create a surface for a hip implant, in accordance with various embodiments of the invention.

FIG. 32 illustrates a 3D guidance template designed to guide a posterior cut using a posterior reference plane, in accordance with an embodiment of the invention. The joint facing surface of the template is, at least in part, a mirror image of portions of the joint that are not altered by the arthritic process.

FIG. 33 illustrates a 3D guidance template designed to guide an anterior cut using an anterior reference plane, in accordance with an embodiment of the invention. The joint facing surface of the template is, at least in part, a mirror image of portions of the joint that are altered by the arthritic process.

FIGS. 40A-C illustrate the use of 3D guidance templates for performing ligament repair, in accordance with an embodiment of the invention.

FIG. 47 shows an example of an optional second femoral neck mold, placed on the femoral neck cut, providing and estimate of anteversion and longitudinal femoral axis.

DETAILED DESCRIPTION OF THE INVENTION

Figure 1:
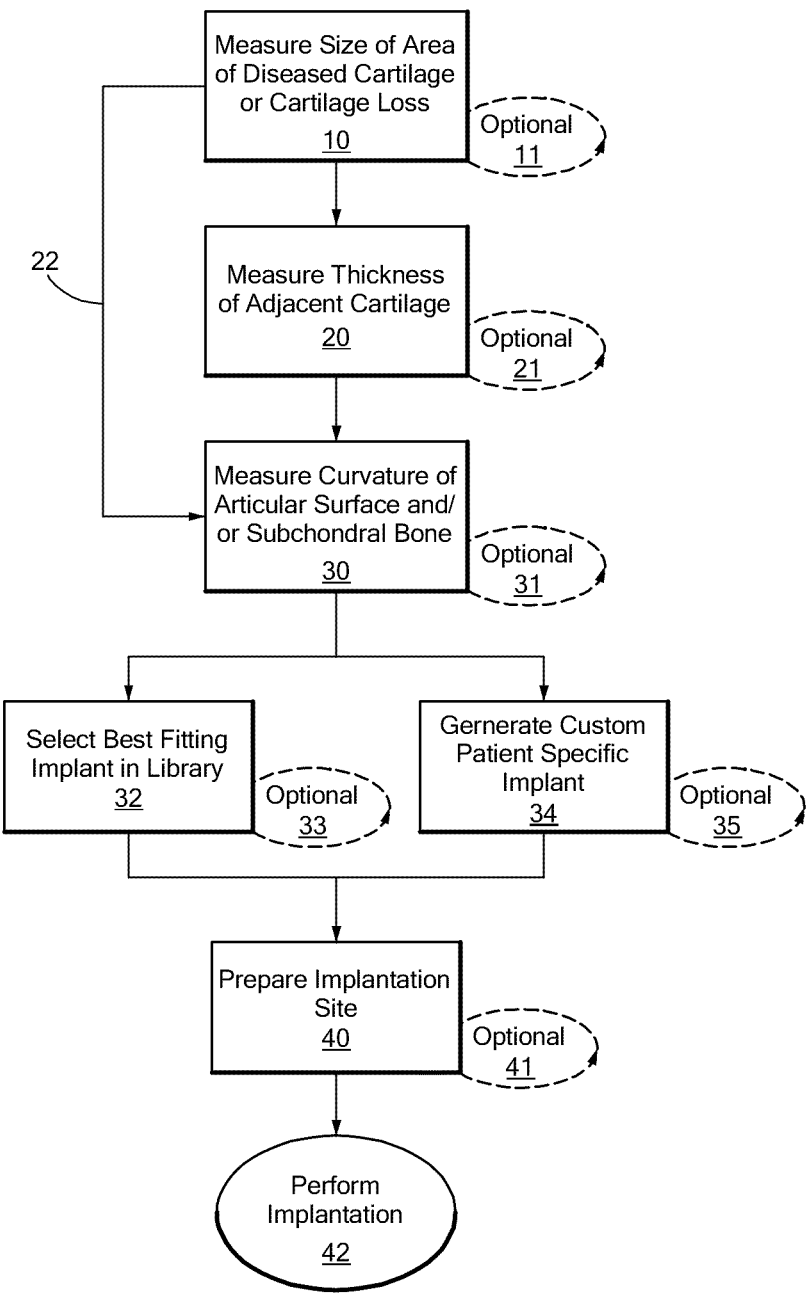
FIG. 1 is a flowchart depicting various methods of the present invention including, measuring the size of an area of diseased cartilage or cartilage loss, measuring the thickness of the adjacent cartilage, and measuring the curvature of the articular surface and/or subchondral bone. Based on this information, a best-fitting implant can be selected from a library of implants or a patient specific custom implant can be generated. The implantation site is subsequently prepared and the implantation is performed.

The following description is presented to enable any person skilled in the art to make and use the invention. Various modifications to the embodiments described will be readily apparent to those skilled in the art, and the generic principles defined herein can be applied to other embodiments and applications without departing from the spirit and scope of the present invention as defined by the appended claims. Thus, the present invention is not intended to be limited to the embodiments shown, but is to be accorded the widest scope consistent with the principles and features disclosed herein. To the extent necessary to achieve a complete understanding of the invention disclosed, the specification and drawings of all issued patents, patent publications, and patent applications cited in this application are incorporated herein by reference.

3D guidance surgical tools, referred to herein as a 3D guidance surgical templates, that may be used for surgical assistance may include, without limitation, using templates, jigs and/or molds, including 3D guidance molds. It is to be understood that the terms "template," "jig," "mold," "3D guidance mold," and "3D guidance template," shall be used interchangeably within the detailed description and appended claims to describe the tool unless the context indicates otherwise.

3D guidance surgical tools that may be used may include guide apertures. It is to be understood that the term guide aperture shall be used interchangeably within the detailed description and appended claims to describe both guide surface and guide elements.

As will be appreciated by those of skill in the art, the practice of the present invention employs, unless otherwise indicated, conventional methods of x-ray imaging and processing, x-ray tomosynthesis, ultrasound including A-scan, B-scan and C-scan, computed tomography (CT scan), magnetic resonance imaging (MRI), optical coherence tomography, single photon emission tomography (SPECT) and positron emission tomography (PET) within the skill of the art. Such techniques are explained fully in the literature and need not be described herein. See, e.g., X-Ray Structure Determination: A Practical Guide, 2nd Edition, editors Stout and Jensen, 1989, John Wiley & Sons, publisher; Body Conn.: A Practical Approach, editor Slone, 1999, McGraw-Hill publisher; X-ray Diagnosis: A Physician's Approach, editor Lam, 1998 Springer-Verlag, publisher; and Dental Radiology: Understanding the X-Ray Image, editor Laetitia Brocklebank 1997, Oxford University Press publisher. See also, The Essential Physics of Medical Imaging ($2^{nd}$ Ed.), Jerrold T. Bushberg, et al.

The present invention provides methods and compositions for repairing joints, particularly for repairing articular cartilage and for facilitating the integration of a wide variety of cartilage repair materials into a subject. Among other things, the techniques described herein allow for the customization of cartilage repair material to suit a particular subject, for example in terms of size, cartilage thickness and/or curvature. When the shape (e.g., size, thickness and/or curvature) of the articular cartilage surface is an exact or near anatomic fit with the non-damaged cartilage or with the subject's original cartilage, the success of repair is enhanced. The repair material can be shaped prior to implantation and such shaping can be based, for example, on electronic images that provide information regarding curvature or thickness of any "normal" cartilage surrounding the defect and/or on curvature of the bone underlying the defect. Thus, the current invention provides, among other things, for minimally invasive methods for partial joint replacement. The methods will require only minimal or, in some instances, no loss in bone stock. Additionally, unlike with current techniques, the methods described herein will help to restore the integrity of the articular surface by achieving an exact or near anatomic match between the implant and the surrounding or adjacent cartilage and/or subchondral bone.

Advantages of the present invention can include, but are not limited to, (i) customization of joint repair, thereby enhancing the efficacy and comfort level for the patient following the repair procedure; (ii) eliminating the need for a surgeon to measure the defect to be repaired intraoperatively in some embodiments; (iii) eliminating the need for a surgeon to shape the material during the implantation procedure; (iv) providing methods of evaluating curvature of the repair material based on bone or tissue images or based on intraoperative probing techniques; (v) providing methods of repairing joints with only minimal or, in some instances, no loss in bone stock; and (vi) improving postoperative joint congruity.

Thus, the methods described herein allow for the design and use of joint repair material that more precisely fits the defect (e.g., site of implantation) and, accordingly, provides improved repair of the joint.

I. Assessment of Joints and Alignment

The methods and compositions described herein can be used to treat defects resulting from disease of the cartilage (e.g., osteoarthritis), bone damage, cartilage damage, trauma, and/or degeneration due to overuse or age. The invention allows, among other things, a health practitioner to evaluate and treat such defects. The size, volume and shape of the area of interest can include only the region of cartilage that has the defect, but preferably will also include contiguous parts of the cartilage surrounding the cartilage defect.

As will be appreciated by those of skill in the art, size, curvature and/or thickness measurements can be obtained using any suitable technique. For example, one-dimensional, two-dimensional, and/or three-dimensional measurements can be obtained using suitable mechanical means, laser devices, electromagnetic or optical tracking systems, molds, materials applied to the articular surface that harden and "memorize the surface contour," and/or one or more imaging techniques known in the art. Measurements can be obtained non-invasively and/or intraoperatively (e.g., using a probe or other surgical device). As will be appreciated by those of skill in the art, the thickness of the repair device can vary at any given point depending upon the depth of the damage to the cartilage and/or bone to be corrected at any particular location on an articular surface.

As illustrated in FIG. 1, typically the process begins by first measuring the size of the area of diseased cartilage or cartilage loss 10. Thereafter the user can optionally measure the thickness of adjacent cartilage 20. Once these steps are performed, the curvature of the articular surface is measured 30. Alternatively, the curvature of subchondral bone can be measured.

Once the size of the defect is known, either an implant can be selected from a library 32 or an implant can be generated based on the patient specific parameters obtained in the measurements and evaluation 34. Prior to installing the implant in the joint, the implantation site is prepared 40 and then the implant is installed 42. One or more of these steps can be repeated as necessary or desired as shown by the optional repeat steps 11, 21, 31, 33, 35, and 41.

A. Imaging Techniques i. Thickness and Curvature

As will be appreciated by those of skill in the art, imaging techniques suitable for measuring thickness and/or curvature (e.g., of cartilage and/or bone) or size of areas of diseased cartilage or cartilage loss include the use of x-rays, magnetic resonance imaging (MRI), computed tomography scanning (CT, also known as computerized axial tomography or CAT), optical coherence tomography, ultrasound imaging techniques, and optical imaging techniques. (See, also, International Patent Publication WO 02/22014 to Alexander, et al., published Mar. 21, 2002; U.S. Pat. No. 6,373,250 to Tsoref et al., issued Apr. 16, 2002; and Vandeberg et al. (2002) *Radiology* 222:430-436). Contrast or other enhancing agents can be employed using any route of administration, e.g. intravenous, intra-articular, etc.

Based on the imaging performed, the software may evaluate the fit of different implants and/or surgical guide templates with regard to dimensions, overall size and shape. The dimensions, overall size and shape may be optimized with regard to cortical bone shape and dimensions, cortical bone thickness, endosteal bone shape, size of marrow cavity, articular surface shape and dimensions, subchondral bone shape and dimensions, or subchondral bone thickness. Thus, for example, an implant may either be custom made or selected from a number of pre-manufactured implants that is optimized with regard to any of the following or combinations thereof: AP dimensions and shape, mediolateral dimensions and shape, superoinferior dimensions and shape, shape of the articulating surface, shape and dimensions of the interface in contact with cortical bone, shape and dimensions of intramedullary portions or components. These parameters may also be optimized for implant function, e.g. for different degrees of joint flexion or extension or abduction or adduction or internal or external rotation.

In certain embodiments, CT or MRI is used to assess tissue, bone, cartilage and any defects therein, for example cartilage lesions or areas of diseased cartilage, to obtain information on subchondral bone or cartilage degeneration and to provide morphologic or biochemical or biomechanical information about the area of damage. Specifically, changes such as fissuring, partial or full thickness cartilage loss, and signal changes within residual cartilage can be detected using one or more of these methods. For discussions of the basic NMR principles and techniques, see MRI Basic Principles and Applications, Second Edition, Mark A. Brown and Richard C. Semelka, Wiley-Liss, Inc. (1999). For a discussion of MRI including conventional T1 and T2-weighted spin-echo imaging, gradient recalled echo (GRE) imaging, magnetization transfer contrast (MTC) imaging, fast spin-echo (FSE) imaging, contrast enhanced imaging, rapid acquisition relaxation enhancement (RARE) imaging, gradient echo acquisition in the steady state (GRASS), and driven equilibrium Fourier transform (DEFT) imaging, to obtain information on cartilage, see Alexander, et al., WO 02/22014. Other techniques include steady state free precision, flexible equilibrium MRI and DESS. Thus, in preferred embodiments, the measurements produced are based on three-dimensional images of the joint obtained as described in Alexander, et al., WO 02/22014 or sets of two-dimensional images ultimately yielding 3D information. Two-dimensional, and three-dimensional images, or maps, of the cartilage alone or in combination with a movement pattern of the joint, e.g. flexion-extension, translation and/or rotation, can be obtained. Three-dimensional images can include information on movement patterns, contact points, contact zone of two or more opposing articular surfaces, and movement of the contact point or zone during joint motion. Two- and three-dimensional images can include information on biochemical composition of the articular cartilage. In addition, imaging techniques can be compared over time, for example to provide up-to-date information on the shape and type of repair material needed.

Traditional CT and MRI scans utilize two dimensional cross-sectional images acquired in different imaging planes to visualize complex three-dimensional articular anatomy. With computed tomography, these slices are typically acquired in the axial plane. The in-plane resolution is typically on the order of 0.25×0.25 millimeters. The slice thickness may vary from one to five millimeters. Thus, the resolution obtained with these imaging studies is not isotropic. Moreover, the CT slices and, similarly with MRI, may be separated by one or more millimeters. This means that the resolution of the images is excellent within the imaging plane. However, two to ten-fold loss in image resolution can be encountered in a plane perpendicular to the slices acquired by the CT or MRI scanner. This limitation in resolution perpendicular to the imaging plane can result in inaccuracies in deriving the three-dimensional shape of, without limitation, an implant and/or a 3-D guidance template, described in more detail below.

In accordance with one embodiment of the invention, spiral CT imaging is utilized to acquire the images rather than standard CT technology. With recent CT technology, slip ring technology is incorporated in the scanner. A slip ring is a circular contact with sliding brushes that allows the gantry to rotate continuously, untethered by electrical wires. The use of slip ring technology eliminates the initial limitations at the end of each slice acquisition. Thus, the rotating gantry is free to rotate continuously throughout the examination of a joint. A slip ring CT scanner design allows greater rotational velocities, thereby shortening scan times. With a spiral CT scan data is acquired while the table is moving. As a result, the x-ray source moves in a spiral or helical rather than a circular pattern around the patient. The speed of the table motion relative to the rotation of the CT gantry is a very important consideration for image quality in helical or spiral CT scanning. This parameter is call pitch. In a preferred embodiment, spiral CT scans will be acquired through the joint wherein these spiral CT scans afford a resolution that is isotropic, for example 1 millimeter by 1 millimeter by 1 millimeter in x, y and z direction, or, more preferred, 0.75×0.75×0.75 millimeters in x, y and z direction, or, more preferred, 0.5×0.5×0.5 millimeters in x, y and z direction, or more preferred 0.25×0.25×0.25 millimeters in x, y and z direction. Near isotropic data sets are also acceptable particularly if the maximum resolution in any one of the three special orientations does not exceed 1.5 millimeters, or, more preferred 1.0 millimeters, or, more preferred 0.75 millimeters, or, more preferred 0.5 millimeters. Thus, the present invention recognizes that the accuracy in placing a 3-D guidance template on an articular surface, or shaping an implant, can be greatly improved with isotropic or near isotropic data sets as compared to traditional 2-D slice based data sets derived from either CT or MRI or other imaging technologies. For example, a knee joint scan data acquired with near isotropic resolution of 0.4×0.4×0.7 millimeters (e.g. a resolution ratio of less than 2:1 between the different dimensions and resolution in all three dimensions preferably better than 1 mm) will yield greater positional accuracy in placing a 3-D guidance template on the articular surface than scan data acquired using traditional CT scans, for example, with a scan resolution of 0.4×0.4×1.2 millimeters.

With MRI, standard acquisition call sequences also result in two dimensional slices for displaying complex three dimensional articular anatomy. The two dimensional slices can be acquired using 2-D or 3-D Fourier transformation. After the 2-D or 3-D transform, 2-D slices are available for image viewing and image processing. Of note, typically the image resolution in the imaging plane will be two or more fold greater than the image resolution perpendicular to the primary imaging plane. Similar to CT, this limitation in spatial resolution in the plane perpendicular to the imaging plane can result in inaccuracies in deriving and subsequently placing 3-D guidance molds. In a preferred embodiment, MRI data is acquired or processed so that the data used for generating the 3-D guidance mold or implant has isotropic or near isotropic resolution. For example, isotropic or near isotropic resolution may be achieved by fusing two non-parallel imaging planes acquired using standard 2-D or 3-D Fourier transform images, registering them relative to each other and performing an image fusion (see U.S. patent application Ser. No. 10/728,731, entitled "FUSION OF MULTIPLE IMAGING PLANES FOR ISOTROPIC IMAGING IN MRI AND QUANTITATIVE IMAGE ANALYSIS USING ISOTROPIC OR NEAR-ISOTROPIC IMAGING," hereby incorporated by reference in its entirety). Alternatively, using latest generation scan technology, for example, with 3-D FSE, 3-D DESS, 3-D MENSA, 3-D PAVA, 3-D LAVA, 3-D MERGE, 3-D MEDIC imaging sequences, multi-channel coils, high field magnets, advanced gradient technology, isotropic or near isotropic acquisition using 3-D Fourier transform can be obtained. Using such advanced imaging technology, image resolution of 0.5 by 0.5 by 0.8 millimeters or greater may be obtained, achieving near isotropic and even isotropic resolution, with preferably resolution in all three dimensions of less than 1 mm.

As will be appreciated by those of skill in the art, imaging techniques can be combined, if desired. For example, C-arm imaging or x-ray fluoroscopy can be used for motion imaging, while MRI can yield high resolution cartilage information. C-arm imaging can be combined with intra-articular contrast to visualize the cartilage.

Figure 2:
FIG. 2 is a reproduction of a three-dimensional thickness map of the articular cartilage of the distal femur. Three-dimensional thickness maps can be generated, for example, from ultrasound, CT or MRI data. Dark holes within the substances of the cartilage indicate areas of full thickness cartilage loss.

Any of the imaging devices described herein can also be used intra-operatively (see, also below), for example using a hand-held ultrasound and/or optical probe to image the articular surface intra-operatively. FIG. 2 illustrates a reproduction of a three-dimensional thickness map of the articular surface on the distal femur. The dark holes within the cartilage indicate areas of full cartilage loss.

ii. Anatomical and Mechanical Axes, Virtual Ligament Balancing

Imaging can be used to determine the anatomical and biomechanical axes of an extremity associated with a joint, which can then be used in creating an implant or surgical guide template or mold. Suitable tests include, for example, an x-ray, or an x-ray combined with an MRI. Typically, anatomical landmarks are identified on the imaging test results (e.g., the x-ray film) and those landmarks are then utilized to directly or indirectly determine the desired axes. Thus, for example, if surgery is contemplated in a hip joint, knee joint, or ankle joint, an x-ray can be obtained. This x-ray can be a weight-bearing film of the extremity, for example, a full-length leg film taken while the patient is standing. This film can be used to determine the femoral and tibial anatomical axes and to estimate the biomechanical axes. As will be appreciated by those of skill in the art, these processes for identifying, e.g., anatomical and biomechanical axis of the joint can be applied to other joints without departing from the scope of the invention.

Anatomical and biomechanical axes can also be determined using other imaging modalities, including but not limited to, computed tomography and MRI. For example, a CT scan can be obtained through the hip joint, the knee joint, and the ankle joint. Optionally, the scan can be reformatted in the sagittal, coronal, or other planes. The CT images can then be utilized to identify anatomical landmarks and to determine the anatomical and biomechanical axes of the hip joint, knee joint, and/or ankle joint.

Similarly, an MRI scan can be obtained for this purpose. For example, an MRI scan of the thigh and pelvic region can be obtained using a body coil or a torso phased array coil. A high resolution scan of the knee joint can be obtained using a dedicated extremity coil. A scan of the calf/tibia region and the ankle joint can be obtained again using a body coil or a torso phased array coil. Anatomical landmarks can be identified in each joint on these scans and the anatomical and biomechanical axes can be estimated using this information.

In various embodiments, the imaging scan can be extended for 5 cm, more preferably 10 cm, or more preferably 15 cm above and/or below the joint thereby deriving anatomic information that can be used to derive the anatomic and biomechanical axis. For example, an MRI or CT scan can be obtained through a knee joint. The scan can extend 15 cm above and below the joint. The mid-femoral line and mid-tibial line as well as other anatomic landmarks such as the femoral transepicondylar line or Whiteside line or posterior condylar line can be determined and can be used to estimate the anatomic and biomechanical axes. Thus, in the example of a knee joint, no additional scanning through the hip joint and ankle joints will be needed.

With, for example, MRI, even larger coverage may be obtained, for example with a series of axial, sagittal or coronal slices obtained with a large field of view, e.g. 20 cm or more preferably 25 cm, or more preferably 30 cm, or more preferably 35 cm. These large field of view scans can be utilized to estimate the anatomic and biomechanical axes as described above. They lack, however, information on the surface detail of the joint due to limitations in spatial resolution. A second or additional scan can be performed with high resolution, e.g. with spatial resolution and x and y axis of less than 1.0 mm, or, more preferably, less than 0.8 mm, or, more preferably, less than 0.6 mm. The additional high resolution scan may be utilized to derive the articular surface detail needed for a good and accurate fit between the guidance template or implant, and the articular surface or adjacent structures.

A biomechanical axis and, in some instances, an anatomical axis may advantageously be defined by imaging the entire extremity in question. Such imaging may include cross-sectional, spiral or volumetric imaging via a CT or MRI scan or optical imaging through the entire extremity, or acquisition of select images or slices or volumes through an area of interest such as a hip joint, a knee joint or ankle joint.

In an illustrative embodiment, scans through the entire or portions of an entire extremity covering multiple joints may be replaced with an extended scan through a single joint such as a knee joint. For example, it may not be sufficient to estimate a biomechanical axis or an anatomical access with a standard knee scan such as a CT scan or MRI scan that includes, for example, only ten centimeter of the area or volume of interest above, or ten centimeters of area or volume of interest below the tibiofemoral joints space. With an extended scan, a larger area adjacent to the target joint can be included in the scan, e.g. fifteen centimeters above and below the medial tibia femoral joint space, twenty centimeters above and below the medial tibia femoral joint space, fifteen centimeters above and twenty centimeters below the medial tibiofemoral joint space, twenty centimeters above and twenty-five centimeters below the medial tibiofemoral joint space. While the extended scan is less involved on the operative side than the scan involving the neighboring joints, it can, optionally be used to provide an estimate of the anatomical axis, biomechanical axis, and/or an implant axes or related planes. Thus, better ease of use is provided at the expense of, possibly, more radiation and possibly, less accuracy.

In another embodiment, cross-sectional or volumetric images such as CT scans or MRI scans may be acquired through more than one joint, typically one or more joints neighboring the one contemplated for surgery. For example, CT or MRI slices, CT spirals, CT or MRI volumes, MRI two plane acquisitions with optional image fusion, or other tomographic acquisitions are acquired through the hip joint, knee joint and ankle joint in a patient scheduled for total knee replacement surgery. The 3D surgical guidance templates may be optimized by using anatomic and/or biomechanical information obtained in the adjacent neighboring joints, for example, resulting in an improved anatomic or functional result. By using cross-sectional or volumetric imaging information, more accurate identification of anatomic landmarks for identifying relevant anatomical and/or biomechanical axis, relevant planes including surgical planes and implant planes, as well as implant axes can be achieved when compared to x-rays or CT scout scans, in particular when the cross-sectional or volumetric data are acquired through neighboring joints. The accuracy of the position, orientation, shape or combinations thereof, of a 3D guide template can thus be improved with resulting improvement in accuracy of the surgical correction of underlying deformities such as varus, valgus, abduction, adduction, or rotation deformities.

An imaging test obtained during weight-bearing conditions has some inherent advantages, in that it demonstrates normal as well as pathological loading and load distribution. A cross-sectional imaging study such as a CT scan or MRI scan has some advantages because it allows one to visualize and demonstrate the anatomical landmarks in three, rather than two, dimensions, thereby adding accuracy. Moreover, measurements can be performed in other planes, such as the sagittal or oblique planes, that may not be easily accessible in certain anatomical regions using conventional radiography. In principle, any imaging test can be utilized for this purpose.

The biomechanical axis can be defined as the axis going from the center of the femoral head, between the condylar surfaces and through the ankle joint The software may automatically, semi-automatically or manually assisted find or identify the relevant anatomic points to calculate the anatomic and biomechanical axes, in accordance with various embodiments of the invention. For example, the software or the user can find the center of the femoral head. Optionally, this can be done in 3D rather than only in 2D. Thus, for example, in the femoral head, the software can find the center of the femoral head relative to its x, y, and z-dimensions. Alternatively, the relevant anatomic points can be selected manually and the axes can be calculated.

In another embodiment the software can compute methods of adjusting varus or valgus or ante- or retroversion deformity or rotational deformity based on such anatomic and biomechanical axis measurements. For example, the surface of a surgical guide template can be adapted so that surgical cuts performed for a total knee implant can be placed to correct an underlying varus or valgus deformity or, for example, ante- or retroversion. Alternatively, the openings/cut planes of a surgical guide template used for drilling, cutting and the like can be adjusted to achieve a varus or valgus correction to a near anatomic or physiologic range. These adjustments can be optimized for the implants of different manufacturers, e.g. Johnson & Johnson, Stryker, Smith & Nephew, Biomet and Zimmer.

In various embodiments, gait, loading and other physical activities of a joint as well as static joint positions may be simulated using a computer workstation. The template and its apertures and the resultant surgical templates and/or procedures, e.g. cuts, drilling, rasping, may be optimized using this information to achieve an optimal functional result. For example, the template and its apertures and the resultant implant position may be optimized for different degrees of flexion and extension, internal or external rotation, abduction or adduction, and ante or retroversion. Thus, the templates may be used to achieve motion that is optimized in one, two or more directions. Not only anatomic, but also functional optimization is possible in this manner.

The origin and insertion of ligaments, e.g. the anterior and posterior cruciate ligaments and the medial and lateral collateral ligaments in the case of a knee, can be visualized on the scan. With MRI, the ligaments are directly visible. If the ligament is torn, the location of the residual fibers at the origin or attachment can be visualized. Different joint positions can then be simulated and changes in ligament length can be determined for different angles of flexion and extension, internal or external rotation, abduction or adduction, and ante or retroversion. These simulations can be performed without but also with the implant in place. Thus, ligament length—and through this presumed tension—can be estimated virtually with any given implant and implant size. Different implants or component(s) can be tested preoperatively on the computer workstation and the implant or component(s) yielding the optimal ligament performance, e.g. minimal change in ligament length, for different joint positions can be determined pre-operatively. Thus, the invention provides among others for pre-operative ligament balancing, including but not limited to by directly visualizing the ligaments or fiber remnants.

For example, in one embodiment a loading apparatus may be applied to the patient to simulate weight-bearing while acquiring the CT scan. A non-limiting example of such a loading apparatus has been described by Dynamed with the Dynawell device. Any loading apparatus that can apply axial or other physiologic or near physiologic loading forces on the hip, knee or ankle joints or two or three of them may be used. Other more sophisticated scanning procedures can be used to derive this information without departing from the scope of the invention.

In a preferred embodiment, when imaging a joint of the lower extremity, a standing, weight-bearing x-ray can be obtained to determine the biomechanical axis. In the case of a knee or hip joint, for example, a standing, weight-bearing x-ray of the hip joint or the knee joint can be obtained. Alternatively, standing, weight-bearing x-rays can be obtained spanning the entire leg from the hip to the foot. The x-ray can be obtained in the antero-posterior or posterior-anterior projection but also in a lateral projection or principally any other projection that is desired. The user can measure the biomechanical axis, for example, by finding the centroid of the femoral head and the centroid of the ankle joint and by connecting these. This measurement can be performed manually, for example, on a x-ray film or electronically, for example, on a digitized or digital image, including with software assistance. The axis measured on the standing, weight-bearing x-ray can be cross referenced with another imaging modality such a CT or MRI scan. For example, a biomechanical axis can be determined on a standing x-ray of the leg. The result and data can be cross referenced, for example, by identifying corresponding bony anatomical landmarks to a CT scan or MRI scan. The result and information can then be utilized to determine the optimal shape of a 3-D guidance template. Specifically, the orientation, position, or shape of the template can be influenced based on the measurement of the biomechanical axis. Moreover, the position or shape of any blocks attached to said templates or linkages or the position or shape instruments attached to the mold, block or linkages can be influenced by this measurement. Combining the standing, weight-bearing imaging modality with CT scanning or MRI scanning has the principle advantage that the joint is evaluated during physiological loading. CT or MRI alone, typically do not afford assessment in loaded, weight-bearing condition.

As described above, the biomechanical axis can be evaluated in different planes or in three dimensions. For example, the actual biomechanical axis can be assessed in the AP plane and a desired biomechanical axis can be determined in this plane. In addition, the actual biomechanical axis can be determined in the lateral plane, for example, in the lateral projection radiograph, and the desired biomechanical axis can be determined in the lateral plane. By measuring the relevant biomechanical and anatomical axis in two or more planes, the shape of a 3-D guidance template and/or implant can be further refined and optimized with result in improvements in clinical and patient function.

The biomechanical or anatomical axis may also be measured using other approaches including a non-weight bearing position. For example, anatomical landmarks can be identified on a CT scout scan and cross referenced to a joint such as a knee joint or a hip joint for which surgery is contemplated. Thus, for example, the user can measure and determine the centroid of the ankle joint and the centroid of the hip joint for knee surgery using the CT scout scan.

In a preferred embodiment, the anatomical landmarks are determined using CT slices or MRI slices rather than a scout scan. A CT scout scan or MRI scout scan can have inherent limitations in spatial resolution. A CT scout scan is typically a single, 2-D radiographic image of the extremity lacking 3-D anatomical information and lacking high spatial resolution. An MRI scout scan is typically composed of multiple 2-D MRI slices, possibly acquired in one, two, or three planes. However, the resolution of the MRI scout scan is typically also limited. By acquiring selective slices and even isotropic or near isotropic data sets through neighboring joints, anatomical landmarks can be identified in a more reliable manner thereby improving the accuracy of anatomical and biomechanical axis determination. This improvement in accuracy translates into an improvement in accuracy in the resultant 3-D guidance mold, for example, a knee or hip joint, including improved accuracy of its shape, orientation, or position.

Computed Tomography imaging has been shown to be highly accurate for the determination of the relative anatomical and biomechanical axes of the leg (Testi Debora, Zannoni Cinzia, Cappello Angelo and Viceconti Marco. "Border tracing algorithm implementation for the femoral geometry reconstruction." *Comp. Meth. and Programs in Biomed.*, Feb. 14, 2000; Farrar M J, Newman R J, Mawhinney R R, King R. "Computed tomography scan scout film for measurement of femoral axis in knee arthroplasty." *J. Arthroplasty.* 1999 December; 14(8): 1030-1; Kim J S, Park T S, Park S B, Kim J S, Kim I Y, Kim S I. "Measurement of femoral neck anteversion in 3D. Part 1: 3D imaging method." *Med. and Biol. Eng. and Computing.* 38(6): 603-609, November 2000; Akagi M, Yamashita E, Nakagawa T, Asano T, Nakamura T. "Relationship between frontal knee alignment and reference axis in the distal femur." *Clin. Ortho. and Related Res.* No. 388,147-156, 2001; Mahaisavariya B, Sitthiseripratip K, Tongdee T, Bohez E, Sloten J V, Oris P. "Morphological study of the proximal femur: a new method of geometrical assessment using 3 dimensional reverse engineering." *Med. Eng. and Phys.* 24 (2002) 617-622; Lam Li On, Shakespeare D. "Varus/Valgus alignment of the femoral component in total knee arthroplasty." *The Knee,* 10 (2003) 237-241).

The angles of the anatomical structures of the proximal and distal femur also show a certain variability level (i.e. standard deviation) comparable with the varus or valgus angle or the angle between the anatomical femoral axis and the biomechanical axis (Mahaisavariya B, Sitthiseripratip K, Tongdee T, Bohez E, Sloten J V, Oris P. "Morphological study of the proximal femur: a new method of geometrical assessment using 3 dimensional reverse engineering." *Med. Eng. and Phys.* 24 (2002) 617-622). Thus, a preferred approach for assessing the axes is based on CT scans of the hip, knee and ankle joint or femur rather than only of the knee region.

CT has been shown to be efficient in terms of the contrast of the bone tissue with respect to surrounding anatomical tissue so the bone structures corresponding to the femur and tibia can be extracted very accurately with semi automated computerized systems (Mahaisavariya B, Sitthiseripratip K, Tongdee T, Bohez E, Sloten J V, Oris P. "Morphological study of the proximal femur: a new method of geometrical assessment using 3 dimensional reverse engineering." *Med. Eng. and Phys.* 24 (2002) 617-622; Testi Debora, Zannoni Cinzia, Cappello Angelo and Viceconti Marco. "Border tracing algorithm implementation for the femoral geometry reconstruction." *Comp. Meth. and Programs in Biomed.*, Feb. 14, 2000).

While 2-D CT has been shown to be accurate in the estimation of the biomechanical axis (Mahaisavariya B, Sitthiseripratip K, Tongdee T, Bohez E, Sloten J V, Oris P. "Morphological study of the proximal femur: a new method of geometrical assessment using 3 dimensional reverse engineering." *Med. Eng. and Phys.* 24 (2002) 617-622; Testi Debora, supra.; Lam Li On, Supra, 3-D CT has been shown to be more accurate for the estimation of the femoral anteversion angle (Kim J S, Park T S, Park S B, Kim J S, Kim I Y, Kim S I. Measurement of femoral neck anteversion in 3D. Part 1: 3D imaging method. Medical and Biological engineering and computing. 38(6): 603-609, November 2000; Kim J S, Park T S, Park S B, Kim J S, Kim I Y, Kim S I. Measurement of femoral neck anteversion in 3D. Part 1: 3D modeling method. Medical and Biological engineering and computing. 38(6): 610-616, November 2000). Farrar used simple CT 2-D scout views to estimate the femoral axis (Farrar M J, Newman R J, Mawhinney R R, King R. Computed tomography scan scout film for measurement of femoral axis in knee arthroplasty. J. Arthroplasty. 1999 December; 14(8): 1030-1).

In one embodiment, 2-D sagittal and coronal reconstructions of CT slice images are used to manually estimate the biomechanical axis. One skilled in the art can easily recognize many different ways to automate this process. For example, a CT scan covering at least the hip, knee and ankle region is acquired. This results in image slices (axial) which can be interpolated to generate the sagittal and coronal views.

Preprocessing (filtering) of the slice images can be used to improve the contrast of the bone regions so that they can be extracted accurately using simple thresholding or a more involved image segmentation tool like LiveWire or active contour models.

Identification of landmarks of interest like the centroid of the tibial shaft, the ankle joint, the intercondylar notch and the centroid of the femoral head can be performed. The biomechanical axis can be defined as the line connecting the proximal and the distal centroids, i.e. the femoral head centroid, the tibial or ankle joint centroid. The position of the intercondylar notch can be used for evaluation of possible deviations, errors or deformations including varus and valgus deformity.

In one embodiment, multiple imaging tests can be combined. For example, the anatomical and biomechanical axes can be estimated using a weight-bearing x-ray of the extremity or portions of the extremity. The anatomical information derived in this fashion can then be combined with a CT or MRI scan of one or more joints, such as a hip, knee, or ankle joint. Landmarks seen on radiography can then, for example, be cross-referenced on the CT or MRI scan. Axis measurements performed on radiography can be subsequently applied to the CT or MRI scans or other imaging modalities. Similarly, the information obtained from a CT scan can be compared with that obtained with an MRI or ultrasound scan. In one embodiment, image fusion of different imaging modalities can be performed. For example, if surgery is contemplated in a knee joint, a full-length weight-bearing x-ray of the lower extremity can be obtained. This can be supplemented by a spiral CT scan, optionally with intra-articular contrast of the knee joint providing high resolution three-dimensional anatomical characterization of the knee anatomy even including the menisci and cartilage. This information, along with the axis information provided by the radiograph can be utilized to select or derive therapies, such as implants or surgical instruments.

In certain embodiments, it may be desirable to characterize the shape and dimension of intra-articular structures, including subchondral bone or the cartilage. This may be done, for example, by using a CT scan, preferably a spiral CT scan of one or more joints. The spiral CT scan can optionally be performed using intra-articular contrast. Alternatively, an MRI scan can be performed. If CT is utilized, a full spiral scan, or a few selected slices, can be obtained through neighboring joints. Typically, a full spiral scan providing full three-dimensional characterization would be obtained in the joint for which therapy is contemplated. If implants, or templates, for surgical instruments are selected or shaped, using this scan, the subchondral bone shape can be accurately determined from the resultant image data. A standard cartilage thickness and, similarly, a standard cartilage loss can be assumed in certain regions of the articular surface. For example, a standard thickness of 2 mm of the articular cartilage can be applied to the subchondral bone in the anterior third of the medial and lateral femoral condyles. Similarly, a standard thickness of 2 mm of the articular cartilage can be applied to the subchondral bone in the posterior third of the medial and lateral femoral condyles. A standard thickness of 0 mm of the articular cartilage can be applied in the central weight-bearing zone of the medial condyle, and a different value can be applied to the lateral condyle. The transition between these zones can be gradual, for example, from 2 mm to 0 mm. These standard values of estimated cartilage thickness and cartilage loss in different regions of the joint can optionally be derived from a reference database. The reference database can include categories such as age, body mass index ("BMI"), severity of disease, pain, severity of varus deformity, severity of valgus deformity, Kellgren-Lawrence score, along with other parameters that are determined to be relative and useful. Use of a standard thickness for the articular cartilage can facilitate the imaging protocols required for pre-operative planning.

Alternatively, however, the articular cartilage can be fully characterized by performing a spiral CT scan of the joint in the presence of intra-articular contrast or by performing an MRI scan using cartilage sensitive pulse sequences.

The techniques described herein can be used to obtain an image of a joint that is stationary, either weight bearing or not, or in motion or combinations thereof. Imaging studies that are obtained during joint motion can be useful for assessing the load bearing surface. This can be advantageous for designing or selecting implants, e.g. for selecting reinforcements in high load areas, for surgical tools and for implant placement, e.g. for optimizing implant alignment relative to high load areas.

iii. Joint Space

In accordance with another embodiment of the invention, a method and system for determining joint space width is provided, in accordance with an embodiment of the invention. Without limitation, a CT scan, MRI scan, optical scan, and/or ultrasound imaging is performed. The medial and lateral joint space width in a knee joint, the joint space in a hip joint, ankle joint or other joint is evaluated. This evaluation may be performed in two dimensions, using a single scan plane orientation, such as sagittal or coronal plane, or it may be performed in three dimensions. The evaluation of joint space width may include measuring the distance from the subchondral bone plate of one articular surface to the subchondral bone plate of the opposing articular surface. Alternatively, the cartilage thickness may be measured directly on one or more articular surfaces. Joint space width or cartilage thickness may be measured for different regions of the joint and joint space width and cartilage loss can be evaluated in anterior, posterior, medial, lateral, superior and/or inferior positions. The measurements may be performed for different positions of the joint such as a neutral position, 45 degrees of flexion, 90 degrees of flexion, 5 degrees of abduction, 5 degrees of internal rotation and so forth. For example, in a knee joint, the joint space width may be evaluated in extension and at 25 degrees of knee flexion and 90 degrees of knee flexion. The medial and lateral joint space width may be compared and differences in medial and lateral joint space width can be utilized to optimize the desired postoperative correction in anatomical or biomechanical axis alignment based on this information. The shape, orientation, or position of a 3D guided template may be adjusted using this information, for example, in knee or hip implant placement or other surgeries.

For example, the measurement may show reduced joint space width or cartilage thickness in the medial compartment when compared to a normal anatomic reference standard, e.g. from age or sex or gender matched controls, and/or lateral compartment. This can coincide with valgus alignment of the knee joint, measured, for example, on the scout scan of an CT-scan or the localizer scan of an MRI scan including multiple localizer scans through the hip, knee and ankle joints.

If the biomechanical axis estimated on the comparison of the medial and lateral joint space width coincides with the biomechanical axis of the extremity measured on the scout scan, no further adjustment may be necessary. If the biomechanical axis estimated on the comparison of the medial and lateral joint space width does not coincide with the biomechanical axis of the extremity measured on the CT or MRI scout scan, additional correction of the valgus deformity (or in other embodiments, varus or other deformities) can be achieved.

This additional correction may be determined, for example, by adding the difference in axis correction desired based on biomechanical axis measured by comparison of the medial lateral joint space width and axis correction desired based on measurement of the biomechanical axis of the extremity measured on the scout or localizer scan to axis correction desired based on measurement of the biomechanical axis of the extremity measured on the scout or localizer scan alone. By combining the information from both, measurement of joint space width of the median and lateral compartment and measurement of the biomechanical axis using the scout scan or localizer scan or, for example, a weight bearing x-ray, an improved assessment of axis alignment during load bearing conditions can be obtained with resultant improvements in the shape, orientation or position of the 3D guidance template and related attachments or linkages.

Optionally, the extremity can be loaded while in the scanner, for example, using a compression harness. Examples for compression harnesses have been published, for example, by Dynawell.

iv. Estimation of Cartilage Loss

In another embodiment, an imaging modality such as spiral CT, spiral CT arthography, MRI, optical imaging, optical coherence tomography, ultrasound and others may be used to estimate cartilage loss in one, two or three dimensions. The information can be used to determine a desired correction of a measured biomechanical or anatomical axis. The correction can be in the anterior-posterior, medio-lateral, and/or superior-inferior direction, or any other direction applicable or desirable, or combinations thereof. The information can be combined with other data e.g., from a standing, weight bearing x-ray or CT scout scan, or an MRI localizer scan or a CT scan or MRI scan that includes axial/spiral or other images through the hip, knee and ankle joints. The information can be used to refine the axis correction desired based on, for example, standing x-rays, non-weight bearing x-rays, CT scout scans, MRI localizer scans and the like.

In another embodiment, any axis correction can be performed in a single plane (e.g., the medial-lateral plane), in two planes (e.g., the medial lateral and anterior-posterior planes), or multiple planes, including oblique planes that are biomechanically or anatomically relevant or desirable.

v. High Resolution Imaging

Additional improvements in accuracy of the 3D guide template and/or implants surfaces may be obtained with use of imaging technology that yields high spatial resolution, not only within the imaging plane, but along all three planes, specifically the X, Y and Z axis. With CT scanning, this can be achieved with the advent of spiral CT Scanning techniques. With MRI, dual or more plane scanning or volumetric acquisition can be performed. If dual or more plane MRI scanning is performed, these multiple scan planes can be fused, for example by cross-registration and resampling along the X, Y and Z axis. The resultant effective resolution in X, Y and Z direction is greatly improved as compared to standard CT scanning or standard MRI scanning. Improvements in resolution have the advantage that the resultant 3D guide templates can be substantially more accurate, for example with regard to their position, shape or orientation.

vi. Phantom Scans

Imaging modalities are subject to scan to scan variations, for example, including spatial distortion. In one embodiment, phantom scans may be performed in order to optimize the scan quality, specifically spatial resolution and spatial distortion. A phantom scan can be performed prior to a patient scan, simultaneously with a patient scan or after a patient scan. Using the phantom scan data, it is possible to make adjustments and optimizations of the scanner and, moreover, to perform image post processing to perform corrections, for example, correction of geometric distortions. Thus, if a phantom scan detects certain geometric distortion in the X, Y or Z axis and the amount of distortion is measured on the phantom scan, a correction factor can be included in the data prior to generating a 3D guide template. The resulting 3D guide template is thus more accurate with resulting improvement in intra-operative cross-reference to the anatomic surface and resultant improved accuracy in any surgical intervention such as drilling or cutting.

In another embodiment, a smoothing operation, e.g. using low frequency filtering, can be performed in order to remove any image related artifacts, such as stepping artifacts between adjacent CT or MRI slices. In some applications, the smoothing operation can be helpful in improving the fit between the joint and the template.

B. Intraoperative Measurements

Alternatively, or in addition to, non-invasive imaging techniques described above, measurements of the size of an area of diseased cartilage or an area of cartilage loss, measurements of cartilage thickness and/or curvature of cartilage or bone can be obtained intraoperatively during arthroscopy or open arthrotomy. Intraoperative measurements can, but need not, involve actual contact with one or more areas of the articular surfaces.

Devices suitable for obtaining intraoperative measurements of cartilage or bone or other articular structures, and to generate a topographical map of the surface include but are not limited to, Placido disks, optical measurements tools and device, optical imaging tools and devices, and laser interferometers, and/or deformable materials or devices. (See, for example, U.S. Pat. No. 6,382,028 to Wooh et al., issued May 7, 2002; U.S. Pat. No. 6,057,927 to Levesque et al., issued May 2, 2000; U.S. Pat. No. 5,523,843 to Yamane et al. issued Jun. 4, 1996; U.S. Pat. No. 5,847,804 to Sarver et al. issued Dec. 8, 1998; and U.S. Pat. No. 5,684,562 to Fujieda, issued Nov. 4, 1997).

Figure 3A:
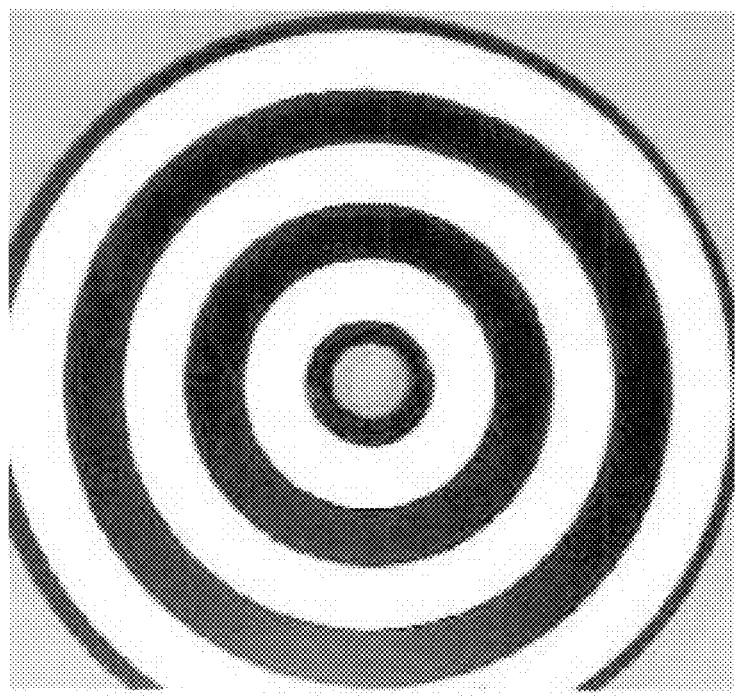
FIG. 3A shows an example of a Placido disc of concentrically arranged circles of light.
Figure 3B:
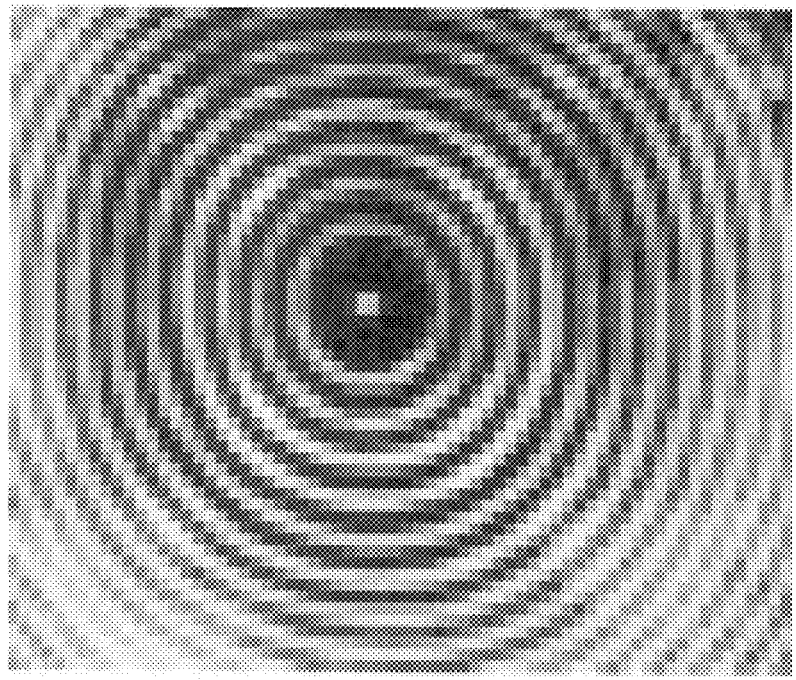
FIG. 3B shows an example of a projected Placido disc on a surface of fixed curvature.

FIG. 3A illustrates a Placido disk of concentrically arranged circles of light. The concentric arrays of the Placido disk project well-defined circles of light of varying radii, generated either with laser or white light transported via optical fiber. The Placido disk can be attached to the end of an endoscopic device (or to any probe, for example a hand-held probe) so that the circles of light are projected onto the cartilage surface. FIG. 3B illustrates an example of a Placido disk projected onto the surface of a fixed curvature. One or more imaging cameras can be used (e.g., attached to the device) to capture the reflection of the circles. Mathematical analysis is used to determine the surface curvature. The curvature can then, for example, be visualized on a monitor as a color-coded, topographical map of the cartilage surface. Additionally, a mathematical model of the topographical map can be used to determine the ideal surface topography to replace any cartilage defects in the area analyzed.

Figure 4:
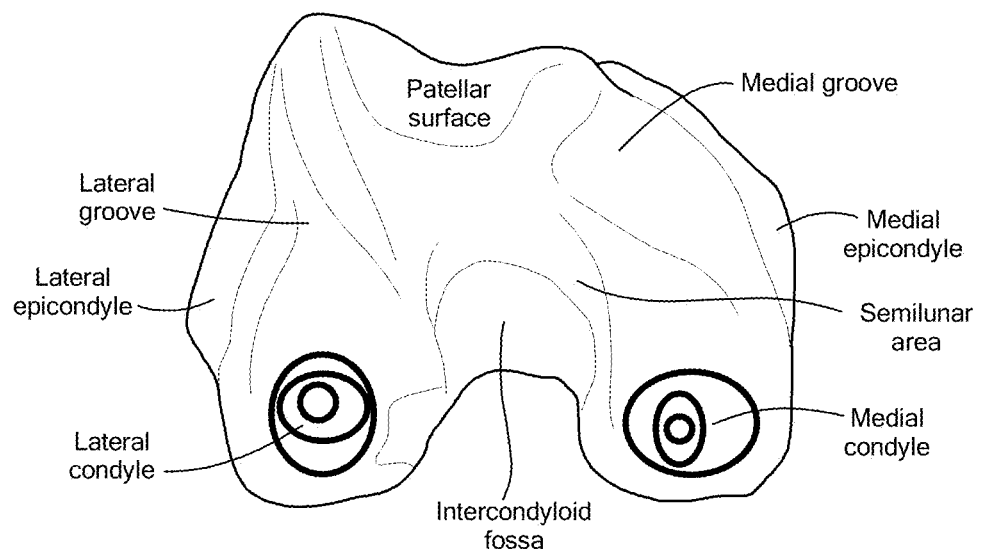
FIG. 4 shows a reflection resulting from a projection of concentric circles of light (Placido Disk) on each femoral condyle, demonstrating the effect of variation in surface contour on the reflected circles.

FIG. 4 shows a reflection resulting from the projection of concentric circles of light (Placido disk) on each femoral condyle, demonstrating the effect of variation in surface contour on reflected circles.

Similarly an optical imaging device or measurement tool, e.g. a laser interferometer, can also be attached to the end of an endoscopic device. Optionally, a small sensor can be attached to the device in order to determine the cartilage surface or bone curvature using phase shift interferometry, producing a fringe pattern analysis phase map (wave front) visualization of the cartilage surface. The curvature can then be visualized on a monitor as a color coded, topographical map of the cartilage surface. Additionally, a mathematical model of the topographical map can be used to determine the ideal surface topography to replace any cartilage or bone defects in the area analyzed. This computed, ideal surface, or surfaces, can then be visualized on the monitor, and can be used to select the curvature, or curvatures, of the replacement cartilage or mold.

Optical imaging techniques can be utilized to generate a 3D visualization or surface map of the cartilage or bone, which can be used to generate an articular repair system or a mold.

Figure 5:
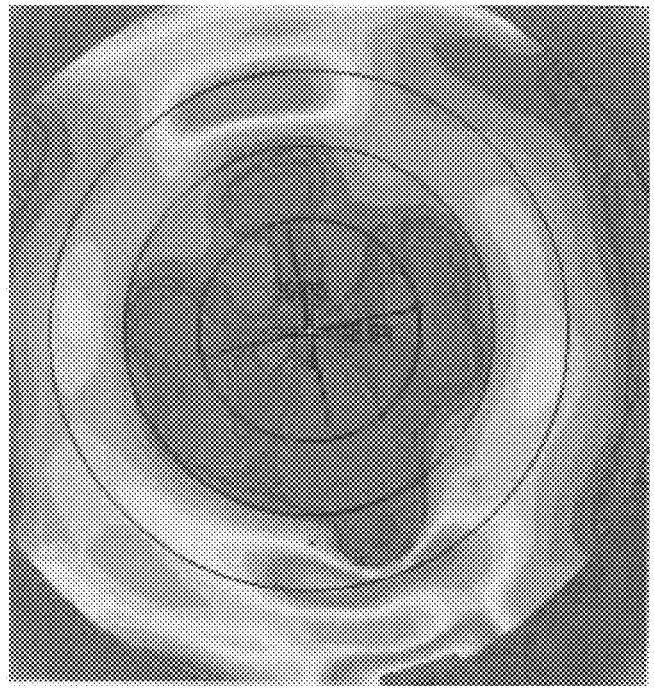
FIG. 5 shows an example of a 2D topographical map of an irregularly curved surface.
Figure 6:
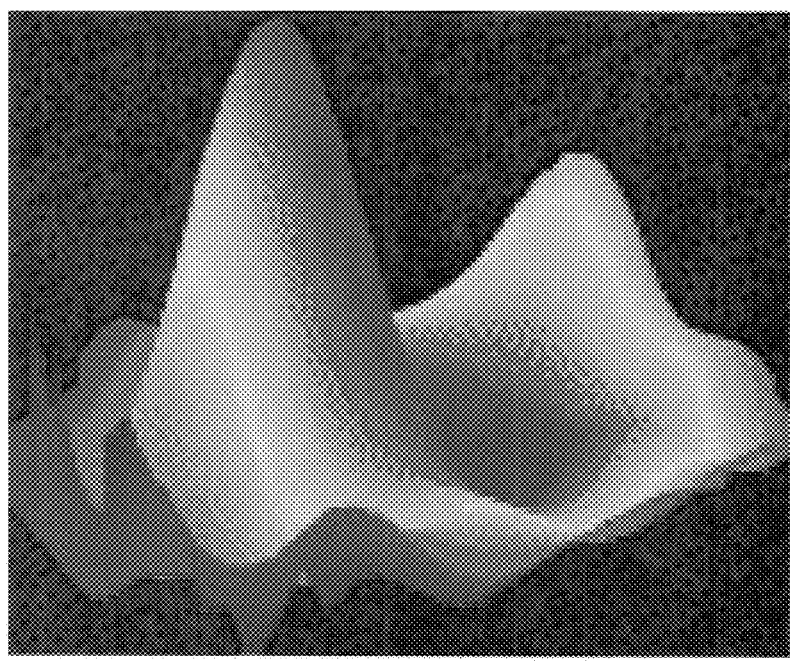
FIG. 6 shows an example of a 3D topographical map of an irregularly curved surface.

One skilled in the art will readily recognize that other techniques for optical measurements of the cartilage surface curvature can be employed without departing from the scope of the invention. For example, a 2-dimensional or 3-dimensional map, such as that shown in FIG. 5 and FIG. 6, can be generated.

Mechanical devices (e.g., probes) can also be used for intraoperative measurements, for example, deformable materials such as gels, molds, any hardening materials (e.g., materials that remain deformable until they are heated, cooled, or otherwise manipulated). See, e.g., WO 02/34310 to Dickson et al., published May 2, 2002. For example, a deformable gel can be applied to a femoral condyle. The side of the gel pointing towards the condyle can yield a negative impression of the surface contour of the condyle. The negative impression can then be used to determine the size of a defect, the depth of a defect and the curvature of the articular surface in and adjacent to a defect. This information can be used to select a therapy, e.g. an articular surface repair system or a mold. It can also be used to make a mold, either directly with use of the impression or, for example, indirectly via scanning the impression. In another example, a hardening material can be applied to an articular surface, e.g. a femoral condyle or a tibial plateau. The hardening material can remain on the articular surface until hardening has occurred. The hardening material can then be removed from the articular surface. The side of the hardening material pointing towards the articular surface can yield a negative impression of the articular surface. The negative impression can then be used to determine the size of a defect, the depth of a defect and the curvature of the articular surface in and adjacent to a defect. This information can then be used to select a therapy, e.g. an articular surface repair system or a mold. It can also be used to make a mold, either directly with use of the impression or, for example, indirectly via scanning the impression. In some embodiments, the hardening system can remain in place and form the actual articular surface repair system.

In certain embodiments, the deformable material comprises a plurality of individually moveable mechanical elements. When pressed against the surface of interest, each element can be pushed in the opposing direction and the extent to which it is pushed (deformed) can correspond to the curvature of the surface of interest. The device can include a brake mechanism so that the elements are maintained in the position that conforms to the surface of the cartilage and/or bone. The device can then be removed from the patient and analyzed for curvature. Alternatively, each individual moveable element can include markers indicating the amount and/or degree it is deformed at a given spot. A camera can be used to intra-operatively image the device and the image can be saved and analyzed for curvature information. Suitable markers include, but are not limited to, actual linear measurements (metric or empirical), different colors corresponding to different amounts of deformation and/or different shades or hues of the same color(s). Displacement of the moveable elements can also be measured using electronic means.

Other devices to measure cartilage and subchondral bone intraoperatively include, for example, ultrasound probes. An ultrasound probe, preferably handheld, can be applied to the cartilage and the curvature of the cartilage and/or the subchondral bone can be measured. Moreover, the size of a cartilage defect can be assessed and the thickness of the articular cartilage can be determined. Such ultrasound measurements can be obtained in A-mode, B-mode, or C-mode. If A-mode measurements are obtained, an operator can typically repeat the measurements with several different probe orientations, e.g. mediolateral and anteroposterior, in order to derive a three-dimensional assessment of size, curvature and thickness.

One skilled in the art will easily recognize that different probe designs are possible using the optical, laser interferometry, mechanical and ultrasound probes. The probes are preferably handheld. In certain embodiments, the probes or at least a portion of the probe, typically the portion that is in contact with the tissue, can be sterile. Sterility can be achieved with use of sterile covers, for example similar to those disclosed in WO 99/08598A1 to Lang, published Feb. 25, 1999.

Analysis on the curvature of the articular cartilage or subchondral bone using imaging tests and/or intraoperative measurements can be used to determine the size of an area of diseased cartilage or cartilage loss. For example, the curvature can change abruptly in areas of cartilage loss. Such abrupt or sudden changes in curvature can be used to detect the boundaries of diseased cartilage or cartilage defects.

As described above, measurements can be made while the joint is stationary, either weight bearing or not, or in motion.

II. Repair Materials

A wide variety of materials find use in the practice of the present invention, including, but not limited to, plastics, metals, crystal free metals, ceramics, biological materials (e.g., collagen or other extracellular matrix materials), hydroxyapatite, cells (e.g., stem cells, chondrocyte cells or the like), or combinations thereof. Based on the information (e.g., measurements) obtained regarding the defect and the articular surface and/or the subchondral bone, a repair material can be formed or selected. Further, using one or more of these techniques described herein, a cartilage replacement or regenerating material having a curvature that will fit into a particular cartilage defect, will follow the contour and shape of the articular surface, and will match the thickness of the surrounding cartilage. The repair material can include any combination of materials, and typically include at least one non-pliable material, for example materials that are not easily bent or changed.

A. Metal and Polymeric Repair Materials

Currently, joint repair systems often employ metal and/or polymeric materials including, for example, prostheses which are anchored into the underlying bone (e.g., a femur in the case of a knee prosthesis). See, e.g., U.S. Pat. No. 6,203,576 to Afriat, et al. issued Mar. 20, 2001 and U.S. Pat. No. 6,322,588 to Ogle, et al. issued Nov. 27, 2001, and references cited therein. A wide-variety of metals are useful in the practice of the present invention, and can be selected based on any criteria. For example, material selection can be based on resiliency to impart a desired degree of rigidity. Non-limiting examples of suitable metals include silver, gold, platinum, palladium, iridium, copper, tin, lead, antimony, bismuth, zinc, titanium, cobalt, stainless steel, nickel, iron alloys, cobalt alloys, such as Elgiloy®, a cobalt-chromium-nickel alloy, and MP35N, a nickel-cobalt-chromium-molybdenum alloy, and Nitinol™, a nickel-titanium alloy, aluminum, manganese, iron, tantalum, crystal free metals, such as Liquidmetal® alloys (available from LiquidMetal Technologies, www.liquidmetal.com), other metals that can slowly form polyvalent metal ions, for example to inhibit calcification of implanted substrates in contact with a patient's bodily fluids or tissues, and combinations thereof.

Suitable synthetic polymers include, without limitation, polyamides (e.g., nylon), polyesters, polystyrenes, polyacrylates, vinyl polymers (e.g., polyethylene, polytetrafluoroethylene, polypropylene and polyvinyl chloride), polycarbonates, polyurethanes, poly dimethyl siloxanes, cellulose acetates, polymethyl methacrylates, polyether ether ketones, ethylene vinyl acetates, polysulfones, nitrocelluloses, similar copolymers and mixtures thereof. Bioresorbable synthetic polymers can also be used such as dextran, hydroxyethyl starch, derivatives of gelatin, polyvinylpyrrolidone, polyvinyl alcohol, poly[N-(2-hydroxypropyl) methacrylamide], poly(hydroxy acids), poly(epsilon-caprolactone), polylactic acid, polyglycolic acid, poly(dimethyl glycolic acid), poly (hydroxy butyrate), and similar copolymers can also be used.

Other materials would also be appropriate, for example, the polyketone known as polyetheretherketone (PEEK™). This includes the material PEEK 450G, which is an unfilled PEEK approved for medical implantation available from Victrex of Lancashire, Great Britain. (Victrex is located at www.matweb.com or see Boedeker www.boedeker.com). Other sources of this material include Gharda located in Panoli, India (www.ghardapolymers.com).

It should be noted that the material selected can also be filled. For example, other grades of PEEK are also available and contemplated, such as 30% glass-filled or 30% carbon filled, provided such materials are cleared for use in implantable devices by the FDA, or other regulatory body. Glass filled PEEK reduces the expansion rate and increases the flexural modulus of PEEK relative to that portion which is unfilled. The resulting product is known to be ideal for improved strength, stiffness, or stability. Carbon filled PEEK is known to enhance the compressive strength and stiffness of PEEK and lower its expansion rate. Carbon filled PEEK offers wear resistance and load carrying capability.

As will be appreciated, other suitable similarly biocompatible thermoplastic or thermoplastic polycondensate materials that resist fatigue, have good memory, are flexible, and/or deflectable have very low moisture absorption, and good wear and/or abrasion resistance, can be used without departing from the scope of the invention. The implant can also be comprised of polyetherketoneketone (PEKK).

Other materials that can be used include polyetherketone (PEK), polyetherketoneetherketoneketone (PEKEKK), and polyetheretherketoneketone (PEEKK), and generally a polyaryletheretherketone. Further other polyketones can be used as well as other thermoplastics.

Reference to appropriate polymers that can be used for the implant can be made to the following documents, all of which are incorporated herein by reference. These documents include: PCT Publication WO 02/02158 A1, dated Jan. 10, 2002 and entitled Bio-Compatible Polymeric Materials; PCT Publication WO 02/00275 A1, dated Jan. 3, 2002 and entitled Bio-Compatible Polymeric Materials; and PCT Publication WO 02/00270 A1, dated Jan. 3, 2002 and entitled Bio-Compatible Polymeric Materials.

The polymers can be prepared by any of a variety of approaches including conventional polymer processing methods. Preferred approaches include, for example, injection molding, which is suitable for the production of polymer components with significant structural features, and rapid prototyping approaches, such as reaction injection molding and stereo-lithography. The substrate can be textured or made porous by either physical abrasion or chemical alteration to facilitate incorporation of the metal coating. Other processes are also appropriate, such as extrusion, injection, compression molding and/or machining techniques. Typically, the polymer is chosen for its physical and mechanical properties and is suitable for carrying and spreading the physical load between the joint surfaces.

More than one metal and/or polymer can be used in combination with each other. For example, one or more metal-containing substrates can be coated with polymers in one or more regions or, alternatively, one or more polymer-containing substrate can be coated in one or more regions with one or more metals.

The system or prosthesis can be porous or porous coated. The porous surface components can be made of various materials including metals, ceramics, and polymers. These surface components can, in turn, be secured by various means to a multitude of structural cores formed of various metals. Suitable porous coatings include, but are not limited to, metal, ceramic, polymeric (e.g., biologically neutral elastomers such as silicone rubber, polyethylene terephthalate and/or combinations thereof) or combinations thereof. See, e.g., U.S. Pat. No. 3,605,123 to Hahn, issued Sep. 20, 1971. U.S. Pat. No. 3,808,606 to Tronzo issued May 7, 1974 and U.S. Pat. No. 3,843,975 to Tronzo issued Oct. 29, 1974; U.S. Pat. No. 3,314,420 to Smith issued Apr. 18, 1967; U.S. Pat. No. 3,987,499 to Scharbach issued Oct. 26, 1976; and German Offenlegungsschrift U.S. Pat. No. 2,306,552. There can be more than one coating layer and the layers can have the same or different porosities. See, e.g., U.S. Pat. No. 3,938,198 to Kahn, et al., issued Feb. 17, 1976.

The coating can be applied by surrounding a core with powdered polymer and heating until cured to form a coating with an internal network of interconnected pores. The tortuosity of the pores (e.g., a measure of length to diameter of the paths through the pores) can be important in evaluating the probable success of such a coating in use on a prosthetic device. See, also, U.S. Pat. No. 4,213,816 to Morris issued Jul. 22, 1980. The porous coating can be applied in the form of a powder and the article as a whole subjected to an elevated temperature that bonds the powder to the substrate. Selection of suitable polymers and/or powder coatings can be determined in view of the teachings and references cited herein, for example based on the melt index of each.

B. Biological Repair Material

Repair materials can also include one or more biological material either alone or in combination with non-biological materials. For example, any base material can be designed or shaped and suitable cartilage replacement or regenerating material(s) such as fetal cartilage cells can be applied to be the base. The cells can be then be grown in conjunction with the base until the thickness (and/or curvature) of the cartilage surrounding the cartilage defect has been reached. Conditions for growing cells (e.g., chondrocytes) on various substrates in culture, ex vivo and in vivo are described, for example, in U.S. Pat. No. 5,478,739 to Slivka et al. issued Dec. 26, 1995; U.S. Pat. No. 5,842,477 to Naughton et al. issued Dec. 1, 1998; U.S. Pat. No. 6,283,980 to Vibe-Hansen et al., issued Sep. 4, 2001, and U.S. Pat. No. 6,365,405 to Salzmann et al. issued Apr. 2, 2002. Non-limiting examples of suitable substrates include plastic, tissue scaffold, a bone replacement material (e.g., a hydroxyapatite, a bioresorbable material), or any other material suitable for growing a cartilage replacement or regenerating material on it.

Biological polymers can be naturally occurring or produced in vitro by fermentation and the like. Suitable biological polymers include, without limitation, collagen, elastin, silk, keratin, gelatin, polyamino acids, cat gut sutures, polysaccharides (e.g., cellulose and starch) and mixtures thereof. Biological polymers can be bioresorbable.

Biological materials used in the methods described herein can be autografts (from the same subject); allografts (from another individual of the same species) and/or xenografts (from another species). See, also, International Patent Publications WO 02/22014 to Alexander et al. published Mar. 21, 2002 and WO 97/27885 to Lee published Aug. 7, 1997. In certain embodiments autologous materials are preferred, as they can carry a reduced risk of immunological complications to the host, including re-absorption of the materials, inflammation and/or scarring of the tissues surrounding the implant site.

In one embodiment of the invention, a probe is used to harvest tissue from a donor site and to prepare a recipient site. The donor site can be located in a xenograft, an allograft or an autograft. The probe is used to achieve a good anatomic match between the donor tissue sample and the recipient site. The probe is specifically designed to achieve a seamless or near seamless match between the donor tissue sample and the recipient site. The probe can, for example, be cylindrical. The distal end of the probe is typically sharp in order to facilitate tissue penetration. Additionally, the distal end of the probe is typically hollow in order to accept the tissue. The probe can have an edge at a defined distance from its distal end, e.g. at 1 cm distance from the distal end and the edge can be used to achieve a defined depth of tissue penetration for harvesting. The edge can be external or can be inside the hollow portion of the probe. For example, an orthopedic surgeon can take the probe and advance it with physical pressure into the cartilage, the subchondral bone and the underlying marrow in the case of a joint such as a knee joint. The surgeon can advance the probe until the external or internal edge reaches the cartilage surface. At that point, the edge will prevent further tissue penetration thereby achieving a constant and reproducible tissue penetration. The distal end of the probe can include one or more blades, saw-like structures, or tissue cutting mechanism. For example, the distal end of the probe can include an iris-like mechanism consisting of several small blades. The blade or blades can be moved using a manual, motorized or electrical mechanism thereby cutting through the tissue and separating the tissue sample from the underlying tissue. Typically, this will be repeated in the donor and the recipient. In the case of an iris-shaped blade mechanism, the individual blades can be moved so as to close the iris thereby separating the tissue sample from the donor site.

In another embodiment of the invention, a laser device or a radiofrequency device can be integrated inside the distal end of the probe. The laser device or the radiofrequency device can be used to cut through the tissue and to separate the tissue sample from the underlying tissue.

In one embodiment of the invention, the same probe can be used in the donor and in the recipient. In another embodiment, similarly shaped probes of slightly different physical dimensions can be used. For example, the probe used in the recipient can be slightly smaller than that used in the donor thereby achieving a tight fit between the tissue sample or tissue transplant and the recipient site. The probe used in the recipient can also be slightly shorter than that used in the donor thereby correcting for any tissue lost during the separation or cutting of the tissue sample from the underlying tissue in the donor material.

Any biological repair material can be sterilized to inactivate biological contaminants such as bacteria, viruses, yeasts, molds, mycoplasmas and parasites. Sterilization can be performed using any suitable technique, for example radiation, such as gamma radiation.

Any of the biological materials described herein can be harvested with use of a robotic device. The robotic device can use information from an electronic image for tissue harvesting.

In certain embodiments, the cartilage replacement material has a particular biochemical composition. For instance, the biochemical composition of the cartilage surrounding a defect can be assessed by taking tissue samples and chemical analysis or by imaging techniques. For example, WO 02/22014 to Alexander describes the use of gadolinium for imaging of articular cartilage to monitor glycosaminoglycan content within the cartilage. The cartilage replacement or regenerating material can then be made or cultured in a manner, to achieve a biochemical composition similar to that of the cartilage surrounding the implantation site. The culture conditions used to achieve the desired biochemical compositions can include, for example, varying concentrations. Biochemical composition of the cartilage replacement or regenerating material can, for example, be influenced by controlling concentrations and exposure times of certain nutrients and growth factors.

III. Devices Design
A. Cartilage Models

Using information on thickness and curvature of the cartilage, a physical model of the surfaces of the articular cartilage and of the underlying bone can be created. This physical model can be representative of a limited area within the joint or it can encompass the entire joint. For example, in the knee joint, the physical model can encompass only the medial or lateral femoral condyle, both femoral condyles and the notch region, the medial tibial plateau, the lateral tibial plateau, the entire tibial plateau, the medial patella, the lateral patella, the entire patella or the entire joint. The location of a diseased area of cartilage can be determined, for example using a 3D coordinate system or a 3D Euclidian distance as described in WO 02/22014.

In this way, the size of the defect to be repaired can be determined. As will be apparent, some, but not all, defects will include less than the entire cartilage. Thus, in one embodiment of the invention, the thickness of the normal or only mildly diseased cartilage surrounding one or more cartilage defects is measured. This thickness measurement can be obtained at a single point or, preferably, at multiple points, for example 2 point, 4-6 points, 7-10 points, more than 10 points or over the length of the entire remaining cartilage. Furthermore, once the size of the defect is determined, an appropriate therapy (e.g., articular repair system) can be selected such that as much as possible of the healthy, surrounding tissue is preserved.

In other embodiments, the curvature of the articular surface can be measured to design and/or shape the repair material. Further, both the thickness of the remaining cartilage and the curvature of the articular surface can be measured to design and/or shape the repair material. Alternatively, the curvature of the subchondral bone can be measured and the resultant measurement(s) can be used to either select or shape a cartilage replacement material. For example, the contour of the subchondral bone can be used to re-create a virtual cartilage surface: the margins of an area of diseased cartilage can be identified. The subchondral bone shape in the diseased areas can be measured. A virtual contour can then be created by copying the subchondral bone surface into the cartilage surface, whereby the copy of the subchondral bone surface connects the margins of the area of diseased cartilage.

Figure 7A:
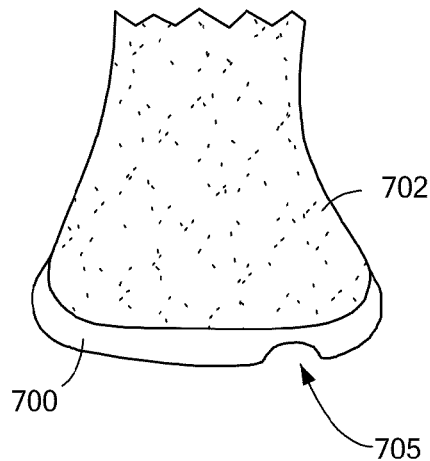
FIGS. 7A-H illustrate, in cross-section, various stages of knee resurfacing, in accordance with various embodiments of the invention.
Figure 7B:
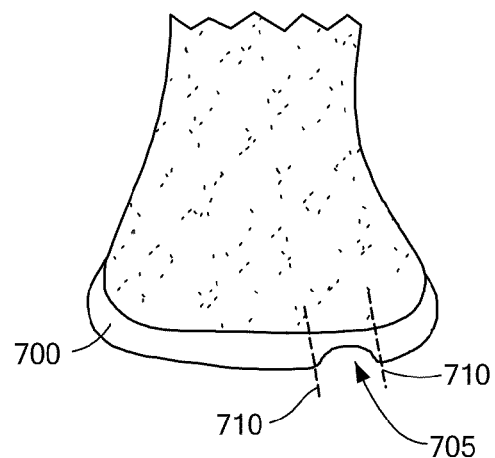
Figure 7C:
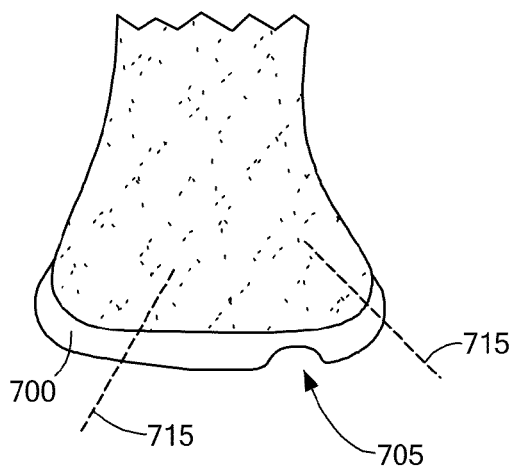

Turning now to FIGS. 7A-H, various stages of knee resurfacing steps are shown. FIG. 7A illustrates an example of normal thickness cartilage 700 in the anterior, central and posterior portion of a femoral condyle 702 with a cartilage defect 705 in the posterior portion of the femoral condyle. FIG. 7B shows the detection of a sudden change in thickness indicating the margins of a cartilage defect 710 that would be observed using the imaging techniques or the mechanical, optical, laser or ultrasound techniques described above. FIG. 7C shows the margins of a weight-bearing surface 715 mapped onto the articular cartilage 700. Cartilage defect 705 is located within the weight-bearing surface 715.

Figure 7D:
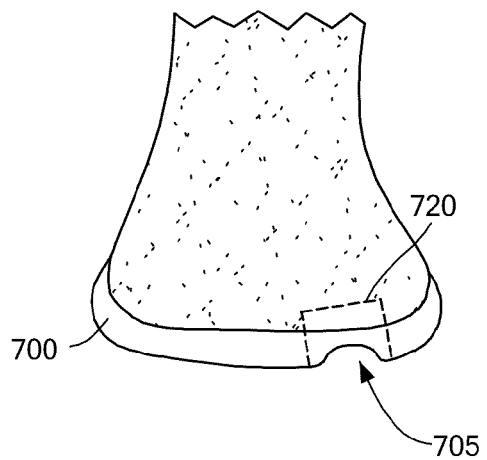
Figure 7E:
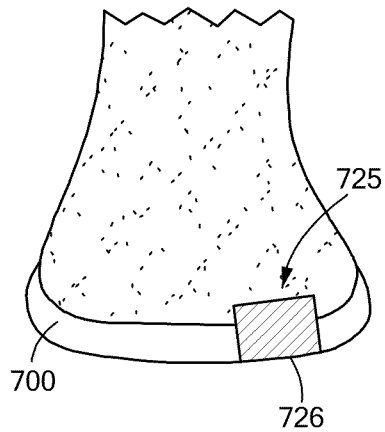

FIG. 7D shows an intended implantation site (stippled line) 720 and cartilage defect 705. In this depiction, the implantation site 720 is slightly larger than the area of diseased cartilage 705. FIG. 7E depicts placement of a single component articular surface repair system 725. The external surface of the articular surface repair system 726 has a curvature that seamlessly extends from the surrounding cartilage 700 resulting in good postoperative alignment between the surrounding normal cartilage 700 and the articular surface repair system 725.

Figure 7F:
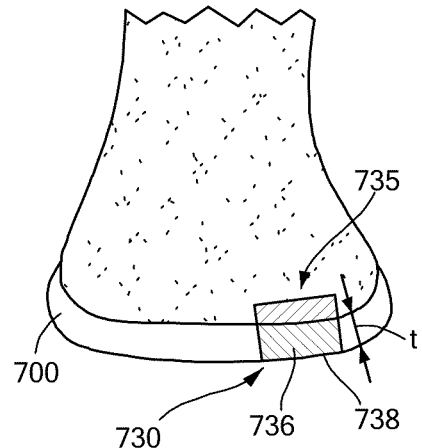

FIG. 7F shows an exemplary multi-component articular surface repair system 730. The distal surface 733 of the second component 732 has a curvature that extends from that of the adjacent subchondral bone 735. The first component 736 has a thickness t and surface curvature 738 that extends from the surrounding normal cartilage 700. In this embodiment, the second component 732 could be formed from a material with a Shore or Rockwell hardness that is greater than the material forming the first component 736, if desired. Thus it is contemplated that the second component 732 having at least portion of the component in communication with the bone of the joint is harder than the first component 736 which extends from the typically naturally softer cartilage material. Other configurations, of course, are possible without departing from the scope of the invention.

By providing a softer first component 736 and a firmer second component 732, the overall implant can be configured so that its relative hardness is analogous to that of the bone-cartilage or bone-meniscus area that it abuts. Thus, the softer material first component 736, being formed of a softer material, could perform the cushioning function of the nearby meniscus or cartilage.

Figure 7G:
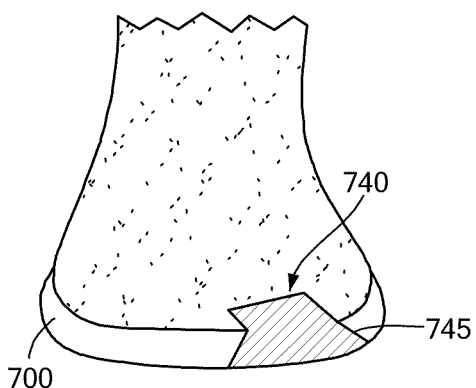
Figure 7H:
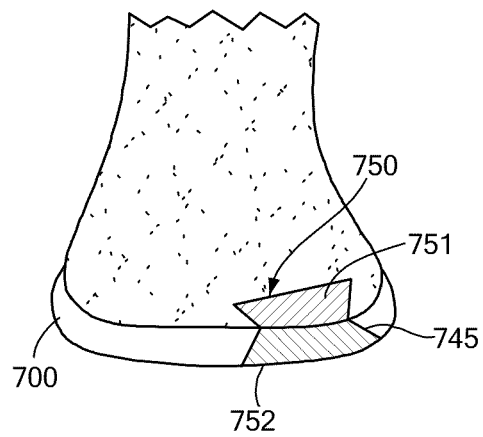

FIG. 7G shows another single component articular surface repair system 740 with a peripheral margin 745 which is configured so that it is substantially non-perpendicular to the surrounding or adjacent normal cartilage 700. FIG. 7H shows a multi-component articular surface repair system 750 with a first component 751 and a second component 752 similar to that shown in FIG. 7G with a peripheral margin 745 of the second component 745 substantially non-perpendicular to the surrounding or adjacent normal cartilage 700.

Figure 8A:
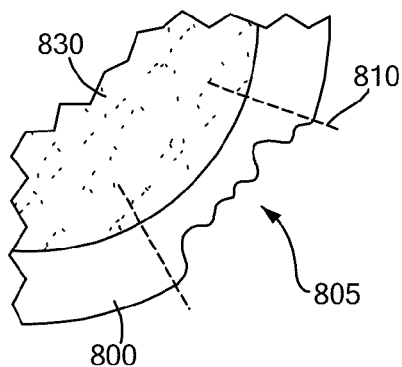
FIGS. 8A-E, illustrate, in cross-section, exemplary knee imaging and resurfacing, in accordance with various embodiments of the invention.
Figure 8B:
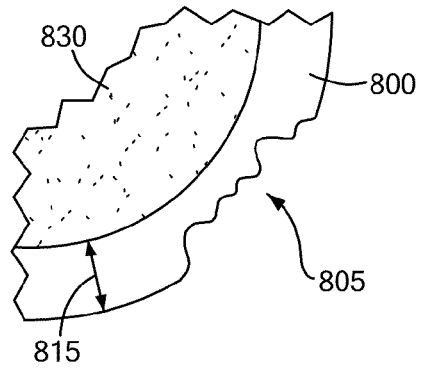
Figure 8C:
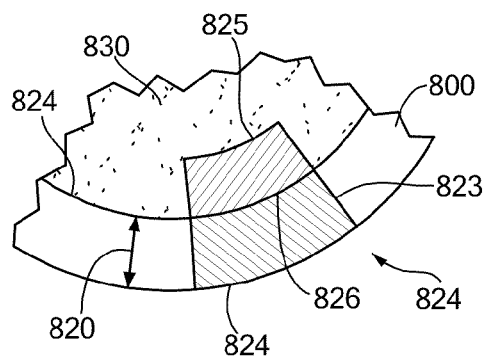

Now turning to FIGS. 8A-E, these figures depict exemplary knee imaging and resurfacing processes. FIG. 8A depicts a magnified view of an area of diseased cartilage 805 demonstrating decreased cartilage thickness when compared to the surrounding normal cartilage 800. The margins 810 of the defect have been determined. FIG. 8B depicts the measurement of cartilage thickness 815 adjacent to the defect 805. FIG. 8C depicts the placement of a multi-component mini-prosthesis 824 for articular resurfacing. The thickness 820 of the first component 823 closely approximates that of the adjacent normal cartilage 800. The thickness can vary in different regions of the prosthesis. The curvature of the distal portion 824 of the first component 823 closely approximates an extension of the normal cartilage 800 surrounding the defect. The curvature of the distal portion 826 of the second component 825 is a projection of the surface 827 of the adjacent subchondral bone 830 and can have a curvature that is the same, or substantially similar, to all or part of the surrounding subchondral bone.

Figure 8D:
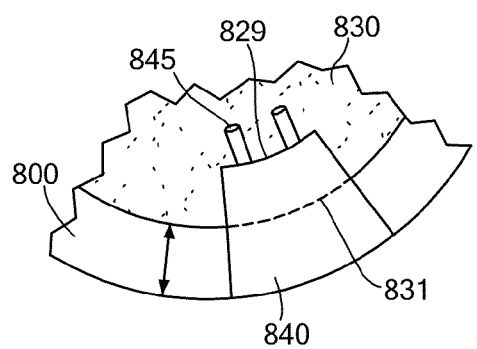

FIG. 8D is a schematic depicting placement of a single component mini-prosthesis 840 utilizing anchoring stems 845. As will be appreciated by those of skill in the art, a variety of configurations, including stems, posts, and nubs can be employed. Additionally, the component is depicted such that its internal surface 829 is located within the subchondral bone 830. In an alternative construction, the interior surface 829 conforms to the surface of the subchondral bone 831.

Figure 8E:
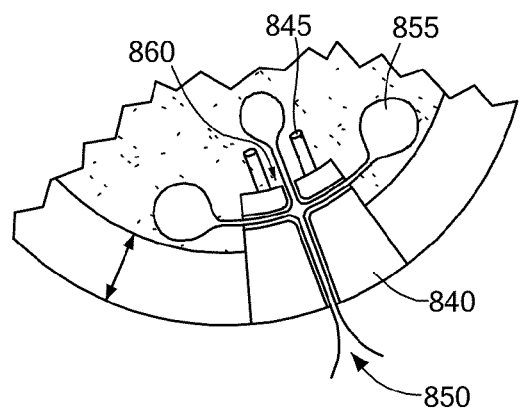

FIG. 8E depicts placement of a single component mini-prosthesis 840 utilizing anchoring stems 845 and an opening at the external surface 850 for injection of bone cement 855 or other suitable material. The injection material 855 can freely extravasate into the adjacent bone and marrow space from several openings at the undersurface of the mini-prosthesis 860 thereby anchoring the mini-prosthesis.

Figure 9A:
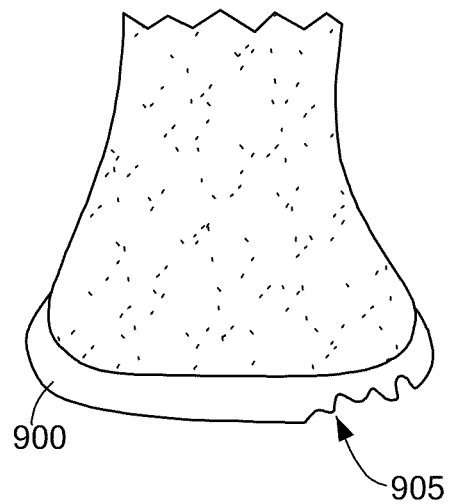
FIGS. 9A-C, illustrate, in cross-section, other exemplary knee resurfacing devices and methods, in accordance with various embodiments of the invention.
Figure 9B:
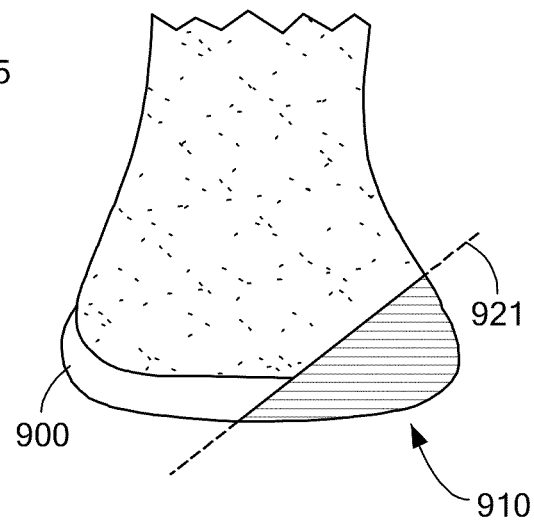
Figure 9C:
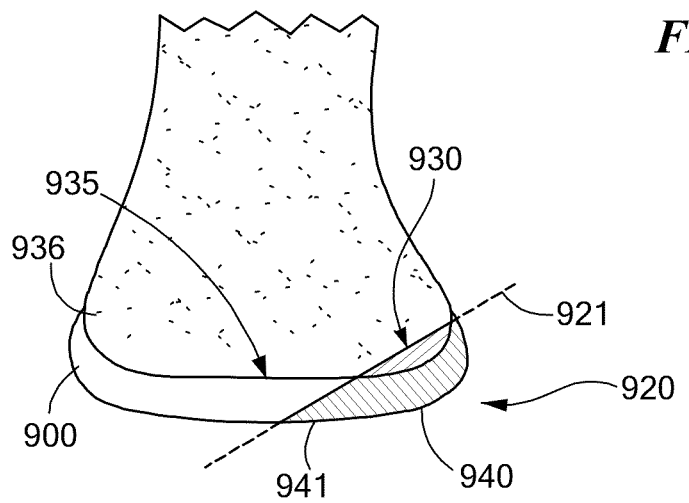

FIGS. 9A-C, depict an alternative knee resurfacing device. FIG. 9A depicts a normal thickness cartilage in the anterior, central and posterior portion of a femoral condyle 900 and a large area of diseased cartilage 905 toward the posterior portion of the femoral condyle. FIG. 9B depicts placement of a single component articular surface repair system 910. Again, the implantation site has been prepared with a single cut 921, as illustrated. However, as will be appreciated by those of skill in the art, the repair system can be perpendicular to the adjacent normal cartilage 900 without departing from the scope of the invention. The articular surface repair system is not perpendicular to the adjacent normal cartilage 900. FIG. 9C depicts a multi-component articular surface repair system 920. Again, the implantation site has been prepared with a single cut (cut line shown as 921). The second component 930 has a curvature similar to the extended surface 930 adjacent subchondral bone 935. The first component 940 has a curvature that extends from the adjacent cartilage 900.

B. Device Modeling In Situ

Figure 10A:
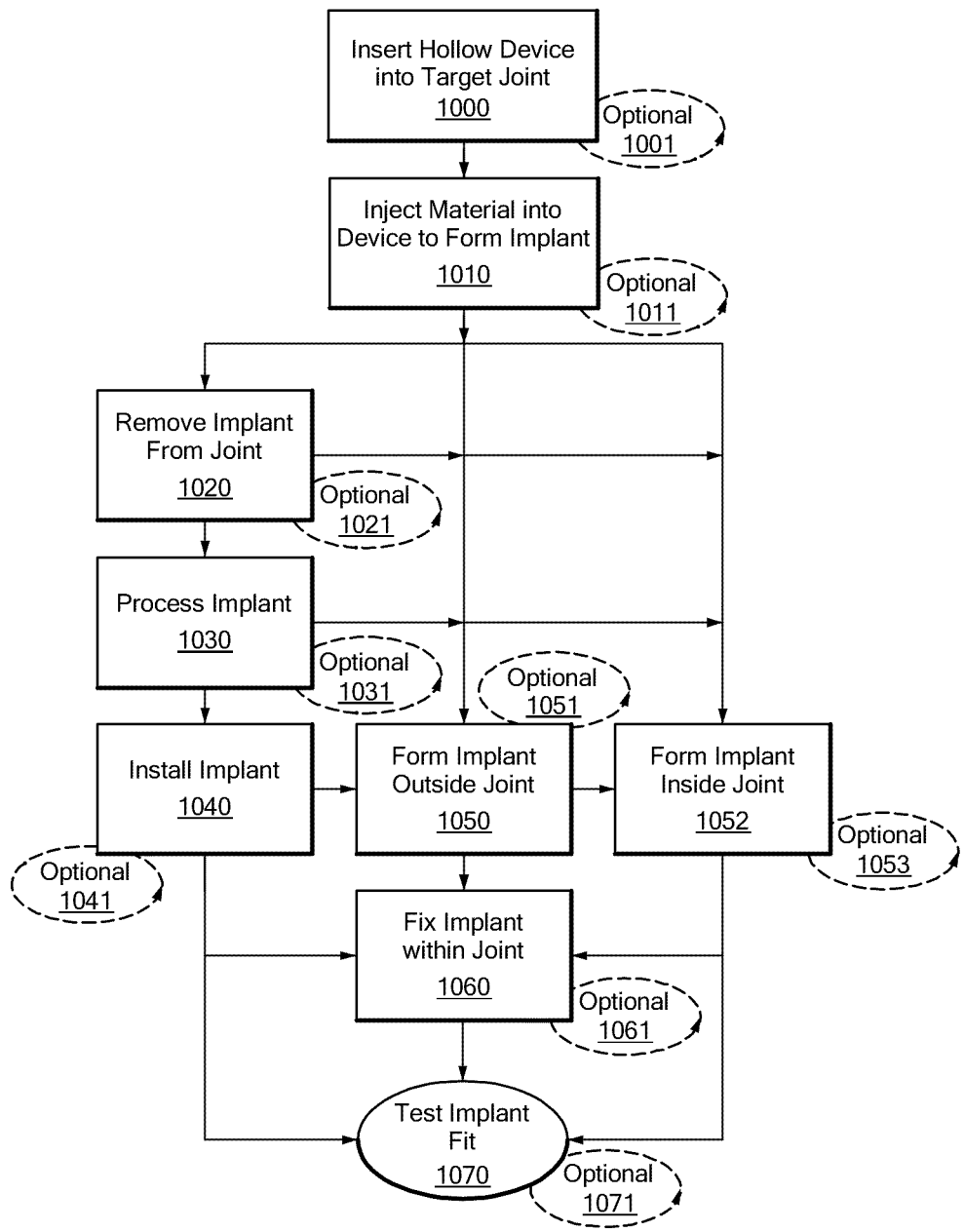
FIGS. 10A-B are flow charts illustrating steps for forming a device in situ, in accordance with various embodiments of the invention.
Figure 10B:
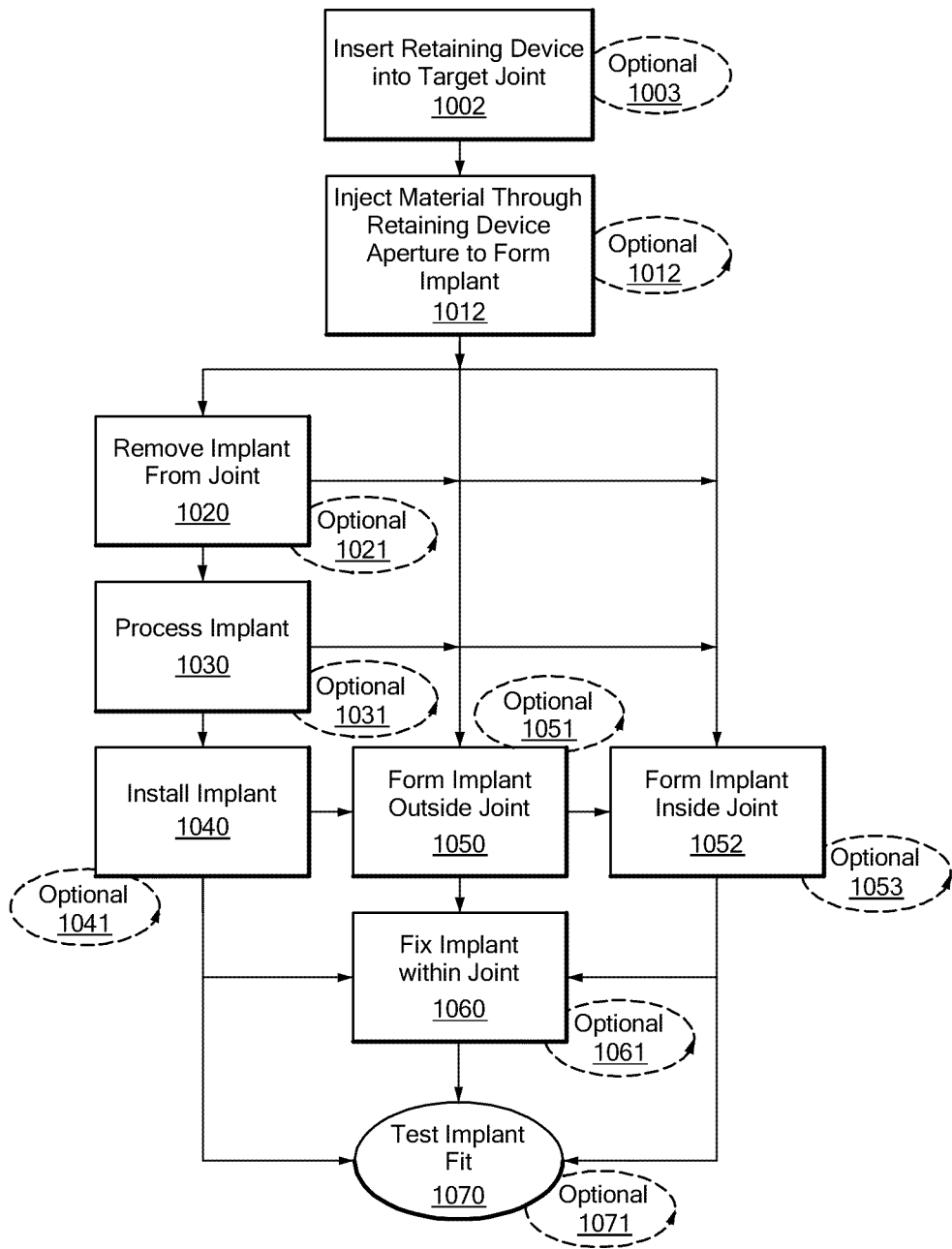

Another approach to repairing a defect is to model defect repair system in situ, as shown in FIGS. 10A-B. As shown in FIG. 10A, one approach would be to insert a hollow device, such as a balloon, into the target joint 1000. Any device capable of accepting, for example, injections of material would be suitable. Suitable injection materials include, for example, polymers and other materials discussed in Section II, above, can be used without departing from the scope of the invention.

In one embodiment it is contemplated that an insertion device has a substantially fixed shape that matches at least one articular surface or subchondral bone of the joint. After inserting the insertion device 1000, material is injected into the joint through the insertion device 1010 where it then hardens in situ, forming an implant 1052. The injection material can optionally bond to the device while hardening.

Alternatively, the implant can be removed after hardening 1020 for further processing 1030, such as polishing, e.g. as described Section IV.

Where the implant is removable after hardening in situ, it can be preferable to have the implant be formed so that it is collapsible, foldable or generally changeable in shape to facilitate removal. After processing, the implant can be reinstalled 1040.

One or more molds can be applied to one or more articular surfaces. The mold can have an internal surface facing the articular surface that substantially conforms to the shape of the articular cartilage and/or the shape of the subchondral bone. A hardening material including a polymer or metals can then be injected through an opening in the mold. The opening can include a membrane that allows insertion of an injection device such as a needle. The membrane helps to avoid reflux of the injected material into the joint cavity. Alternatively, the mold can be made of a material that provides sufficient structural rigidity to allow hardening of the injected substance with the proper shape while allowing for placement of needles and other devices through the mold.

Additionally, the implant device can be composed of a plurality of subcomponents, where the volume or size of each of the subcomponents is smaller than the volume of the implant. The different subcomponents can be connected or assembled prior to insertion into the joint 1050 (whether outside the body or adjacent the joint but within or substantially within the body), or, in some instances, can be assembled after insertion to the joint 1052. The subcomponents can be disassembled inside the joint, or adjacent the joint, once hardening of the injectable material has occurred.

Additionally, the implant can be fixed to the surface of the bone after implantation 1060 For example, fixation mechanisms can include mechanical structures such as fins, keels, teeth and pegs or non-mechanical means, such as bone cement, etc. Typically after the device is implanted and/or fixed within the joint, the functionality of the implant is tested 1070 to determine whether it enables the joint to engage in a desired range of motion. As will be appreciated by those of skill in the art, one or more of these steps can be repeated without departing from the scope of the invention, as shown by the optional repeat steps 1001, 1011, 1021, 1031, 1041, 1051, 1053, 1061 and 1071.

As shown in FIG. 10B, another approach would be to insert a retaining device into the target joint 1002. Any device capable of accepting, for example, injections of material would be suitable. Suitable materials include, for example, polymers and other materials discussed in Section II, above, can be used without departing from the scope of the invention.

In one embodiment it is contemplated that an insertion device has a substantially fixed shape that matches at least one articular surface or subchondral bone of the joint. After inserting the retaining device 1002, material is injected into a hollow area formed between the retaining device and the joint surface through an aperture 1012 where it then hardens in situ, forming an implant 1052. The injection material can optionally bond to the device while hardening.

Alternatively, the implant can be removed after hardening 1020 for further processing 1030, such as polishing, e.g. as described Section IV.

Where the implant is removable after hardening in situ, it can be preferable to have the implant be formed so that it is collapsible, foldable or generally changeable in shape to facilitate removal. After processing, the implant can be reinstalled 1040.

Additionally, the implant device can be composed of a plurality of subcomponents, where the volume or size of each of the subcomponents is smaller than the volume of the implant. The different subcomponents can be connected or assembled prior to insertion into the joint 1050 (whether outside the body or adjacent the joint but within or substantially within the body), or, in some instances, can be assembled after insertion to the joint 1052. The subcomponents can be disassembled inside the joint, or adjacent the joint, once hardening of the injectable material has occurred.

Additionally, the implant can be fixed to the surface of the bone after implantation 1060 For example, fixation mechanisms can include mechanical structures such as fins, keels, teeth and pegs or non-mechanical means, such as bone cement, etc. Typically after the device is implanted and/or fixed within the joint, the functionality of the implant is tested 1070 to determine whether it enables the joint to engage in a desired range of motion. As will be appreciated by those of skill in the art, one or more of these steps can be repeated without departing from the scope of the invention, as shown by the optional repeat steps 1003, 1013, 1021, 1031, 1041, 1051, 1053, 1061 and 1071.

Prior to performing the method shown in FIG. 10B, one or more holes or apertures can be drilled into the surface of the bone at an angle either perpendicular to the bone surface or set at an angle. Upon injecting material underneath the retaining device, the material embeds within the holes and form pegs upon hardening.

In one contemplated embodiment, at least a portion of the implantation device remains in situ after hardening of the injection material. In this scenario, the implantation device can be formed from a bio-resorbable material. In this instance, the container forming the implantation device can be resorbed, typically some time after hardening of the injection material.

The shape of the implantation device can be fixed. Where the shape is fixed, an imaging test or intraoperative measurement can be used to either shape or select the best fitting device for a particular patient, for example, using the imaging techniques and intraoperative measurement techniques described in SECTIONS IA-B, above.

In other embodiments, portions of the device can be rigid, or substantially rigid, while other portions of the device are deformable or malleable. Alternatively, a portion of the device can be relatively more rigid than another portion, without any requirement that any section be rigid, deformable or malleable, but that sections vary in hardness relative to another section. In this manner the shape of the rigid, substantially rigid, or relatively more rigid section can be determined, for example, using an imaging test. In contrast, it is possible that the malleable, deformable, or relatively more deformable portion of the implantation device can then take the shape of one or more articular surface in situ. This occurs particularly after the implantation material has been injected and while the material is hardening in situ. In still other embodiments, the entire device can be deformable.

In other embodiments, the implantation device can be expandable or collapsible. For example, a support structure such as a Nitinol™ mesh can be inserted into the joint. Insertion can occur via, for example, a catheter or an arthroscopy portal. Once inside the joint, the implantation device can then be expanded. The implantation device can include a receptacle, such as a bag, to receive the injection of hardening material, such as polyethylene or other liquid including metal preparations. The receptacle portion of the implantation device can be bio-resorbable and/or can bond with the injected material. Alternatively, the implantation device can be removed subsequent to injecting the material. Where a supporting material is used, the supporting material can be removed concurrently or subsequent to the removal of the implantation device, either via an incision or by collapsing the implantation device and removing it via, for example, the catheter or arthroscopy portal.

In another embodiment, a balloon such as that shown in FIGS. 11A-E, can be used as the implantation device. Different balloon shapes and sizes can be made available. A detailed description of all possible shapes and sizes for the balloons is not included to avoid obscuring the invention, but would be apparent to those of skill in the art. Where a balloon is used, it can be inserted into a joint and inflated. The size, height, shape and position of the balloon can be evaluated arthroscopically or via an open incision or using, for example, an imaging test relative to the articular surface and the other articular strictures. Range of motion testing can be performed in order to ensure adequate size, shape and position of the device during the full range of motion.

After insertion, the balloon can be slowly injected with, for example, a self-hardening material, or material that hardens upon activation. Suitable materials are described below and would be apparent to those of skill in the art. Typically, upon injection, the material is in a fluid or semi-fluid state. The material expands the balloon as it is injected which results in the balloon taking on the shape of the articular surface, for example as shown in FIG. 11A, and other articular structures such that it fills the defect.

The balloon can be slowly injected with a self hardening or hardening material such as a polymer and even metals. The material is initially in a fluid or semi-fluid state. The material expands the balloon whereby the shape of the balloon will take substantially the shape of the articular surface(s) and other articular structures. The polymer will subsequently harden inside the balloon thereby substantially taking the shape of the articular cavity and articular surface(s)/structures. The balloon can also be composed of a bio-resorbable material. The balloon can also be removed after the procedure.

Comparing, for example, the embodiments illustrated in FIGS. 11A-C, FIG. 11A illustrates a single balloon 1100 inserted between two joint surfaces 1102, 1104 of a joint 1110. In this figure, the joint surfaces are illustrated with associated cartilage 1106, 1108. The proximal end 1112 of the balloon is configured to communicate with a device that enables the balloon to be inflated, e.g. by filling the balloon 1100 with a substance. Substances include, but are not limited to, air, polymers, crystal free metals, or any other suitable material, such as those discussed in Section II above. The balloon 1100 of FIG. 11A is configured such that the distal end of the balloon 1114 does not extend beyond distal end of the joint 1120 (where the distal end of the joint is defined relative to the area of the joint where the balloon entered the joint).

FIG. 11B illustrates an alternative balloon 1130 wherein the distal end 1114 of the balloon 1130 and the proximal end 1113 of the balloon 1130 extends beyond the distal 1120 and proximal 1122 end of the joint. This extension can be optimized for flexion and extension by using different balloon sizes. FIG. 11C illustrates a balloon 1140 wherein the balloon 1140 is configured such that the distal end 1114 of the balloon 1140 extends beyond the distal 1120 of the joint while the proximal end 1114 of the balloon 1140 does not extend beyond the end of the joint. As will be appreciated by those of skill in the art, other permutations are possible without departing from the scope of the invention.

Additionally, a sharp instrument such as a scalpel can be inserted into the balloon or adjacent to the balloon and the balloon can be cut or slit. The balloon can then be pulled back from the hardened material and removed from the joint, preferably through a catheter or an arthroscopy portal.

More than one balloon can be used as illustrated in FIGS. 11D-G. Where a plurality of balloons used, the balloons can be configured such that the balloons are inserted side-by-side as shown by 1150, 1152 in FIG. 11D, inserted in different compartments as shown by 1154, 1156 in FIG. 11E, one or more balloons are encompassed within the lumen of another balloon, as shown by 1160, 1162 and 1170, 1172, 1174 in FIGS. 11F-G, in a top-bottom relationship, and/or combinations thereof.

Each balloon can have the same or different wall thickness or can be composed of the same or different materials. As a result of differences in material, a person of skill in the art will appreciate that the amount of pressure required to expand each of the balloons can vary either uniformly or in a non-uniform fashion. These pressures would be known to a person of skill in the art and are not discussed at length herein to avoid obscuring the invention.

For example, in one scenario the superior and inferior surface of a first, inner balloon, can have a low inflation pressure relative to a second balloon. Thus, as the material is injected, the pressure created inside the lumen of the balloon is directly transmitted to one or more articular surface. In this manner, the distance between the two articular surfaces can be controlled and a minimum distance can be obtained ensuring a sufficient thickness of the resultant implant. This embodiment can be useful in areas within or bordering the contact zone of the articular surface.

A second outer or peripheral balloon can be provided that requires a higher inflation pressure relative to the first balloon. The inner, low inflation pressure balloon can be placed in the weight-bearing zone. The same balloon can also have different wall properties in different regions of the balloon, e.g. a rigid wall with high inflation pressures in the periphery and a less rigid wall with intermediate or low inflation pressures in the center.

Alternatively, a first balloon, having a low inflation pressure relative to a second balloon is provided in an area bordering the contact zone of the articular surface. Again, as material is injected, the pressure created inside the lumen of the balloon is directly transmitted to one or more articular surface. In this manner, the distance between the two articular surfaces can be controlled and a minimum distance can be obtained ensuring a sufficient thickness of the resultant implant.

A second balloon can be provided at an area where there is relatively more weight bearing. This balloon can be configured to require a higher inflation pressure relative to the first balloon.

Differences in wall thickness, pressure tolerances and expandability of balloons can also be used to influence the resulting shape of the injected material.

Figure 12A:
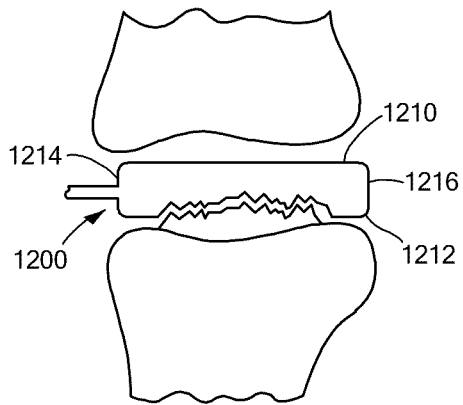
FIGS. 12A-E illustrate a variety of cross-sectional shapes achieved using balloons with variable wall thicknesses or material compositions, in accordance with various embodiments of the invention.

The results of using inflation devices, or balloons, with differing wall thicknesses or pressure tolerances is shown in FIGS. 12A-F. As shown in FIG. 12A the balloon 1200 has an upper surface 1210 and a lower surface 1212 along with a proximal end 1214 and a distal end 1216. The relative pressure tolerance of the balloon or inflation device 1200 is lower on the lower surface 1212 than the upper surface 1210. As a result, the upper surface of the balloon 1210 has a relatively flat configuration relative to its corresponding joint surface while the lower surface 1212 has a relatively conforming shape relative to its corresponding joint surface.

Figure 12B:
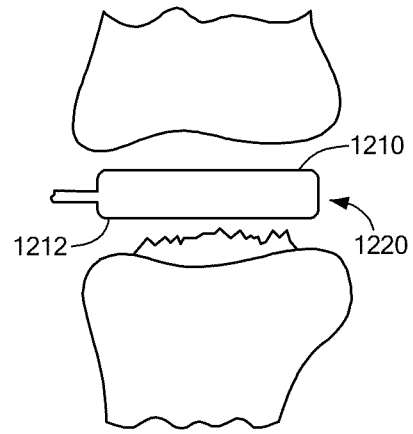

Turning now to FIG. 12B, the inflation device used 1220 has a relatively constant pressure tolerance that is relatively high which results in both the upper surface 1210 and the lower surface 1212 having relatively flat configurations relative to each of its corresponding joint surfaces, regardless of the joint surface anatomy.

Figure 12C:
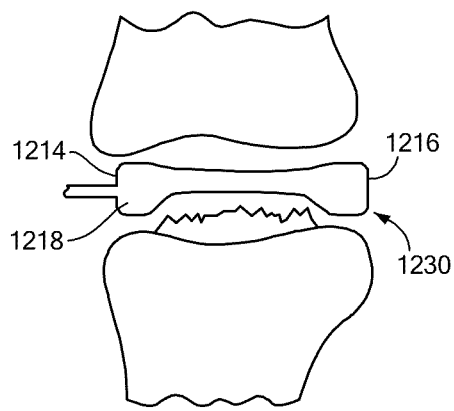

FIG. 12C illustrates a balloon 1230 having a low inflation pressure at its proximal 1214 and distal 1216 ends, with a higher inflation pressure at a central region 1218. The result of this configuration is that when the balloon is inflated, the proximal and distal ends inflate to a greater profile (e.g., height) than the central region. The inflation pressure of the central region, although higher than the proximal and distal ends, can be set such that the central region has a relatively flat configuration relative to the corresponding joint surfaces, as shown, or can be configured to achieve the result shown in FIG. 12A.

As will be appreciated by those of skill in the art, any of these balloons can be configured to have varying properties resulting in portions of the wall being less rigid than other portions, within the same balloon, e.g. a rigid wall with high inflation pressures in the periphery and a less rigid wall with intermediate or low inflation pressures in the center. Where there is more than one thickness to the balloon, it could, for example, have less stiffness anteriorly; greater stiffness centrally, and less stiffness posteriorly. The wall thickness variability will enable the device to accommodate shape formation. Central thickness will help prevent the device from fully conforming to the irregular surface of the joint, which may be important where there are irregularities to the joint surface, such as bone spurs. Alternatively, if the central portion is of less stiffness than the anterior and posterior sections, the device would be configured to conform more closely to the shape of the joint surface, including any irregularities. The closer the device conforms to the joint shape, the more the device seats within the joint.

Optionally, the surgeon can elect to remove surface irregularities, including bone spurs. This can be done using known techniques such as arthroscopy or open arthrotomy.

Where more than one balloon is used, the different balloons can have different shapes and sizes. Shape and size can be adjusted or selected for a given patient and joint. In addition to size and shape differences of the balloons, each of the balloons can also be configured to have different and/or varying wall thicknesses. For example, one balloon could be configured with a central portion that is less stiff than the anterior and posterior sections while a second balloon could be configured so that the central portion is of greater stiffness than the anterior and posterior section.

Figure 12D:
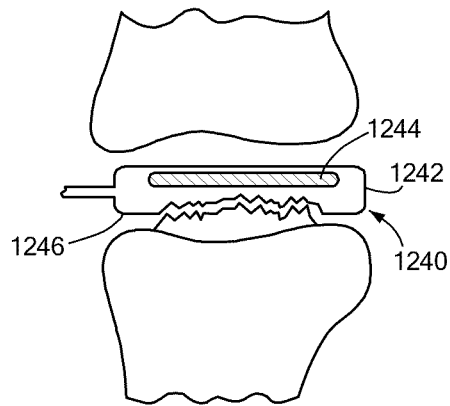
Figure 12E:
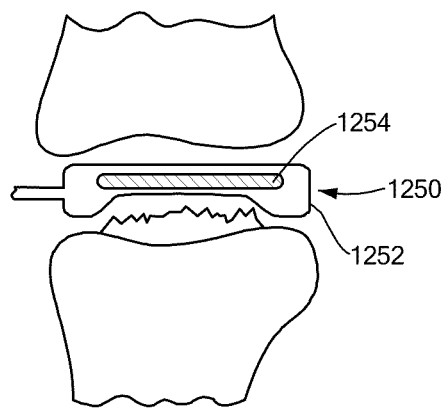

FIGS. 12D-E illustrate configurations using two balloons. As shown in FIG. 12D the first balloon 1244 sits within a second balloon 1242 to form an inflation device 1240. In this embodiment, the inferior surface 1246 of the external second balloon 1242 is configured with an inflation pressure that enables at least one surface of the device to conform, or substantially conform, to the corresponding joint surface.

FIG. 12E also illustrates a two balloon configuration 1250 with a first balloon 1254 and a second balloon 1252. In this embodiment, the inflation pressure of the device is configured such that the surface does not substantially conform to the corresponding joint surface.

FIGS. 13A-J(1-3) illustrate a variety of cross-sections possible for the embodiments shown in FIGS. 11-12. These embodiments illustrate possible profiles achieved with a single balloon (FIGS. 13A(1-3)); a dual balloon embodiment wherein one balloon fits within a second balloon in approximately a central position (FIG. 13B(1-3)) or in an off-centered position within a second balloon (FIGS. 13D(1-3)); a tri-balloon set-up where two balloons fit within a first balloon (FIGS. 13C(1-3)), three balloons are positioned next to each other (FIGS. 13 H(1-3)), or two balloons are adjacent each other while one balloon has another balloon within its lumen (FIGS. 13E(2-3), F(2), G(2)); a four balloon set-up where two balloons are adjacent each other and each one has a balloon within its lumen (FIG. 13G(3)) or three balloons are adjacent each other with at least one of the three balloons having another balloon within its lumen (FIGS. 13I(2-3)), or a five balloon set up where three balloons are positioned adjacent each other and two of the three balloons have balloons within its lumen (FIG. 13J(1)). As will be appreciated by those of skill in the art, other combinations and profiles are achievable using the teachings of the invention without departing from the scope of the invention. All possible combinations have not been illustrated in order to avoid obscuring the invention.

In another embodiment, a probe can be inserted into the balloon or the device. The probe can be utilized for measuring the device thickness (e.g. minima and maxima). In this and other embodiments, the balloon can be initially injected with a test material that is typically not hardening. Once inside the balloon or the device, the thickness of the device or the balloon can be measured, e.g. for a given inflation pressure. In this manner, a sufficient minimum implant thickness can be ensured. Probes to measure the thickness of the device or the balloon include, but are not limited to ultrasound, including A-, B- or C-scan.

Figure 14A:
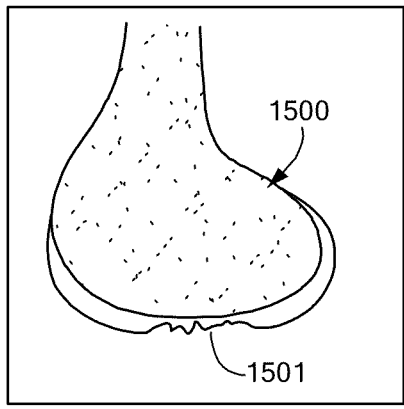
Figure 14D:
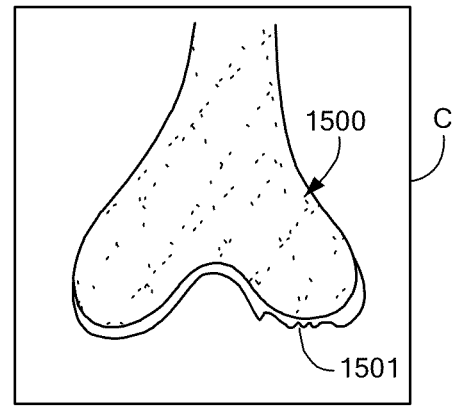
Figure 14B:
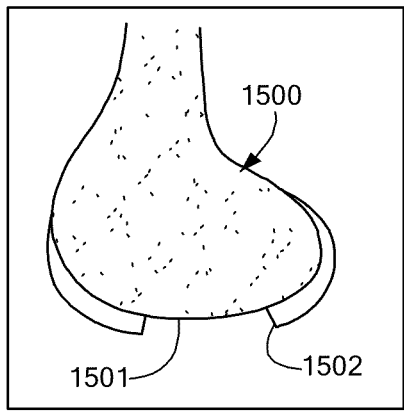
Figure 14E:
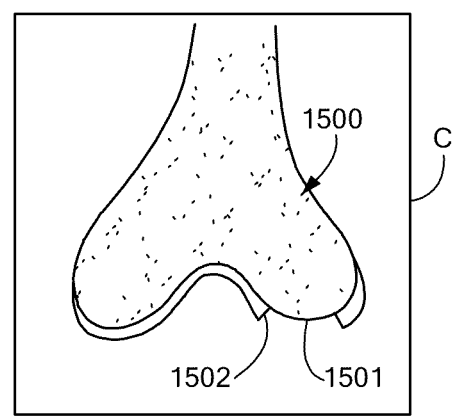
Figure 14C:
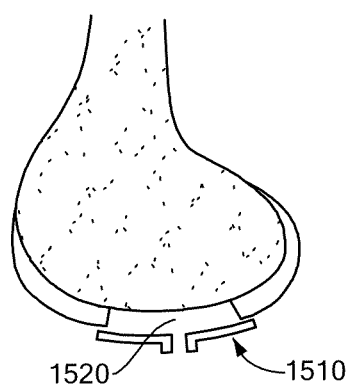
Figure 14F:
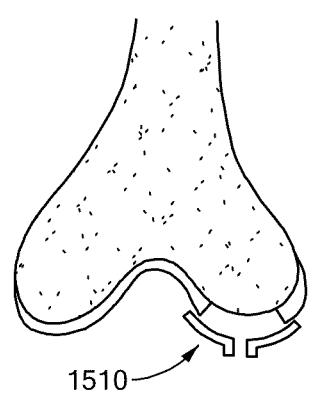

Turning now to FIGS. 14A-J which illustrate the cartilage repair system described in FIG. 10B utilizing the retaining device. FIGS. 14A and D illustrate a cartilage defect 1501 on an articular surface 1500 in the sagittal plane S and the coronal plane C. The surgeon debrides the defect thereby optionally creating smooth margins 1502.

A retaining device 1510 is applied to the defect 1501 to define a cavity 1520. A hardening material can be injected into an aperture 1512 in the retaining device 1510. Suitable materials include, but are not limited to, a polymer or a crystal free metal. Additionally, as will be appreciated by those of skill in the art, the material injected can be initially in powder form with a liquid catalyst or hardening material injected thereafter.

As illustrated in FIG. 14G, the surface of the bone 1550 can be prepared, e.g. by curette or drill, so that the surface of the bone 1550 defines small teeth, holes, or anchoring members, 1552 that help anchor the resulting device to the articular surface 1550. As shown in FIGS. 14G(2) and (5) the drill holes can be drilled parallel in relation to one another, where there are more than two, and perpendicular to the surface of the subchondral bone 1552. Alternatively, the drill holes can be drilled at an angle in relationship to each other and at a angle that is not perpendicular to the subchondral bone 1553 as illustrated in FIG. 15G(3-4). As will be appreciated by those of skill in the art, one or more pegs can be created on the surface of the bone. For example FIG. 14G(2) illustrates a two peg set-up while FIG. 14G(8) illustrates a single peg scenario and FIG. 14G(4) illustrates a four peg scenario where some pegs are in parallel relationship while others are not. As shown in FIG. 14G(9), the aperture (1552 or 1553) can be formed so that the bore does not form a cylinder, but rather has channel protrusions 1572 into the bone that, when filled, form the turning channel for a screw, thus resulting in the filled aperture forming a screw that enables the anchored device to be removed by turning in a clockwise or counter-clockwise direction.

As shown in FIG. 14H, a ridge 1546, typically circumferential, can be used. The circumferential ridge can help achieve a tight seal between the detaining device and the cartilage in order to avoid spillage of the injected material in the joint cavity. Alternatively, the periphery of the mold can include a soft, compressible material that helps achieve a tight seal between the mold and the surrounding cartilage.

FIG. 14I illustrates the retaining mold with a handle placed on the surface of a bone.

As shown in FIG. 14J, the retaining device 1510 can have one or more handles 1547 attached to it. The handle can facilitate the surgeon maintaining the retaining device in position while the injected material hardens. The aperture 1512 of the retaining device accepts injections and can include a membrane 1513 as shown in FIG. 14J. The configuration assists in creating a tight seal after a needle 1560 or injection instrument used to inject the material 1570 into the cavity 1520 is removed. Additionally, or in place of the membrane 1513, a cap 1514 can be provided that seals the aperture 1512 after the material 1570 is injected. Additionally, anchoring teeth 1590 can be provided that communicate with the meniscus 1591 or cartilage surrounding a defect. The anchoring teeth 1590 help keep the device stable when placed over the defect.

As illustrated in FIG. 14G(4) more than one aperture 1512, 1512' can be provided without departing from the scope of the invention.

The retaining device system can be designed to inject an area equal to or slightly greater than the area of diseased cartilage. Alternatively, the retaining device system can be designed for the entire weight-bearing surface or the entire articular surface of a compartment. Retaining devices can be used on opposing articular surfaces, e.g. on a femoral condyle and a tibial plateau, thereby recreating a smooth gliding surface on both articular surfaces.

The retaining device can be designed to allow for light exposure including UV light. For example, the retaining device can be made using a transparent plastic. The retaining device can also be made to allow for passage of ultrasound waves.

C. Customized Containers

In another embodiment of the invention, a container or well can be formed to the selected specifications, for example to match the material needed for a particular subject or to create a stock of repair materials in a variety of sizes. The size and shape of the container can be designed using the thickness and curvature information obtained from the joint and from the cartilage defect. More specifically, the inside of the container can be shaped to follow any selected measurements, for example as obtained from the cartilage defect(s) of a particular subject. The container can be filled with a cartilage replacement or regenerating material, for example, collagen-containing materials, plastics, bioresorbable materials and/or any suitable tissue scaffold. The cartilage regenerating or replacement material can also consist of a suspension of stem cells or fetal or immature or mature cartilage cells that subsequently develop to more mature cartilage inside the container. Further, development and/or differentiation can be enhanced with use of certain tissue nutrients and growth factors.

The material is allowed to harden and/or grow inside the container until the material has the desired traits, for example, thickness, elasticity, hardness, biochemical composition, etc. Molds can be generated using any suitable technique, for example computer devices and automation, e.g. computer assisted design (CAD) and, for example, computer assisted modeling (CAM). Because the resulting material generally follows the contour of the inside of the container it will better fit the defect itself and facilitate integration.

D. Designs Encompassing Multiple Component Repair Materials

The articular repair system or implants described herein can include one or more components.

Figure 15A:
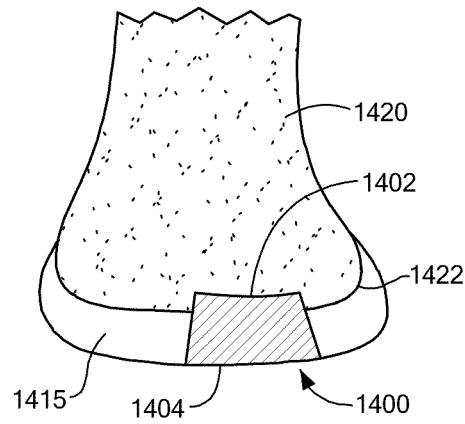
FIGS. 15A-B show single and multiple component devices, in accordance with various embodiments of the invention.
Figure 15B:
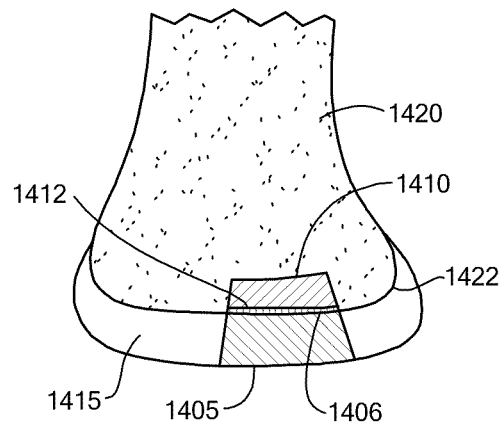

FIGS. 15A-B shows single and multiple component devices. FIG. 15A illustrates an example of a single component articular surface repair system 1400 with varying curvature and radii that fits within the subchondral bone 1420 such that the interior surface 1402 of the system 1400 does not form an extension of the surface of the subchondral bone 1422. The articular surface repair system is chosen to include convex 1402 and concave 1404 portions. Such devices can be preferable in a lateral femoral condyle or small joints such as the elbow joint. FIG. 15B depicts a multi-component articular surface repair system with a second component 1410 with a surface 1412 that forms an extension of the surface 1422 of the subchondral bone 1420 and a first component 1405 with an interior surface 1406 that forms an extension of the curvature and shape of the surrounding normal cartilage 1415. The second component 1410 and the first component 1405 demonstrate varying curvatures and radii with convex and concave portions that correspond to the curvature of the subchondral bone 1420 and/or the normal cartilage 1415. As will be appreciated by those of skill in the art, these two components can be formed such that the parts are integrally formed with each other, or can be formed such that each part abuts the other. Additionally, the relationship between the parts can be by any suitable mechanism including adhesives and mechanical means.

Figure 16A:
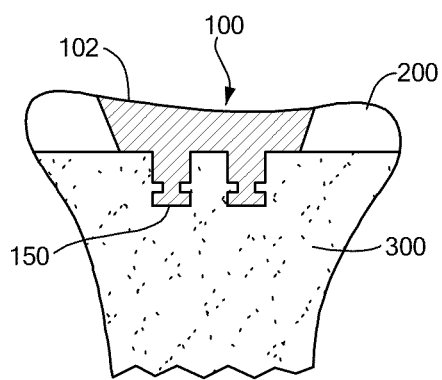
FIGS. 16A-B show exemplary articular repair systems having an outer contour matching the surrounding normal cartilage, in accordance with various embodiments of the invention. The systems are implanted into the underlying bone using one or more pegs.
Figure 16B:
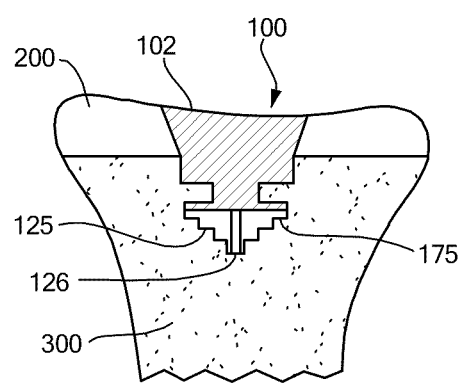

FIGS. 16A-B show articular repair systems 100 having an outer contour 102 forming an extension of the surrounding normal cartilage 200. The systems are implanted into the underlying bone 300 using one or more pegs 150, 175. The pegs, pins, or screws can be porous-coated and can have flanges 125 as shown in FIG. 15B.

Figure 17:
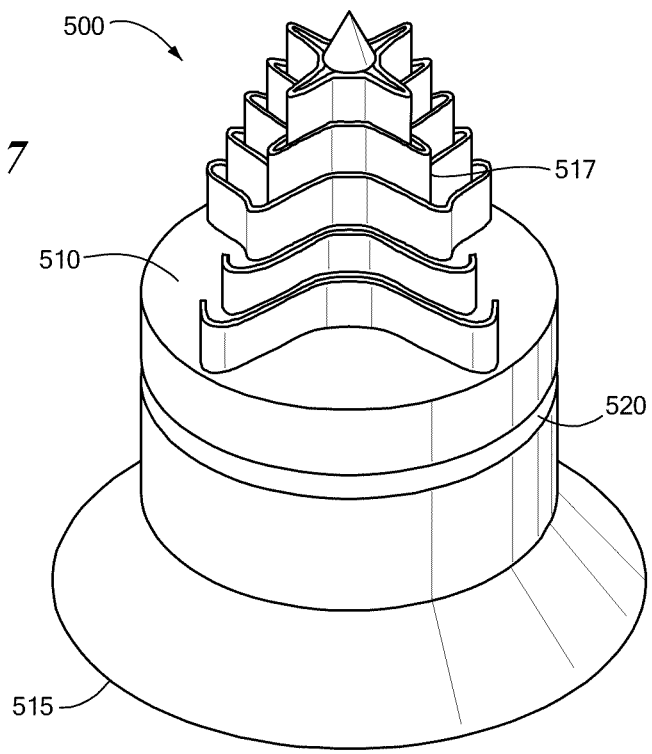
FIG. 17 shows a perspective view of an exemplary articular repair device including a flat surface to control depth and prevent toggle; an exterior surface having the contour of normal cartilage; flanges to prevent rotation and control toggle; a groove to facilitate tissue in-growth, in accordance with one embodiment of the invention.

FIG. 17 shows an exemplary articular repair device 500 including a flat surface 510 to control depth and prevent toggle; an exterior surface 515 having the contour of normal cartilage; flanges 517 to prevent rotation and control toggle; a groove 520 to facilitate tissue in-growth.

Figure 18A:
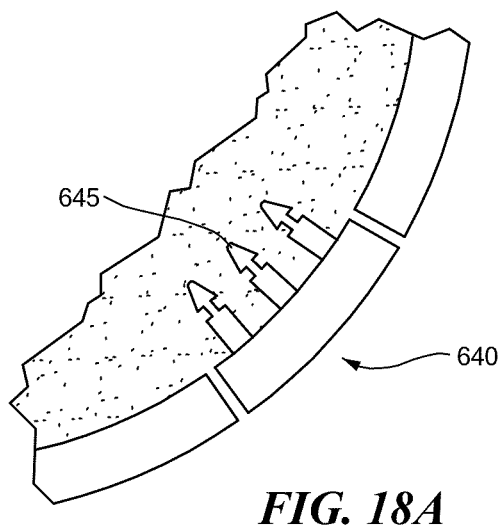
FIGS. 18A-D depict, in cross-section, another example of an implant with multiple anchoring pegs, in accordance with various embodiments of the invention.
Figure 18B:
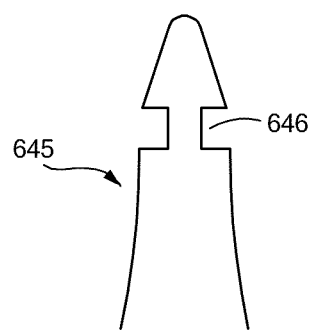
Figure 18C:
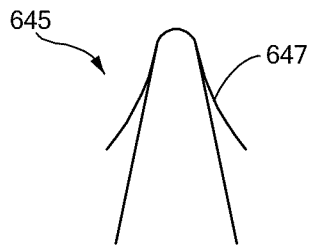
Figure 18D:
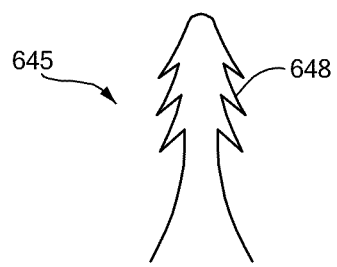

FIGS. 18A-D depict, in cross-section, another example of an implant 640 with multiple anchoring pegs, stems, or screws 645. FIG. 18B-D show various cross-sectional representations of various possible embodiments of the pegs, or anchoring stems. FIG. 18B shows a peg 645 having a notch 646 or groove around its circumference; FIG. 18C shows a peg 645 with radially-extending arms 647 that help anchor the device in the underlying bone; and FIG. 18D shows a peg 645 with multiple grooves or flanges 648.

Figure 19A:
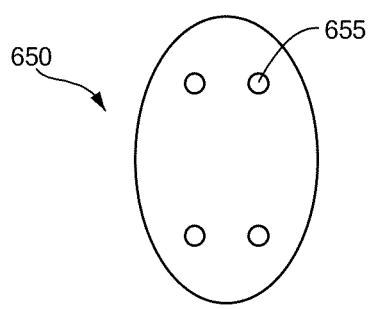
FIG. 19A-B depict an overhead view of an exemplary implant with multiple anchoring pegs and depict how the pegs are not necessarily linearly aligned along the longitudinal axis of the device, in accordance with various embodiments of the invention.
Figure 19B:
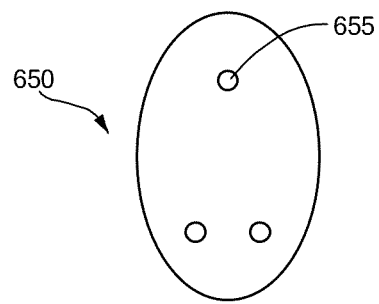

FIGS. 19A-B depict an overhead view of an exemplary implant 650 with multiple anchoring pegs 655 which illustrates that the pegs are not necessarily linearly aligned along the longitudinal axis of the device.

Figure 20A:
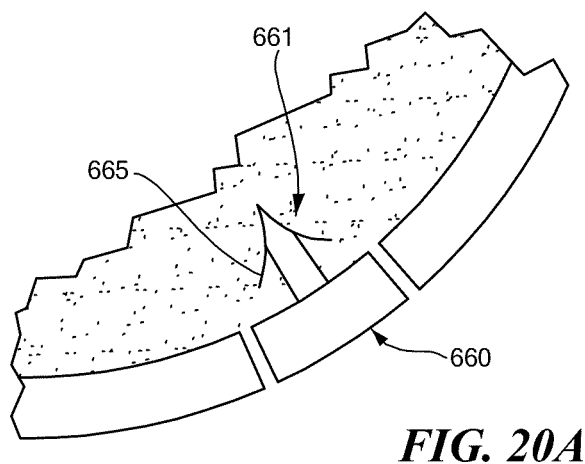
FIGS. 20A-E depict an exemplary implant having radially extending arms, in accordance with various embodiments of the invention.
Figure 20B:
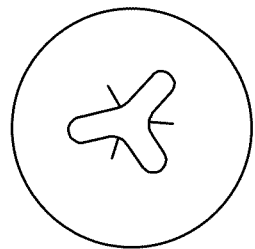
Figure 20C:
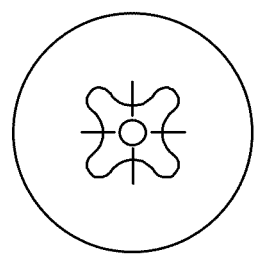
Figure 20D:
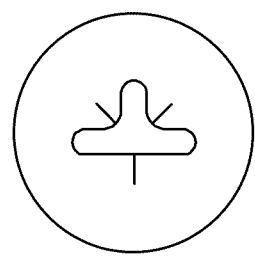
Figure 20E:
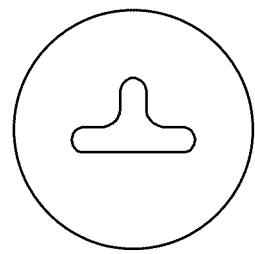

FIG. 20A depicts an implant 660 with a peg 661 having radially extending arms 665. FIGS. 20B-E are top views of the implant pegs illustrating a variety of suitable alternative shapes.

Examples of one-component systems include, but are not limited to, a plastic, a polymer, a metal, a metal alloy, crystal free metals, a biologic material or combinations thereof. In certain embodiments, the surface of the repair system facing the underlying bone can be smooth. In other embodiments, the surface of the repair system facing the underlying bone can be porous or porous-coated. In another aspect, the surface of the repair system facing the underlying bone is designed with one or more grooves, for example to facilitate the in-growth of the surrounding tissue. The external surface of the device can have a step-like design, which can be advantageous for altering biomechanical stresses. Optionally, flanges can also be added at one or more positions on the device (e.g., to prevent the repair system from rotating, to control toggle and/or prevent settling into the marrow cavity). The flanges can be part of a conical or a cylindrical design. A portion or all of the repair system facing the underlying bone can also be flat which can help to control depth of the implant and to prevent toggle.

Non-limiting examples of multiple-component systems include combinations of metal, plastic, metal alloys, crystal free metals, and one or more biological materials. One or more components of the articular surface repair system can be composed of a biologic material (e.g. a tissue scaffold with cells such as cartilage cells or stem cells alone or seeded within a substrate such as a bioresorable material or a tissue scaffold, allograft, autograft or combinations thereof) and/or a non-biological material (e.g., polyethylene or a chromium alloy such as chromium cobalt).

Thus, the repair system can include one or more areas of a single material or a combination of materials, for example, the articular surface repair system can have a first and a second component. The first component is typically designed to have size, thickness and curvature similar to that of the cartilage tissue lost while the second component is typically designed to have a curvature similar to the subchondral bone. In addition, the first component can have biomechanical properties similar to articular cartilage, including but not limited to similar elasticity and resistance to axial loading or shear forces. The first and the second component can consist of two different metals or metal alloys. One or more components of the system (e.g., the second portion) can be composed of a biologic material including, but not limited to bone, or a non-biologic material including, but not limited to hydroxyapatite, tantalum, a chromium alloy, chromium cobalt or other metal alloys.

One or more regions of the articular surface repair system (e.g., the outer margin of the first portion and/or the second portion) can be bioresorbable, for example to allow the interface between the articular surface repair system and the patient's normal cartilage, over time, to be filled in with hyaline or fibrocartilage. Similarly, one or more regions (e.g., the outer margin of the first portion of the articular surface repair system and/or the second portion) can be porous. The degree of porosity can change throughout the porous region, linearly or non-linearly, for where the degree of porosity will typically decrease towards the center of the articular surface repair system. The pores can be designed for in-growth of cartilage cells, cartilage matrix, and connective tissue thereby achieving a smooth interface between the articular surface repair system and the surrounding cartilage.

The repair system (e.g., the second component in multiple component systems) can be attached to the patient's bone with use of a cement-like material such as methylmethacrylate, injectable hydroxy- or calcium-apatite materials and the like.

In certain embodiments, one or more portions of the articular surface repair system can be pliable or liquid or deformable at the time of implantation and can harden later. Hardening can occur, for example, within 1 second to 2 hours (or any time period therebetween), preferably with in 1 second to 30 minutes (or any time period therebetween), more preferably between 1 second and 10 minutes (or any time period therebetween).

One or more components of the articular surface repair system can be adapted to receive injections. For example, the external surface of the articular surface repair system can have one or more openings therein. The openings can be sized to receive screws, tubing, needles or other devices which can be inserted and advanced to the desired depth, for example, through the articular surface repair system into the marrow space. Injectables such as methylmethacrylate and injectable hydroxy- or calcium-apatite materials can then be introduced through the opening (or tubing inserted therethrough) into the marrow space thereby bonding the articular surface repair system with the marrow space. Similarly, screws or pins, or other anchoring mechanisms. can be inserted into the openings and advanced to the underlying subchondral bone and the bone marrow or epiphysis to achieve fixation of the articular surface repair system to the bone. Portions or all components of the screw or pin can be bioresorbable, for example, the distal portion of a screw that protrudes into the marrow space can be bioresorbable. During the initial period after the surgery, the screw can provide the primary fixation of the articular surface repair system. Subsequently, ingrowth of bone into a porous coated area along the undersurface of the articular cartilage repair system can take over as the primary stabilizer of the articular surface repair system against the bone.

The articular surface repair system can be anchored to the patient's bone with use of a pin or screw or other attachment mechanism. The attachment mechanism can be bioresorbable. The screw or pin or attachment mechanism can be inserted and advanced towards the articular surface repair system from a non-cartilage covered portion of the bone or from a non-weight-bearing surface of the joint.

The interface between the articular surface repair system and the surrounding normal cartilage can be at an angle, for example oriented at an angle of 90 degrees relative to the underlying subchondral bone. Suitable angles can be determined in view of the teachings herein, and in certain cases, non-90 degree angles can have advantages with regard to load distribution along the interface between the articular surface repair system and the surrounding normal cartilage.

The interface between the articular surface repair system and the surrounding normal cartilage and/or bone can be covered with a pharmaceutical or bioactive agent, for example a material that stimulates the biological integration of the repair system into the normal cartilage and/or bone. The surface area of the interface can be irregular, for example, to increase exposure of the interface to pharmaceutical or bioactive agents.

E. Pre-Existing Repair Systems

As described herein, repair systems, including surgical instruments, templates, guides and/or molds, of various sizes, curvatures and thicknesses can be obtained. These repair systems, including surgical instruments, guides, templates and/or molds, can be catalogued and stored to create a library of systems from which an appropriate system for an individual patient can then be selected. In other words, a defect, or an articular surface, is assessed in a particular subject and a pre-existing repair system, including surgical instruments, templates, guides and/or molds, having a suitable shape and size is selected from the library for further manipulation (e.g., shaping) and implantation.

F. Mini-Prosthesis

As noted above, the methods and compositions described herein can be used to replace only a portion of the articular surface, for example, an area of diseased cartilage or lost cartilage on the articular surface. In these systems, the articular surface repair system can be designed to replace only the area of diseased or lost cartilage or it can extend beyond the area of diseased or lost cartilage, e.g., 3 or 5 mm into normal adjacent cartilage. In certain embodiments, the prosthesis replaces less than about 70% to 80% (or any value therebetween) of the articular surface (e.g., any given articular surface such as a single femoral condyle, etc.), preferably, less than about 50% to 70% (or any value therebetween), more preferably, less than about 30% to 50% (or any value therebetween), more preferably less than about 20% to 30% (or any value therebetween), even more preferably less than about 20% of the articular surface.

The prosthesis can include multiple components, for example a component that is implanted into the bone (e.g., a metallic device) attached to a component that is shaped to cover the defect of the cartilage overlaying the bone. Additional components, for example intermediate plates, meniscal repair systems and the like can also be included. It is contemplated that each component replaces less than all of the corresponding articular surface. However, each component need not replace the same portion of the articular surface. In other words, the prosthesis can have a bone-implanted component that replaces less than 30% of the bone and a cartilage component that replaces 60% of the cartilage. The prosthesis can include any combination, provided each component replaces less than the entire articular surface.

The articular surface repair system can be formed or selected so that it will achieve a near anatomic fit or match with the surrounding or adjacent cartilage. Typically, the articular surface repair system is formed and/or selected so that its outer margin located at the external surface will be aligned with the surrounding or adjacent cartilage.

Thus, the articular repair system can be designed to replace the weight-bearing portion (or more or less than the weight bearing portion) of an articular surface, for example in a femoral condyle. The weight-bearing surface refers to the contact area between two opposing articular surfaces during activities of normal daily living (e.g., normal gait). At least one or more weight-bearing portions can be replaced in this manner, e.g., on a femoral condyle and on a tibia.

In other embodiments, an area of diseased cartilage or cartilage loss can be identified in a weight-bearing area and only a portion of the weight-bearing area, specifically the portion containing the diseased cartilage or area of cartilage loss, can be replaced with an articular surface repair system.

In another embodiment, the articular repair system can be designed or selected to replace substantially all of the articular surface, e.g. a condyle.

In another embodiment, for example, in patients with diffuse cartilage loss, the articular repair system can be designed to replace an area slightly larger than the weight-bearing surface.

In certain aspects, the defect to be repaired is located only on one articular surface, typically the most diseased surface. For example, in a patient with severe cartilage loss in the medial femoral condyle but less severe disease in the tibia, the articular surface repair system can only be applied to the medial femoral condyle. Preferably, in any methods described herein, the articular surface repair system is designed to achieve an exact or a near anatomic fit with the adjacent normal cartilage.

In other embodiments, more than one articular surface can be repaired. The area(s) of repair will be typically limited to areas of diseased cartilage or cartilage loss or areas slightly greater than the area of diseased cartilage or cartilage loss within the weight-bearing surface(s).

The implant and/or the implant site can be sculpted to achieve a near anatomic alignment between the implant and the implant site. In another embodiment of the invention, an electronic image is used to measure the thickness, curvature, or shape of the articular cartilage or the subchondral bone, and/or the size of a defect, and an articular surface repair system is selected using this information. The articular surface repair system can be inserted arthroscopically. The articular surface repair system can have a single radius. More typically, however, as shown in FIG. 15A, discussed above, the articular surface repair system 1500 has varying curvatures and radii within the same plane, e.g. anteroposterior or mediolateral or superoinferior or oblique planes, or within multiple planes. In this manner, the articular surface repair system can be shaped to achieve a near anatomic alignment between the implant and the implant site. This design allows not only allows for different degrees of convexity or concavity, but also for concave portions within a predominantly convex shape or vice versa 1500.

In another embodiment the articular surface repair system has an anchoring stem, used to anchor the device, for example, as described in U.S. Pat. No. 6,224,632 to Pappas et al issued May 1, 2001. The stem, or peg, can have different shapes including conical, rectangular, fin among others. The mating bone cavity is typically similarly shaped as the corresponding stem.

As shown in FIG. 16, discussed above, the articular surface repair system 100 can be affixed to the subchondral bone 300, with one or more stems, or pegs, 150 extending through the subchondral plate into the marrow space. In certain instances, this design can reduce the likelihood that the implant will settle deeper into the joint over time by resting portions of the implant against the subchondral bone. The stems, or pegs, can be of any shape suitable to perform the function of anchoring the device to the bone. For example, the pegs can be cylindrical or conical. Optionally, the stems, or pegs, can further include notches or openings to allow bone in-growth. In addition, the stems can be porous coated for bone in-growth. The anchoring stems or pegs can be affixed to the bone using bone cement. An additional anchoring device can also be affixed to the stem or peg. The anchoring device can have an umbrella shape (e.g., radially expanding elements) with the wider portion pointing towards the subchondral bone and away from the peg. The anchoring device can be advantageous for providing immediate fixation of the implant. The undersurface of the articular repair system facing the subchondral bone can be textured or rough thereby increasing the contact surface between the articular repair system and the subchondral bone. Alternatively, the undersurface of the articular repair system can be porous coated thereby allowing in-growth. The surgeon can support the in-growth of bone by treating the subchondral bone with a rasp, typically to create a larger surface area and/or until bleeding from the subchondral bone occurs.

In another embodiment, the articular surface repair system can be attached to the underlying bone or bone marrow using bone cement. Bone cement is typically made from an acrylic polymeric material. Typically, the bone cement is comprised of two components: a dry powder component and a liquid component, which are subsequently mixed together. The dry component generally includes an acrylic polymer, such as polymethylmethacrylate (PMMA). The dry component can also contain a polymerization initiator such as benzoylperoxide, which initiates the free-radical polymerization process that occurs when the bone cement is formed. The liquid component, on the other hand, generally contains a liquid monomer such as methyl methacrylate (MMA). The liquid component can also contain an accelerator such as an amine (e.g., N,N-dimethyl-p-toluidine). A stabilizer, such as hydroquinone, can also be added to the liquid component to prevent premature polymerization of the liquid monomer. When the liquid component is mixed with the dry component, the dry component begins to dissolve or swell in the liquid monomer. The amine accelerator reacts with the initiator to form free radicals that begin to link monomer units to form polymer chains. In the next two to four minutes, the polymerization process proceeds changing the viscosity of the mixture from a syrup-like consistency (low viscosity) into a dough-like consistency (high viscosity). Ultimately, further polymerization and curing occur, causing the cement to harden and affix a prosthesis to a bone.

In certain aspects of the invention, as shown in FIG. 7E, above, bone cement 755 or another liquid attachment material such as injectable calciumhydroxyapatite can be injected into the marrow cavity through one or more openings 750 in the prosthesis. These openings in the prosthesis can extend from the articular surface to the undersurface of the prosthesis 760. After injection, the openings can be closed with a polymer, silicon, metal, metal alloy or bioresorbable plug.

In another embodiment, one or more components of the articular surface repair (e.g., the surface of the system that is pointing towards the underlying bone or bone marrow) can be porous or porous coated. A variety of different porous metal coatings have been proposed for enhancing fixation of a metallic prosthesis by bone tissue in-growth. Thus, for example, U.S. Pat. No. 3,855,638 to Pilliar issued Dec. 24, 2974, discloses a surgical prosthetic device, which can be used as a bone prosthesis, comprising a composite structure consisting of a solid metallic material substrate and a porous coating of the same solid metallic material adhered to and extending over at least a portion of the surface of the substrate. The porous coating consists of a plurality of small discrete particles of metallic material bonded together at their points of contact with each other to define a plurality of connected interstitial pores in the coating. The size and spacing of the particles, which can be distributed in a plurality of monolayers, can be such that the average interstitial pore size is not more than about 200 microns. Additionally, the pore size distribution can be substantially uniform from the substrate-coating interface to the surface of the coating. In another embodiment, the articular surface repair system can contain one or more polymeric materials that can be loaded with and release therapeutic agents including drugs or other pharmacological treatments that can be used for drug delivery. The polymeric materials can, for example, be placed inside areas of porous coating. The polymeric materials can be used to release therapeutic drugs, e.g. bone or cartilage growth stimulating drugs. This embodiment can be combined with other embodiments, wherein portions of the articular surface repair system can be bioresorbable. For example, the first layer of an articular surface repair system or portions of its first layer can be bioresorbable. As the first layer gets increasingly resorbed, local release of a cartilage growth-stimulating drug can facilitate in-growth of cartilage cells and matrix formation.

In any of the methods or compositions described herein, the articular surface repair system can be pre-manufactured with a range of sizes, curvatures and thicknesses. Alternatively, the articular surface repair system can be custom-made for an individual patient.

IV. Manufacturing

A. Shaping

In certain instances shaping of the repair material will be required before or after formation (e.g., growth to desired thickness), for example where the thickness of the required cartilage material is not uniform (e.g., where different sections of the cartilage replacement or regenerating material require different thicknesses).

The replacement material can be shaped by any suitable technique including, but not limited to, mechanical abrasion, laser abrasion or ablation, radiofrequency treatment, cryoablation, variations in exposure time and concentration of nutrients, enzymes or growth factors and any other means suitable for influencing or changing cartilage thickness. See, e.g., WO 00/15153 to Mansmann published Mar. 23, 2000; If enzymatic digestion is used, certain sections of the cartilage replacement or regenerating material can be exposed to higher doses of the enzyme or can be exposed longer as a means of achieving different thicknesses and curvatures of the cartilage replacement or regenerating material in different sections of said material.

The material can be shaped manually and/or automatically, for example using a device into which a pre-selected thickness and/or curvature has been input and then programming the device using the input information to achieve the desired shape.

In addition to, or instead of, shaping the cartilage repair material, the site of implantation (e.g., bone surface, any cartilage material remaining, etc.) can also be shaped by any suitable technique in order to enhance integration of the repair material.

B. Sizing

The articular repair system can be formed or selected so that it will achieve a near anatomic fit or match with the surrounding or adjacent cartilage or subchondral bone or menisci and other tissue. The shape of the repair system can be based on the analysis of an electronic image (e.g. MRI, CT, digital tomosynthesis, optical coherence tomography or the like). If the articular repair system is intended to replace an area of diseased cartilage or lost cartilage, the near anatomic fit can be achieved using a method that provides a virtual reconstruction of the shape of healthy cartilage in an electronic image.

In one embodiment of the invention, a near normal cartilage surface at the position of the cartilage defect can be reconstructed by interpolating the healthy cartilage surface across the cartilage defect or area of diseased cartilage. This can, for example, be achieved by describing the healthy cartilage by means of a parametric surface (e.g. a B-spline surface), for which the control points are placed such that the parametric surface follows the contour of the healthy cartilage and bridges the cartilage defect or area of diseased cartilage. The continuity properties of the parametric surface will provide a smooth integration of the part that bridges the cartilage defect or area of diseased cartilage with the contour of the surrounding healthy cartilage. The part of the parametric surface over the area of the cartilage defect or area of diseased cartilage can be used to determine the shape or part of the shape of the articular repair system to match with the surrounding cartilage.

In another embodiment, a near normal cartilage surface at the position of the cartilage defect or area of diseased cartilage can be reconstructed using morphological image processing. In a first step, the cartilage can be extracted from the electronic image using manual, semi-automated and/or automated segmentation techniques (e.g., manual tracing, region growing, live wire, model-based segmentation), resulting in a binary image. Defects in the cartilage appear as indentations that can be filled with a morphological closing operation performed in 2-D or 3-D with an appropriately selected structuring element. The closing operation is typically defined as a dilation followed by an erosion. A dilation operator sets the current pixel in the output image to 1 if at least one pixel of the structuring element lies inside a region in the source image. An erosion operator sets the current pixel in the output image to 1 if the whole structuring element lies inside a region in the source image. The filling of the cartilage defect or area of diseased cartilage creates a new surface over the area of the cartilage defect or area of diseased cartilage that can be used to determine the shape or part of the shape of the articular repair system to match with the surrounding cartilage or subchondral bone.

As described above, the articular repair system, including surgical tools and instruments, molds, in situ repair systems, etc. can be formed or selected from a library or database of systems of various sizes, curvatures and thicknesses so that it will achieve a near anatomic fit or match with the surrounding or adjacent cartilage and/or subchondral bone. These systems can be pre-made or made to order for an individual patient. In order to control the fit or match of the articular repair system with the surrounding or adjacent cartilage or subchondral bone or menisci and other tissues preoperatively, a software program can be used that projects the articular repair system over the anatomic position where it will be implanted. Suitable software is commercially available and/or readily modified or designed by a skilled programmer.

In yet another embodiment, the articular repair system including unicompartmental and total knee implants as well as hip devices can be projected over the implantation site using one or more 2-D or 3-D images. The cartilage and/or subchondral bone and other anatomic structures can be optionally extracted from a 2-D or 3-D electronic image such as an MRI or a CT using manual, semi-automated and/or automated segmentation techniques. A 2-D or 3-D representation of the cartilage and/or bone and other anatomic structures as well as the articular repair system can be generated, for example using a polygon or NURBS surface or other parametric surface representation. Ligaments, menisci and other articular structures can be displayed in 2-D and 3-D. For a description of various parametric surface representations see, for example Foley, J. D. et al., Computer Graphics Principles and Practice in C; Addison-Wesley, $2^{nd}$ edition, 1995).

The 2-D or 3-D representations of the cartilage and/or subchondral bone and other anatomic structures and the articular repair system can be merged into a common coordinate system. The articular repair system, including surgical tools and instruments, molds, in situ repair systems, etc. can then be placed at the desired implantation site. The representations of the cartilage, subchondral bone, ligaments, menisci and other anatomic structures and the articular repair system are rendered into a 2-D or 3-D image, for example application programming interfaces (APIs) OpenGL® (standard library of advanced 3-D graphics functions developed by SGI, Inc.; available as part of the drivers for PC-based video cards, for example from www.nvidia.com for NVIDIA video cards or www.3dlabs.com for 3Dlabs products, or as part of the system software for Unix workstations) or DirectX® (multimedia API for Microsoft Windows® based PC systems; available from www.microsoft.com). The 2-D or 3-D image can be rendered or displayed showing the cartilage, subchondral bone, ligaments, menisci or other anatomic objects, and the articular repair system from varying angles, e.g. by rotating or moving them interactively or non-interactively, in real-time or non-real-time.

In another embodiment, the implantation site may be visualized using one or more cross-sectional 2-D images, as described in U.S. Ser. No. 10/305,652, entitled "Methods and Compositions for Articular Repair," filed Nov. 27, 2002, which is hereby incorporated by reference in its entirety. Typically, a series of 2-D cross-sectional images will be used. The 2-D images can be generated with imaging tests such as CT, MRI, digital tomosynthesis, ultrasound, optical imaging, optical coherence tomography, other imaging modalities using methods and tools known to those of skill in the art. The articular repair system or implant can then be superimposed onto one or more of these 2-D images. The 2-D cross-sectional images may be reconstructed in other planes, e.g. from sagittal to coronal, etc. Isotropic data sets (e.g., data sets where the slice thickness is the same or nearly the same as the in-plane resolution) or near isotropic data sets can also be used. Multiple planes may be displayed simultaneously, for example using a split screen display. The operator may also scroll through the 2-D images in any desired orientation in real time or near real time; the operator can rotate the imaged tissue volume while doing this. The articular repair system or implant may be displayed in cross-section utilizing different display planes, e.g. sagittal, coronal or axial, typically matching those of the 2-D images demonstrating the cartilage, subchondral bone, ligaments, menisci or other tissue. Alternatively, a three-dimensional display may be used for the articular repair system. The 2-D electronic image and the 2-D or 3-D representation of the articular repair system or implant may be merged into a common coordinate system. The cartilage repair system or implant can then be placed at the desired implantation site. The series of 2-D cross-sections of the anatomic structures, the implantation site and the articular repair system or implant may be displayed interactively (e.g. the operator can scroll through a series of slices) or non-interactively (e.g. as an animation that moves through the series of slices), in real-time or non-real-time.

The software can be designed so that the articular repair system, including surgical tools and instruments, molds, in situ repair systems, etc. with the best fit relative to the cartilage and/or subchondral bone is automatically selected, for example using one or more of the techniques described above. Alternatively, the operator can select an articular repair system, including surgical tools and instruments, molds, in situ repair systems, etc. and project it or drag it onto the implantation site displayed on the cross-sectional 2-D or the 3-D images. The operator can then move and rotate the articular repair system relative to the implantation site and scroll through a cross-sectional 2-D or 3-D display of the articular repair system and of the anatomic structures. The operator can perform a visual and/or computer-assisted inspection of the fit between the articular repair system and the implantation site. This can be performed for different positions of the joint, e.g. extension, 45, 90 degrees of flexion, adduction, abduction, internal or external rotation. The procedure can be repeated until a satisfactory fit has been achieved. The procedure can be entirely manual by the operator; it can, however, also be computer-assisted. For example, the software can select a first trial implant that the operator can test (e.g., evaluate the fit). Software that highlights areas of poor alignment between the implant and the surrounding cartilage or subchondral bone or menisci or other tissues can also be designed and used. Based on this information, the software or the operator can select another implant and test its alignment.

In all of the above embodiments, the biomechanical axis and relevant anatomical axes or planes can be displayed simultaneous with the joint and/or articular repair device in the 2-D or 3-D display. Simultaneous display of at least one or more biomechanical axes or anatomical axes or planes can help improve the assessment of fit of the articular repair system. Biomechanical axis or relevant anatomical axes or planes can also be displayed for different positions of the joint.

C. Rapid Prototyping, Other Manufacturing Techniques

Rapid protyping is a technique for fabricating a three-dimensional object from a computer model of the object. A special printer is used to fabricate the prototype from a plurality of two-dimensional layers. Computer software sections the representations of the object into a plurality of distinct two-dimensional layers and then a three-dimensional printer fabricates a layer of material for each layer sectioned by the software. Together the various fabricated layers form the desired prototype. More information about rapid prototyping techniques is available in US Patent Publication No 2002/0079601A1 to Russell et al., published Jun. 27, 2002. An advantage to using rapid prototyping is that it enables the use of free form fabrication techniques that use toxic or potent compounds safely. These compounds can be safely incorporated in an excipient envelope, which reduces worker exposure A powder piston and build bed are provided. Powder includes any material (metal, plastic, etc.) that can be made into a powder or bonded with a liquid. The power is rolled from a feeder source with a spreader onto a surface of a bed. The thickness of the layer is controlled by the computer. The print head then deposits a binder fluid onto the powder layer at a location where it is desired that the powder bind. Powder is again rolled into the build bed and the process is repeated, with the binding fluid deposition being controlled at each layer to correspond to the three-dimensional location of the device formation. For a further discussion of this process see, for example, US Patent Publication No 2003/017365A1 to Monkhouse et al. published Sep. 18, 2003.

The rapid prototyping can use the two dimensional images obtained, as described above in Section I, to determine each of the two-dimensional shapes for each of the layers of the prototyping machine. In this scenario, each two dimensional image slice would correspond to a two dimensional prototype slide. Alternatively, the three-dimensional shape of the defect can be determined, as described above, and then broken down into two dimensional slices for the rapid prototyping process. The advantage of using the three-dimensional model is that the two-dimensional slices used for the rapid prototyping machine can be along the same plane as the two-dimensional images taken or along a different plane altogether.

Rapid prototyping can be combined or used in conjunction with casting techniques. For example, a shell or container with inner dimensions corresponding to an articular repair system including surgical instruments, molds, alignment guides or surgical guides, can be made using rapid prototyping. Plastic or wax-like materials are typically used for this purpose. The inside of the container can subsequently be coated, for example with a ceramic, for subsequent casting. Using this process, personalized casts can be generated.

Rapid prototyping can be used for producing articular repair systems including surgical tools, molds, alignment guides, cut guides etc. Rapid prototyping can be performed at a manufacturing facility. Alternatively, it may be performed in the operating room after an intraoperative measurement has been performed.

Alternatively, milling techniques can be utilized for producing articular repair systems including surgical tools, molds, alignment guides, cut guides etc.

Alternatively, laser based techniques can be utilized for producing articular repair systems including surgical tools, molds, alignment guides, cut guides etc.

V. Implantation

Following one or more manipulations (e.g., shaping, growth, development, etc), the cartilage replacement or regenerating material can then be implanted into the area of the defect. Implantation can be performed with the cartilage replacement or regenerating material still attached to the base material or removed from the base material. Any suitable methods and devices can be used for implantation, for example, devices as described in U.S. Pat. No. 6,375,658 to Hangody et al. issued Apr. 23, 2002; U.S. Pat. No. 6,358,253 to Torrie et al. issued Mar. 19, 2002; U.S. Pat. No. 6,328,765 to Hardwick et al. issued Dec. 11, 2001; and International Publication WO 01/19254 to Cummings et al. published Mar. 22, 2001.

In selected cartilage defects, the implantation site can be prepared with a single cut across the articular surface, for example, as shown in FIG. 8. In this case, single 810 and multi-component 820 prostheses can be utilized.

A. The Joint Replacement Procedure i. Knee Joint

Performing a total knee arthroplasty is a complicated procedure. In replacing the knee with an artificial knee, it is important to get the anatomical and mechanical axes of the lower extremity aligned correctly to ensure optimal functioning of the implanted knee.

Figure 21A:
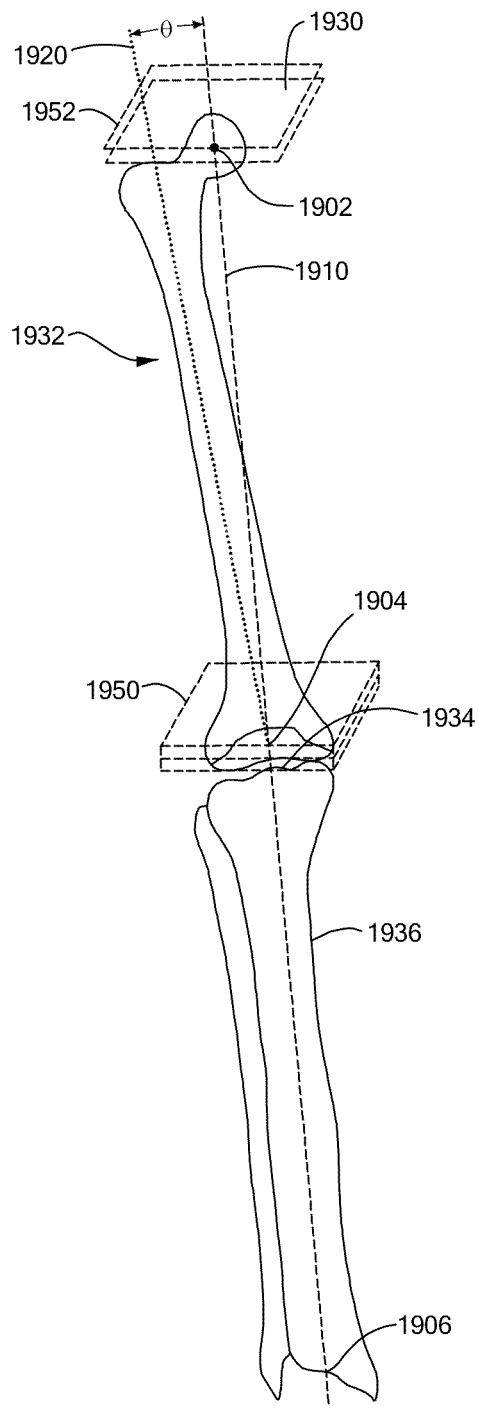
FIG. 21A illustrates a femur, tibia and fibula along with the mechanical and anatomic axes.

As shown in FIG. 21A, the center of the hip 1902 (located at the head 1930 of the femur 1932), the center of the knee 1904 (located at the notch where the intercondular tubercle 1934 of the tibia 1936 meet the femur) and ankle 1906 lie approximately in a straight line 1910 which defines the mechanical axis of the lower extremity. The anatomic axis 1920 aligns 5-7° offset θ from the mechanical axis in the valgus, or outward, direction.

The long axis of the tibia 1936 is collinear with the mechanical axis of the lower extremity 1910. From a three-dimensional perspective, the lower extremity of the body ideally functions within a single plane known as the median anterior-posterior plane (MAP-plane) throughout the flexion-extension arc. In order to accomplish this, the femoral head 1930, the mechanical axis of the femur, the patellar groove, the intercondylar notch, the patellar articular crest, the tibia and the ankle remain within the MAP-plane during the flexion-extension movement. During movement, the tibia rotates as the knee flexes and extends in the epicondylar axis which is perpendicular to the MAP-plane.

A variety of image slices can be taken at each individual joint, e.g., the knee joint $1950\text{-}1950_n$, and the hip joint $1952\text{-}1950_n$. These image slices can be used as described above in Section I along with an image of the full leg to ascertain the axis.

With disease and malfunction of the knee, alignment of the anatomic axis is altered. Performing a total knee arthroplasty is one solution for correcting a diseased knee. Implanting a total knee joint, such as the PFC Sigma RP Knee System by Johnson & Johnson, requires that a series of resections be made to the surfaces forming the knee joint in order to facilitate installation of the artificial knee. The resections should be made to enable the installed artificial knee to achieve flexion-extension movement within the MAP-plane and to optimize the patient's anatomical and mechanical axis of the lower extremity.

First, the tibia 1930 is resected to create a flat surface to accept the tibial component of the implant. In most cases, the tibial surface is resected perpendicular to the long axis of the tibia in the coronal plane, but is typically sloped 4-7° posteriorly in the sagittal plane to match the normal slope of the tibia. As will be appreciated by those of skill in the art, the sagittal slope can be 0° where the device to be implanted does not require a sloped tibial cut. The resection line 1958 is perpendicular to the mechanical axis 1910, but the angle between the resection line and the surface plane of the plateau 1960 varies depending on the amount of damage to the knee.

Figure 21B:
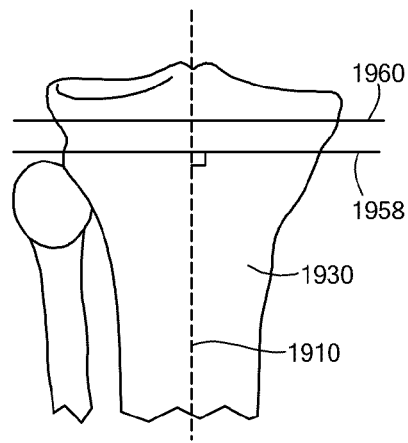
FIGS. 21B-E illustrate the tibia with the anatomic and mechanical axis used to create a cutting plane along with a cut femur and tibia.
Figure 21C:
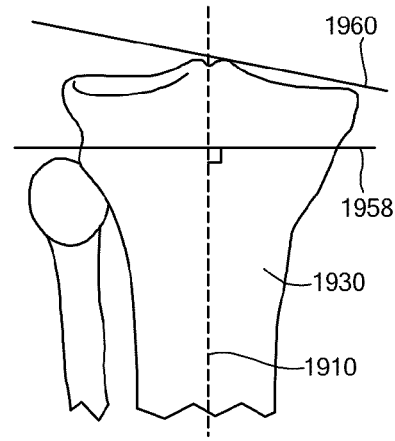
Figure 21D:
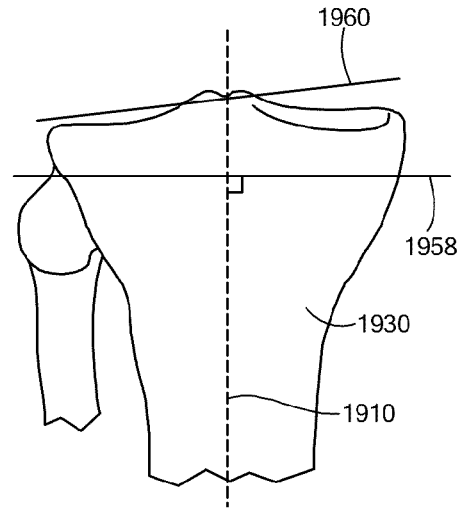

FIGS. 21B-D illustrate an anterior view of a resection of an anatomically normal tibial component, a tibial component in a varus knee, and a tibial component in a valgus knee, respectively. In each figure, the mechanical axis 1910 extends vertically through the bone and the resection line 1958 is perpendicular to the mechanical axis 1910 in the coronal plane, varying from the surface line formed by the joint depending on the amount of damage to the joint. FIG. 21B illustrates a normal knee wherein the line corresponding to the surface of the joint 1960 is parallel to the resection line 1958. FIG. 21C illustrates a varus knee wherein the line corresponding to the surface of the joint 1960 is not parallel to the resection line 1958. FIG. 21D illustrates a valgus knee wherein the line corresponding to the surface of the joint 1960 is not parallel to the resection line 1958.

Once the tibial surface has been prepared, the surgeon turns to preparing the femoral condyle.

The plateau of the femur 1970 is resected to provide flat surfaces that communicate with the interior of the femoral prosthesis. The cuts made to the femur are based on the overall height of the gap to be created between the tibia and the femur. Typically, a 20 mm gap is desirable to provide the implanted prosthesis adequate room to achieve full range of motion. The bone is resected at a 5-7° angle valgus to the mechanical axis of the femur. Resected surface 1972 forms a flat plane with an angular relationship to adjoining surfaces 1974, 1976. The angle $\theta'$, $\theta''$ between the surfaces 1972-1974, and 1972-1976 varies according to the design of the implant.

ii. Hip Joint

Figure 21E:
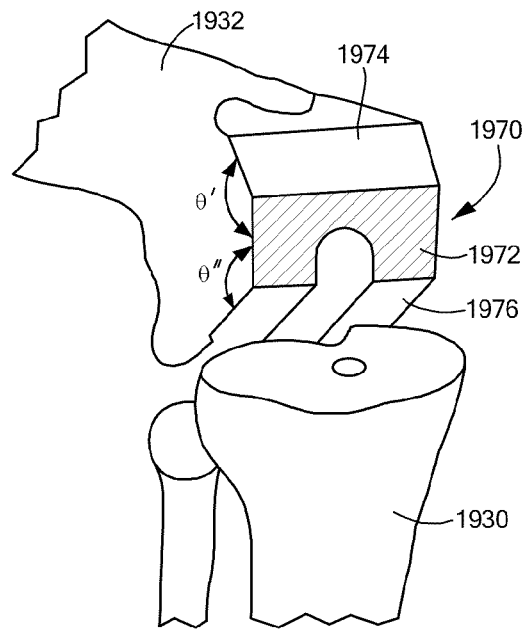
Figure 21F:
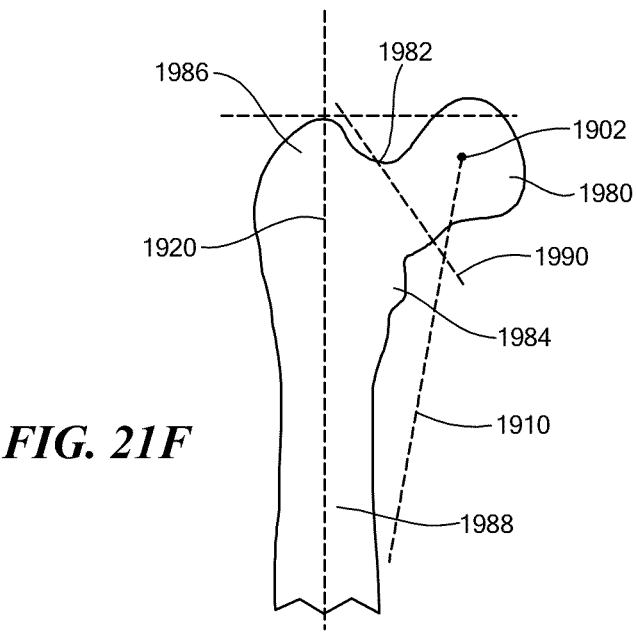
FIG. 21F illustrates the proximal end of the femur including the head of the femur.

As illustrated in FIG. 21F, the external geometry of the proximal femur includes the head 1980, the neck 1982, the lesser trochanter 1984, the greater trochanter 1986 and the proximal femoral diaphysis. The relative positions of the trochanters 1984, 1986, the femoral head center 1902 and the femoral shaft 1988 are correlated with the inclination of the neck-shaft angle. The mechanical axis 1910 and anatomic axis 1920 are also shown. Assessment of these relationships can change the reaming direction to achieve neutral alignment of the prosthesis with the femoral canal.

Using anteroposterior and lateral radiographs, measurements are made of the proximal and distal geometry to determine the size and optimal design of the implant.

Typically, after obtaining surgical access to the hip joint, the femoral neck 1982 is resected, e.g. along the line 1990. Once the neck is resected, the medullary canal is reamed. Reaming can be accomplished, for example, with a conical or straight reamer, or a flexible reamer. The depth of reaming is dictated by the specific design of the implant. Once the canal has been reamed, the proximal reamer is prepared by serial rasping, with the rasp directed down into the canal.

B. Surgical Tools

Further, surgical assistance can be provided by using a device applied to the outer surface of the articular cartilage or the bone, including the subchondral bone, in order to match the alignment of the articular repair system and the recipient site or the joint. The device can be round, circular, oval, ellipsoid, curved or irregular in shape. The shape can be selected or adjusted to match or enclose an area of diseased cartilage or an area slightly larger than the area of diseased cartilage or substantially larger than the diseased cartilage. The area can encompass the entire articular surface or the weight bearing surface. Such devices are typically preferred when replacement of a majority or an entire articular surface is contemplated.

Mechanical devices can be used for surgical assistance (e.g., surgical tools), for example using gels, molds, plastics or metal. One or more electronic images or intraoperative measurements can be obtained providing object coordinates that define the articular and/or bone surface and shape. These objects' coordinates can be utilized to either shape the device, e.g. using a CAD/CAM technique, to be adapted to a patient's articular anatomy or, alternatively, to select a typically premade device that has a good fit with a patient's articular anatomy. The device can have a surface and shape that will match all or portions of the articular cartilage, subchondral bone and/or other bone surface and shape, e.g. similar to a "mirror image." The device can include, without limitation, one or more cut planes, apertures, slots and/or holes to accommodate surgical instruments such as drills, reamers, curettes, k-wires, screws and saws.

The device may have a single component or multiple components. The components may be attached to the unoperated and operated portions of the intra- or extra-articular anatomy. For example, one component may be attached to the femoral neck, while another component may be in contact with the greater or lesser trochanter. Typically, the different components can be used to assist with different parts of the surgical procedure. When multiple components are used, one or more components may also be attached to a different component rather than the articular cartilage, subchondral bone or other areas of osseous or non-osseous anatomy. For example, a tibial mold may be attached to a femoral mold and tibial cuts can be performed in reference to femoral cuts.

Components may also be designed to fit to the joint after an operative step has been performed. For example, in a knee, one component may be designed to fit all or portions of a distal femur before any cuts have been made, while another component may be designed to fit on a cut that has been made with the previously used mold or component. In a hip, one component may be used to perform an initial cut, for example through the femoral neck, while another subsequently used component may be designed to fit on the femoral neck after the cut, for example covering the area of the cut with a central opening for insertion of a reamer. Using this approach, subsequent surgical steps may also be performed with high accuracy, e.g. reaming of the marrow cavity.

In another embodiment, a guide may be attached to a mold to control the direction and orientation of surgical instruments. For example, after the femoral neck has been cut, a mold may be attached to the area of the cut, whereby it fits portions or all of the exposed bone surface. The mold may have an opening adapted for a reamer. Before the reamer is introduced a femoral reamer guide may be inserted into the mold and advanced into the marrow cavity. The position and orientation of the reamer guide may be determined by the femoral mold. The reamer can then be advanced over the reamer guide and the marrow cavity can be reamed with improved accuracy. Similar approaches are feasible in the knee and other joints.

All mold components may be disposable. Alternatively, some molds components may be re-usable. Typically, mold components applied after a surgical step such as a cut as been performed can be reuseable, since a reproducible anatomic interface will have been established.

Interconnecting or bridging components may be used. For example, such interconnecting or bridging components may couple the mold attached to the joint with a standard, preferably unmodified or only minimally modified cut block used during knee or hip surgery. Interconnecting or briding components may be made of plastic or metal. When made of metal or other hard material, they can help protect the joint from plastic debris, for example when a reamer or saw would otherwise get into contact with the mold.

The accuracy of the attachment between the component or mold and the cartilage or subchondral bone or other osseous structures is typically better than 2 mm, more preferred better than 1 mm, more preferred better than 0.7 mm, more preferred better than 0.5 mm, or even more preferred better than 0.5 mm. The accuracy of the attachment between different components or between one or more molds and one or more surgical instruments is typically better than 2 mm, more preferred better than 1 mm, more preferred better than 0.7 mm, more preferred better than 0.5 mm, or even more preferred better than 0.5 mm.

The angular error of any attachments or between any components or between components, molds, instruments and/or the anatomic or biomechanical axes is preferably less than 2 degrees, more preferably less than 1.5 degrees, more preferably less than 1 degree, and even more preferably less than 0.5 degrees. The total angular error is preferably less than 2 degrees, more preferably less than 1.5 degrees, more preferably less than 1 degree, and even more preferably less than 0.5 degrees.

Typically, a position will be chosen that will result in an anatomically desirable cut plane, drill hole, or general instrument orientation for subsequent placement of an articular repair system or for facilitating placement of the articular repair system. Moreover, the device can be designed so that the depth of the drill, reamer or other surgical instrument can be controlled, e.g., the drill cannot go any deeper into the tissue than defined by the device, and the size of the hole in the block can be designed to essentially match the size of the implant. Information about other joints or axis and alignment information of a joint or extremity can be included when selecting the position of these slots or holes. Alternatively, the openings in the device can be made larger than needed to accommodate these instruments. The device can also be configured to conform to the articular shape. The apertures, or openings, provided can be wide enough to allow for varying the position or angle of the surgical instrument, e.g., reamers, saws, drills, curettes and other surgical instruments. An instrument guide, typically comprised of a relatively hard material, can then be applied to the device. The device helps orient the instrument guide relative to the three-dimensional anatomy of the joint.

The mold may contact the entire articular surface. In various embodiments, the mold can be in contact with only a portion of the articular surface. Thus, the mold can be in contact, without limitation, with: 100% of the articular surface; 80% of the articular surface; 50% of the articular surface; 30% of the articular surface; 30% of the articular surface; 20% of the articular surface; or 10% or less of the articular surface. An advantage of a smaller surface contact area is a reduction in size of the mold thereby enabling cost efficient manufacturing and, more important, minimally invasive surgical techniques. The size of the mold and its surface contact areas have to be sufficient, however, to ensure accurate placement so that subsequent drilling and cutting can be performed with sufficient accuracy.

In various embodiments, the maximum diameter of the mold is less than 10 cm. In other embodiments, the maximum diameter of the mold may be less than: 8 cm; 5 cm; 4 cm; 3 cm; or even less than 2 cm.

The mold may be in contact with three or more surface points rather than an entire surface. These surface points may be on the articular surface or external to the articular surface. By using contact points rather than an entire surface or portions of the surface, the size of the mold may be reduced.

Reductions in the size of the mold can be used to enable minimally invasive surgery (MIS) in the hip, the knee, the shoulder and other joints. MIS technique with small molds will help to reduce intraoperative blood loss, preserve tissue including possibly bone, enable muscle sparing techniques and reduce postoperative pain and enable faster recovery. Thus, in one embodiment of the invention the mold is used in conjunction with a muscle sparing technique. In another embodiment of the invention, the mold may be used with a bone sparing technique. In another embodiment of the invention, the mold is shaped to enable MIS technique with an incision size of less than 15 cm, or, more preferred, less than 13 cm, or, more preferred, less than 10 cm, or, more preferred, less than 8 cm, or, more preferred, less than 6 cm.

The mold may be placed in contact with points or surfaces outside of the articular surface. For example, the mold can rest on bone in the intercondylar notch or the anterior or other aspects of the tibia or the acetabular rim or the lesser or greater trochanter. Optionally, the mold may only rest on points or surfaces that are external to the articular surface. Furthermore, the mold may rest on points or surfaces within the weight-bearing surface, or on points or surfaces external to the weight-bearing surface.

The mold may be designed to rest on bone or cartilage outside the area to be worked on, e.g. cut, drilled etc. In this manner, multiple surgical steps can be performed using the same mold. For example, in the knee, the mold may be stabilized against portions of the intercondylar notch, which can be selected external to areas to be removed for total knee arthroplasty or other procedures. In the hip, the mold may be attached external to the acetabular fossa, providing a reproducible reference that is maintained during a procedure, for example total hip arthroplasty. The mold may be affixed to the underlying bone, for example with pins or drills etc.

In additional embodiments, the mold may rest on the articular cartilage. The mold may rest on the subchondral bone or on structures external to the articular surface that are within the joint space or on structures external to the joint space. If the mold is designed to rest on the cartilage, an imaging test demonstrating the articular cartilage can be used in one embodiment. This can, for example, include ultrasound, spiral CT arthrography, MRI using, for example, cartilage displaying pulse sequences, or MRI arthrography. In another embodiment, an imaging test demonstrating the subchondral bone, e.g. CT or spiral CT, can be used and a standard cartilage thickness can be added to the scan. The standard cartilage thickness can be derived, for example, using an anatomic reference database, age, gender, and race matching, age adjustments and any method known in the art or developed in the future for deriving estimates of cartilage thickness. The standard cartilage thickness may, in some embodiments, be uniform across one or more articular surfaces or it can change across the articular surface.

The mold may be adapted to rest substantially on subchondral bone. In this case, residual cartilage can create some offset and inaccurate result with resultant inaccuracy in surgical cuts, drilling and the like. In one embodiment, the residual cartilage is removed in a first step in areas where the mold is designed to contact the bone and the subchondral bone is exposed. In a second step, the mold is then placed on the subchondral bone.

With advanced osteoarthritis, significant articular deformity can result. The articular surface(s) can become flattened. There can be cyst formation or osteophyte formation. "Tram track" like structures can form on the articular surface. In one embodiment of the invention, osteophytes or other deformities may be removed by the computer software prior to generation of the mold. The software can automatically, semi-automatically or manually with input from the user simulate surgical removal of the osteophytes or other deformities, and predict the resulting shape of the joint and the associated surfaces. The mold can then be designed based on the predicted shape. Intraoperatively, these osteophytes or other deformities can then also optionally be removed prior to placing the mold and performing the procedure. Alternatively, the mold can be designed to avoid such deformities. For example, the mold may only be in contact with points on the articular surface or external to the articular surface that are not affected or involved by osteophytes. The mold can rest on the articular surface or external to the articular surface on three or more points or small surfaces with the body of the mold elevated or detached from the articular surface so that the accuracy of its position cannot be affected by osteophytes or other articular deformities. The mold can rest on one or more tibial spines or portions of the tibial spines. Alternatively, all or portions of the mold may be designed to rest on osteophytes or other excrescences or pathological changes.

The surgeon can, optionally, make fine adjustments between the alignment device and the instrument guide. In this manner, an optimal compromise can be found, for example, between biomechanical alignment and joint laxity or biomechanical alignment and joint function, e.g. in a knee joint flexion gap and extension gap. By oversizing the openings in the alignment guide, the surgeon can utilize the instruments and insert them in the instrument guide without damaging the alignment guide. Thus, in particular if the alignment guide is made of plastic, debris will not be introduced into the joint. The position and orientation between the alignment guide and the instrument guide can be also be optimized with the use of, for example, interposed spacers, wedges, screws and other mechanical or electrical methods known in the art.

A surgeon may desire to influence joint laxity as well as joint alignment. This can be optimized for different flexion and extension, abduction, or adduction, internal and external rotation angles. For this purpose, for example, spacers can be introduced that are attached or that are in contact with one or more molds. The surgeon can intraoperatively evaluate the laxity or tightness of a joint using spacers with different thickness or one or more spacers with the same thickness. For example, spacers can be applied in a knee joint in the presence of one or more molds and the flexion gap can be evaluated with the knee joint in flexion. The knee joint can then be extended and the extension gap can be evaluated. Ultimately, the surgeon will select an optimal combination of spacers for a given joint and mold. A surgical cut guide can be applied to the mold with the spacers optionally interposed between the mold and the cut guide. In this manner, the exact position of the surgical cuts can be influenced and can be adjusted to achieve an optimal result. Thus, the position of a mold can be optimized relative to the joint, bone or cartilage for soft-tissue tension, ligament balancing or for flexion, extension, rotation, abduction, adduction, anteversion, retroversion and other joint or bone positions and motion. The position of a cut block or other surgical instrument may be optimized relative to the mold for soft-tissue tension or for ligament balancing or for flexion, extension, rotation, abduction, adduction, anteversion, retroversion and other joint or bone positions and motion. Both the position of the mold and the position of other components including cut blocks and surgical instruments may be optimized for soft-tissue tension or for ligament balancing or for flexion, extension, rotation, abduction, adduction, anteversion, retroversion and other joint or bone positions and motion.

Figure 37A:
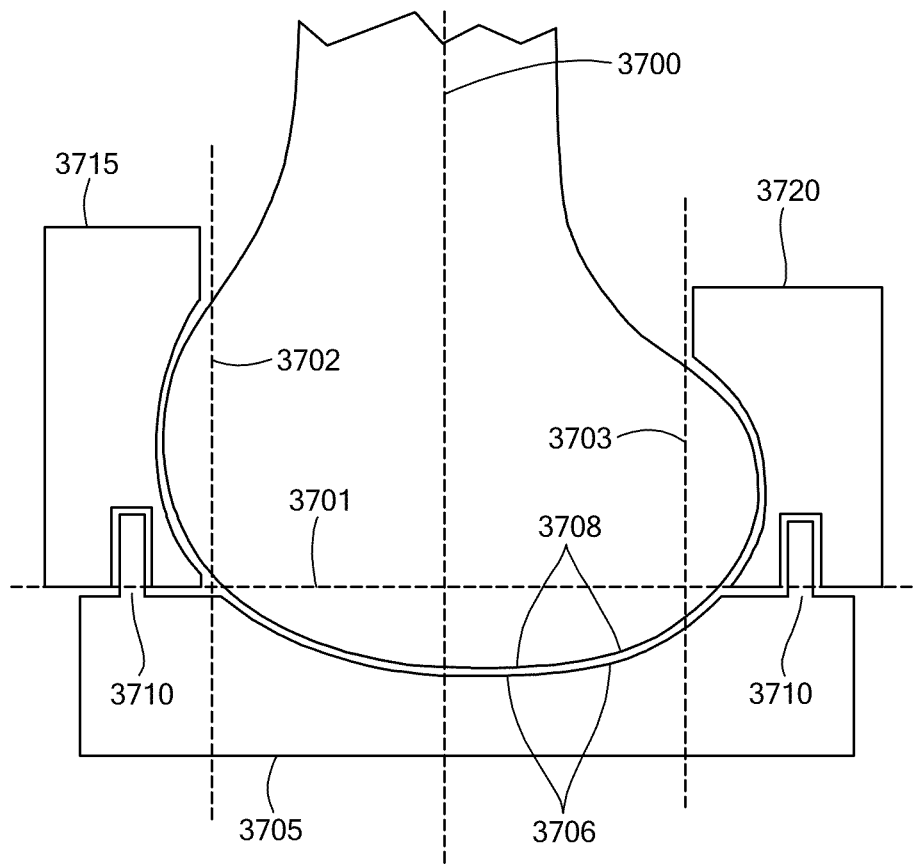
FIGS. 37A-D show multiple molds with linkages on the same articular surface (A-C) and to an opposing articular surface (D), in accordance with various embodiments of the invention.
Figure 37C:
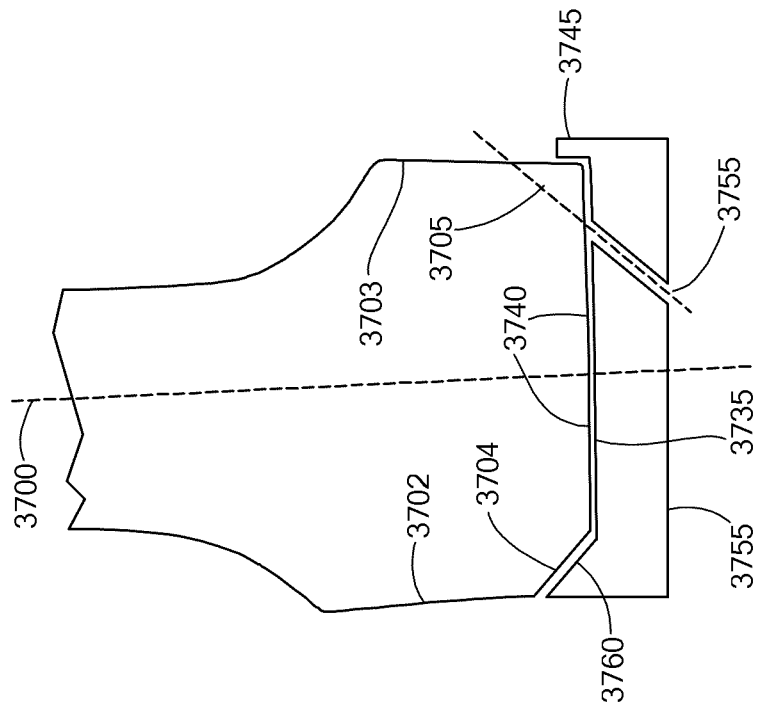
Figure 37B:
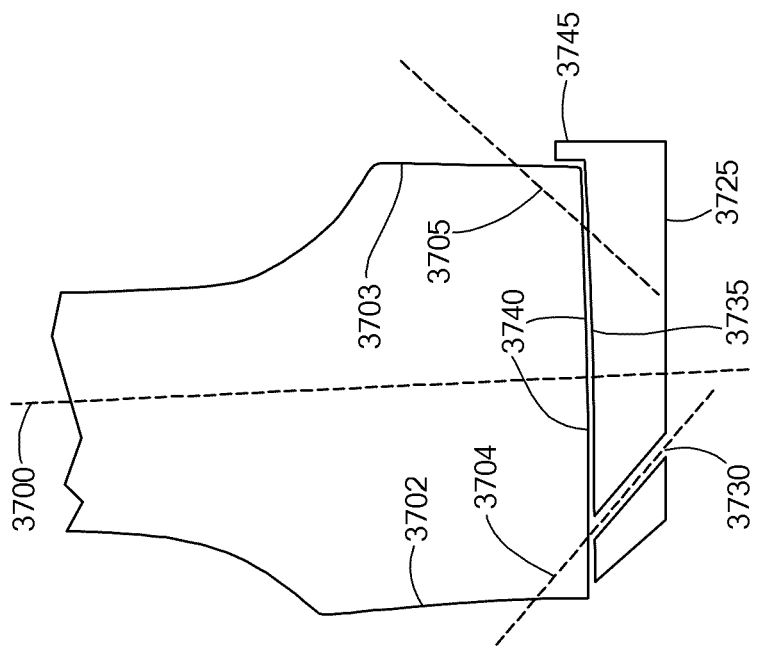
Figure 37D:
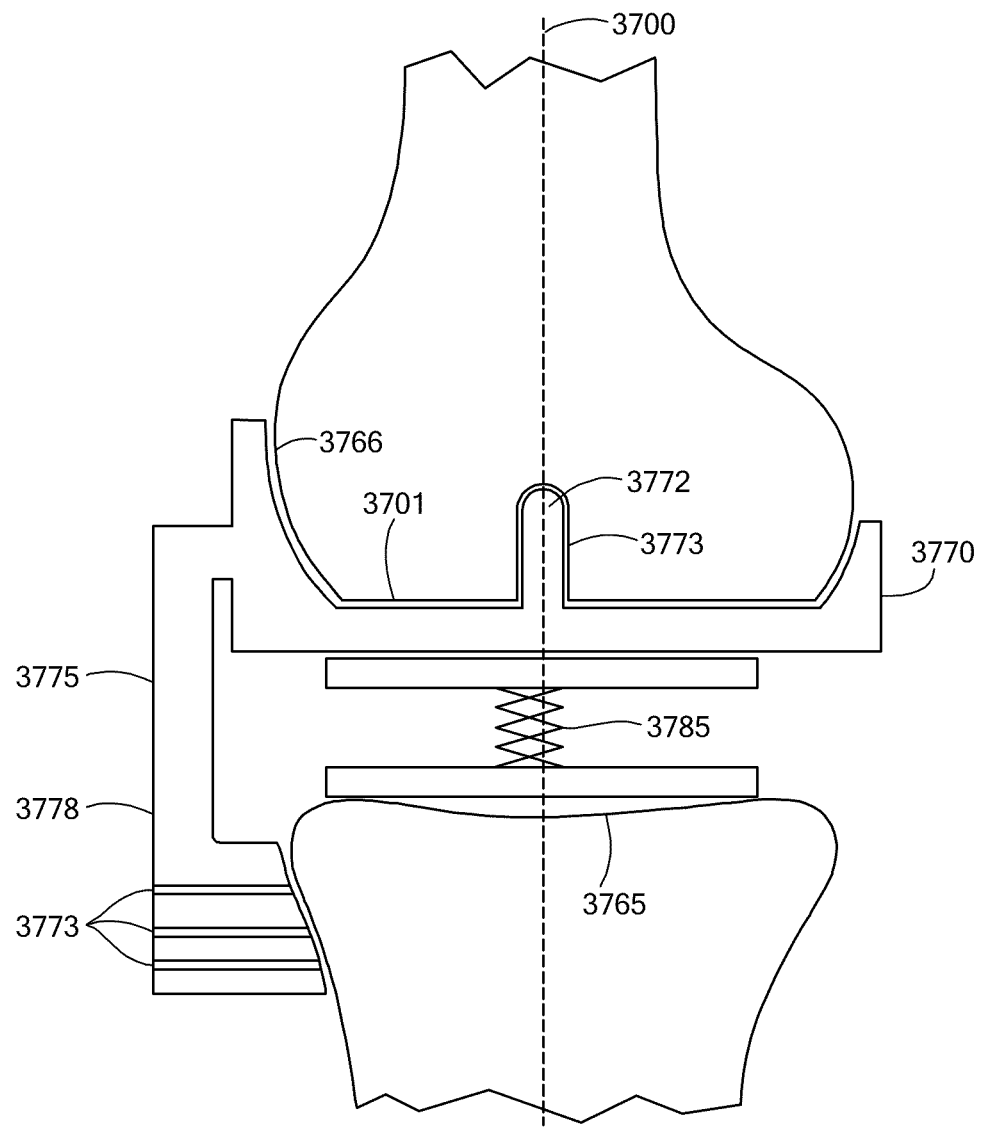

Someone skilled in the art will recognize other means for optimizing the position of the surgical cuts or other interventions. As stated above, expandable or ratchet-like devices may be utilized that can be inserted into the joint or that can be attached or that can touch the mold (see also FIG. 37D). Such devices can extend from a cutting block or other devices attached to the mold, optimizing the position of drill holes or cuts for different joint positions or they can be integrated inside the mold. Integration in the cutting block or other devices attached to the mold is preferable, since the expandable or ratchet-like mechanisms can be sterilized and re-used during other surgeries, for example in other patients. Optionally, the expandable or ratchet-like devices may be disposable. The expandable or ratchet like devices may extend to the joint without engaging or contacting the mold; alternatively, these devices may engage or contact the mold. Hinge-like mechanisms are applicable. Similarly, jack-like mechanisms are useful. In principal, any mechanical or electrical device useful for fine-tuning the position of the cut guide relative to the molds may be used. These embodiments are helpful for soft-tissue tension optimization and ligament balancing in different joints for different static positions and during joint motion.

A surgeon may desire to influence joint laxity as well as joint alignment. This can be optimized for different flexion and extension, abduction, or adduction, internal and external rotation angles. For this purpose, for example, spacers or expandable or ratchet-like can be utilized that can be attached or that can be in contact with one or more molds. The surgeon can intraoperatively evaluate the laxity or tightness of a joint using spacers with different thickness or one or more spacers with the same thickness or using such expandable or ratchet like devices. For example, spacers or a ratchet like device can be applied in a knee joint in the presence of one or more molds and the flexion gap can be evaluated with the knee joint in flexion. The knee joint can then be extended and the extension gap can be evaluated. Ultimately, the surgeon will select an optimal combination of spacers or an optimal position for an expandable or ratchet-like device for a given joint and mold. A surgical cut guide can be applied to the mold with the spacers or the expandable or ratchet-like device optionally interposed between the mold and the cut guide or, in select embodiments, between the mold and the joint or the mold and an opposite articular surface. In this manner, the exact position of the surgical cuts can be influenced and can be adjusted to achieve an optimal result. Someone skilled in the art will recognize other means for optimizing the position of the surgical cuts or drill holes. For example, expandable or ratchet-like devices can be utilized that can be inserted into the joint or that can be attached or that can touch the mold. Hinge-like mechanisms are applicable. Similarly, jack-like mechanisms are useful. In principal, any mechanical or electrical device useful for fine-tuning the position of the cut guide relative to the molds can be used.

The template and any related instrumentation such as spacers or ratchets can be combined with a tensiometer to provide a better intraoperative assessment of the joint. The tensiometer can be utilized to further optimize the anatomic alignment and tightness of the joint and to improve post-operative function and outcomes. Optionally, local contact pressures may be evaluated intraoperatively, for example using a sensor like the ones manufactured by Tekscan, South Boston, Mass. The contact pressures can be measured between the mold and the joint or between the mold and any attached devices such as a surgical cut block.

The template may be a mold that can be made of a plastic or polymer. The mold may be produced by rapid prototyping technology, in which successive layers of plastic are laid down, as know in the art. In other embodiments, the template or portions of the template can be made of metal. The mold can be milled or made using laser based manufacturing techniques.

The template may be casted using rapid prototyping and, for example, lost wax technique. It may also be milled. For example, a preformed mold with a generic shape can be used at the outset, which can then be milled to the patient specific dimensions. The milling may only occur on one surface of the mold, preferably the surface that faces the articular surface. Milling and rapid prototyping techniques may be combined.

Curable materials may be used which can be poured into forms that are, for example, generated using rapid prototyping. For example, liquid metal may be used. Cured materials may optionally be milled or the surface can be further refined using other techniques.

Metal inserts may be applied to plastic components. For example, a plastic mold may have at least one guide aperture to accept a reaming device or a saw. A metal insert may be used to provide a hard wall to accept the reamer or saw. Using this or similar designs can be useful to avoid the accumulation of plastic or other debris in the joint when the saw or other surgical instruments may get in contact with the mold. Other hard materials can be used to serve as inserts. These can also include, for example, hard plastics or ceramics.

In another embodiment, the mold does not have metallic inserts to accept a reaming device or saw. The metal inserts or guides may be part of an attached device, that is typically in contact with the mold. A metallic drill guide or a metallic saw guide may thus, for example, have metallic or hard extenders that reach through the mold thereby, for example, also stabilizing any devices applied to the mold against the physical body of the mold.

The template may not only be used for assisting the surgical technique and guiding the placement and direction of surgical instruments. In addition, the templates can be utilized for guiding the placement of the implant or implant components. For example, in the hip joint, tilting of the acetabular component is a frequent problem with total hip arthroplasty. A template can be applied to the acetabular wall with an opening in the center large enough to accommodate the acetabular component that the surgeon intends to place. The template can have receptacles or notches that match the shape of small extensions that can be part of the implant or that can be applied to the implant. For example, the implant can have small members or extensions applied to the twelve o'clock and six o'clock positions. See, for example, FIG. 9A-D, discussed below. By aligning these members with notches or receptacles in the mold, the surgeon can ensure that the implant is inserted without tilting or rotation. These notches or receptacles can also be helpful to hold the implant in place while bone cement is hardening in cemented designs.

One or more templates can be used during the surgery. For example, in the hip, a template can be initially applied to the proximal femur that closely approximates the 3D anatomy prior to the resection of the femoral head. The template can include an opening to accommodate a saw (see FIGS. 8-9). The opening is positioned to achieve an optimally placed surgical cut for subsequent reaming and placement of the prosthesis. A second template can then be applied to the proximal femur after the surgical cut has been made. The second template can be useful for guiding the direction of a reamer prior to placement of the prosthesis. As can be seen in this, as well as in other examples, templates can be made for joints prior to any surgical intervention. However, it is also possible to make templates that are designed to fit to a bone or portions of a joint after the surgeon has already performed selected surgical procedures, such as cutting, reaming, drilling, etc. The template can account for the shape of the bone or the joint resulting from these procedures.

In certain embodiments, the surgical assistance device comprises an array of adjustable, closely spaced pins (e.g., plurality of individually moveable mechanical elements). One or more electronic images or intraoperative measurements can be obtained providing object coordinates that define the articular and/or bone surface and shape. These objects' coordinates can be entered or transferred into the device, for example manually or electronically, and the information can be used to create a surface and shape that will match all or portions of the articular and/or bone surface and shape by moving one or more of the elements, e.g. similar to an "image." The device can include slots and holes to accommodate surgical instruments such as drills, curettes, k-wires, screws and saws. The position of these slots and holes may be adjusted by moving one or more of the mechanical elements. Typically, a position will be chosen that will result in an anatomically desirable cut plane, reaming direction, or drill hole or instrument orientation for subsequent placement of an articular repair system or for facilitating the placement of an articular repair system.

Information about other joints or axis and alignment information of a joint or extremity can be included when selecting the position of the, without limitation, cut planes, apertures, slots or holes on the template, in accordance with an embodiment of the invention. The biomechanical and/or anatomic axes may be derived using above-described imaging techniques including, without limitation, a standard radiograph, including a load bearing radiograph, for example an upright knee x-ray or a whole leg length film (e.g., hip to foot) These radiographs may be acquired in different projections, for example anteroposterior, posteroanterior, lateral, oblique etc. The biomechanical and anatomic axes may also be derived using other imaging modalities such as CT scan or MRI scan, a CT scout scan or MRI localized scans through portions or all of the extremity, either alone or in combination, as described in above embodiments. For example, when total or partial knee arthroplasty is contemplated, a spiral CT scan may be obtained through the knee joint. The spiral CT scan through the knee joint serves as the basis for generating the negative contour template(s)/mold(s) that will be affixed to portions or all of the knee joint. Additional CT or MRI scans may be obtained through the hip and ankle joint. These may be used to define the centroids or centerpoints in each joint or other anatomic landmarks, for example, and then to derive the biomechanical and other axes.

In another embodiment, the biomechanical axis may be established using non-image based approaches including traditional surgical instruments and measurement tools such as intramedullary rods, alignment guides and also surgical navigation. For example, in a knee joint, optical or radiofrequency markers can be attached to the extremity. The lower limb may then be rotated around the hip joint and the position of the markers can be recorded for different limb positions. The center of the rotation will determine the center of the femoral head. Similar reference points may be determined in the ankle joint etc. The position of the templates or, more typically, the position of surgical instruments relative to the templates may then be optimized for a given biomechanical load pattern, for example in varus or valgus alignment. Thus, by performing these measurements pre- or intraoperatively, the position of the surgical instruments may be optimized relative to the molds and the cuts can be placed to correct underlying axis errors such as varus or valgus malalignment or ante- or retroversion.

Upon imaging, a physical template of a joint, such as a knee joint, or hip joint, or ankle joint or shoulder joint is generated, in accordance with an embodiment of the invention. The template can be used to perform image guided surgical procedures such as partial or complete joint replacement, articular resurfacing, or ligament repair. The template may include reference points or opening or apertures for surgical instruments such as drills, saws, burrs and the like.

In order to derive the preferred orientation of drill holes, cut planes, saw planes and the like, openings or receptacles in said template or attachments will be adjusted to account for at least one axis. The axis can be anatomic or biomechanical, for example, for a knee joint, a hip joint, an ankle joint, a shoulder joint or an elbow joint.

In one embodiment, only a single axis is used for placing and optimizing such drill holes, saw planes, cut planes, and or other surgical interventions. This axis may be, for example, an anatomical or biomechanical axis. In a preferred embodiment, a combination of axis and/or planes can be used for optimizing the placement of the drill holes, saw planes, cut planes or other surgical interventions. For example, two axes (e.g., one anatomical and one biomechanical) can be factored into the position, shape or orientation of the 3D guided template and related attachments or linkages. For example, two axes, (e.g., one anatomical and biomechanical) and one plane (e.g., the top plane defined by the tibial plateau), can be used. Alternatively, two or more planes can be used (e.g., a coronal and a sagittal plane), as defined by the image or by the patients anatomy.

Angle and distance measurements and surface topography measurements may be performed in these one or more, preferably two or more, preferably three or more multiple planes, as necessary. These angle measurements can, for example, yield information on varus or valgus deformity, flexion or extension deficit, hyper or hypo-flexion or hyper- or hypo-extension, abduction, adduction, internal or external rotation deficit, or hyper- or hypo-abduction, hyper- or hypo-adduction, hyper- or hypo-internal or external rotation.

Single or multi-axis line or plane measurements can then be utilized to determine preferred angles of correction, e.g., by adjusting surgical cut or saw planes or other surgical interventions. Typically, two axis corrections will be preferred over a single axis correction, a two plane correction will be preferred over a single plane correction and so forth.

In accordance with another embodiment of the invention, more than one drilling, cut, boring and/or reaming or other surgical intervention is performed for a particular treatment such as the placement of a joint resurfacing or replacing implant, or components thereof. These two or more surgical interventions (e.g., drilling, cutting, reaming, sawing) are made in relationship to a biomechanical axis, and/or an anatomical axis and/or an implant axis. The 3D guidance template or attachments or linkages thereto include two or more openings, guides, apertures or reference planes to make at least two or more drillings, reamings, borings, sawings or cuts in relationship to a biomechanical axis, an anatomical axis, an implant axis or other axis derived therefrom or related thereto.

While in simple embodiments it is possible that only a single cut or drilling will be made in relationship to a biomechanical axis, an anatomical axis, an implant axis and/or an axis related thereto, in most meaningful implementations, two or more drillings, borings, reamings, cutting and/or sawings will be performed or combinations thereof in relationship to a biomechanical, anatomical and/or implant axis.

For example, an initial cut may be placed in relationship to a biomechanical axis of particular joint. A subsequent drilling, cut or other intervention can be performed in relation to an anatomical axis. Both can be designed to achieve a correction in a biomechanical axis and/or anatomical axis. In another example, an initial cut can be performed in relationship to a biomechanical axis, while a subsequent cut is performed in relationship to an implant axis or an implant plane. Any combination in surgical interventions and in relating them to any combination of biomechanical, anatomical, implant axis or planes related thereto is possible. In many embodiments of the invention, it is desirable that a single cut or drilling be made in relationship to a biomechanical or anatomical axis. Subsequent cuts or drillings or other surgical interventions can then be made in reference to said first intervention. These subsequent interventions can be performed directly off the same 3D guidance template or they can be performed by attaching surgical instruments or linkages or reference frames or secondary or other templates to the first template or the cut plane or hole and the like created with the first template.

Figure 22:
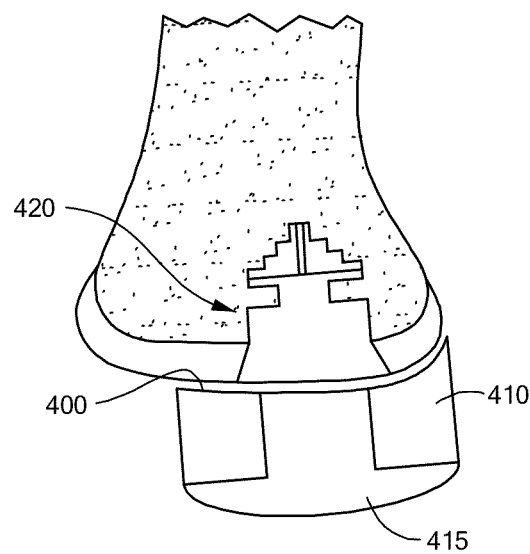
FIG. 22 shows an example of a surgical tool having one surface matching the geometry of an articular surface of the joint, in accordance with one embodiment of the invention. Also shown is an aperture in the tool capable of controlling drill depth and width of the hole and allowing implantation of an insertion of implant having a press-fit design.

FIG. 22 shows an example of a surgical tool 410 having one surface 400 matching the geometry of an articular surface of the joint. Also shown is an aperture 415 in the tool 410 capable of controlling drill depth and width of the hole and allowing implantation or insertion of implant 420 having a press-fit design.

In another embodiment, a frame can be applied to the bone or the cartilage in areas other than the diseased bone or cartilage. The frame can include holders and guides for surgical instruments. The frame can be attached to one or preferably more previously defined anatomic reference points. Alternatively, the position of the frame can be cross-registered relative to one, or more, anatomic landmarks, using an imaging test or intraoperative measurement, for example one or more fluoroscopic images acquired intraoperatively. One or more electronic images or intraoperative measurements including using mechanical devices can be obtained providing object coordinates that define the articular and/or bone surface and shape. These objects' coordinates can be entered or transferred into the device, for example manually or electronically, and the information can be used to move one or more of the holders or guides for surgical instruments. Typically, a position will be chosen that will result in a surgically or anatomically desirable cut plane or drill hole orientation for subsequent placement of an articular repair system. Information about other joints or axis and alignment information of a joint or extremity can be included when selecting the position of these slots or holes.

Furthermore, re-useable tools (e.g., molds) can be also be created and employed. Non-limiting examples of re-useable materials include putties and other deformable materials (e.g., an array of adjustable closely spaced pins that can be configured to match the topography of a joint surface). In other embodiments, the molds may be made using balloons. The balloons can optionally be filled with a hardening material. A surface can be created or can be incorporated in the balloon that allows for placement of a surgical cut guide, reaming guide, drill guide or placement of other surgical tools. The balloon or other deformable material can be shaped intraoperatively to conform to at least one articular surface. Other surfaces can be shaped in order to be parallel or perpendicular to anatomic or biomechanical axes. The anatomic or biomechanical axes can be found using an intraoperative imaging test or surgical tools commonly used for this purpose in hip, knee or other arthroplasties.

In various embodiments, the template may include a reference element, such as a pin, that upon positioning of the template on the articular surface, establishes a reference plane relative to a biomechanical axis or an anatomical axis or plane of a limb. For example, in a knee surgery the reference element may establish a reference plane from the center of the hip to the center of the ankle. In other embodiments, the reference element may establish an axis that subsequently be used a surgical tool to correct an axis deformity.

In these embodiments, the template can be created directly from the joint during surgery or, alternatively, created from an image of the joint, for example, using one or more computer programs to determine object coordinates defining the surface contour of the joint and transferring (e.g., dialing-in) these co-ordinates to the tool. Subsequently, the tool can be aligned accurately over the joint and, accordingly, the surgical instrument guide or the implant will be more accurately placed in or over the articular surface.

In both single-use and re-useable embodiments, the tool can be designed so that the instrument controls the depth and/or direction of the drill, i.e., the drill cannot go any deeper into the tissue than the instrument allows, and the size of the hole or aperture in the instrument can be designed to essentially match the size of the implant. The tool can be used for general prosthesis implantation, including, but not limited to, the articular repair implants described herein and for reaming the marrow in the case of a total arthroplasty.

These surgical tools (devices) can also be used to remove an area of diseased cartilage and underlying bone or an area slightly larger than the diseased cartilage and underlying bone. In addition, the device can be used on a "donor," e.g., a cadaveric specimen, to obtain implantable repair material. The device is typically positioned in the same general anatomic area in which the tissue was removed in the recipient. The shape of the device is then used to identify a donor site providing a seamless or near seamless match between the donor tissue sample and the recipient site. This can be achieved by identifying the position of the device in which the articular surface in the donor, e.g. a cadaveric specimen, has a seamless or near seamless contact with the inner surface when applied to the cartilage.

The device can be molded, rapid prototyped, machine and/or formed based on the size of the area of diseased cartilage and based on the curvature of the cartilage or the underlying subchondral bone or a combination of both or using adjacent structures inside or external to the joint space. The device can take into consideration surgical removal of, for example, the meniscus, in arriving at a joint surface configuration.

In one embodiment, the device can then be applied to the donor, (e.g., a cadaveric specimen) and the donor tissue can be obtained with use of a blade or saw or other tissue removing device. The device can then be applied to the recipient in the area of the joint and the diseased cartilage, where applicable, and underlying bone can be removed with use of a blade or saw or other tissue cutting device whereby the size and shape of the removed tissue containing the diseased cartilage will closely resemble the size and shape of the donor tissue. The donor tissue can then be attached to the recipient site. For example, said attachment can be achieved with use of screws or pins (e.g., metallic, non-metallic or bioresorable) or other fixation means including but not limited to a tissue adhesive. Attachment can be through the cartilage surface or alternatively, through the marrow space.

The implant site can be prepared with use of a robotic device. The robotic device can use information from an electronic image for preparing the recipient site.

Identification and preparation of the implant site and insertion of the implant can be supported by a surgical navigation system. In such a system, the position or orientation of a surgical instrument with respect to the patient's anatomy can be tracked in real-time in one or more 2D or 3D images. These 2D or 3D images can be calculated from images that were acquired preoperatively, such as MR or CT images. Non-image based surgical navigation systems that find axes or anatomical structures, for example with use of joint motion, can also be used. The position and orientation of the surgical instrument as well as the mold including alignment guides, surgical instrument guides, reaming guides, drill guides, saw guides, etc. can be determined from markers attached to these devices. These markers can be located by a detector using, for example, optical, acoustical or electromagnetic signals.

Identification and preparation of the implant site and insertion of the implant can also be supported with use of a C-arm system. The C-arm system can afford imaging of the joint in one or, preferably, multiple planes. The multiplanar imaging capability can aid in defining the shape of an articular surface. This information can be used to selected an implant with a good fit to the articular surface. Currently available C-arm systems also afford cross-sectional imaging capability, for example for identification and preparation of the implant site and insertion of the implant. C-arm imaging can be combined with administration of radiographic contrast.

In various embodiments, the surgical devices described herein can include one or more materials that harden to form a mold of the articular surface. In preferred embodiments, the materials used are biocompatible, such as, without limitation, acylonitrile butadiene styrene, polyphenylsulfone and polycarbonate. As used herein "biocompatible" shall mean any material that is not toxic to the body (e.g., produces a negative reaction undert ISO 10993 standards, incorporated herein by reference). In various embodiments, these biocompatible materials may be compatible with rapid prototyping techniques.

In further embodiments, the mold material is capable of heat sterilization without deformation. An exemplary mold material is polyphenylsulfone, which does not deform up to a temperature of 207° celcius. Alternatively, the mold may be capable of sterilization using gases, e.g. ethyleneoxide. The mold may be capable of sterilization using radiation, e.g. γ-radiation. The mold may be capable of sterilization using hydrogen peroxide or other chemical means. The mold may be capable of sterilization using any one or more methods of sterilization known in the art or developed in the future.

A wide-variety of materials capable of hardening in situ include polymers that can be triggered to undergo a phase change, for example polymers that are liquid or semi-liquid and harden to solids or gels upon exposure to air, application of ultraviolet light, visible light, exposure to blood, water or other ionic changes. (See, also, U.S. Pat. No. 6,443,988 to Felt et al. issued Sep. 3, 2002 and documents cited therein). Non-limiting examples of suitable curable and hardening materials include polyurethane materials (e.g., U.S. Pat. No. 6,443,988 to Felt et al., U.S. Pat. No. 5,288,797 to Khalil issued Feb. 22, 1994, U.S. Pat. No. 4,098,626 to Graham et al. issued Jul. 4, 1978 and U.S. Pat. No. 4,594,380 to Chapin et al. issued Jun. 10, 1986; and Lu et al. (2000) BioMaterials 21(15):1595-1605 describing porous poly(L-lactide acid foams); hydrophilic polymers as disclosed, for example, in U.S. Pat. No. 5,162,430; hydrogel materials such as those described in Wake et al. (1995) Cell Transplantation 4(3): 275-279, Wiese et al. (2001) J. Biomedical Materials Research 54(2):179-188 and Marler et al. (2000) Plastic Reconstruct. Surgery 105(6):2049-2058; hyaluronic acid materials (e.g., Duranti et al. (1998) Dermatologic Surgery 24(12):1317-1325); expanding beads such as chitin beads (e.g., Yusof et al. (2001) J. Biomedical Materials Research 54(1):59-68); crystal free metals such as Liquidmetals®, and/or materials used in dental applications (See, e.g., Brauer and Antonucci, "Dental Applications" pp. 257-258 in "Concise Encyclopedia of Polymer Science and Engineering" and U.S. Pat. No. 4,368,040 to Weissman issued Jan. 11, 1983). Any biocompatible material that is sufficiently flowable to permit it to be delivered to the joint and there undergo complete cure in situ under physiologically acceptable conditions can be used. The material can also be biodegradable.

The curable materials can be used in conjunction with a surgical tool as described herein. For example, the surgical tool can be a template that includes one or more apertures therein adapted to receive injections and the curable materials can be injected through the apertures. Prior to solidifying in situ the materials will conform to the articular surface (subchondral bone and/or articular cartilage) facing the surgical tool and, accordingly, will form a mirror image impression of the surface upon hardening, thereby recreating a normal or near normal articular surface.

In addition, curable materials or surgical tools can also be used in conjunction with any of the imaging tests and analysis described herein, for example by molding these materials or surgical tools based on an image of a joint. For example, rapid prototyping may be used to perform automated construction of the template. The rapid prototyping may include the use of, without limitation, 3D printers, stereolithography machines or selective laser sintering systems. Rapid prototyping is a typically based on computer-aided manufacturing (CAM). Although rapid prototyping traditionally has been used to produce prototypes, they are now increasingly being employed to produce tools or even to manufacture production quality parts. In an exemplary rapid prototyping method, a machine reads in data from a CAD drawing, and lays down successive millimeter-thick layers of plastic or other engineering material, and in this way the template can be built from a long series of cross sections. These layers are glued together or fused (often using a laser) to create the cross section described in the CAD drawing.

Figure 23:
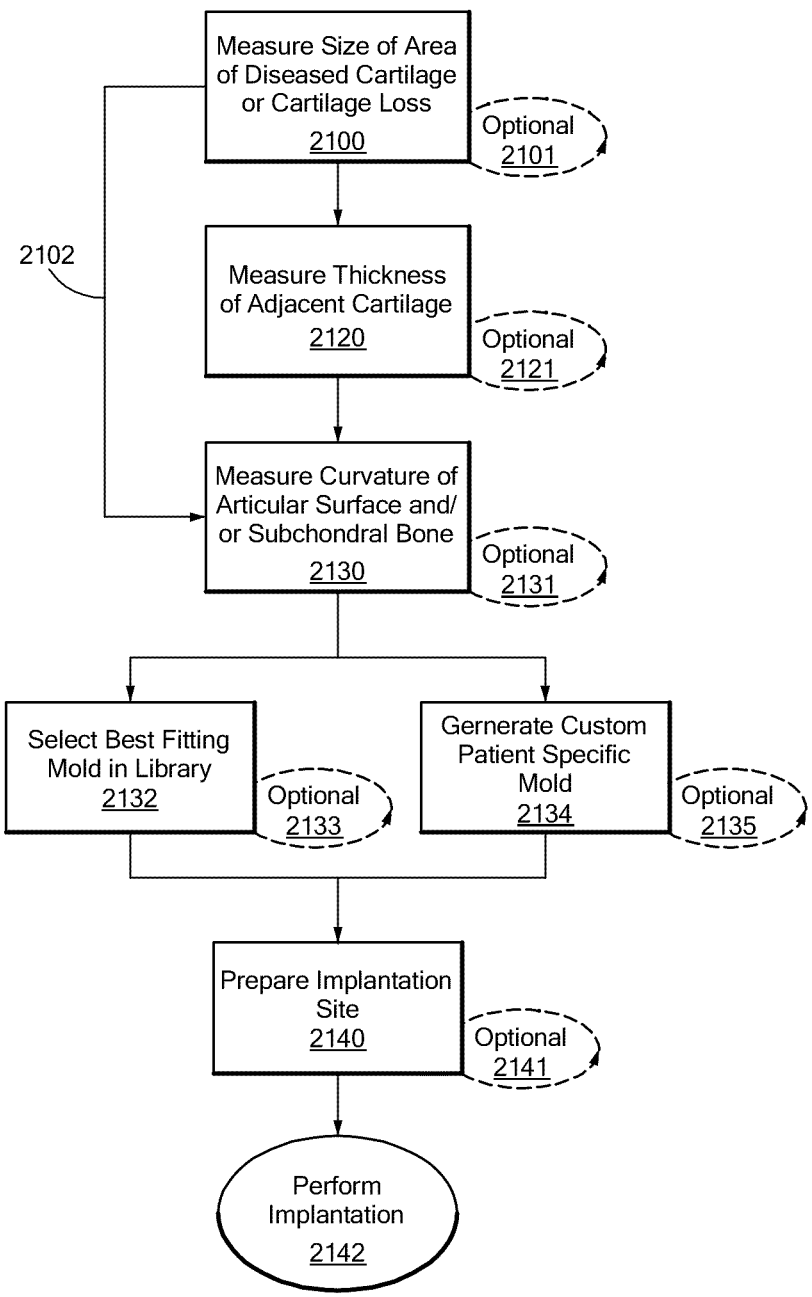
FIG. 23 is a flow chart depicting various methods of the invention used to create a mold for preparing a patient's joint for arthroscopic surgery, in accordance with one embodiment of the invention.

FIG. 23 is a flow chart illustrating the steps involved in designing a mold for use in preparing a joint surface. Optionally, the first step can be to measure the size of the area of the diseased cartilage or cartilage loss 2100, Once the size of the cartilage loss has been measured, the user can measure the thickness of the adjacent cartilage 2120, prior to measuring the curvature of the articular surface and/or the subchondral bone 2130. Alternatively, the user can skip the step of measuring the thickness of the adjacent cartilage 2102. Once an understanding and determination of the shape of the subchondral bone is determined, either a mold can be selected from a library of molds 3132 or a patient specific mold can be generated 2134. In either event, the implantation site is then prepared 2140 and implantation is performed 2142. Any of these steps can be repeated by the optional repeat steps 2101, 2121, 2131, 2133, 2135, 2141.

A variety of techniques can be used to derive the shape of the template, as described above. For example, a few selected CT slices through the hip joint, along with a full spiral CT through the knee joint and a few selected slices through the ankle joint can be used to help define the axes if surgery is contemplated of the knee joint. Once the axes are defined, the shape of the subchondral bone can be derived, followed by applying standardized cartilage loss.

Methodologies for stabilizing the 3D guidance templates will now be described. The 3D guide template may be stabilized using multiple surgical tools such as, without limitation: K-wires, a drill bit anchored into the bone and left within the template to stabilize it against the bone; one or more convexities or cavities on the surface facing the cartilage; bone stabilization against intra/extra articular surfaces, optionally with extenders, for example, from an articular surface onto an extra-articular surface; and/or stabilization against newly placed cuts or other surgical interventions.

Specific anatomic landmarks may be selected in the design and make of the 3D guide template in order to further optimize the anatomic stabilization. For example, a 3D guidance template may be designed to cover portions or all off an osteophyte or bone spur in order to enhance anchoring of the 3D guide template against the underlying articular anatomy. The 3D guidance template may be designed to the shape of a trochlear or intercondylar notch and can encompass multiple anatomic areas such as a trochlea, a medial and a lateral femoral condyle at the same time. In the tibia, a 3D guide template may be designed to encompass a medial and lateral tibial plateau at the same time and it can optionally include the tibial spine for optimized stabilization and cross-referencing. In a hip, the fovea capitis may be utilized in order to stabilize a 3D guide template. Optionally, the surgeon may elect to resect the ligamentum capitis femoris in order to improve the stabilization. Also in the hip, an acetabular mold can be designed to extend into the region of the tri-radiate cartilage, the medial, lateral, superior, inferior, anterior and posterior acetabular wall or ring. By having these extensions and additional features for stabilization, a more reproducible position of the 3D template can be achieved with resulted improvement in accuracy of the surgical procedure. Typically, a template with more than one convexity or concavity or multiple convexities or concavities will provide better cross-referencing in the anatomic surface and higher accuracy and higher stabilization than compared to a mold that has only few surface features such as a singular convexity. Thus, in order to improve the implementation and intraoperative accuracy, careful surgical planning and preoperative planning is desired, that encompasses preferably more than one convexity, more preferred more than two convexities and even more preferred more than three convexities, or that encompasses more than one concavity, more preferred more than two concavities or even more preferred more than three concavities on an articular surface or adjoined surface, including bone and cartilage outside the weight-bearing surface.

In an even more preferred embodiment, more than one convexity and concavity, more preferred more than two convexities and concavities and even more preferred more then three convexities and concavities are included in the surface of the mold in order to optimize the interoperative cross-referencing and in order to stabilize the mold prior to any surgical intervention.

Turning now to particular 3D surgical template configurations and to templates for specific joint applications which are intended to teach the concept of the design as it would then apply to other joints in the body:

i. 3D Guidance Template Configurations/Positioning

The 3D guidance template may include a surface that duplicates the inner surface of an implant or an implant component, and/or that conforms to an articular surface, at least partially, in accordance with an embodiment of the invention. More than one of the surfaces of the template may match or conform to one or more of the surfaces or portions of one or more of these surfaces of an implant, implant component, and/or articular surface.

Figures 30, 31:
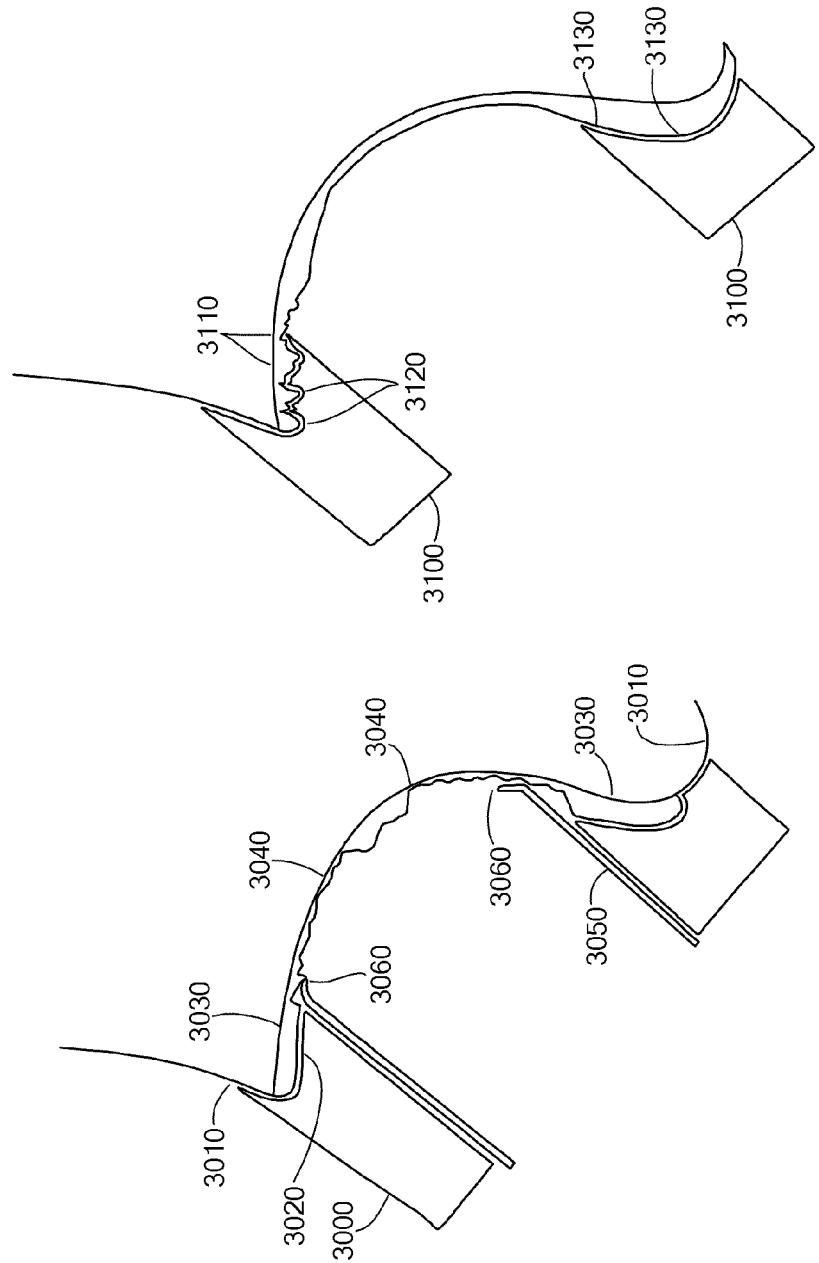
FIG. 30 illustrates a 3D guidance template in a hip joint, wherein the surface of the template facing the joint is a mirror image of a portion of the joint that is not affected by the arthritic process, in accordance with one embodiment of the invention.
FIG. 31 illustrates a 3D guidance template for an acetabulum, wherein the surface of the template facing the joint is a mirror image of a portion of the joint that is affected by the arthritic process, in accordance with an embodiment of the invention.

FIG. 30 shows an example of a 3D guidance template 3000 in a hip joint, in accordance with one embodiment of the invention, wherein the template has extenders 3010 extending beyond the margin of the joint to provide for additional stability and to fix the template in place. The surface of the template facing the joint 3020 is a mirror image of a portion of the joint that is not affected by the arthritic process 3030. By designing the template to be a mirror image of at least a portion of the joint that is not affected by the arthritic process, greater reproducibility in placing the template can be achieved. In this design, the template spares the arthritic portions 3040 of the joint and does not include them in its joint facing surface. The template can optionally have metal sleeves 3050 to accommodate a reamer or other surgical instruments, to protect a plastic. The metal sleeves or, optionally, the template can also include stops 3060 to limit the advancement of a surgical instrument once a predefined depth has been reached.

FIG. 31 shows another embodiment of a 3D guidance template 3100 for an acetabulum, in accordance with an embodiment of the invention. The articular surface is roughened 3110 in some sections by the arthritic process. At least a portion of the template 3120 is made to be a mirror image of the articular surface altered by the arthritic process 3110. By matching the template to the joint in areas where it is altered by the arthritic process improved intraoperative localization and improved fixation can be achieved. In other section, the template can be matched to portions of the joint that are not altered by the arthritic process 3130.

FIG. 32 shows another embodiment of a 3D guidance template 3200 designed to guide a posterior cut 3210 using a posterior reference plane 3220. The joint facing surface of the template 3230 is, at least in part, a mirror image of portions of the joint that are not altered by the arthritic process. The arthritic process includes an osteophyte 3240. The template includes a recess 3250 that helps avoid the osteophyte 3240. The template is at least in part substantially matched to portions of the joint that are not involved by the arthritic process.

FIG. 33 shows another embodiment of a 3D guidance template 3300 designed to guide an anterior cut 3310 using an anterior reference plane 3320. The joint facing surface of the template 3230 is, at least in part, a mirror image of portions of the joint that are altered by the arthritic process. The arthritic process includes an osteophyte 3240. The joint facing surface of the template 3230 is a mirror image of the arthritic process, at least in part, including the osteophyte 3240. The template is at least in part substantially matched to portions of the joint that are involved by the arthritic process.

Figure 34:
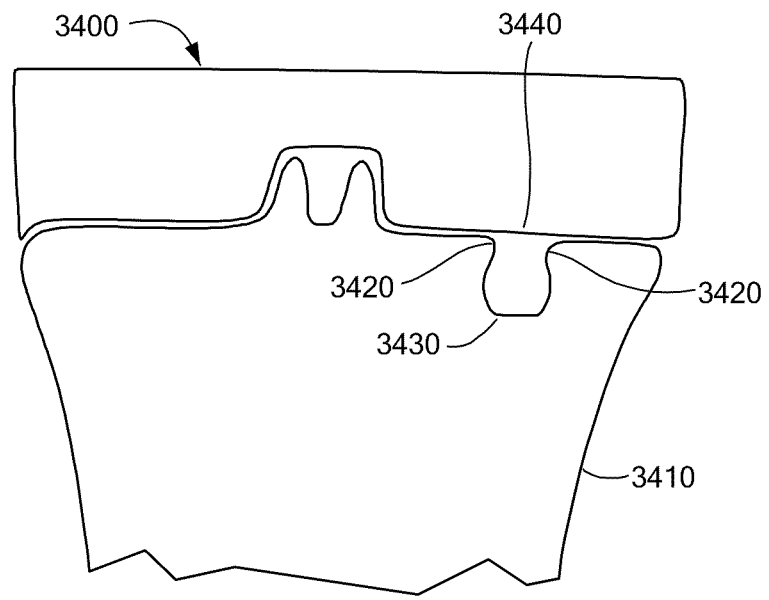
FIG. 34 illustrates a 3D guidance template for guiding a tibial cut (not shown), wherein the tibia includes an arthritic portion, in accordance with an embodiment of the invention. The template is designed to avoid the arthritic process by spanning across a defect or cyst.

FIG. 34 shows another embodiment of a 3D guidance template 3400 for guiding a tibial cut (not shown), wherein the tibia 3410 includes an arthritic portion 3420, in this example a subchondral cyst 3430. The template is designed to avoid the arthritic process by spanning across 3440 the defect or cyst.

Figure 35:
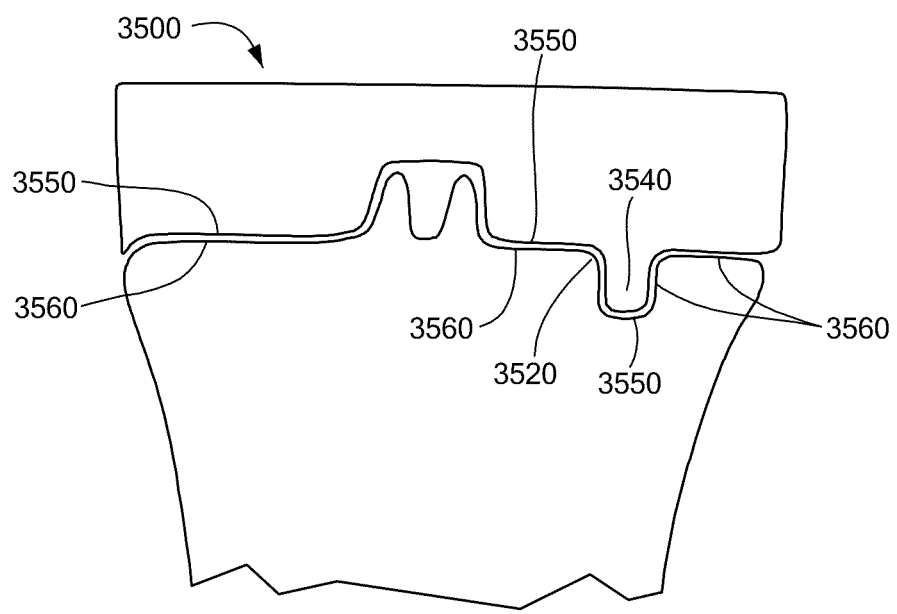
FIG. 35 illustrates a 3D guidance template for guiding a tibial cut, in accordance with an embodiment of the invention. The interface between normal and arthritic tissue is included in the shape of the template.

FIG. 35 shows another embodiment of a 3D guidance template 3500 for guiding a tibial cut (not shown), wherein the tibia 3510 includes an arthritic portion 3520, in this example a subchondral cyst 3530. The template is designed to include the arthritic process 3520 by extending into 3540 the defect or cyst 3530. The surface of the template facing the joint 3550 is a mirror image of portions of normal joint 3560 and portions of the joint that are altered by the arthritic process 3530. The interface between normal and arthritic tissue is included in the shape of the template 3520.

FIGS. 36A-D show a knee joint with a femoral condyle 3600 including a normal 3610 and arthritic 3620 region, in accordance with various embodiments of the invention. The interface 3630 between normal 3610 and arthritic 3620 tissue is shown. The template is designed to guide a posterior cut 3640 using a guide plane 3650 or guide aperture 3660.

Figure 36A:
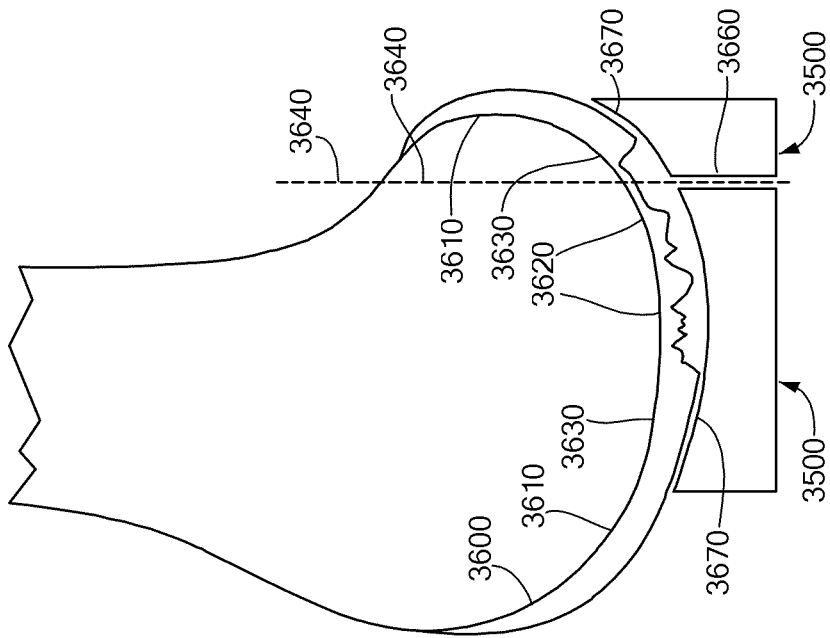
FIG. 36A illustrates a 3D guidance template wherein the surface of the template facing the joint is a mirror image of at least portions of the surface of a joint that is healthy or substantially unaffected by the arthritic process, in accordance with an embodiment of the invention.

In one embodiment shown in FIG. 36A the surface of the template facing the joint 3670 is a mirror image of at least portions of the surface of the joint that is healthy or substantially unaffected by the arthritic process. A recessed area 3670 can be present to avoid contact with the diseased joint region. This design can be favorable when an imaging test is used that does not provide sufficient detail about the diseased region of the joint to accurately generate a template.

Figure 36B:
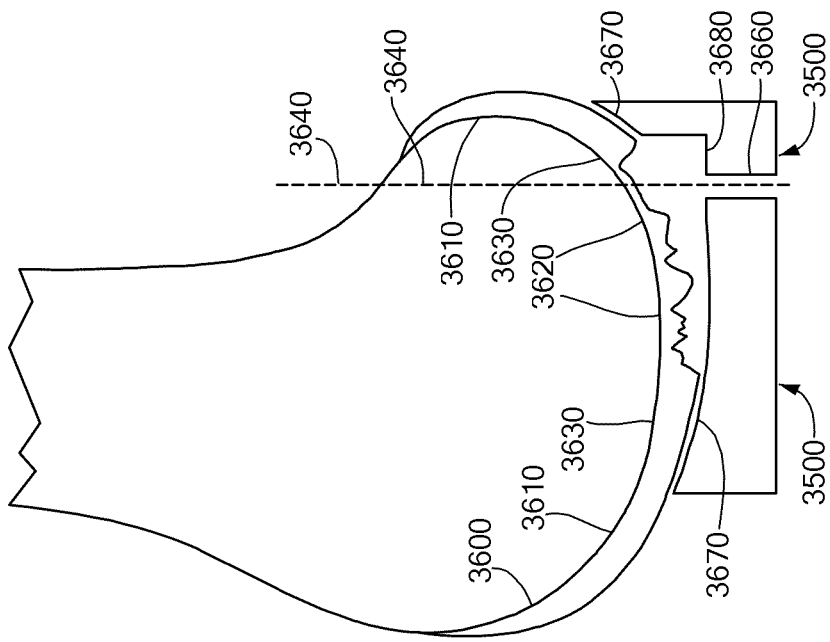
FIG. 36B illustrates the 3D guidance template wherein the surface of the template facing the joint is a mirror image of at least portions of the surface of the joint that is healthy or substantially unaffected by the arthritic process, in accordance with an embodiment of the invention. The diseased area is covered by the template, but the mold is not substantially in contact with it.

In a similar embodiment shown in FIG. 36B the surface of the template facing the joint 3670 is a mirror image of at least portions of the surface of the joint that is healthy or substantially unaffected by the arthritic process. The diseased area 3620 is covered by the template, but the template is not substantially in contact with it.

Figure 36D:
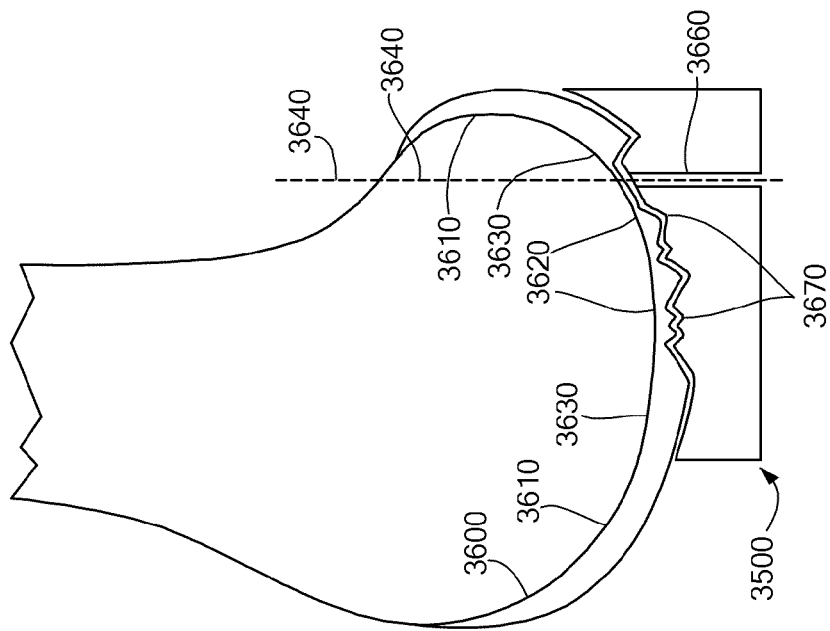
FIG. 36D illustrates the 3D guidance template wherein the template closely mirrors the shape of the interface between substantially normal or near normal and diseased joint tissue, in accordance with an embodiment of the invention.
Figure 36C:
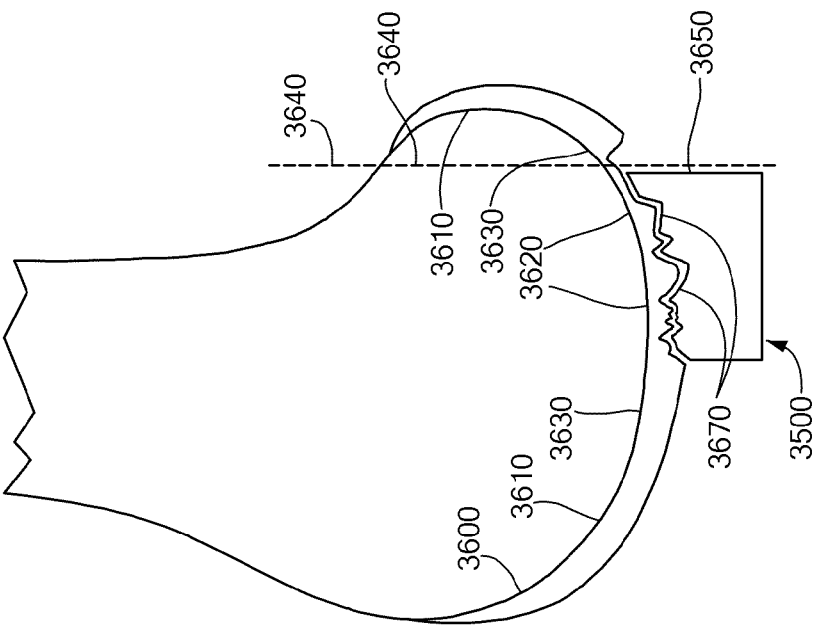
FIG. 36C illustrates the 3D guidance template wherein the surface of the template facing the joint is a mirror image of at least portions of the surface of the joint that are arthritic, in accordance with an embodiment of the invention.

In another embodiment shown in FIG. 36C the surface of the template facing the joint 3670 is a mirror image of at least portions of the surface of the joint that are arthritic. The diseased area 3620 is covered by the template, and the template is in close contact with it. This design can be advantageous to obtain greater accuracy in positioning the template if the arthritic area is well defined on the imaging test, e.g. with high resolution spiral CT or near isotropic MRI acquisitions or MRI with image fusion. This design can also provide enhanced stability during surgical interventions by more firmly fixing the template against the irregular underlying surface.

In another embodiment shown in FIG. 36D the surface of the template facing the joint 3670 is a mirror image of at least portions of the surface of the joint that are arthritic. The diseased area 3620 is covered by the template, and the template is in close contact with it. Moreover, healthy or substantially normal regions 3610 are covered by the template and the template is in close contact with them. The template is also closely mirroring the shape of the interface between substantially normal or near normal and diseased joint tissue 3630. This design can be advantageous to obtain even greater accuracy in positioning the template due to the change in surface profile or contour at the interface and resultant improved placement of the template on the joint surface. This design can also provide enhanced stability during surgical interventions by more firmly fixing and anchoring the template against the underlying surface and the interface 3630.

The template may include guide apertures or reference points for two or more planes, or at least one of a cut plane and one of a drill hole or reaming opening for a peg or implant stem, in accordance with an embodiment of the invention.

The distance between two opposing, articulating implant components may be optimized intraoperatively for different pose angles of the joint or joint positions, such as different degrees of section, extension, abduction, adduction, internal and external rotation. For example, spacers, typically at least partially conforming to the template, may be placed between the template of the opposite surface, where the opposite surface can be the native, uncut joint, the cut joint, the surgically prepared joint, the trial implant, or the definitive implant component for that articular surface. Alternatively, spacers may be placed between the template and the articular surface for which it will enable subsequent surgical interventions. For example, by placing spacers between a tibial template and the tibia, the tibial cut height can be optimized. The thicker the spacer, or the more spacers interposed between the tibial template and the tibial plateau the less deep the cut will be, i.e. the less bone will be removed from the top of the tibia.

The spacers may be non-conforming to the template, e.g. they may be of a flat nature. The spacers may be convex or concave or include multiple convexities or concavities. The spacers may be partially conforming to the template. For example, in one embodiment, the surface of the spacer optionally facing the articular surface can be molded and individualized to the articular surface, thereby forming a template/mold, while the opposite surface of the spacer can be flat or curved or have any other non-patient specific design. The opposite surface may allow for placement of blocks or other surgical instruments or for linkages to other surgical instruments and measurement devices.

In another embodiment, the template may include multiple slots spaced at equal distance or at variable distances wherein these slots allow to perform cuts at multiple cut heights or cut depths that can be decided on intraoperatively. In another embodiment, the template may include a ratchet-like mechanism wherein the ratchet can be placed between the articular surface and the template or between the template and the opposite surface wherein the opposite surface may include the native, uncut opposite surface, the cut opposite surface, an opposite surface template, a trial implant or the implant component designed for the opposite surface. By using a ratchet-like device, soft tissue tension can be optimized, for example, for different pose angles of the joint or joint positions such as flexion, extension, abduction, adduction, internal rotation and external rotation at one or more degrees for each direction.

Optimizing soft tissue tension will improve joint function that advantageously enhances postoperative performance. Soft tissue tension may, for example, be optimized with regard to ligament tension or muscle tension but also capsular tension. In the knee joint, soft tissue tension optimization includes typically ligament balancing, e.g. the cruciate ligaments and/or the collateral ligaments, for different degrees of knee flexion and knee extension.

In a preferred embodiment, a 3D guidance template may attach to two or more points on the joint. In an even more preferred embodiment, a template may attach to three or more points on the joint, even more preferred four or more points on the joint, even more preferred five or more points on the joint, even more preferred six or more points on the joint, even more preferred seven or more points on the joint, even more preferred ten or more points on the joint, even more preferred portions for the entire surface to be replaced.

In another embodiment, the template may include one or more linkages for surgical instruments. The linkages may also be utilized for attaching other measurement devices such as alignment guides, intramedullary guides, laser pointing devices, laser measurement devices, optical measurement devices, radio frequency measurement devices, surgical navigation and the like. Someone skilled in the art will recognize many surgical instruments and measurement in alignment devices may be attached to the template. Alternatively, these surgical instruments or alignment devices may be included within the template.

In another embodiment, a link or a linkage may be attached or may be incorporated or may be part of a template that rests on a first articular surface. Said link or linkage may further extend to a second articular surface which is typically an opposing articular surface. Said link or linkage can thus help cross-reference the first articular surface with the second articular surface, ultimately assisting the performance of surgical interventions on the second articular surface using the cross reference to the first articular surface. The second articular surface may optionally be cut with a second template. Alternatively, the second articular surface may be cut using a standard surgical instrument, non-individualized, that is cross referenced via the link to the surgical mold placed on the first articular surface. The link or linkage may include adjustment means, such as ratchets, telescoping devices and the like to optimize the spatial relationship between the first articular surface and the second, opposing articular surface. This optimization may be performed for different degrees of joint flexion, extension, abduction, adduction and rotation.

In another embodiment, the linkage may be made to the cut articular surface or, more general, an articular surface that has been altered using a template and related surgical intervention. Thus, cross reference can be made from the first articular surface from a mold attached to said first articular surface, the mold attached to a surgically altered, for example, cut articular surface, the surgical instrument attached to said articular surface altered using the mold, e.g. cut or drilled, and the like. Someone skilled in the art will easily recognize multiple different variations of this approach. Irrespective of the various variations, in a first step the articular surface is surgically altered, for example, via cutting, drilling or reaming using a mold while in the second step cross reference is established with a second articular surface.

By establishing cross reference between said first and said second articular surface either via the template and/or prior to or after a surgical intervention, the surgical intervention performed on the second articular surface can be performed using greater accuracy and improved usability in relation to said articulating, opposing first articular surface.

FIGS. 37A-D show multiple templates with linkages on the same articular surface (A-C) and to an opposing articular surface (D), in accordance with various embodiments of the invention. The biomechanical axis is denoted as 3700. A horizontal femoral cut 3701, an anterior femoral cut 3702, a posterior femoral cut 3703, an anterior chamfer cut 3704 and a posterior chamfer cut 3705 are planned in this example. A first template 3705 is applied in order to determine the horizontal cut plane and to perform the cut. The cut is perpendicular to the biomechanical axis 3700. The first template 3705 has linkages or extenders 3710 for connecting a second template 3715 for the anterior cut 3702 and for connecting a third template 3720 for the posterior cut 3703. The linkages 3710 connecting the first template 3705 with the second 3715 and third template 3720 help in achieving a reproducible position of the templates relative to each other. At least one of the templates, preferably the first template 3705, will have a surface 3706 that is a mirror image of the articular surface 3708. In this example, all three templates have surface facing the joint that is a mirror image of the joint, although one template having a surface conforming to the joint suffices in many applications of the invention.

A fourth template 3725 may optionally be used in order to perform an anterior chamfer cut 3704. The fourth template may have a guide aperture or reference plane 3730 that can determine the anterior chamfer cut 3704. The fourth template can, but must not have at least one surface 3735 matching one or more cut articular surfaces 3740. The fourth template may have one or more outriggers or extenders 3745 stabilizing the template against the cut or uncut articular surface.

A fifth template 3750 may optionally be used to perform a anterior chamfer cut 3705. The fifth template may have a guide aperture or reference plane 3755 that can determine the posterior chamfer cut 3705. The fifth template may have at least one surface 3735 matching one or more cut articular surfaces 3740. Oblique planes 3760 may help to further stabilize the template during the procedure. The fifth template may have one or more outriggers or extenders 3745 stabilizing the template against the cut or uncut articular surface.

In another embodiment, an opposite articular side 3765 may be cut in reference to a first articular side 3766. Any order or sequence of cutting is possible: femur first then tibia, tibia first then femur, patella first, and so forth. A template 3770 may be shaped to the uncut or, in this example, cut first articular side. The template may have stabilizers against the first articular surface, for example with extenders 3772 into a previously created peg hole 3773 for an implant. The template may have a linkage or an extender 3775 to a second articular surface 3765. Surgical instruments may be attached to the linkage or extender 3775. In this example, a tibial cut guide 3778 with multiple apertures or reference planes 3779 for a horizontal tibial cut is attached. The tibial cut guide may but may not have a surface matching the tibial surface.

By referencing a first, e.g. femoral, to a second, e.g. tibial cut greater accuracy can be achieved in the alignment of these cuts, which will result in improved implant component alignment and less wear. Ratchet like devices 3785 or hinge like devices or spacers may be inserted into the space between the first and the second articular surface and soft-tissue tension and ligament balancing can be evaluated for different distances achieved between the first 3766 and second 3765 articular surface, with one or more of them being cut or uncut. In this manner, soft-tissue tension and ligament balancing can be tested during different pose angles, e.g. degrees of flexion or extension. Optionally, tensiometers can be used. Once an ideal soft-tissue tension and/or ligament balancing has been achieved, the tibial cut may be performed through one of the guide apertures 3779 in reference to the femoral cut.

Figure 38:
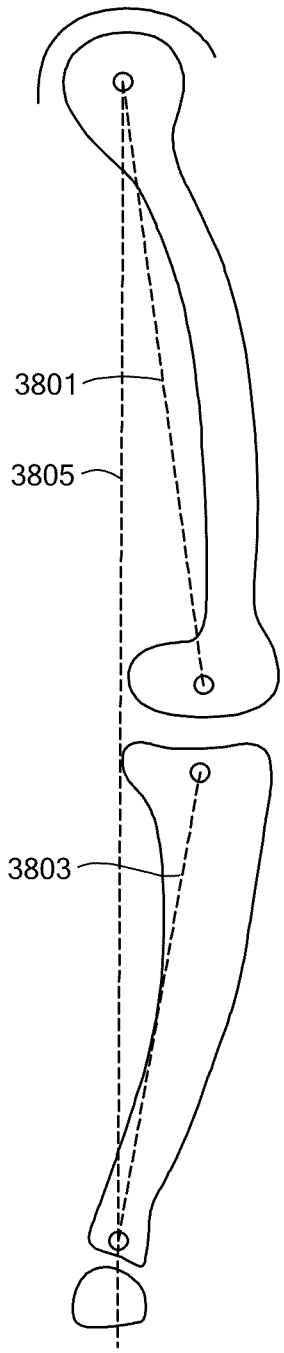
FIG. 38 illustrates a deviation in the AP plane of the femoral and tibial axes in a patient, in accordance with an embodiment of the invention.

FIG. 38 is an example demonstrating a deviation in the AP plane of the femoral 3801 and tibial 3803 axes in a patient. Axis deviations can be determined in any desired plane including the AP plane, not only the ML plane. The axis deviation can be measured. The desired correction can be determined and the position, orientation and shape of a 3D guidance template can be adjusted in order to achieve the necessary correction. The correction may, for example, be designed to achieve a result wherein the femoral 3801 and tibial 3803 axes will coincide with the biomechanical axis 3805.

The invention optionally provides for trial implants and trial devices that help test intraoperatively the result of the surgical intervention achieved using the 3D guidance mold. Trial implants or devices can be particularly useful for subsequent adjustments and fine-tuning of the surgical intervention, for example, optimizing soft tissue tension in different articular pose angles.

In another embodiment, the templates may also allow for intraoperative adjustments. For example, the template may include an opening for a pin. The pin can be placed in the bone and the template can be rotated around the pin thereby optimizing, for example, medial and lateral ligament tension in a knee joint or thereby optimizing the cut orientation and resultant rotation and alignment of an implant relative to the anatomic or biomechanical axis.

In another embodiment, standard tools including alignment guides may be attached to the mold, via linkages for example, and the attachment can allow for additional adjustments in mold and subsequently implant alignment and rotation.

The above-described embodiments can be particularly useful for optimization of soft tissue tension including ligament balancing, for example, in a knee joint. Optimization of soft tissue tension can advantageously improve post-operative function and range of motion.

Linkages may also be utilized to stabilize and fix additional molds or surgical instruments on the articular surface.

Moreover, linkages can allow separation of one large mold into multiple smaller molds. The use of multiple smaller, linked molds advantageously enable smaller surgical axis with the potential to enhance muscle sparing and to reduce the size of the skin cut.

In another embodiment, all or portions of the template may be made of metal, metal-alloys, teflon, ceramics. In a more preferred embodiment, metal, metal-alloys, teflon, ceramics and other hard materials, typically materials that offer a hardness of, without limitation, greater than shore 60D, is placed in areas where the surgical instruments will be in contact with the template.

ii. 3D Guidance Molds for Ligament Repair and Replacement 3D guidance molds may also be utilized for planning the approach and preparing the surgical intervention and conducting the surgical intervention for ligament repair and replacement, in accordance with an embodiment of the invention.

In one example, the anterior cruciate ligament is replaced using a 3D guidance mold. The anterior cruciate ligament is a collagenous structure located in the center of the knee joint, and is covered by the synovial sheath. The ligament has an average length of thirty (30) to thirty-eight (38) millimeters and an average width of ten (10) to eleven (11) millimeters. The ligament is proximally attached to the posterior aspect of the lateral femoral condyle's medial surface. The ligament passes anteriorly, medially and distally within the joint to its attachment at the anteromedial region of the tibial plateau, between the tibial eminences. The distal portion of the ligament fans out to create a large tibial attachment known as the footprint of the ligament. The ligament has two functional subdivisions which include the anteromedial band and the posterolateral band. The posterolateral band is taut when the knee is extended and the anteromedial band becomes taut when the knee is flexed. Because of its internal architecture and attachments sides on femur and tibia, the ACL provides restraint to anterior translation and internal rotation of the tibia in angulation and hyperextension of the knee. The prevalence of ACL injuries are about 1 in 3,000 subjects in the United States and approximately 250,000 new injuries each year.

Other tendon and ligament injuries, for example, including the rotator cuff, the ankle tendons and ligaments, or the posterior cruciate ligament can also be highly prevalent and frequent.

Selecting the ideal osseous tunnel sights is a crucial step in ligament reconstruction, for example, the anterior and posterior cruciate ligament.

In the following paragraphs, embodiments will be described in detail as they can be applied to the anterior cruciate ligament. However, clearly all embodiments mentioned below and modifications thereof are applicable to other ligaments, including the posterior cruciate ligament and also tendons such as tendons around the ankle joint or rotator cuff and shoulder joint.

Anterior Cruciate Ligament

The normal anterior cruciate ligament is composed of a large number of fibers. Each fiber can have a different length, a different origin and a different insertion and is frequently under different tension during the range of motion of the knee joint. One of the limitations of today's ACL graft is that they have parallel fibers. Thus, even with ideal selection of the placement of the osseous tunnels, fibers of an ACL graft will undergo length and tension changes with range of motion. Therefore, today's ACL replacement cannot duplicate the original ligament. However, placing the center of the osseous tunnels at the most isometric points, maximizes the stability that can be obtained during motion and minimizes later on graft wear and ultimately resultant failure.

In illustrative embodiments, 3D guidance templates may be selected and designed to enable highly accurate, reproducible and minimally invasive graft tunnels in the femur and the tibia.

In one embodiment, imaging such as MRI is performed pre-operatively. The images can be utilized to identify the origin of the ligament and its insertion onto the opposing articular surface, in the case of an anterior cruciate ligament, the tibia. Once the estimated location of the origin and the footprint, i.e. the insertion of the ligament has been identified, 3D guidance templates may be made to be applied to these areas or their vicinity.

The 3D guidance templates may be made and shaped to the articular surface, for example, adjacent to the intended tunnel location or they may be shaped to bone or cartilage outside the weight bearing zone, for example, in the intercondylar notch. A 3D guidance template for femoral or tibial tunnel placement for ACL repair may include blocks, attachments or linkages for reference points or guide aperture to guide and direct the direction and orientation of a drill, and optionally, also the drill depth. Optionally, the 3D guidance templates may be hollow. The 3D guidance templates may be circular, semi-circular or ellipsoid. The 3D guidance templates may have a central opening to accommodate a drill.

In one embodiment, the 3D guidance template is placed on, over or near the intended femoral or tibial entry point and subsequently the drill hole. Once proper anatomic positioning has been achieved, the ligament tunnel can be created. The 3D guidance template, its shape, position, and orientation, may be optimized to reflect the desired tunnel location in the femur and the tibia, wherein the tunnel location, position, orientation and angulation is selected to achieve the best possible functional results. Additional considerations in placing the femoral or tibial tunnel includes a sufficient distance to the cortical bone in order to avoid failure or fracture of the tunnel.

Thus, optionally, the distance of the tunnel to the adjacent cortical bone and also other articular structures may optionally be factored into the position, shape and orientation of the femoral or tibial 3D guidance templates in order to achieve the optimal compromise between optimal ligament function and possible post-operative complications such as failure of the tunnel.

In another embodiment, the imaging test may be utilized to determine the origin and insertion of the ligament. This determination can be performed on the basis of bony landmarks identified on the scan, e.g. a CT scan or MRI scan. Alternatively, this determination can be performed by identifying ligament remnants, for example, in the area of the ligament origin and ligament attachment. By determining the origin and the insertion of the ligament the intended graft length may be estimated and measured. This measurement may be performed for different pose angles of the joint such as different degrees of flexion, extension, abduction, adduction, internal and external rotation.

In another embodiment, the imaging test may be utilized to identify the ideal graft harvest site wherein the graft harvest site can optionally be chosen to include sufficiently long ligament portion and underlying bone block proximally and distally in order to fulfill the requirement for graft length as measured earlier in the imaging test. An additional 3D guidance template for the same 3D guidance templates, possibly with linkages, may be utilized to harvest the ligament and bone from the donor site in the case of an autograft. Optionally, 3D guidance templates may also be utilized or designed or shaped or selected to guide the extent of an optional notchplasty. This can include, for example, the removal of osteophytes.

In the case of an ACL replacement, the 3D guidance templates may in this manner optimize selection of femoral and tibial tunnel sites. Tunnel sites may even be optimized for different knee pose angles, i.e. joint positions, and different range of motion. Selecting the properly positioned femoral tunnel site ensures maximum post operative knee stability.

The intra-articular site of the tibial tunnel has less effect on changes in graft length but its position can be optimized using proper placement, position, and shape of 3D guidance templates to prevent intercondular notch impingement.

Moreover, the 3D guidance templates may include an optional stop for the drill, for example, to avoid damage to adjacent neurovascular bundles or adjacent articular structures, including the articular cartilage or other ligaments.

Optionally, the 3D guidance templates may also include a stop, for example, for a drill in order to include the drill depth.

The direction and orientation of the tibial tunnel and also the femoral tunnel may be determined with use of the 3D guidance template, whereby it will also include selection of an optimal tunnel orientation in order to match graft length as measured pre-operatively with the tunnel length and the intra-articular length of the graft ligament.

In one embodiment, a tibial 3D guidance template is, for example, selected so that its opening is located immediately posterior to the anatomic center of the ACL tibial footprint. Anatomic landmarks may be factored into the design, shape, orientation, and position of the tibial guidance template, optionally. These include, without limitation, the anterior horn of the lateral meniscus, the medial tibial spine, the posterior cruciate ligament, and the anterior cruciate ligament stump.

The tunnel site may be located utilizing the 3D guidance template in the anterior posterior plane by extending a line in continuation with the inner edge of the anterior horn of the lateral meniscus. This plane will typically be located six (6) to seven (7) millimeters anterior to the interior border of the PCL. The position, shape and orientation of the 3D guidance template will be typically so that the resultant tibial tunnel and the resultant location and orientation of the ACL graft, once in place, may touch the lateral aspect of the PCL, but will not significantly deflect it. Similarly, the location of the tibial guidance template and the resultant ligament tunnel and the resultant location of the ACL graft, once in place, may be chosen so that the graft will neither abrade nor impinge against the medial aspect of the lateral femoral condyle or the roof of the intercondylar notch when the knee is, for example, in full extension. In this manner, highly accurate graft placement is possible thereby avoiding the problems of impingement and subsequent graft failure.

In another embodiment, the pre-operative scan can be evaluated to determine the maximal possible graft length, for example, patella tendon graft. If there is concern that the maximal graft length is not sufficient for the intended ACL replacement, the tunnel location and orientation, specifically the exits from the femur or the tibia can be altered and optimized in order to match the graft length with the tunnel length and intra-articular length.

In a preferred embodiment, the graft length is measured or simulated pre-operatively, for example, by measuring the optimal graft length for different flexion and extension angles. Using this approach, an optimal position, shape, orientation and design of the 3D guidance template may be derived at an optimal compromise between isometric graft placement, avoidance of impingement onto the PCL, and/or avoidance of impingement onto the femoral condyle, maximizing achievable graft lengths.

Intraoperatively, the femoral and/or tibial 3D guidance templates may include adjustment means. These adjustment means can, for example, allow movement of the template by one or two or more millimeters intervals in posterior or medial or lateral orientation, with resultant movement of the femoral or tibial tunnel. Additionally, intraoperative adjustment may also allow for rotation of the template, with resultant rotation of the resultant femoral or tibial tunnels.

A single template may be utilized to derive the femoral tunnel. A single template may also be utilized to derive the tibial tunnel. More than one template may be used on either side.

Optionally, the templates may include linkages, for example, for attaching additional measurement devices, guide wires, or other surgical instruments. Alignment guides including mechanical, electrical or optical devices may be attached or incorporated in this manner.

In another embodiment, the opposite articular surface may be cross referenced against a first articular surface. For example, in the case of an ACL repair, the femoral tunnel may be prepared first using a 3D guidance template, whereby the 3D guidance template helps determine the optimal femoral tunnel position, location, orientation, diameter, and shape. The femoral guidance template may include a link inferiorly to the tibia or an attachable linkage, wherein said link or said attachable linkage may be utilized to determine the ideal articular entry point for the tibial tunnel. In this manner, the tibial tunnel can be created in an anatomic environment and in mechanical cross reference with the femoral tunnel. The reverse approach is possible, whereby the tibial tunnel is created first using the 3D guidance template with a link or linkage to a subsequently created femoral tunnel. Creating the femoral or tibial tunnel in reference to each other advantageously helps reduce the difficulty in performing the ligament repair and also can improve the accuracy of the surgery in select clinical situations.

In another embodiment, the template for ligament repair may include optional flanges or extenders. These flanges or extenders may have the function of tissue retractors. By having tissue retractor function, the intra-articular template for ligament repair can provide the surgeon with a clearer entry to the intended site of surgical intervention and improve visualization. Moreover, flanges or extenders originating from or attached to the 3D guidance templates may also serve as tissue protectors, for example, protecting the posterior cruciate ligament, the articular cartilage, or other articular structures as well as extra-articular structures.

In another embodiment, an additional 3D guidance template or linkages to a first or second articular 3D guidance templates can be utilized to place ligament attachment means, for example, interference crews.

If an allograft is chosen and the allograft length and optionally, dimensions are known pre-operatively, additional adjustments may be made to the position, shape and orientation of the 3D guidance templates and additional tunnels in order to match graft dimensions with tunnel dimensions and graft length with intra-femoral tunnel length, intra-articular length and intra-tibial tunnel length. Optionally, this adjustment and optimization can be performed for different pose angles of the joint, e.g. different degrees of flexion or extension.

FIGS. 40A-C illustrate an exemplary use of 3D guidance templates for performing ligament repair; in this case repair of the anterior cruciate ligament (ACL). A 3D guidance template 4000 is placed in the intercondylar notch region 4005. At least one surface 4010 of the template 4000 is a mirror image of at least portions of the notch 4005 or the femur. The template 4000 may be optionally placed against the trochlea and/or the femoral condyle (not shown). The mold 4000 includes an opening 4020 and, optionally, metal sleeves 4030, wherein the position, location and orientation of the opening 4020 and/or the metal sleeves 4030 determine the position and orientation of the femoral graft tunnel 4040.

A tibial template 4050 may be used to determine the location and orientation of the tibial tunnel 4060. Specifically, an opening 4065 within the tibial mold 4050 will determine the position, angle and orientation of the tibial tunnel 4060. The opening may include optional metal sleeves 4068. At least one surface 4070 of the tibial template 4050 will substantially match the surface of the tibia 4075. The template may be matched to a tibial spine 4080 wherein the tibial spine can help identify the correct position of the mold and help fix the template in place during the surgical intervention. Of note, the sleeves 4030 and 4068 may be made of other hard materials, e.g. ceramics. The femoral and/or tibial template may be optionally attached to the femoral or tibial articular surface during the procedure, for example using K-wires or screws.

FIG. 40C shows a top view of the tibial plateau 4085. The PCL 4086 is seen as are the menisci 4087. The original site of ACL attachment 4090 is shown. The intended tunnel site 4092 may be slightly posterior to the original ACL attachment 4090. The template 4095 may placed over the intended graft tunnel 4092. The template will typically have a perimeter slightly greater than the intended tunnel site. The templates may allow for attachments, linkages or handles.

PCL Repair

All of the embodiments described above may also be applied to PCL repair as well as the repair of other ligaments or tendons.

For PCL repair, 3D guidance templates may be designed for single, as well as double bundle surgical technique. With single bundle surgical technique, a 3D guidance template may be created with a position, orientation and shape of the template or associated reference points or guide apertures for surgical instruments that will help create a femoral tunnel in the location of the anatomic origin of the ligament. Alternatively, the template and any related reference points or guide apertures or linkages may be designed and placed so that an anterior placement of the femoral tunnel in the anatomic footprint is performed. A more anterior placement of the femoral tunnel can restore normal knee laxity better than isometric graft placement. The 3D guidance templates may be designed so that optimal tension is achieved not only in knee extension but also in knee flexion, particularly ninety degrees of knee flexion. Thus, the origin and the insertion of the PCL may be identified pre-operatively on the scan, either by identifying residual fiber bundles or by identifying the underlying anatomic landmarks. The distance between the origin and the insertion may thus be determined in the extension and can be simulated for different flexion degrees or other articular positions. Femoral and tibial tunnel placement and orientation may then be optimized in order to achieve an isometric or near isometric ligament placement. Intraoperative adjustments are feasible as described in the foregoing embodiments.

A 3D guidance template may also be designed both on the femoral as well as on the tibial side using double bundle reconstruction techniques. With double bundle reconstruction techniques, the femoral or tibial template can include or incorporate links or can have attachable linkages so that a femoral tunnel can be created and cross referenced with a tibial tunnel, or a tibial tunnel can be created and cross referenced to a femoral tunnel.

As described for the ACL, the templates may include stops for drills and reaming devices or other surgical instruments, for example, to protect popliteal neurovascular structures. The templates may include extenders or flanges to serve as tissue retractors as well as tissue protectors.

In principle, templates may be designed to be compatible with any desired surgical technique. In the case of PCL repair, templates may be designed to be compatible with single bundle, or a double bundle reconstruction, tibial inlay techniques as well as other approaches.

As previously stated, 3D guidance templates are applicable to any type of ligament or tendon repair and can provide reproducible, simple intraoperative location of intended attachment sites or tunnels. The shape, orientation and position of the 3D guidance templates may be individualized and optimized for articular anatomy, as well as the biomechanical situation, and may incorporate not only the articular shape but also anatomic lines, anatomic planes, biomechanical lines or biomechanical planes, as well as portions or all of the shape of devices or anchors or instruments to be implanted or to be used during implantation or to be used during surgical repair of a ligament or tendon tear.

iii. Impingement Syndromes, Removal of Exophytic Bone Growth Including Osteophytes 3D guidance templates may also be utilized to treat impingement syndromes, for example, by template guided removal of osteophytes or exophytic bone growth. In one embodiment of the invention, an imaging test such as a CT scan or an MRI scan is obtained through the area of concern. If a joint is imaged, the images can demonstrate an osteophyte or, more generally, exophytic bone growth in intra and extra-articular locations. The scan data may then be utilized to design a template that matches the surface adjacent to the exophytic bone growth or osteophyte, the surface overlying the exophytic bone growth or osteophyte or both or portions of one or both. The template may have openings or apertures or linkages that allow placement of surgical tools for removal of the exophytic bone growth or the osteophyte, such as reamers, drills, rotating blades and the like. Someone skilled in the art will recognize many different surgical instruments that can be utilized in this manner.

Two representative examples where a 3D guidance template can be applied to treat local impingement syndromes are the pincer and Cam impingement syndromes in the hip joint. Pincer and Cam impingement represent femoro-acetabular impingement syndromes caused by an abutment between the proximal femur and the acetabular rim during the end range of motion. Untreated femoral-acetabular impingement can cause osteoarthritis of the hip.

In Cam impingement, a non-spherical portion of the femoral head, typically located near the head-neck junction, is jammed into the acetabulum during hip joint motion. The Cam impingement can lead to considerable shear forces and subsequently chondral erosion.

In one embodiment of the invention, an imaging test, such as a CT scan or MRI scan may be performed pre-operatively. The imaging test may be used to identify the non-spherical portion of the femoral head at the head-neck junction that is responsible for the impingement. A 3D guidance template may be designed that can be applied intraoperatively to this region. The template is designed to fulfill three principle functions:

1. Intraoperative highly accurate identification of the non-spherical portion of the femoral head by placement of the individualized portion of the 3D template onto the area or immediately adjacent to the area.

2. Guidance of surgical instrumentation to remove the non-spherical portion and to re-establish a spherical or essentially spherical shape.

3. Control of the depth of the bone removal and the shape of the bone removal. For this purpose, a stop may be incorporated into the design of the 3D guidance template. Of note, the stop may be asymmetrical and can even be designed to be a mirror image of the desired articular contour.

Figure 41:
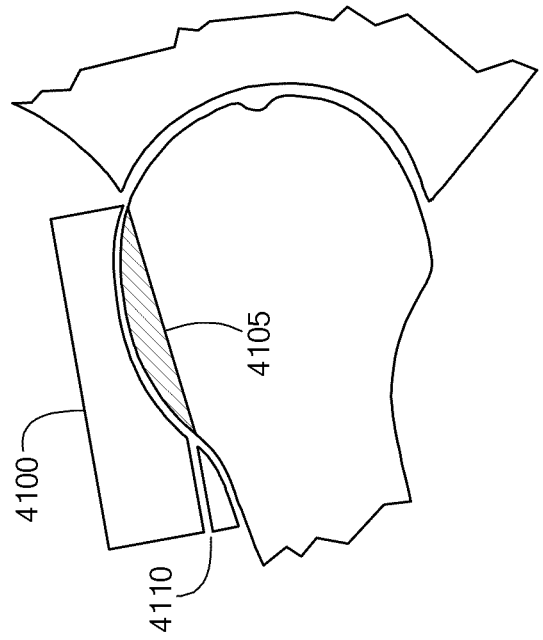
FIG. 41 shows an example of treatment of CAM impingement using a 3D guidance template, in accordance with an embodiment of the invention.

FIG. 41 shows an example of treatment of CAM impingement using a 3D guidance template 4100. The impinging area 4105 may be removed with a saw (not shown) inserted into the guide aperture 4110. The guide aperture may be designed and placed so that only the impinging portion of the joint is removed.

In Pincer impingement, linear bony contact occurs between the normal femoral head-neck junction and enlarged or hypertrophied portion of the acetabulum. Pre-operatively an imaging test may be performed in order to identify the abnormal, over covered or enlarged area of the acetabulum. The amount of bone removal may be determined on the imaging study, e.g. a CT scan or MRI scan. A 3D guidance template may then be designed that will achieve the identical three functions described above in Cam impingement.

Figure 42:
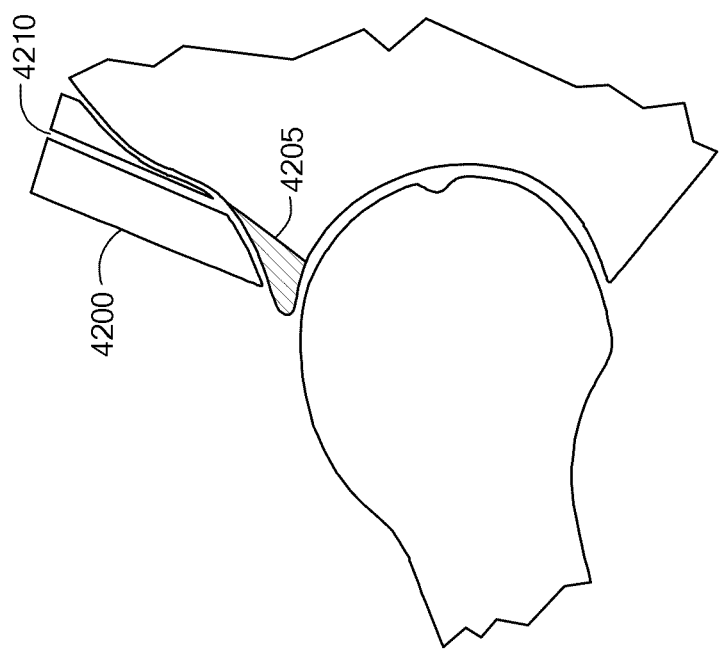
FIG. 42 shows an example of treatment of Pincer impingement using a 3D guidance template, in accordance with an embodiment of the invention.

FIG. 42 shows an example of treatment of Pincer impingement using a 3D guidance template 4200. The impinging area 4205 may be removed with a saw (not shown) inserted into the guide aperture 4210. The guide aperture may be designed and placed so that only the impinging portion of the joint is removed.

Accurate and reproducible identification of the abnormal bony surface causing the impingement is critical in any form of musculoskeletal impingement syndrome. 3D guidance template systems are ideally suited to achieve this purpose and to guide the surgical instrumentation for removal of the source of impingement. Moreover, since the localization of the impinging area is performed pre-operatively during the imaging test, and intra-operatively using the 3D guidance template, this approach allows for minimally invasive, tissue, specifically muscle sparing approaches.

iv. Surgical Navigation and 3D Guidance Templates 3D guidance template technology as described herein may be combined with surgical navigation techniques. Surgical navigation techniques may be image guided or non-image guided for this purpose. Passive or active surgical navigation systems may be employed. Surgical navigation systems that use optical or radiofrequency transmission or registration may be used. A representative example is the Vector Vision navigation system manufactured by Brain Lab, Germany. This is a passive infrared navigation system. Once the patient is positioned appropriately in the operating room, retro-reflective markers can be applied to the extremity near the area of intended surgery. With image guided navigation, an imaging study such as a CT scan or MRI scan, can be transferred into the workstation of the navigation system. For registration purposes, the surgeon can, for example, utilize a pointer navigation tool to touch four or more reference points that are simultaneously co-identified and cross registered on the CT or MRI scan on the workstation. In the knee joint, reference points may include the trochlear groove, the most lateral point of the lateral condyle, the most medial femoral condyle, the tip of the tibial spines and so forth. Using image guided navigation, anatomical and biomechanical axis of the joint can be determined reliably.

Alternatively, non-image guided navigation may be utilized. In this case, retro-reflective markers or small radio frequency transmitters are positioned on the extremity. Movement of the extremity and of the joints is utilized, for example, to identify the center of rotation. If surgery of the knee joint is contemplated, the knee joint may be rotated around the femur. The marker or radiofrequency transmitter motion may be utilized to identify the center of the rotation, which will coincide with the center of the femoral head. In this manner, the biomechanical axis may be determined non-invasively.

The information resulting in imaging guided navigation, pertaining to either anatomical or biomechanical axis can be may be utilized to optimize the position of any molds, blocks, linkages or surgical instruments attached to or guided through the 3D guidance molds.

In one embodiment, the joint or more specifically the articular surface, may be scanned intra-operatively, for example, using ultrasound or optical imaging methods. The optical imaging methods may include stereographic or stereographic like imaging approaches, for example, multiple light path stereographic imaging of the joint and the articular surface or even single light path 3D optical imaging. Other scan technologies that are applicable are, for example, C-arm mounted fluoroscopic imaging systems that can optionally also be utilized to generate cross-sectional images such as a CT scan. Intraoperative CT scanners are also applicable. Utilizing the intraoperative scan, a point cloud of the joint or the articular surface or a 3D reconstruction or a 3D visualization and other 3D representations may be generated that can be utilized to generate an individualized template wherein at least a portion of said template includes a surface that is a mirror image of the joint or the articular surface. A rapid prototyping or a milling or other manufacturing machine can be available in or near the operating room and the 3D guidance template may be generated intraoperatively.

The intraoperative scan in conjunction with the rapid production of an individualized 3D guidance template matching the joint or the articular surface, in whole or at least in part, has the advantage to generate rapidly a tool for rapid intraoperative localization of anatomical landmarks, including articular landmarks. A 3D guidance template may then optionally be cross-registered, for example, using optical markers or radiofrequency transmitters attached to the template with the surgical navigation system. By cross-referencing the 3D guidance template with the surgical navigation system, surgical instruments can now be reproducibly positioned in relationship to the 3D guidance template to perform subsequent procedures in alignment with or in a defined relationship to at least one or more anatomical axis and/or at least one or more biomechanical axis or planes.

v. Stereoscopy, Stereoscopic Imaging:

In addition to cross-sectional or volumetric imaging technologies including CT, spiral CT, and MRI, stereoscopic imaging modalities may be utilized. Stereoscopic imaging is any technique capable of recording three-dimensional information from two two-dimensional, projectional imaging. Traditional stereoscopic imaging includes creating a 3D visualization or representation starting from a pair of 2D images. The projection path of the 2D images is offset. The offset is, for example, designed to create an impression of object depth for the eyes of the viewer. The offset or minor deviation between the two images is similar to the prospectors that both eyes naturally receive inbinocular vision. Using two or more images with an offset or minor deviation in perspective, it is possible to generate a point cloud or 3D surface or 3D visualization of a joint or an articular surface, which can then be input into a manufacturing system such as a rapid prototyping or milling machine. Dual or more light path, as well as single light path, systems can be employed vi. Knee Joint When a total knee arthroplasty is contemplated, the patient can undergo an imaging test, as discussed in more detail above, that will demonstrate the articular anatomy of a knee joint, e.g. width of the femoral condyles, the tibial plateau etc. Additionally, other joints can be included in the imaging test thereby yielding information on femoral and tibial axes, deformities such as varus and valgus and other articular alignment. The imaging test can be an x-ray image, preferably in standing, load-bearing position, a CT or spiral CT scan or an MRI scan or combinations thereof. A spiral CT scan may be advantageous over a standard CT scan due to its improved spatial resolution in z-direction in addition to x and y resolution. The articular surface and shape as well as alignment information generated with the imaging test can be used to shape the surgical assistance device, to select the surgical assistance device from a library of different devices with pre-made shapes and sizes, or can be entered into the surgical assistance device and can be used to define the preferred location and orientation of saw guides or drill holes or guides for reaming devices or other surgical instruments. Intraoperatively, the surgical assistance device is applied to the tibial plateau and subsequently the femoral condyle(s) by matching its surface with the articular surface or by attaching it to anatomic reference points on the bone or cartilage. The surgeon can then introduce a reamer or saw through the guides and prepare the joint for the implantation. By cutting the cartilage and bone along anatomically defined planes, a more reproducible placement of the implant can be achieved. This can ultimately result in improved postoperative results by optimizing biomechanical stresses applied to the implant and surrounding bone for the patient's anatomy and by minimizing axis malalignment of the implant. In addition, the surgical assistance device can greatly reduce the number of surgical instruments needed for total or unicompartmental knee arthroplasty. Thus, the use of one or more surgical assistance devices can help make joint arthroplasty more accurate, improve postoperative results, improve long-term implant survival, reduce cost by reducing the number of surgical instruments used. Moreover, the use of one or more surgical assistance device can help lower the technical difficulty of the procedure and can help decrease operating room ("OR") times.

Thus, surgical tools described herein can also be designed and used to control drill alignment, depth and width, for example when preparing a site to receive an implant. For example, the tools described herein, which typically conform to the joint surface, can provide for improved drill alignment and more accurate placement of any implant. An anatomically correct tool can be constructed by a number of methods and can be made of any material, preferably a substantially translucent and/or transparent material such as plastic, Lucite, silastic, SLA or the like, and typically is a block-like shape prior to molding.

Figure 24A:
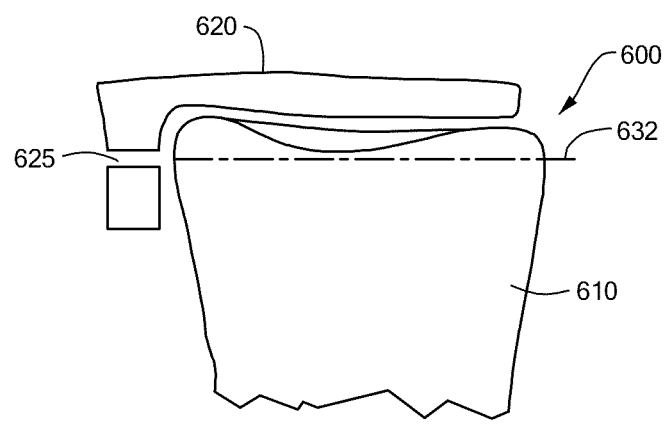
FIG. 24A depicts, in cross-section, an example of a surgical tool containing an aperture through which a surgical drill or saw can fit, in accordance with one embodiment of the invention. The aperture guides the drill or saw to make the proper hole or cut in the underlying bone. Dotted lines represent where the cut corresponding to the aperture will be made in bone.

FIG. 24A depicts, in cross-section, an example of a mold 600 for use on the tibial surface having an upper surface 620. The mold 600 contains an aperture 625 through which a surgical drill or saw can fit. The aperture guides the drill or saw to make the proper hole or cut in the underlying bone 610 as illustrated in FIGS. 21B-D. Dotted lines 632 illustrate where the cut corresponding to the aperture will be made in bone.

Figure 24B:
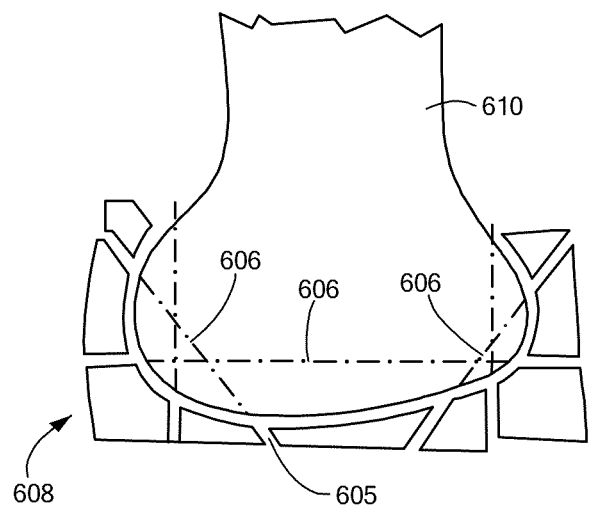
FIG. 24B depicts, in cross-section, an example of a surgical tool containing apertures through which a surgical drill or saw can fit and which guide the drill or saw to make cuts or holes in the bone, in accordance with one embodiment of the invention. Dotted lines represent where the cuts corresponding to the apertures will be made in bone.

FIG. 24B depicts, a mold 608 suitable for use on the femur. As can be appreciated from this perspective, additional apertures are provided to enable additional cuts to the bone surface. The apertures 605 enable cuts 606 to the surface of the femur. The resulting shape of the femur corresponds to the shape of the interior surface of the femoral implant, typically as shown in FIG. 21E. Additional shapes can be achieved, if desired, by changing the size, orientation and placement of the apertures. Such changes would be desired where, for example, the interior shape of the femoral component of the implant requires a different shape of the prepared femur surface.

Turning now to FIG. 25, a variety of illustrations are provided showing a tibial cutting block and mold system. FIG. 25A illustrates the tibial cutting block 2300 in conjunction with a tibia 2302 that has not been resected. In this depiction, the cutting block 2300 consists of at least two pieces. The first piece is a patient specific interior piece 2310 or mold that is designed on its inferior surface 2312 to mate, or substantially mate, with the existing geography of the patient's tibia 2302. The superior surface 2314 and side surfaces 2316 of the first piece 2310 are configured to mate within the interior of an exterior piece 2320. The reusable exterior piece 2320 fits over the interior piece 2310. The system can be configured to hold the mold onto the bone.

The reusable exterior piece has a superior surface 2322 and an inferior surface 2324 that mates with the first piece 2310. The reusable exterior piece 2320 includes cutting guides 2328, to assist the surgeon in performing the tibial surface cut described above. As shown herein a plurality of cutting guides can be provided to provide the surgeon a variety of locations to choose from in making the tibial cut. If necessary, additional spacers can be provided that fit between the first patient configured, or molded, piece 2310 and the second reusable exterior piece, or cutting block, 2320.

Clearly, the mold may be a single component or multiple components. In a preferred embodiment, one or more components are patient specific while other components such as spacers or connectors to surgical instruments are generic. In one embodiment, the mold can rest on portions of the joint on the articular surface or external to the articular surface. Other surgical tools then may connect to the mold. For example, a standard surgical cut block as described for standard implants, for example in the knee the J&J PFC Sigma system, the Zimmer Nexgen system or the Stryker Duracon system, can be connected or placed on the mold. In this manner, the patient specific component can be minimized and can be made compatible with standard surgical instruments.

The mold may include receptacles for standard surgical instruments including alignment tools or guides. For example, a tibial mold for use in knee surgery may have an extender or a receptacle or an opening to receive a tibial alignment rod. In this manner, the position of the mold can be checked against the standard alignment tools and methods. Moreover, the combined use of molds and standard alignment tools including also surgical navigation techniques can help improve the accuracy of or optimize component placement in joint arthroplasty, such as hip or knee arthroplasty. For example, the mold can help define the depth of a horizontal tibial cut for placement of a tibial component. A tibial alignment guide, for example an extramedullary or intramedullary alignment guide, used in conjunction with a tibial mold can help find the optimal anteroposterior angulation, posterior slope, tibial slant, or varus-valgus angle of the tibial cut. The mold may be designed to work in conjunction with traditional alignment tools known in the art.

The mold may include markers, e.g. optoelectronic or radiofrequency, for surgical navigation. The mold may have receptacles to which such markers can be attached, either directly or via a linking member.

The molds can be used in combination with a surgical navigation system. They can be used to register the bones associated with a joint into the coordinate system of the surgical navigation system. For example, if a mold for a joint surface includes tracking markers for surgical navigation, the exact position and orientation of the bone can be detected by the surgical navigation system after placement of the mold in its unique position. This helps to avoid the time-consuming need to acquire the coordinates of tens to hundreds of points on the joint surface for registration.

Referring back to FIG. 25, the variable nature of the interior piece facilitates obtaining the most accurate cut despite the level of disease of the joint because it positions the exterior piece 2320 such that it can achieve a cut that is perpendicular to the mechanical axis. Either the interior piece 2310 or the exterior piece 2320 can be formed out of any of the materials discussed above in Section II, or any other suitable material. Additionally, a person of skill in the art will appreciate that the invention is not limited to the two piece configuration described herein. The reusable exterior piece 2320 and the patient specific interior piece 2310 can be a single piece that is either patient specific (where manufacturing costs of materials support such a product) or is reusable based on a library of substantially defect conforming shapes developed in response to known or common tibial surface sizes and defects.

The interior piece 2310 is typically molded to the tibia including the subchondral bone and/or the cartilage. The surgeon will typically remove any residual meniscal tissue prior to applying the mold. Optionally, the interior surface 2312 of the mold can include shape information of portions or all of the menisci.

Turning now to FIG. 25B-D, a variety of views of the removable exterior piece 2320. The top surface 2322 of the exterior piece can be relatively flat. The lower surface 2324 which abuts the interior piece conforms to the shape of the upper surface of the interior piece. In this illustration the upper surface of the interior piece is flat, therefore the lower surface 2324 of the reusable exterior surface is also flat to provide an optimal mating surface.

A guide plate 2326 is provided that extends along the side of at least a portion of the exterior piece 2320. The guide plate 2326 provides one or more slots or guides 2328 through which a saw blade can be inserted to achieve the cut desired of the tibial surface. Additionally, the slot, or guide, can be configured so that the saw blade cuts at a line perpendicular to the mechanical axis, or so that it cuts at a line that is perpendicular to the mechanical axis, but has a 4-7° slope in the sagittal plane to match the normal slope of the tibia.

Optionally, a central bore 2330 can be provided that, for example, enables a drill to ream a hole into the bone for the stem of the tibial component of the knee implant.

FIGS. 25E-H illustrate the interior, patient specific, piece 2310 from a variety of perspectives. FIG. 25E shows a side view of the piece showing the uniform superior surface 2314 and the uniform side surfaces 2316 along with the irregular inferior surface 2316. The inferior surface mates with the irregular surface of the tibia 2302. FIG. 25F illustrates a superior view of the interior, patient, specific piece of the mold 2310. Optionally having an aperture 2330. FIG. 25G illustrates an inferior view of the interior patient specific mold piece 2310 further illustrating the irregular surface which includes convex and concave portions to the surface, as necessary to achieve optimal mating with the surface of the tibia. FIG. 25H illustrates cross-sectional views of the interior patient specific mold piece 2310. As can be seen in the cross-sections, the surface of the interior surface changes along its length.

As is evident from the views shown in FIGS. 25B and D, the length of the guide plate 2326 can be such that it extends along all or part of the tibial plateau, e.g. where the guide plate 2326 is asymmetrically positioned as shown in FIG. 25B or symmetrical as in FIG. 23D. If total knee arthroplasty is contemplated, the length of the guide plate 2326 typically extends along all of the tibial plateau. If unicompartmental arthroplasty is contemplated, the length of the guide plate typically extends along the length of the compartment that the surgeon will operate on. Similarly, if total knee arthroplasty is contemplated, the length of the molded, interior piece 2310 typically extends along all of the tibial plateau; it can include one or both tibial spines. If unicompartmental arthroplasty is contemplated, the length of the molded interior piece typically extends along the length of the compartment that the surgeon will operate on; it can optionally include a tibial spine.

Turning now to FIG. 25I, an alternative embodiment is depicted of the aperture 2330. In this embodiment, the aperture features lateral protrusions to accommodate using a reamer or punch to create an opening in the bone that accepts a stem having flanges.

FIGS. 25J and M depict alternative embodiments of the invention designed to control the movement and rotation of the cutting block 2320 relative to the mold 2310. As shown in FIG. 25J a series of protrusions, illustrated as pegs 2340, are provided that extend from the superior surface of the mold. As will be appreciated by those of skill in the art, one or more pegs or protrusions can be used without departing from the scope of the invention. For purposes of illustration, two pegs have been shown in FIG. 25J. Depending on the control desired, the pegs 2340 are configured to fit within, for example, a curved slot 2342 that enables rotational adjustment as illustrated in FIG. 23K or within a recess 2344 that conforms in shape to the peg 2340 as shown in FIG. 25L. As will be appreciated by those of skill in the art, the recess 2344 can be sized to snugly encompass the peg or can be sized larger than the peg to allow limited lateral and rotational movement. The recess can be composed of a metal or other hard insert 544.

Figure 25M:
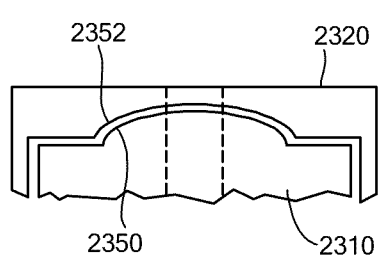
FIGS. 25A-R illustrate tibial cutting blocks and molds used to create a surface perpendicular to the anatomic axis for receiving the tibial portion of a knee implant, in accordance with various embodiments of the invention.

As illustrated in FIG. 25M the surface of the mold 2310 can be configured such that the upper surface forms a convex dome 2350 that fits within a concave well 2352 provided on the interior surface of the cutting block 2320. This configuration enables greater rotational movement about the mechanical axis while limiting lateral movement or translation.

Other embodiments and configurations could be used to achieve these results without departing from the scope of the invention.

As will be appreciated by those of skill in the art, more than two pieces can be used, where appropriate, to comprise the system. For example, the patient specific interior piece 2310 can be two pieces that are configured to form a single piece when placed on the tibia. Additionally, the exterior piece 2320 can be two components. The first component can have, for example, the cutting guide apertures 2328. After the resection using the cutting guide aperture 2328 is made, the exterior piece 2320 can be removed and a secondary exterior piece 2320' can be used which does not have the guide plate 2326 with the cutting guide apertures 2328, but has the aperture 2330 which facilitates boring into the tibial surface an aperture to receive a stem of the tibial component of the knee implant. Any of these designs could also feature the surface configurations shown in FIGS. 25J-M, if desired.

Figure 25N:
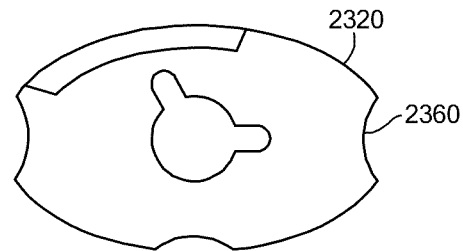

FIG. 25N illustrates an alternative design of the cutting block 2320 that provides additional structures 2360 to protect, for example, the cruciate ligaments, from being cut during the preparation of the tibial plateau. These additional structures can be in the form of indented guides 2360, as shown in FIG. 25N or other suitable structures.

Figure 25O:
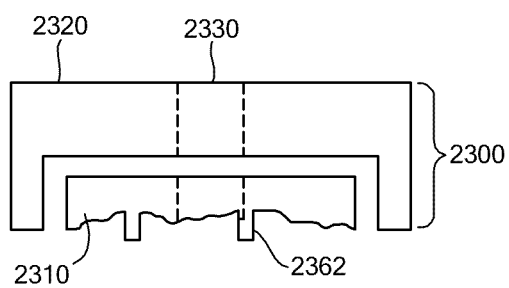

FIG. 25O illustrates a cross-section of a system having anchoring pegs 2362 on the surface of the interior piece 2310 that anchor the interior piece 2310 into the cartilage or meniscal area.

Figure 25P:
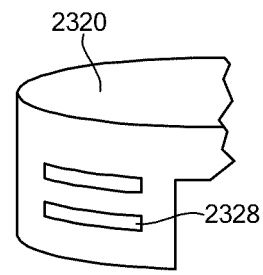
Figure 25Q:
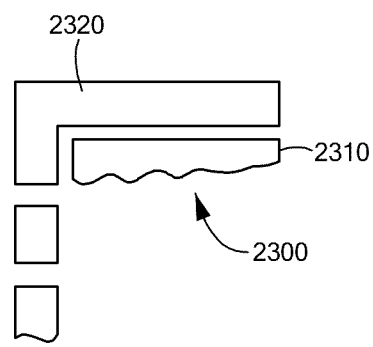

FIGS. 25P AND Q illustrate a device 2300 configured to cover half of a tibial plateau such that it is unicompartmental.

Figure 25R:
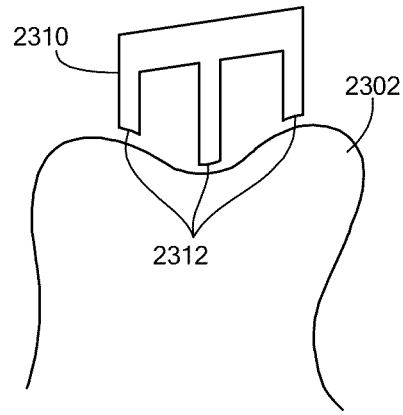

FIG. 25R illustrates an interior piece 2310 that has multiple contact surfaces 2312 with the tibial 2302, in accordance with one embodiment of the invention. As opposed to one large contact surface, the interior piece 2310 includes a plurality of smaller contact surfaces 2312. In various embodiments, the multiple contact surfaces 2312 are not on the sample plane and are at angles relative to each other to ensure proper positioning on the tibia 2302. Two or three contact surfaces 2312 may be required to ensure proper positioning. In various embodiments, only the contact surfaces 2312 of the interior piece may be molded, the molds attached to the rest of the template using methodologies known in the art, such as adhesives. The molds may be removably attached to the template. It is to be understood that multiple contact surfaces 2312 may be utilized in template embodiments that include one or a plurality of pieces.

Turning now to FIG. 26, a femoral mold system is depicted that facilitates preparing the surface of the femur such that the finally implanted femoral implant will achieve optimal mechanical and anatomical axis alignment.

Figure 26A:
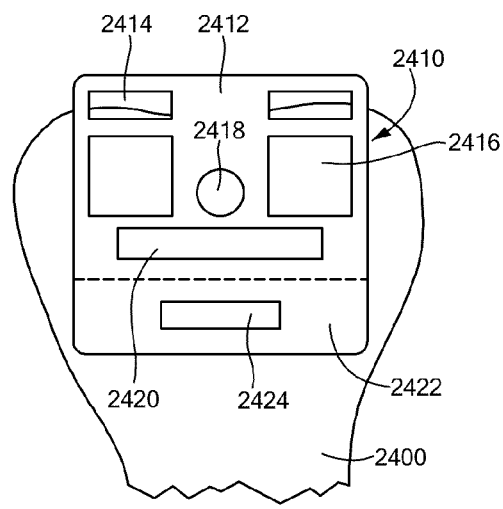
FIGS. 26A-O illustrate femur cutting blocks and molds used to create a surface for receiving the femoral portion of a knee implant, in accordance with various embodiments of the invention.

FIG. 26A illustrates the femur 2400 with a first portion 2410 of the mold placed thereon. In this depiction, the top surface of the mold 2412 is provided with a plurality of apertures. In this instance the apertures consist of a pair of rectangular apertures 2414, a pair of square apertures 2416, a central bore aperture 2418 and a long rectangular aperture 2420. The side surface 2422 of the first portion 2410 also has a rectangular aperture 2424. Each of the apertures is larger than the eventual cuts to be made on the femur so that, in the event the material the first portion of the mold is manufactured from a soft material, such as plastic, it will not be inadvertently cut during the joint surface preparation process. Additionally, the shapes can be adjusted, e.g., rectangular shapes made trapezoidal, to give a greater flexibility to the cut length along one area, without increasing flexibility in another area. As will be appreciated by those of skill in the art, other shapes for the apertures, or orifices, can be changed without departing from the scope of the invention.

Figure 26B:
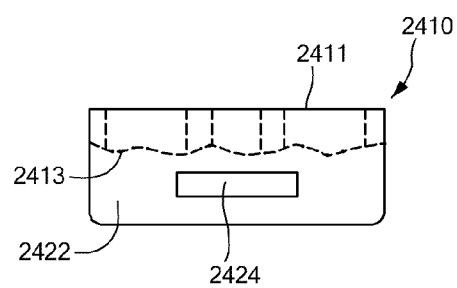
FIG. 26P illustrates an axis defined by the center of the tibial plateau and the center of the distal tibia.
FIG. 26q shows an axis defining the center of the tibial plateau to the femoral head.
FIGS. 26R and 26S show isometric views of a femoral template and a tibial template, respectively, in accordance with various embodiments of the invention.
FIG. 26T illustrates a femoral guide reference tool attached to the femoral template, in accordance with an embodiment of the invention.
FIG. 26U illustrates a sample implant template positioned on the condyle, in accordance with an embodiment of the invention.
FIG. 26V is an isometric view of the interior surface of the sample implant template, in accordance with an embodiment of the invention.
FIG. 26W is an isometric view of the tibial template attached to the sample implant, in accordance with an embodiment of the invention.
FIG. 26X shows a tibial template that may be used, after the tibial cut has been made, to further guide surgical tools, in accordance with an embodiment of the invention.
FIG. 26Y shows a tibial implant 2415 and femoral implant inserted onto the tibia and femur, respectively, after the above-described cuts have been made, in accordance with an embodiment of the invention.

FIG. 26B illustrates a side view of the first portion 2410 from the perspective of the side surface 2422 illustrating the aperture 2424. As illustrated, the exterior surface 2411 has a uniform surface which is flat, or relatively flat configuration while the interior surface 2413 has an irregular surface that conforms, or substantially conforms, with the surface of the femur.

Figure 26C:
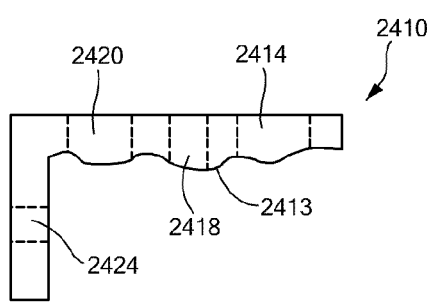
Figure 26D:
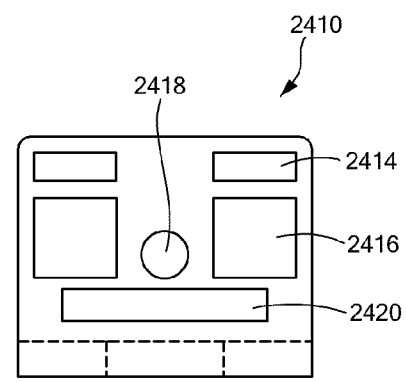

FIG. 26C illustrates another side view of the first, patient specific molded, portion 2410, more particularly illustrating the irregular surface 2413 of the interior. FIG. 26D illustrates the first portion 2410 from a top view. The center bore aperture 2418 is optionally provided to facilitate positioning the first piece and to prevent central rotation.

FIG. 26D illustrates a top view of the first portion 2410. The bottom of the illustration corresponds to an anterior location relative to the knee joint. From the top view, each of the apertures is illustrated as described above. As will be appreciated by those of skill in the art, the apertures can be shaped differently without departing from the scope of the invention.

Figure 26E:
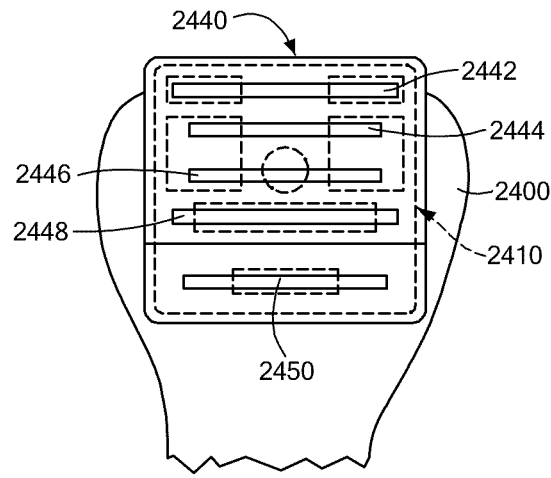

Turning now to FIG. 26E, the femur 2400 with a first portion 2410 of the cutting block placed on the femur and a second, exterior, portion 2440 placed over the first portion 2410 is illustrated. The second, exterior, portion 2440 features a series of rectangular grooves (2442-2450) that facilitate inserting a saw blade therethrough to make the cuts necessary to achieve the femur shape illustrated in FIG. 21E. These grooves can enable the blade to access at a 90° angle to the surface of the exterior portion, or, for example, at a 45° angle. Other angles are also possible without departing from the scope of the invention.

As shown by the dashed lines, the grooves (2442-2450) of the second portion 2440, overlay the apertures of the first layer.

Figure 26F:
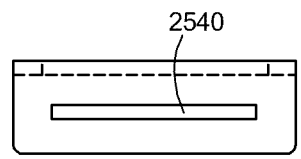
Figure 26G:
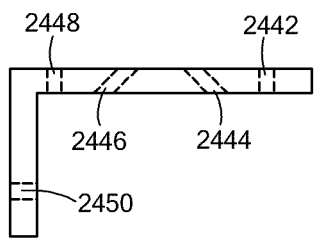
Figure 26H:
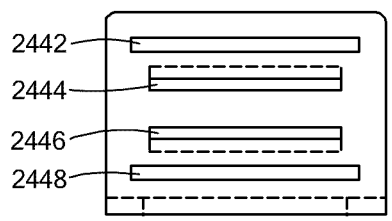

FIG. 26F illustrates a side view of the second, exterior, cutting block portion 2440. From the side view a single aperture 2450 is provided to access the femur cut. FIG. 26G is another side view of the second, exterior, portion 2440 showing the location and relative angles of the rectangular grooves. As evidenced from this view, the orientation of the grooves 2442, 2448 and 2450 is perpendicular to at least one surface of the second, exterior, portion 2440. The orientation of the grooves 2444, 2446 is at an angle that is not perpendicular to at least one surface of the second, exterior portion 2440. These grooves (2444, 2446) facilitate making the angled chamfer cuts to the femur. FIG. 26H is a top view of the second, exterior portion 2440. As will be appreciated by those of skill in the art, the location and orientation of the grooves will change depending upon the design of the femoral implant and the shape required of the femur to communicate with the implant.

Figure 26I:
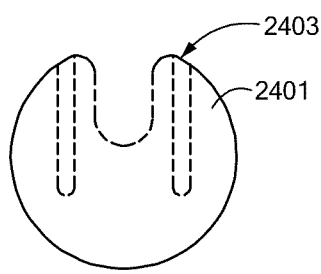

FIG. 26I illustrates a spacer 2401 for use between the first portion 2410 and the second portion 2440. The spacer 2401 raises the second portion relative to the first portion, thus raising the area at which the cut through groove 2424 is made relative to the surface of the femur. As will be appreciated by those of skill in the art, more than one spacer can be employed without departing from the scope of the invention. Spacers can also be used for making the tibial cuts. Optional grooves or channels 2403 can be provided to accommodate, for example, pins 2460 shown in FIG. 26J.

Figure 26J:
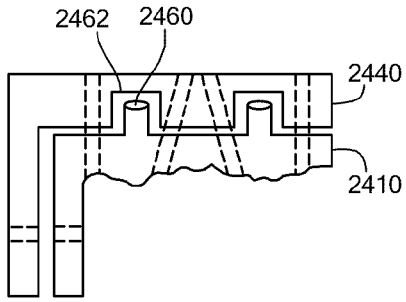

Similar to the designs discussed above with respect to FIG. 25, alternative designs can be used to control the movement and rotation of the cutting block 2440 relative to the mold 2410. As shown in FIG. 26J a series of protrusions, illustrated as pegs 2460, are provided that extend from the superior surface of the mold. These pegs or protrusions can be telescoping to facilitate the use of molds if necessary. As will be appreciated by those of skill in the art, one or more pegs or protrusions can be used without departing from the scope of the invention. For purposes of illustration, two pegs have been shown in FIG. 26J. Depending on the control desired, the pegs 2460 are configured to fit within, for example, a curved slot that enables rotational adjustment similar to the slots illustrated in FIG. 25K or within a recess that conforms in shape to the peg, similar to that shown in FIG. 25L and described with respect to the tibial cutting system. As will be appreciated by those of skill in the art, the recess 2462 can be sized to snugly encompass the peg or can be sized larger than the peg to allow limited lateral and rotational movement.

Figure 26K:
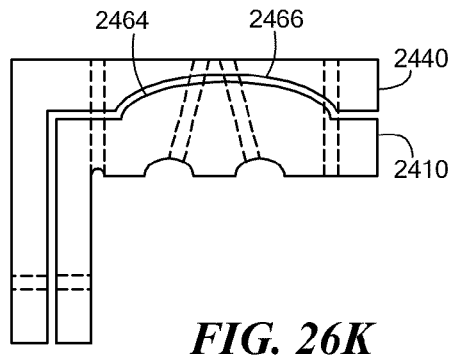
Figure 26L:
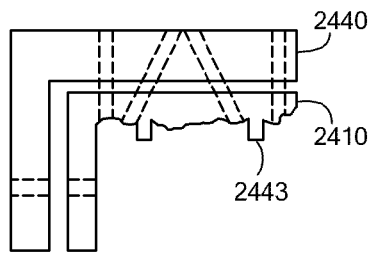
Figure 26M:
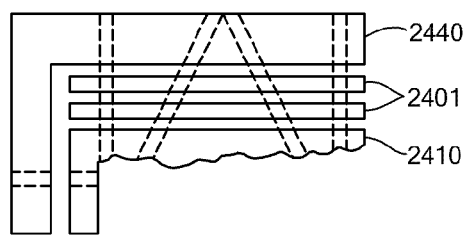

As illustrated in FIG. 26K the surface of the mold 2410 can be configured such that the upper surface forms a convex dome 2464 that fits within a concave well 2466 provided on the interior surface of the cutting block 2440. This configuration enables greater rotational movement about the mechanical axis while limiting lateral movement or translation.

In installing an implant, first the tibial surface is cut using a tibial block, such as those shown in FIG. 26. The patient specific mold is placed on the femur. The knee is then placed in extension and spacers 2401, such as those shown in FIG. 26M, or shims are used, if required, until the joint optimal function is achieved in both extension and flexion. The spacers, or shims, are typically of an incremental size, e.g., 5 mm thick to provide increasing distance as the leg is placed in extension and flexion. A tensiometer can be used to assist in this determination or can be incorporated into the mold or spacers in order to provide optimal results. The design of tensiometers are known in the art and are not included herein to avoid obscuring the invention. Suitable designs include, for example, those described in U.S. Pat. No. 5,630,820 to Todd issued May 20, 1997.

Figure 26N:
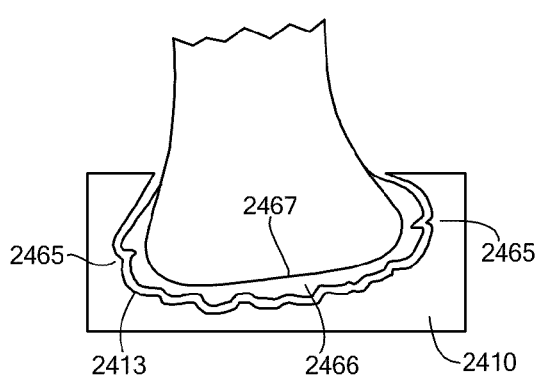
Figure 26O:
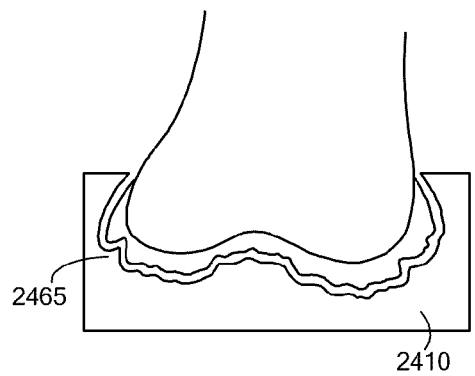

As illustrated in FIGS. 26N (sagittal view) and 26O (coronal view), the interior surface 2413 of the mold 2410 can include small teeth 2465 or extensions that can help stabilize the mold against the cartilage 2466 or subchondral bone 2467.

3D guidance templates may be used to create more that one cut on the same and/or on the opposite articular surface or opposite articular bone, in accordance with an embodiment of the invention. These cuts may be cross-referenced with other cuts using one or more guidance template(s).

In accordance with one embodiment of the invention, the 3D guidance template(s) are utilized to perform more than one cut on the same articular side such as the femoral side of a knee joint. In another embodiment, a 3D guidance template may be utilized to cross reference surgical interventions on an opposing articular surface. In a knee, for example, the first articular surface can be the femoral surface. The opposing articular surface can be the tibial surface or the patella surface. In a hip, the first articular surface can be the acetabulum. The opposing articular surface or the opposing bone can be the proximal femur.

Thus, in a knee, a horizontal femur cut can be cross-referenced with an anterior or posterior femur cut or optionally also chamfer, oblique cuts. Similarly, a tibial horizontal cut can be cross-referenced with any tibial oblique or vertical cuts on the same articular side or surface.

In accordance with another embodiment, one or more femur cuts can be crossed-referenced with one or more tibial cuts. Or, in a hip, one or more acetabular cuts or surgical interventions can be cross-referenced with one or more femoral cuts or surgical interventions such as drilling, reaming or boring. Similarly, in a knee again, one or more femur cuts can be cross-referenced with one or more patella cuts. Any combination and order is possible.

The cross-referencing can occur via attachments or linkages including spacers or hinge or ratchet like devices from a first articular bone and/or cartilage surface, to a second articular, bone and/or cartilage surface. The resulting positioning of the cut on the opposing articular, bone or cartilage surface can be optimized by testing the cut for multiple pose angles or joint positions such as flexion, extension, internal or external rotation, abduction or adduction. Thus, for example, in a knee a distal femur cut can be performed with a mold. Via a linkage or an attachment, a tibial template may be attached thereto or to the cut or other surgical intervention, thus a cross-reference can be related from the femoral cut to a tibial cut or other surgical intervention. Cross-referencing from a first articular surface to a second articular surface via, without limitation, attachments or linkages to a template has the advantage of insuring an optimal alignment between the implant or other therapeutic device components of the first articular surface to that on a second articular surface. Moreover, by cross-referencing surgical interventions on a first articular surface to a second articular surface, improved efficiencies and time savings can be obtained with the resulted surgical procedure.

Cross-referencing the first, the second and, optionally a third or more articular surface, such as in a knee joint, may be performed with a single linkage or attachment or multiple linkages or attachments. A single pose angle or position of a joint or multiple pose angles or positions of a joint may be tested and optimized during the entire surgical intervention. Moreover, any resulting surgical interventions on the opposite, second articular surface, bone or cartilage may be further optimized by optionally cross-referencing to additional measurement tools such as standard alignment guides.

For example, in a knee joint, a 3D template may be utilized to perform one or more surgical interventions on the femoral side, such as a femoral cut. This can then be utilized via a linkage, an attachment or via indirect cross-referencing directly onto the site of surgical intervention, to guide a surgical intervention such as a cut of the tibial side. Prior to performing the surgical intervention on the tibial side, a traditional tibial alignment guide with cross-reference to the medial and lateral malleolus of the ankle turn may be used to optimize the position, orientation and/or depth and extent of the planned surgical intervention such as the cut. For example, cross-referencing to the femoral cut can aid in defining the relative superior inferior height of the tibial cut, while cross-referencing a tibial alignment guide can optionally be utilized to determine the slant of the cut in the interior posterior direction.

An exemplary system and methodology is now described in which a femoral template is used to make a cut on the femur, which is then cross-referenced to properly align a tibial template for making a cut on the tibial plateau. Initially, an electronic image(s) of the leg is obtained using imaging techniques elaborated in above-described embodiments. For example, a pre-operative CT scan of a patient's leg may be obtained to obtain electronic image data.

Image processing is then applied to the image data to derive, without limitation, relevant joint surfaces, axis, and/or cut planes. Image processing techniques may include, without limitation, segmentation and propagation of point clouds.

Figure 26P:
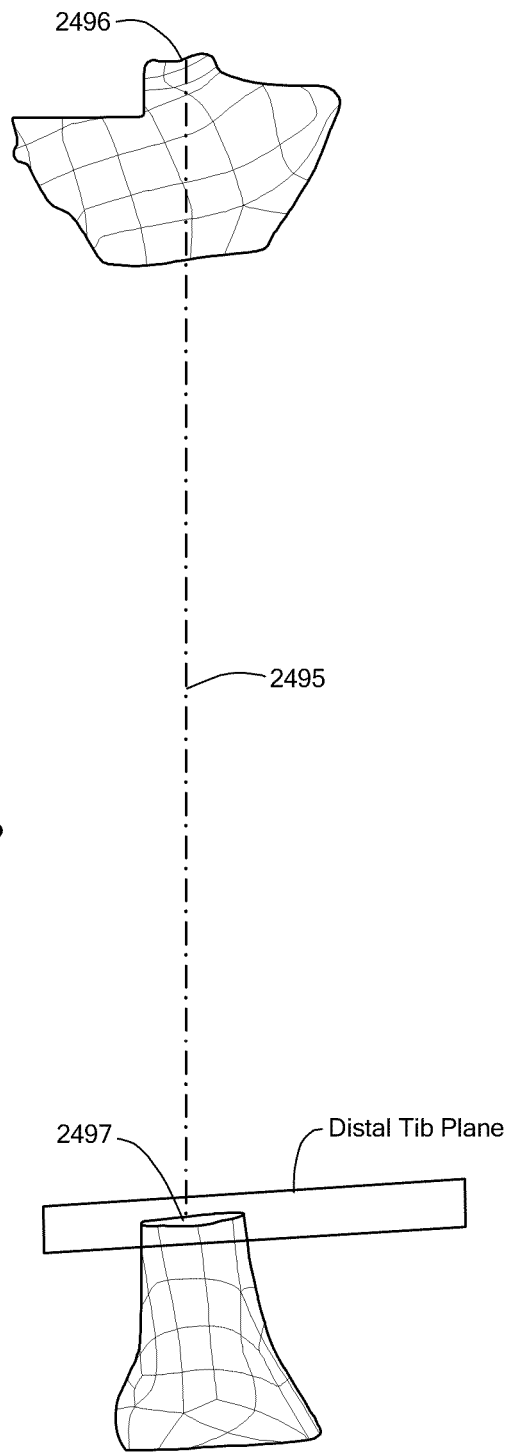
Figure 26Q:
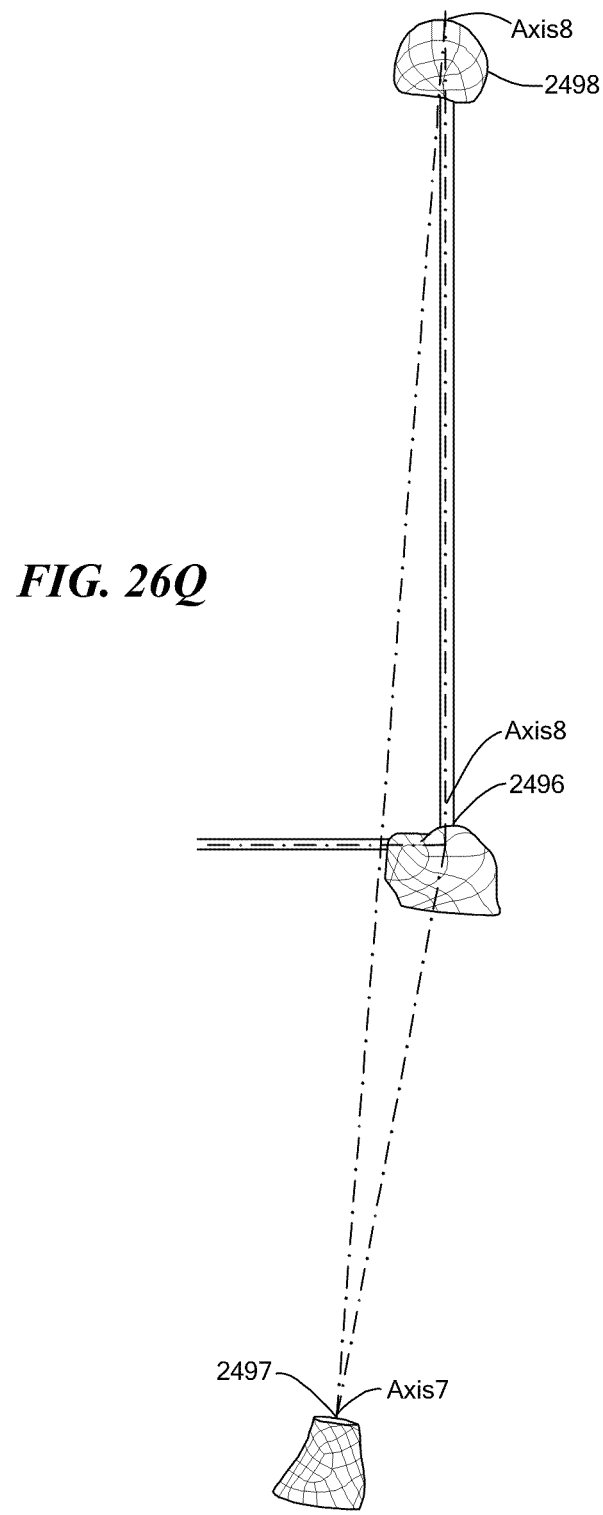

Relevant biomechanical and/or anatomical axis data may be obtained by identifying, for example, the central femoral head, central knee joint and center of the distal tibia. The cutting planes may then be defined based on at least one of these axis. For example, the tibial implant bearing surface may be defined as being perpendicular to the axis defined by the center of the tibial plateau 2496 and the center of the distal tibia 2497, as illustrated in FIG. 26P; the tibial implant's medial margin may project towards the femoral head, as illustrated in FIG. 26Q; and the anterior to posterior slope of the tibia may be approximated by the natural anatomical slope (alternatively, excessive tibial slope may be corrected).

Figure 26R:
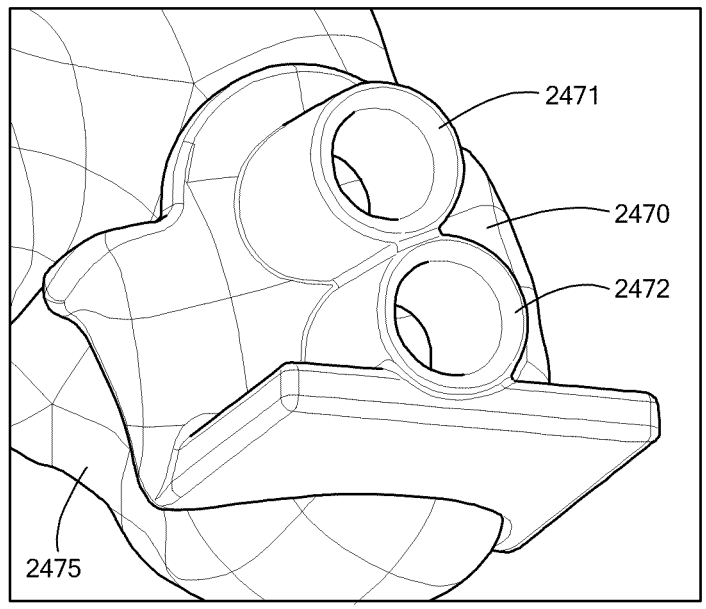
Figure 26S:
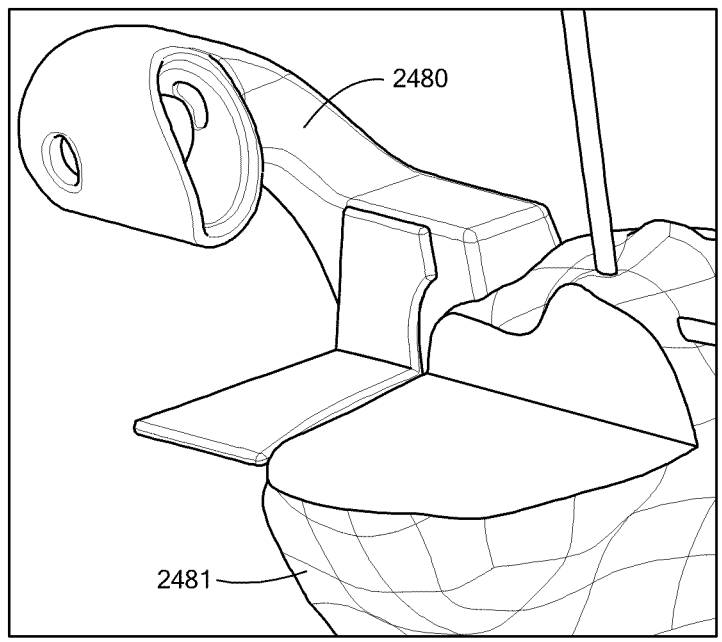

The tibial and femoral templates and implants may be designed based, at least in part, on the derived joint surfaces, axis and/or cut planes. FIGS. 26R and 26S show isometric views of a femoral template 2470 and a tibial template 2480, respectively, in accordance with an embodiment of the invention. The femoral template 2470 has an interior surface that, in various embodiments, conforms, or substantially conforms, with the anatomic surface (bone and/or cartilage) of the femur 2475. Furthermore, the interior surface of the femoral template may extend a desired amount around the anatomical boney surfaces of the condyle to further ensure proper fixation. The interior surface of the tibial cutting block 2480 may conform, or substantially conform to the surface (bone and/or cartilage) of the tibia 2481.

In an exemplary use, the femoral template 2470 is placed on the femoral condyle 2475, for example, when the knee is flexed. The femoral template 2470 may be fixed to the femoral condyle 2475 using, without limitation, anchoring screws/drill pins inserted through drill bushing holes 2471 and 2472. The position of holes 2471 and 2472 on the condyle may be the same used to anchor the final implant to the femur. In various embodiments, the holes 2471 and 2472 may include metal inserts/bushings to prevent degradation when drilling. Fixing the template 2470 to the femoral condyle 2475 advantageously prevents movement of the template during subsequent cutting or other surgical interventions thereby ensuring the accuracy of the resultant surgical cuts.

Figure 26T:
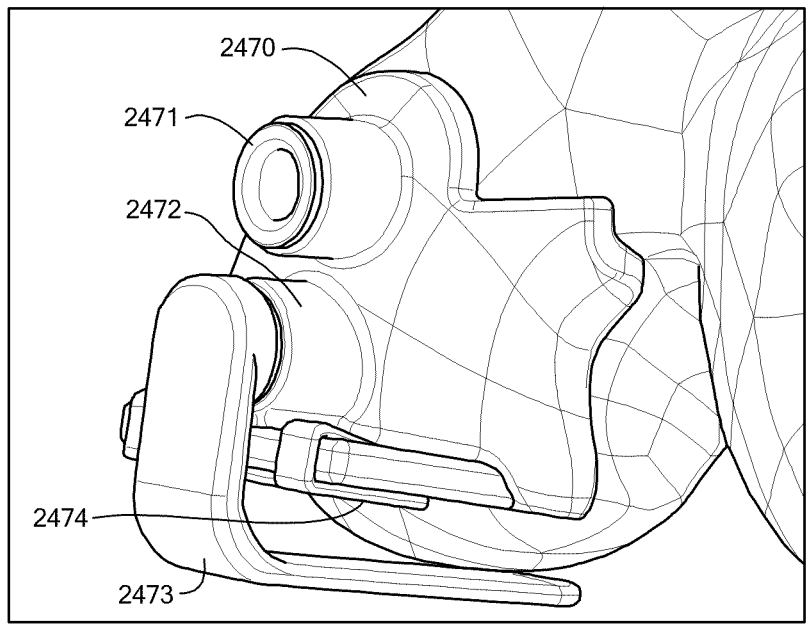

To assist in accurately positioning the femoral template 2470, a femoral guide reference tool 2473 may be attached to the femoral template 2470, as shown in FIG. 26T. The femoral guide reference tool 2473 may, without limitation, attach to one of holes 2471 and 2472. The femoral guide reference tool 2473 may reference off the tangential margin of the posterior condyle, and aid, for example, in correct anterior-posterior positioning of the femoral template 2470.

Upon proper fixation of the femoral template 2470 to the femoral condyle 2475, a cut to the femoral condyle is made using cut guide surface or element 2474. The cut guide surface or element 2474 may be integral to the femoral template 2470, or may be an attachment to the femoral template 2470, with the attachment made of a harder material than the femoral template 2470. For example, the cut guide surface or element 2474 may be a metal tab that slides onto the femoral template 2470, which may be made, without limitation, of a softer, plastic material.

Figure 26U:
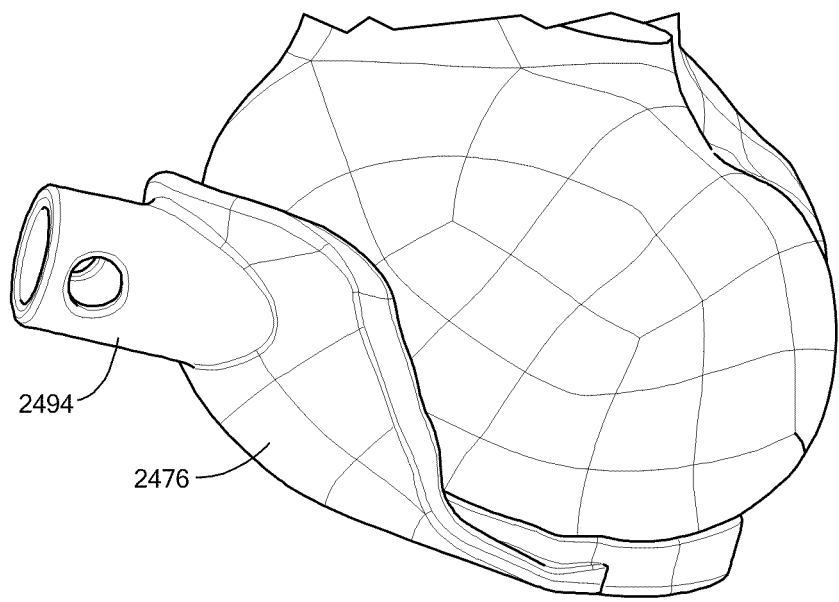

Upon making the femoral cut and removing the femoral template 2475, a sample implant template 2476 (not the final implant) is optionally positioned on the condyle, as shown in FIG. 26U, in accordance with an embodiment of the invention. The sample implant template 2474 may be attached to the condyle by using without limitation, anchoring screws/drill pins inserted through the same holes used to anchor the final implant to the femur.

The sample implant template 2476 includes an attachment mechanism 2494 for attaching the tibial template 2480, thereby cross-referencing the placement of the distal tibial cut with respect to the femoral cut/implant's placement. The attachment mechanism 2494 may be, without limitation, a boss, as shown in FIG. 26U, or other attachment mechanism known in the art, such as a snap-fit mechanism. Note that in alternative embodiments, a sample implant template 2476 is not required. For example, the tibial template 2480 may attach directly to the femoral template 2470. However, in the subject embodiment, the drill bushing features of the femoral template 2475 will interfere with the knee going into extension, preventing the tibial cut.

In illustrative embodiments, the thickness of the sample implant template 2476 may not only include the thickness of the final femoral implant, but may include an additional thickness that corresponds to a preferred joint space between tibial and femoral implants. For example, the additional thickness may advantageously provide a desired joint space identified for proper ligament balancing or for flexion, extension, rotation, abduction, adduction, anteversion, retroversion and other joint or bone positions and motion.

Figure 26V:
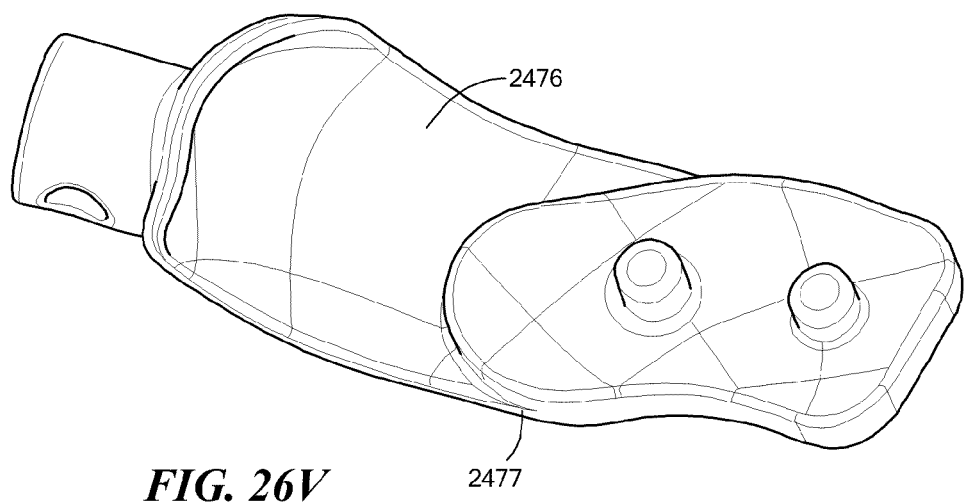

FIG. 26V is an isometric view of the interior surface of the sample implant template 2476, in accordance with an embodiment of the invention. In various embodiments, the femoral implant often rests on subchondral bone, with the cartilage being excised. In embodiments where the sample implant template 2474 extends beyond the dimensions of the femoral implant such that portions of the sample implant template 2476 rests on cartilage, an offset 2477 in the interior surface of the sample implant template 2476 may be provided.

Figure 26W:
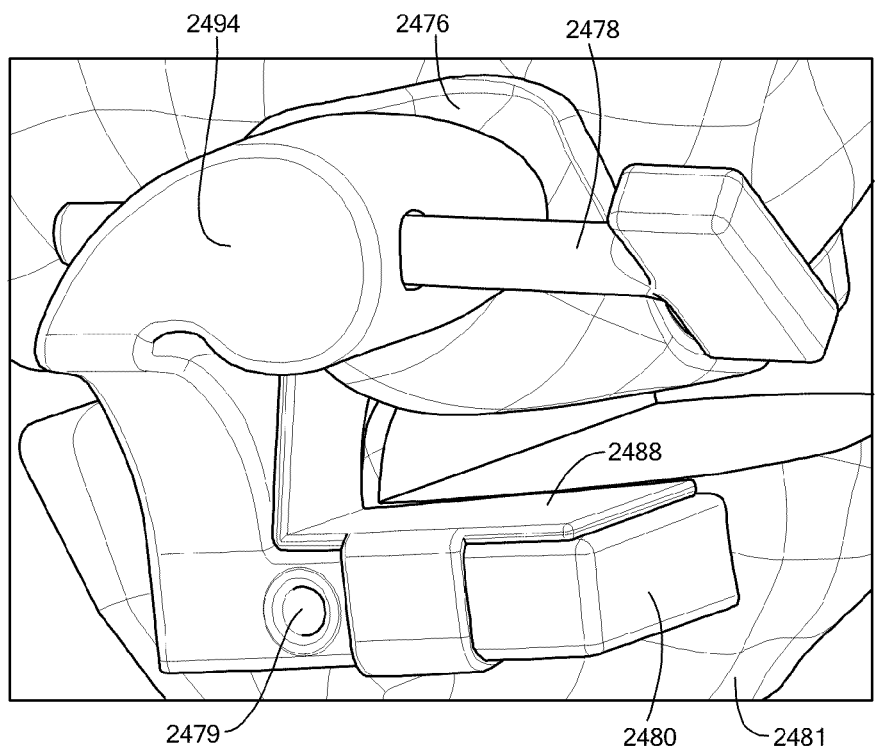

FIG. 26W is an isometric view of the tibial template 2480 attached to the sample implant 2476 when the knee is in extension, in accordance with an embodiment of the invention. A crosspin 2478 inserted through boss 2494 fixes the tibial template 2480 to the sample implant template 2474. Of course, other attachment mechanisms may be used, as described above. In preferred embodiments, the tibial template 2480 may also be fixed to the tibia 2481 using, without limitation, anchoring screws/drill pins inserted through drill bushing hole 2479. In various embodiments, the holes 2479 include metal inserts (or other hard material) to prevent degradation when drilling. As with the femoral template 2475, the cut guide surface or element of the tibial template 2480 may be integral to the tibial template 2475, or may be an attachment to the tibial template 2480, the attachment made of a harder material than the tibial template 2480. Upon fixing the position of the tibial template 2480, the cut guide of the tibial template 2475 assists in guiding the desired cut on the tibia.

Figure 26X:
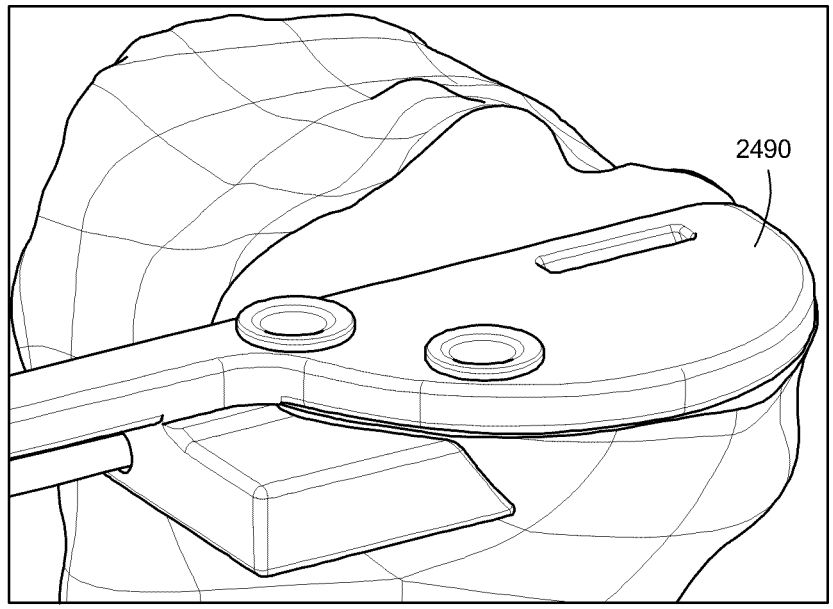

FIG. 26X shows a tibial template 2490 that may be used, after the tibial cut has been made, to further guide surgical tools in forming anchoring apertures in the tibia for utilization by the tibial implant (e.g., the tibial implant may include pegs and/or keels that are used to anchor the tibial implant into the tibia), in accordance with an embodiment of the invention. The outer perimeter of a portion of the tibial template 2490 may mimic the perimeter of the tibial implant. Guide apertures in the tibial template 2490 correspond to the tibial implants fixation features. A portion of the tibial template 2490 conforms to, without limitation, the anterior surface of the tibia to facilitate positioning and anchoring of the template 2490.

Figure 26Y:
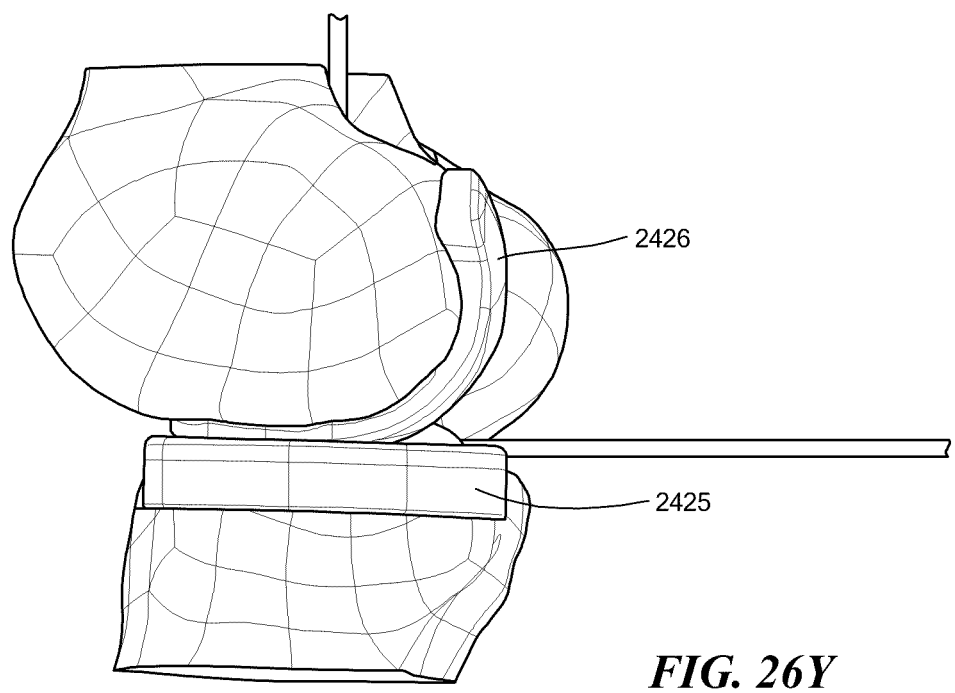

FIG. 26Y shows a tibial implant 2425 and femoral implant 2426 inserted onto the tibia and femur, respectively, after the above-described cuts have been made, in accordance with an embodiment of the invention.

Thus, the tibial template 2480 used on the tibia can be cross-referenced to the femoral template 2476, femoral cut and/or sample implant 2474. Similarly, in the hip, femoral templates can be placed in reference to an acetabular mold or vice versa. In general, when two or more articular surfaces will be repaired or replaced, a template can be placed on one or more of them and surgical procedures including cutting, drilling, sawing or rasping can be performed on the other surface or other surfaces in reference to said first surface(s).

In illustrative embodiments, three-dimensional guidance templates may be utilized to determine an optimized implant rotation. Examples are provided below with reference to the knee, however it is to be understood that optimizing implant rotation may be applied other joints as well.

Femoral Rotation:

The optimal rotation of a femoral component or femoral implant for a uni-compartmental, patello femoral replacement or total knee replacement may be ascertained in a number of different ways. Implant rotation is typically defined using various anatomic axes or planes. These anatomic axes may include, without limitation, the transepicondylar axis; the Whiteside line, i.e. the trochlea anteroposterior axis, which is typically perpendicular to at least one of the cuts; and/or the posterior condylar axis. Another approach for optimizing femoral component rotation is a so-called balancing gap technique. With the balancing gap technique, a femoral cut is made parallel to the tibia, i.e. the tibia is cut first typically. Prior to performing the femoral cut, the femoral cut plate is optimized so that the medial and lateral ligament and soft tissue tension are approximately equal.

By measuring the relevant anatomic axis or planes, the optimal implant rotation may be determined. The measurement may be factored into the shape, position or orientation of the 3D guidance template, in accordance with an embodiment of the invention. Any resultant surgical interventions including cuts, drilling, or sawings are then made incorporating this measurement, thereby achieving an optimal femoral component rotation.

Moreover in order to achieve an optimal balancing, the rotation of the template may be changed so that the cuts are parallel to the tibial cut with substantially equal tension medially and laterally applied.

Tibial Rotation:

A 3D guidance template may also be utilized to optimize tibial component rotation for uni-compartmental or total knee replacements, in accordance with an embodiment of the invention. Tibial component rotation may be measured using a number of different approaches known in the art. In one example of a tibial component rotation measurement, the anteroposterior axis of the tibia is determined. For a total knee replacement, the tibial component can be placed so that the axis of the implant coincides with the medial one-third of the tibial tuberosity. This approach works well when the tibia is symmetrical.

In another embodiment, the symmetrical tibial component is placed as far as possible posterolateral and externally rotated so that the posteromedial corner of the tibial plateau is uncovered to an extent of between three (3) and five (5) millimeters.

The above examples are only representative of the different approaches that have been developed in the literature. Clearly, other various anatomic axis, plane and area measurements may be performed in order to optimize implant rotation.

In illustrative embodiments, these measurements may be factored into the design of a 3D guidance template and the position, shape or orientation of the 3D guidance template may be optimized utilizing this information. Thus, any subsequent surgical intervention such as cutting, sawing and/or drilling will result in an optimized implant rotation, for example, in the horizontal or in a near horizontal plane.

Turning now to FIG. 27, a variety of illustrations are provided showing a patellar cutting block and mold system. FIGS. 27A-C illustrates the patellar cutting block 2700 in conjunction with a patella 2702 that has not been resected. In this depiction, the cutting block 2700 can consist of only one piece or a plurality of pieces, if desired. The inner surface 2703 is patient specific and designed to mate, or substantially mate, with the existing geography of the patient's patella 2702. Small openings are present 2707 to accept the saw. The mold or block can have only one or multiple openings. The openings can be larger than the saw in order to allow for some rotation or other fine adjustments. FIG. 27A is a view in the sagittal plane S. The quadriceps tendon 2704 and patellar tendon 2705 are shown.

FIG. 27B is a view in the axial plane A. The cartilage 2706 is shown. The mold can be molded to the cartilage or the subchondral bone or combinations thereof. FIG. 27C is a frontal view F of the mold demonstrating the opening for the saw 2707. The dashed line indicates the relative position of the patella 2702.

FIGS. 27D (sagittal view) and E (axial view) illustrate a patellar cutting block 2708 in conjunction with a patella 2702 that has not been resected. In this depiction, the cutting block 2708 consists of at least two pieces. The first piece is a patient specific interior piece 2710 or mold that is designed on its inferior surface 2712 to mate, or substantially mate, with the existing geography of the patient's patella 2702. The posterior surface 2714 and side surfaces 2716 of the first piece 2710 are configured to mate within the interior of an exterior piece 2720. The reusable exterior piece 2720 fits over the interior piece 2710 and holds it onto the patella. The reusable exterior piece has an interior surface 2724 that mates with the first piece 2710. The reusable exterior piece 2720 includes cutting guides 2707, to assist the surgeon in performing the patellar surface cut. A plurality of cutting guides can be provided to provide the surgeon a variety of locations to choose from in making the patellar cut. If necessary, additional spacers can be provided that fit between the first patient configured, or molded, piece 2710 and the second reusable exterior piece, or cutting block, 2720.

The second reusable exterior piece, or cutting block, 2720, can have grooves 2722 and extensions 2725 designed to mate with surgical instruments such as a patellar clamp 2726. The patellar clamp 2726 can have ring shaped graspers 2728 and locking mechanisms, for example ratchet-like 2730. The opening 2732 in the grasper fits onto the extension 2725 of the second reusable exterior piece 2720. Portions of a first portion of the handle of the grasper can be at an oblique angle 2734 relative to the second portion of the handle, or curved (not shown), in order to facilitate insertion. Typically the portion of the grasper that will be facing towards the intra-articular side will have an oblique or curved shaped thereby allowing a slightly smaller incision.

The variable nature of the interior piece facilitates obtaining the most accurate cut despite the level of disease of the joint because it positions the exterior piece 2720 in the desired plane. Either the interior piece 2710 or the exterior piece 2720 can be formed out of any of the materials discussed above in Section II, or any other suitable material. Additionally, a person of skill in the art will appreciate that the invention is not limited to the two piece configuration described herein. The reusable exterior piece 2720 and the patient specific interior piece 2710 can be a single piece that is either patient specific (where manufacturing costs of materials support such a product) or is reusable based on a library of substantially defect conforming shapes developed in response to known or common tibial surface sizes and defects.

The interior piece 2710 is typically molded to the patella including the subchondral bone and/or the cartilage.

From this determination, an understanding of the amount of space needed to balance the knee is determined and an appropriate number of spacers is then used in conjunction with the cutting block and mold to achieve the cutting surfaces and to prevent removal of too much bone. Where the cutting block has a thickness of, for example, 10 mm, and each spacer has a thickness of 5 mm, in preparing the knee for cuts, two of the spacers would be removed when applying the cutting block to achieve the cutting planes identified as optimal during flexion and extension. Similar results can be achieved with ratchet or jack like designs interposed between the mold and the cut guide.

vii. Hip Joint

Turning now to FIG. 28, a variety of views showing sample mold and cutting block systems for use in the hip joint are shown. FIG. 28A illustrates femur 2510 with a mold and cutting block system 2520 placed to provide a cutting plane

2530 across the femoral neck 2512 to facilitate removal of the head 2514 of the femur and creation of a surface 2516 for the hip ball prosthesis.

FIG. 28B illustrates a top view of the cutting block system 2520. The cutting block system 2520 includes an interior, patient specific, molded section 2524 and an exterior cutting block surface 2522. The interior, patient specific, molded section 2524 can include a canal 2526 to facilitate placing the interior section 2524 over the neck of the femur. As will be appreciated by those of skill in the art, the width of the canal will vary depending upon the rigidity of the material used to make the interior molded section. The exterior cutting block surface 2522 is configured to fit snugly around the interior section. Additional structures can be provided, similar to those described above with respect to the knee cutting block system, that control movement of the exterior cutting block 2524 relative to interior mold section 2522, as will be appreciated by those of skill in the art. Where the interior section 2524 encompasses all or part of the femoral neck, the cutting block system can be configured such that it aids in removal of the femoral head once the cut has been made by, for example, providing a handle 2501 as shown in FIG. 28G.

Figure 28E:
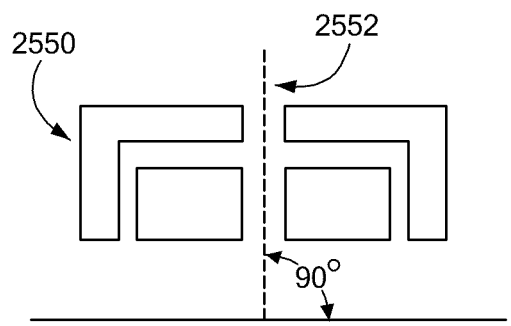
Figure 28F:
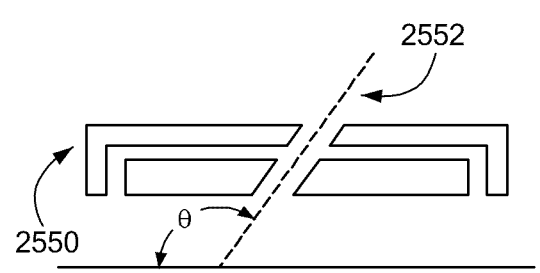
Figure 28G:
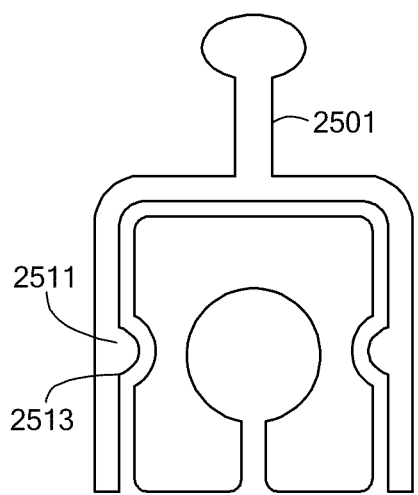

FIG. 28C illustrates a second cutting block system 2550 that can be placed over the cut femur to provide a guide for reaming after the femoral head has been removed using the cutting block shown in FIG. 28A. FIG. 28D is a top view of the cutting block shown in FIG. 28C. As will be appreciated by those of skill in the art, the cutting block shown in FIG. 28C-D, can be one or more pieces. As shown in FIG. 28E, the aperture 2552 can be configured such that it enables the reaming for the post of the implant to be at a 90° angle relative to the surface of femur. Alternatively, as shown in FIG. 28F, the aperture 2552 can be configured to provide an angle other than 90° for reaming, if desired.

FIGS. 29A (sagittal view) and 29B (frontal view, down onto mold) illustrates a mold system 2955 for the acetabulum 2957. The mold can have grooves 2953 that stabilize it against the acetabular rim 2960. Surgical instruments, e.g. reamers, can be passed through an opening in the mold 2956. The side wall of the opening 2962 can guide the direction of the reamer or other surgical instruments. Metal sleeves 2964 can be inserted into the side wall 2962 thereby protecting the side wall of the mold from damage. The metal sleeves 2964 can have lips 2966 or overhanging edges that secure the sleeve against the mold and help avoid movement of the sleeve against the articular surface.

FIG. 29C is a frontal view of the same mold system shown in FIGS. 29A and 29B. A groove 2970 has been added at the 6 and 12 o'clock positions. The groove can be used for accurate positioning or placement of surgical instruments. Moreover, the groove can be useful for accurate placement of the acetabular component without rotational error. Someone skilled in the art will recognize that more than one groove or internal guide can be used in order to not only reduce rotational error but also error related to tilting of the implant. As seen FIG. 29D, the implant 2975 can have little extensions 2977 matching the grooves thereby guiding the implant placement. The extensions 2977 can be a permanent part of the implant design or they can be detachable. Note metal rim 2979 and inner polyethylene cup 2980 of the acetabular component.

Figure 28H:
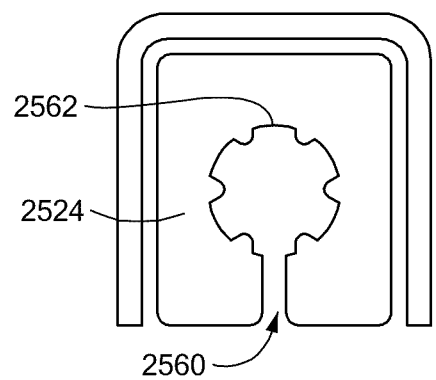

FIG. 28H illustrates a cross-section of a system where the interior surface 2560 of the molded section 2524 has teeth 2562 or grooves to facilitate grasping the neck of the femur.

Various steps may be performed in order to design and make 3D guidance templates for hip implants, in accordance with an embodiment of the invention.

For example, in an initial step, a discrepancy in the length of the left leg and right leg may be determined, for example, in millimeters. Leg length discrepancy may be determined, for example, using standing x-rays, typically including the entire leg but also cross-sectional imaging modalities such as CT or MRI.

A CT scout scan may be utilized to estimate leg length. Alternatively, select image slices through the hip and ankle joint may be utilized to estimate leg length either using CT or MRI.

Figure 39:
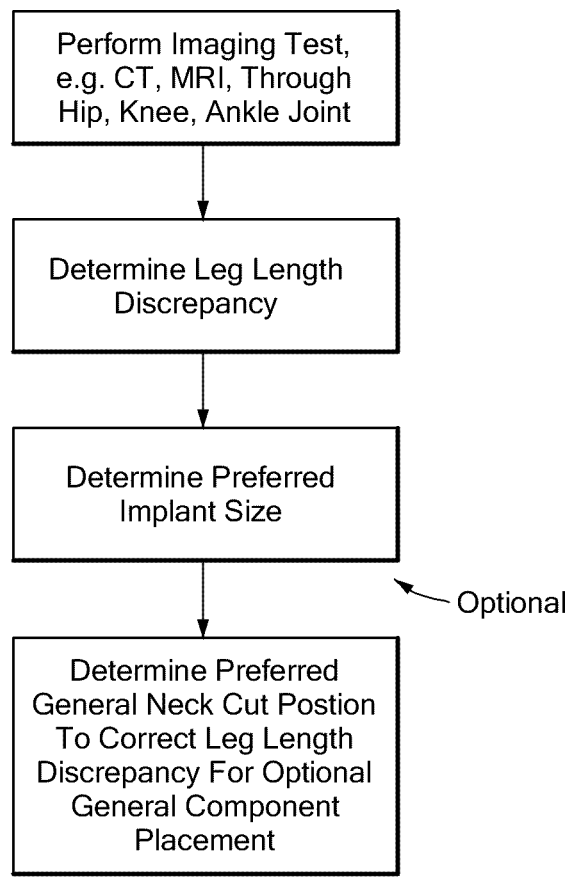
FIG. 39 is a flow diagram showing a method wherein measured leg length discrepancy is utilized to determine the optimal cut height of a femoral neck cut for total hip arthroplasty, in accordance with an embodiment of the invention.
Figure 43:
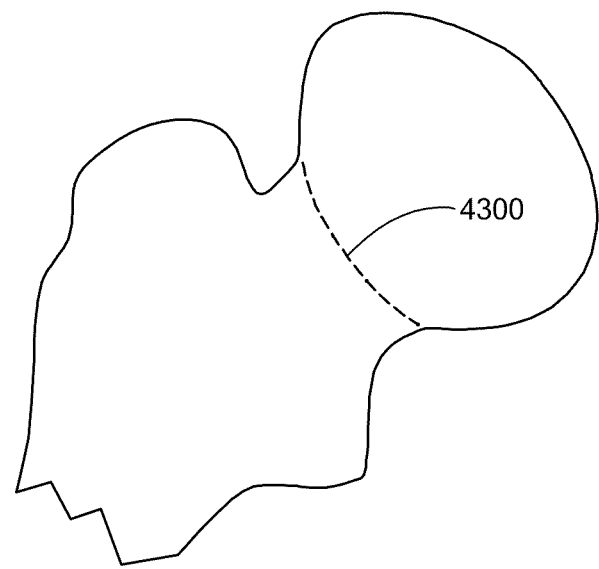
FIG. 43 shows an example of an intended site for placement of a femoral neck mold for total hip arthroplasty, in accordance with one embodiment of the invention.

Pre-operative planning is then performed using the image data. A first 3D guidance template is designed to rest on the femoral neck. FIG. 43 shows an example of an intended site 4300 for placement of a femoral neck mold for total hip arthroplasty A cut or saw plane integrated into this template can be derived. The position, shape and orientation of the 3D guidance mold or jig or template may be determined on the basis of anatomical axis such as the femoral neck axis, the biomechanical axis and/or also any underlying leg length discrepancy (FIG. 39). Specifically, the superoinferior cut or saw guide height can be adapted to account for leg length discrepancy. For example, if the left leg is five (5) millimeters shorter than the right leg, then the cut height can be moved by five (5) millimeters to account for this difference. The femoral neck cut height ultimately determines the position of the femoral stem. Thus, in this manner, using this type of pre-operative planning, the femoral neck cut height can be optimized using a 3D guidance template.

FIG. 39 is a flow diagram of a method wherein measurement of leg length discrepancy can be utilized to determine the optimal cut height of the femoral neck cut for total hip arthroplasty. Initially, imaging is performed, e.g. CT and/or MRI, through, without limitation, the hip, knee and ankle joint, step 3902. Leg length discrepancy is determined, using the imaging data obtained, step 3904. The preferred implant size may then be optionally determined, step 3906. The preferred femoral neck cut position is determined based, at least in part, on correcting the leg length discrepancy for optimal femoral component placement.

Figure 44:
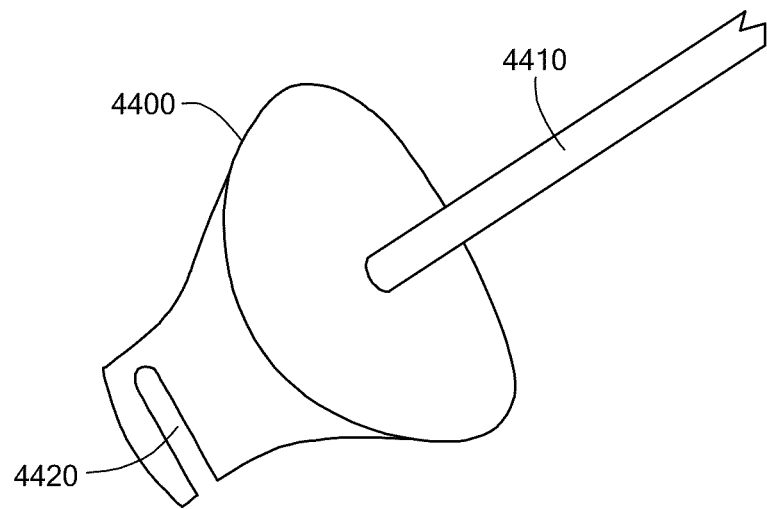
FIG. 44 shows an example of a femoral neck mold with handle and slot, in accordance with an embodiment of the invention.

FIG. 44 shows another example of a femoral neck mold 4400 with handle 4410 and optional slot 4420.

Acetabulum:

In the acetabulum, the position and orientation of the acetabular component or acetabular cup is also critical for the success of hip surgery. For example, the lowest portion of the acetabular cup may be placed so that it is five (5) millimeters lateral to an anatomic landmark on a pelvic x-ray coinciding with the inferior border of the radiographic tear drop. If the acetabular component is, for example, placed too far superiorly, significant bone may be lost.

Placing the acetabular component using the 3D guidance template may include, for example, the following steps:

Step One: Imaging, e.g. using optical imaging methods, CT or MRI.

Step Two: Determining the anterior rotation of the acetabulum and the desired rotation of the acetabular cup.

Step Three: Find best fitting cup size.

Step Four: Determine optimal shape, orientation and/or position of 3D guidance template.

The template may be optionally designed to rest primarily on the margin of the acetabular fossa. In this manner, it is possible to ream through the template.

Figure 45:
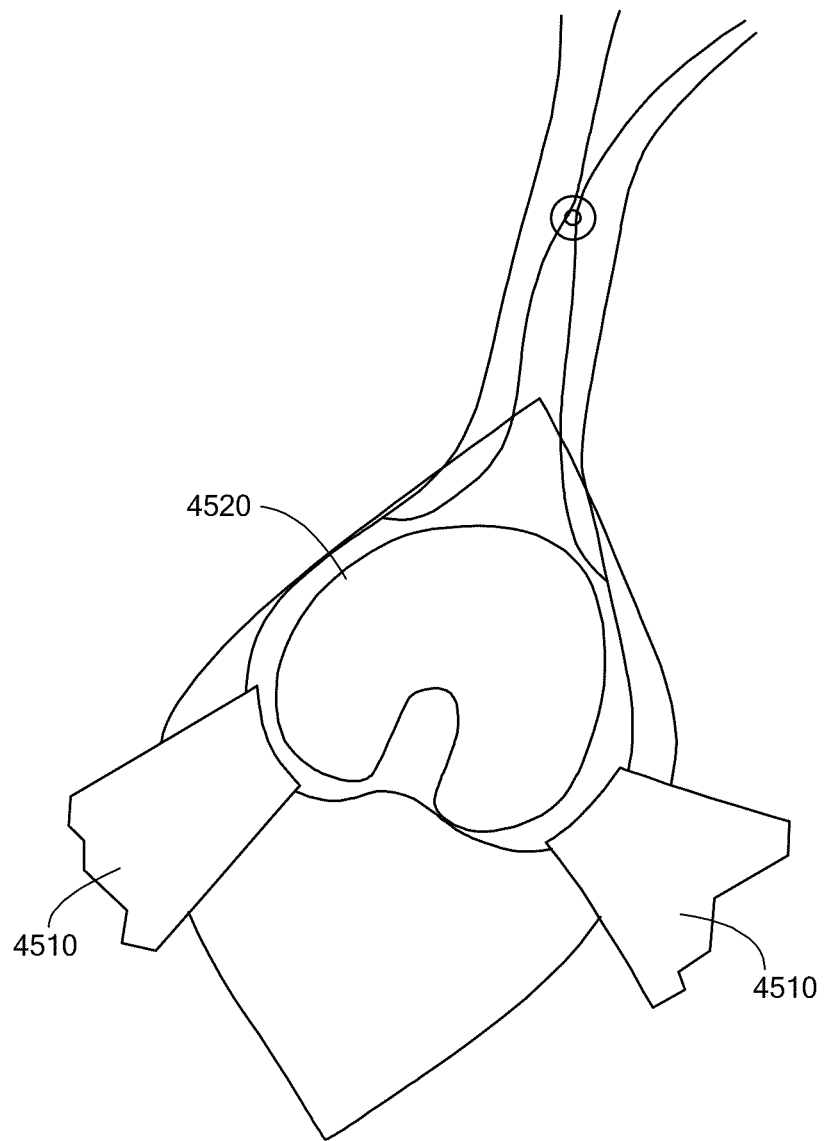
FIG. 45 shows an example of a posterior acetabular approach for total hip replacement, in accordance with an embodiment of the invention.

FIG. 45 shows an example of a posterior acetabular approach for total hip replacement. Tissue retractors 4510 are in place. The acetabular fossa is visible 4520.

Figure 46:
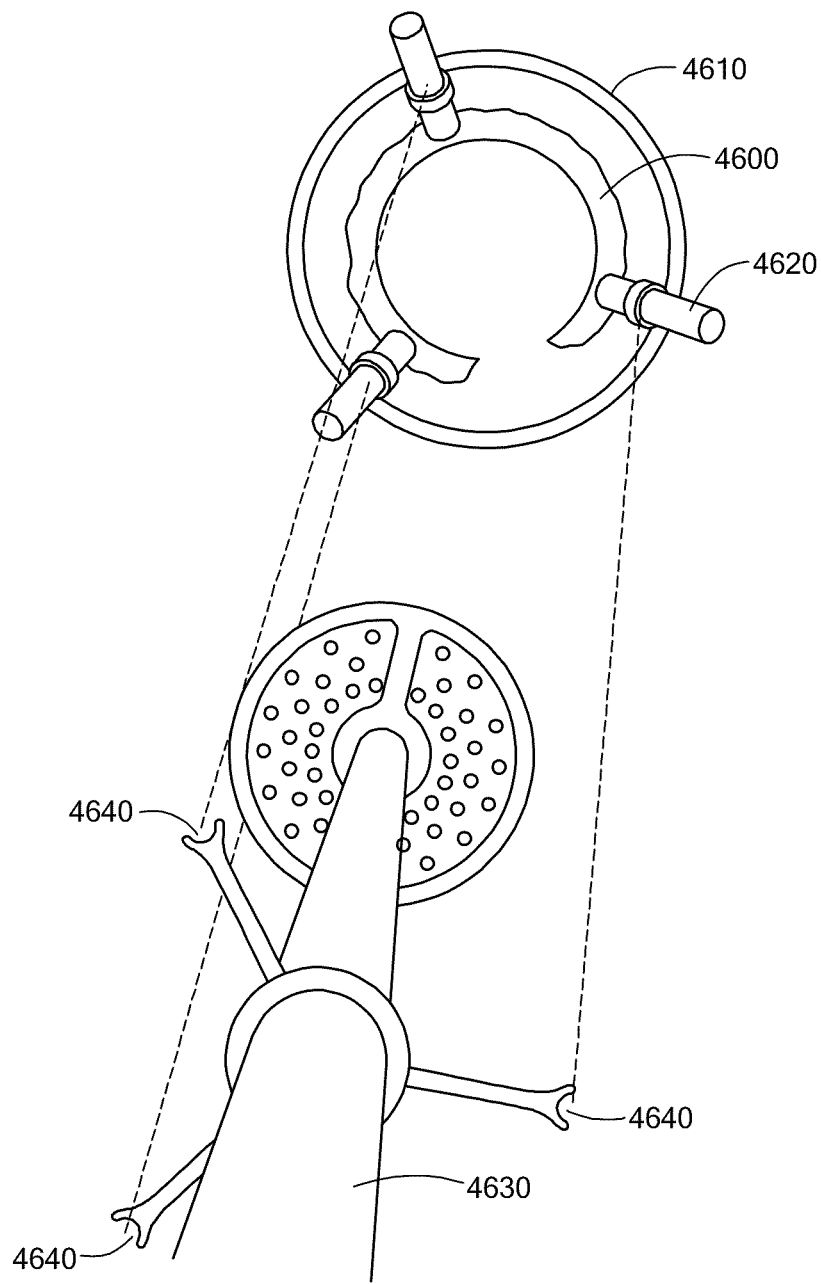
FIG. 46 shows an example of a guidance mold used for reaming the site for an acetabular cup, in accordance with an embodiment of the invention.

FIG. 46 shows an example of a guidance mold used for reaming the site for an acetabular cup. The mold 4600 can be optionally attached to a generic frame 4610. A guide for the reamer is shown 4620. The reamer 4630 or the mold can have optional stops 4640. In this example, the stops 4640 are attached to the reamer 4630 and engage the guide 4620 for the reamer.

For purposes of reaming, the template may be fixed to the pelvis, for example, using metal spikes or K-wires. The template may also have a grip for fixing it to the bone. Thus, a surgeon may optionally press the template against the bone while a second surgeon will perform the reaming through the opening in the template. The grip or any stabilizers can extend laterally, and optionally serve as tissue retractors, keeping any potentially interfering soft tissue out of the surgical field. The template may also include stoppers 4640 to avoid over penetration of the reamer. These stoppers may be designed in the form of metal stops defining the deepest penetration area for the peripheral portion or other portions of the reamer. Optionally, the template may also taper and decrease in inner radius thereby creating a stop once the reamer once the reaches the innermost portion of the template. Any stop known in the art can be used. The imaging test can be used to design or shape the mold in a manner that will help achieve the optimal reaming depth. The stops can be placed on the mold or reamer in reference to the imaging test in order to achieve the optional reaming depth.

A 3D guidance template may be utilized to optimize the anteversion of the acetabular cup. For example, with the posteral lateral approach, typically an anteversion of forty to forty-five degrees is desired in both males and females. With an anterolateral approach, zero degrees anteversion may be desired. Irrespective of the desired degree of anti-version, the shape, orientation and/or position of the template may be optimized to include the desired degree of anteversion.

Similarly, on the femoral side, the 3D guidance template may be optimized with regard to its shape, orientation and position in order to account for neutral, varus or valgus position of the femoral shaft. A 3D guidance template may also be utilized to optimize femoral shaft anteversion.

Thus, after a first template has been utilized for performing the femoral neck cut and a second template has been utilized for performing the surgical intervention on the acetabular side, a third template may optionally be utilized to be placed onto the femoral cut.

FIG. 47 shows an example of an optional third mold 4700, placed on the femoral neck cut, providing and estimate of anteversion and longitudinal femoral axis.

The third template may optionally include a handle. The third template may be shaped, designed, oriented and/or positioned so that it is optimized to provide the surgeon with information and reference points for the long axis of the femur 4710 and femoral anteversion 4720. A broach 4730 with broach handle 4740 is seen in place. The cut femoral neck 4750 is seen. The third mold 4700 attaches to it. By providing information on the long axis of the femur and femoral anteversion, an intra-operative x-ray can be saved which would otherwise be necessitated in order to obtain this information.

Optionally, modular hip implant components may be utilized such as a modular stem. Such modular designs can be helpful in further optimizing the resultant femoral anteversion by selecting, for example, different stem shapes.

In another embodiment, the surgeon may perform a femur first technique wherein a first cut is applied to the femur using a first 3D guidance mold. Optionally, the broach in the cut femoral shaft may be left in place. Optionally, a trial implant head may be applied to the broach. The trial implant head may be variable in radius and superoinferior diameter and may be utilized to determine the optimal soft tissue tension. Optionally, the trial head may also be utilized to determine the acetabular cup position wherein said acetabular cup position is derived on the basis of the femoral cut. Thus, the acetabular position can be optionally derived using the opposite articular surface. In a reverse acetabulum first technique, the acetabulum can be prepared first and, using soft tissue balancing techniques, the femoral component can be placed in reference to the acetabular component. Optionally, the femoral cut may even be placed intentionally too proximal and is subsequently optimized by measuring soft tissue tension utilizing various trial heads with the option to then change the height of the optimal femoral cut.

Positioning of Template

In an illustrative embodiment of the invention, in order to make a guidance template reliably and reproducibly, a portion of the joint is identified in a first step wherein said portion of the joint has not been altered by the arthritic process. In a second step, the surface or a point cloud of said portion of the joint is derived, and may, optionally, be used to derive a virtual 3D model and, in a third step, to generate a physical model as part of the guidance template. Using a portion of the joint that has not been altered by the arthritic process can advantageously improve the reproducibility and the accuracy of the resultant mold or jig or template.

The step of identifying said portion of the joint may be visual, semiautomatic or fully automatic. Anatomic models may assist in the process. Anatomic reference standards may be utilized.

As known in the art, various methods for image segmentation may be used to derive the point cloud or the surface. Suitable algorithms include, for example, but are not limited to snakes, live wire, thresholding, active contours, deformable models and the like. Artificial neural networks may be employed to improve the accuracy of the molds.

In another embodiment, the current biomechanical axis may determined or estimated in a first step. In a second step, the desired biomechanical axis is determined. In a third step adjustments, for example via change in slot position or position for openings for saws and drills and the like, may be made to alter the cut or drill position in order to correct the biomechanical axis in a fourth step. In a fifth step, the position of the slot or openings for saws and drills and the like may be adjusted for ligament balancing and/or for optimizing flexion and extension gap. This adjustment may be performed in the 3D model prior to the manufacturing process. Alternatively, adjustments may be made intraoperatively, for example via spacers or ratchet like devices or pins to allow for some degree of rotation.

In another embodiment, at least a portion of the surface of the mold or jig or template is derived from a portion of the joint that is affected by the arthritic process. Optionally, adjustment means can be performed, for example via the software, to simulate a normal shape. The difference between the actual shape and the adjusted shape can be utilized the optimize the position of the slots or openings in the mold or template or jig.

In a preferred embodiment, at least a portion of the surface of the mold or jig or template that is in contact with the joint may be derived from a portion of the joint that is affected by the arthritic process and a portion of the joint that has not been altered by the arthritic process. By spanning both normal and diseased portions of the joint, the interface between normal and diseased portions of the joint is included in the surface of the mold. The interface between normal and diseased portions of the joint is typically characterized by a sudden change in contour or shape, e.g. a reduction in cartilage thickness, a change in subchondral bone contour, a cyst or a bone spur. This change in joint contour or shape provides additional reference points for accurately placing the mold or jig or template. In addition, this change in joint contour or shape provides also additional stabilization or fixation of the mold or jig or template on the surface of the joint, in particular while performing surgical interventions such as cutting, drilling or sawing.

viii. Patellar Template

Figure 48A:
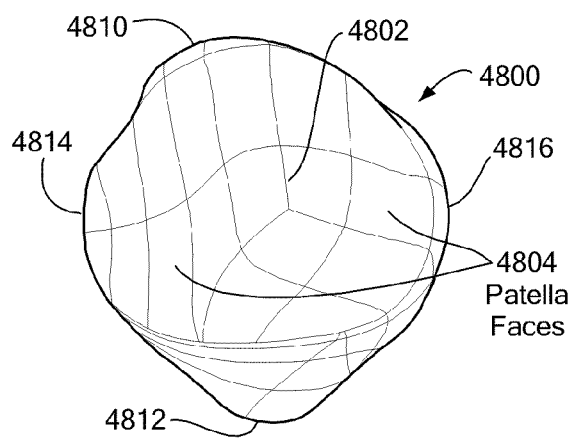
FIG. 48A illustrates a patella modeled from CT data.

FIG. 48A illustrates a patella 4800 having a patellar ridge 4802, patellar facets 4804, 4804. Also depicted are the superior 4810, inferior 4812, lateral 4814, and medial 4816 surfaces.

Figure 48B:
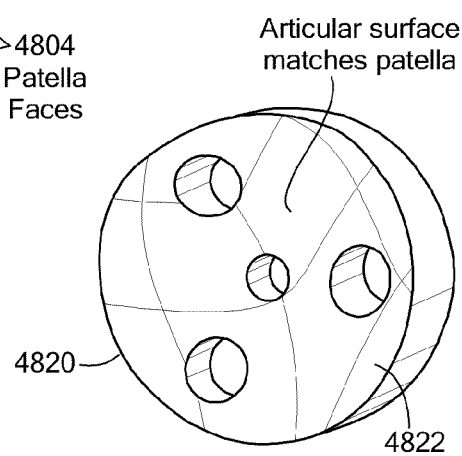
FIGS. 48B-D illustrate a mold guide, and then the mold guide placed on an articular surface of the patella.

FIG. 48B illustrates a mold drill guide 4820 from the perspective of the patella matching surface 4822. The mold drill guide 4820 is configured so that it is substantially a round cylinder. However, other shapes can be employed without departing from the scope of the invention. Such shapes can be strictly geometrical, e.g. ovoid, or non-geometrical.

The patella matching surface 4822 has an articular surfaces that matches, or closely conforms to, the surface of the patella. The design is proposed such that the guide is molded to precisely fit the anatomy of the articular surface of the patella for each patient, thus providing precise location of the patella planing needed. As will be appreciated by those of skill in the art, while an exact or precise fit is desired, deviations from a precise fit can occur without departing from the scope of the invention. Thus, it is anticipated that a certain amount of error in the design can be tolerated.

Figure 48C:
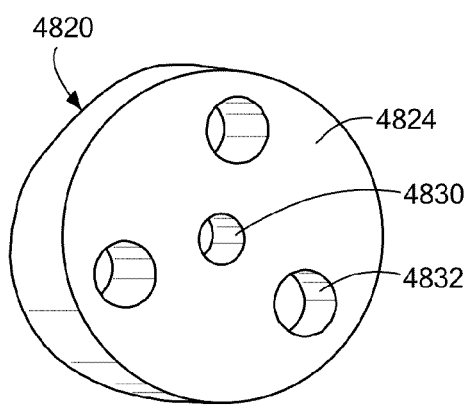

FIG. 48C illustrates the guide 4820 from the opposite perspective. The planar guide surface or element 4824 is depicted as flat, or substantially flat. However, as will be appreciated by those of skill in the art, other surface configurations can be employed without departing from the scope of the invention. Both FIGS. 48A and B depict apertures 4830, 4832. A central aperture 4830 is provided that accommodates, for example, a ⅛ drill bit. The central aperture 4830 can be located such that it is centered within the guide, off-centered, or slightly off-centered, without departing from the scope of the invention. An off-center or slightly off-center configure could be used with the round cylindrical configuration, but could also be used with the other configurations as well. One or more additional apertures 4832 can be provided to enable peg holes to be drilled. The apertures 4832 can be configured to have a larger diameter as the first aperture 4830, a smaller diameter, or an identical diameter.

Figure 48D:
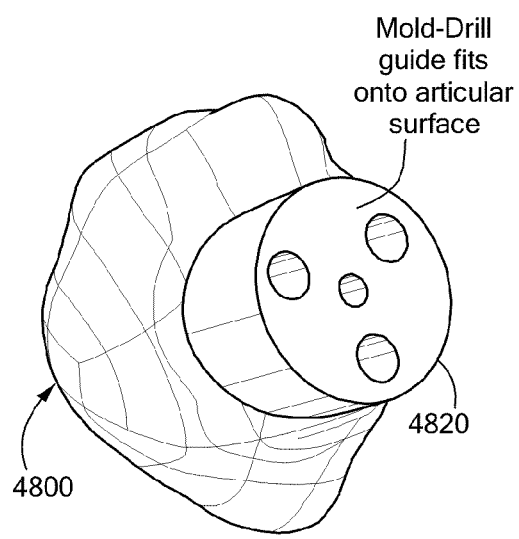
Figure 48E:
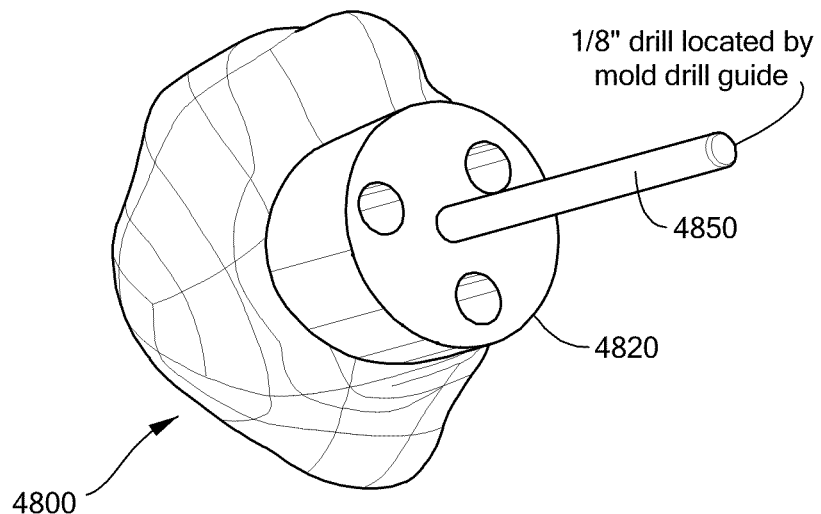
FIG. 48E illustrates a drill placed into a patella through mold drill guide.
Figure 48F:
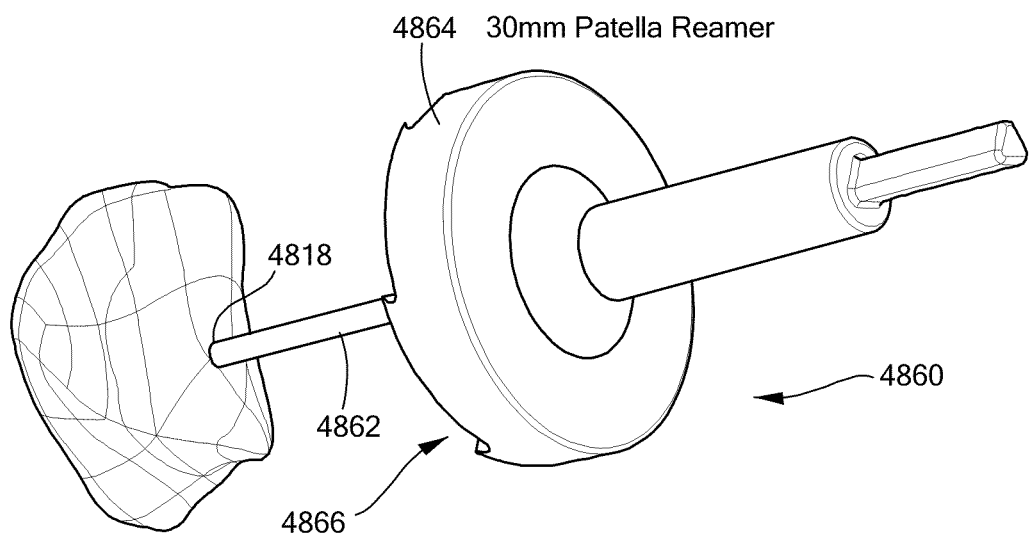
FIG. 48F illustrates a reamer used to prepare the patella.

As shown in FIG. 48D the mold drill guide is fitted onto the articular surface of the patella. Because the articular facing surface (shown in FIG. 48A) is configured to match or substantially match the articular surface of the patella, the drill guide mates with the patellar surface to enable the drill holes to line-up in the desired place for the implant. FIG. 48E illustrates the mold drill guide fitted onto the articular surface of the patella with a ⅛" drill 4850 positioned within the central aperture 4830.

Once a central aperture 4818 has been formed into the patella, a patella reamer 4860 is used to resurface the patella 4800. The reamer 4860 has a guide 4862, which fits within the aperture 4818, and a reamer 4864 having a planing surface or blade surface 1066.

Figure 49A:
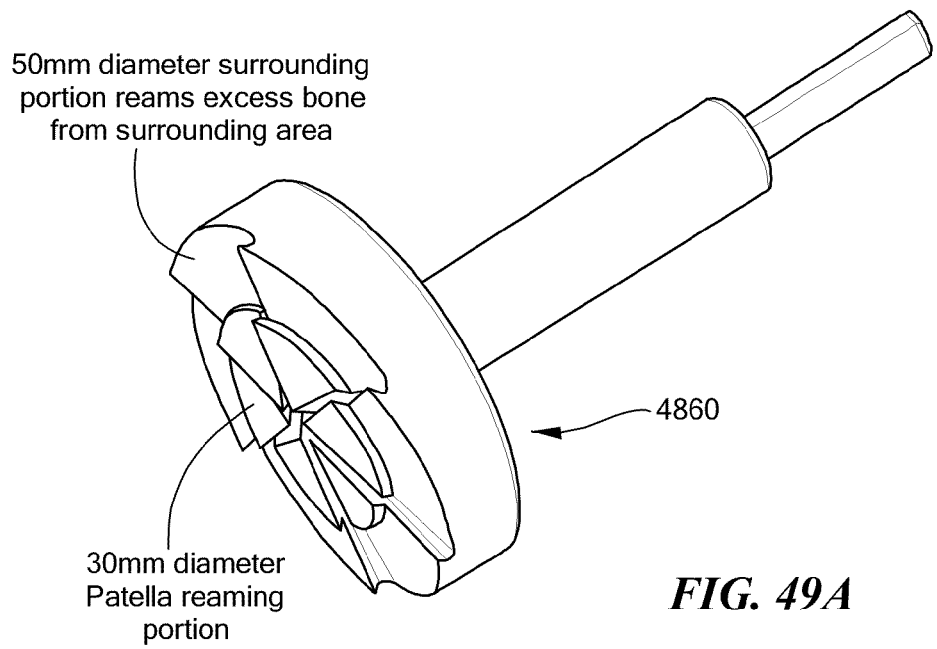
FIG. 49A illustrates a reamer made for each patella size.
Figure 49B:
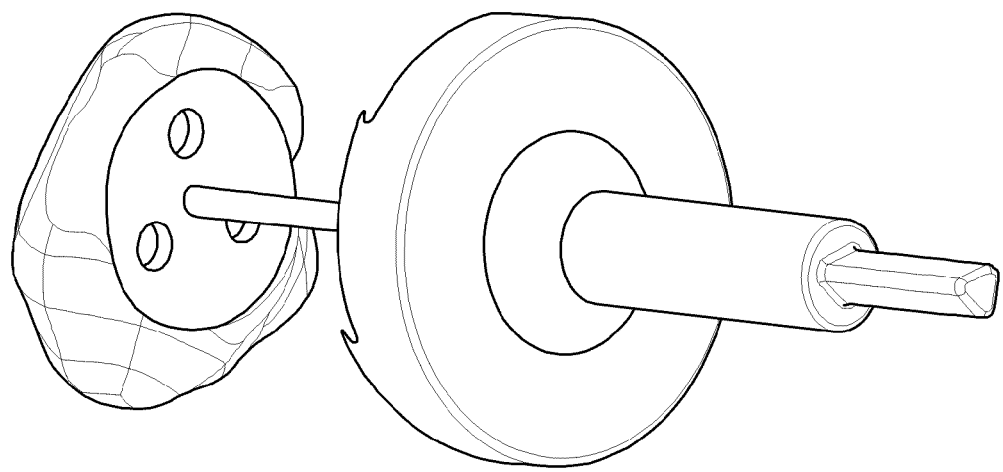
FIG. 49B illustrates a reamed patella ready for patella implantation.

Turning to FIG. 49A the reamer 1060 is shown. The planing surface 1066 has is configured to provide dual planing surfaces in order to recess the patella and clear surrounding bone. Providing dual planing surfaces helps to insure poly-metal articulation only. FIG. 49B illustrates the reamer relative to a patella. An area is prepared 1062 for a 30 mm patella insert, and a surrounding area 1061 is reamed.

Figure 50A:
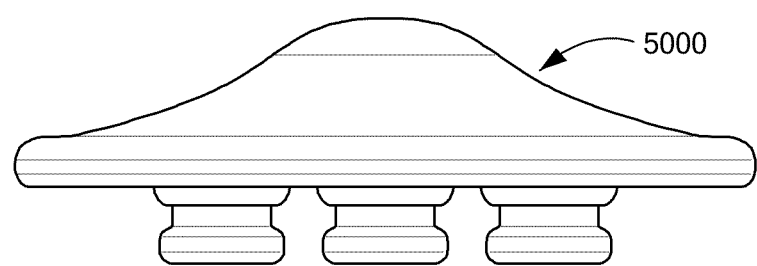
FIGS. 50A-F illustrate a recessed patella implanted on a patella.
Figure 50B:
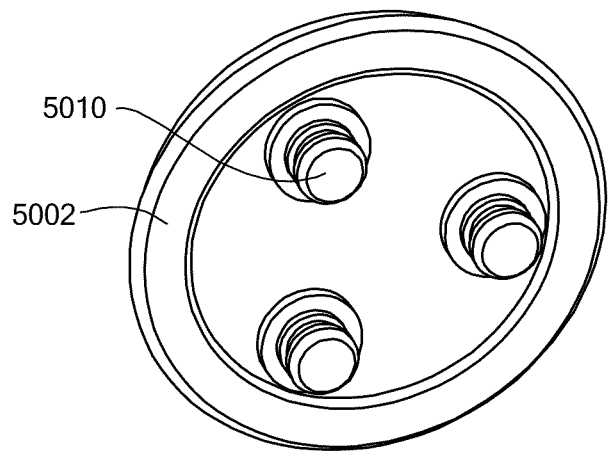
Figure 50C:
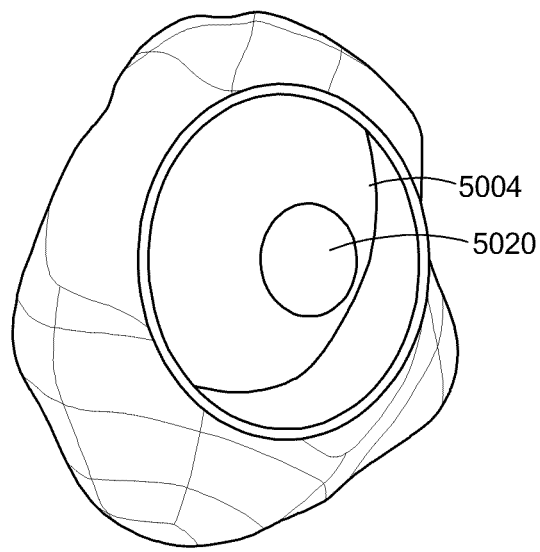
Figure 50D:
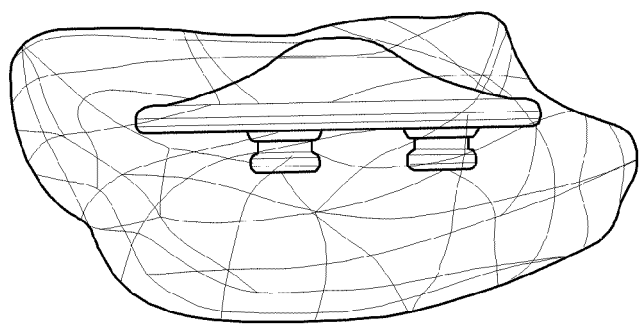
Figure 50E:
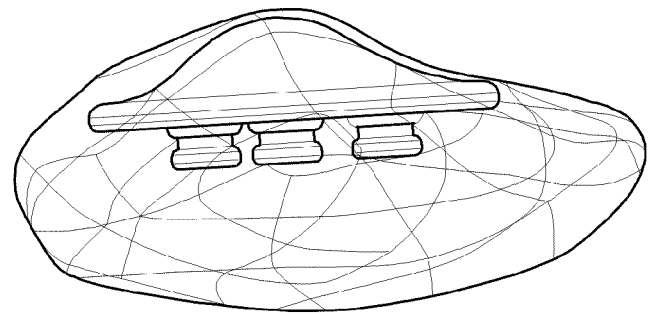
Figure 50F:
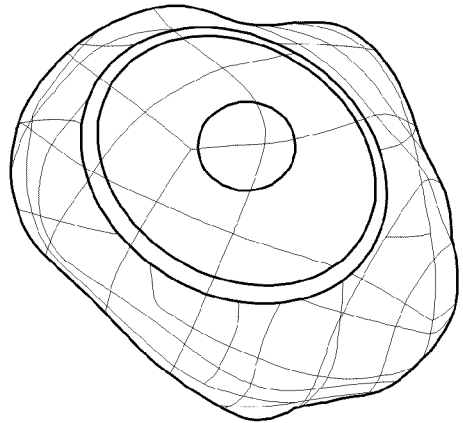

FIG. 50A illustrates a patella implant 5000. The inferior surface of the implant 5000, has one or more pegs 5010. In this instance, the inferior surface 5002 is depicted with three pegs 5010. The implant 5000 is positioned on a patella as shown in FIG. 50C such that a protuberance 5020 on the superior surface 5004 of the implant is positioned approximately at the apex of the natural patella. FIGS. 50D-F illustrate the implant superimposed within a patella, more clearly showing the protuberance corresponding to the apex of the natural patella.

B. Small, Focal Cartilage Defect

After identification of the cartilage defect and marking of the skin surface using the proprietary U-shaped cartilage defect locator device as described herein, a 3 cm incision is placed and the tissue retractors are inserted. The cartilage defect is visualized.

A first Lucite block matching the 3D surface of the femoral condyle is placed over the cartilage defect. The central portion of the Lucite block contains a drill hole with an inner diameter of, for example, 1.5 cm, corresponding to the diameter of the base plate of the implant. A standard surgical drill with a drill guide for depth control is inserted through the Lucite block, and the recipient site is prepared for the base component of the implant. The drill and the Lucite block are then removed.

A second Lucite block of identical outer dimensions is then placed over the implant recipient site. The second Lucite block has a rounded, cylindrical extension matching the size of the first drill hole (and matching the shape of the base component of the implant), with a diameter 0.1 mm smaller than the first drill hole and 0.2 mm smaller than that of the base of the implant. The cylindrical extension is placed inside the first drill hole.

The second Lucite block contains a drill hole extending from the external surface of the block to the cylindrical extension. The inner diameter of the second drill hole matches the diameter of the distal portion of the fin-shaped stabilizer strut of the implant, e.g. 3 mm. A drill, e.g. with 3 mm diameter, with a drill guide for depth control is inserted into the second hole and the recipient site is prepared for the stabilizer strut with a four fin and step design. The drill and the Lucite block are then removed.

A plastic model/trial implant matching the 3-D shape of the final implant with a diameter of the base component of 0.2 mm less than that of the final implant and a cylindrical rather than tapered strut stabilizer with a diameter of 0.1 mm less than the distal portion of the final implant is then placed inside the cartilage defect. The plastic model/trial implant is used to confirm alignment of the implant surface with the surrounding cartilage. The surgeon then performs final adjustments.

The implant is subsequently placed inside the recipient site. The anterior fin of the implant is marked with red color and labeled "A." The posterior fin is marked green with a label "P" and the medial fin is color coded yellow with a label "M." The Lucite block is then placed over the implant. A plastic hammer is utilized to advance the implant slowly into the recipient site. A press fit is achieved with help of the tapered and four fin design of the strut, as well as the slightly greater diameter (0.1 mm) of the base component relative to the drill hole. The Lucite block is removed. The tissue retractors are then removed. Standard surgical technique is used to close the 3 cm incision. The same procedure described above for the medial femoral condyle can also be applied to the lateral femoral condyle, the medial tibial plateau, the lateral tibial plateau and the patella. Immediate stabilization of the device can be achieved by combining it with bone cement if desired.

IV. Kits

Also described herein are kits comprising one or more of the methods, systems and/or compositions described herein. In particular, a kit can include one or more of the following: instructions (methods) of obtaining electronic images; systems or instructions for evaluating electronic images; one or more computer means capable of analyzing or processing the electronic images; and/or one or more surgical tools for implanting an articular repair system. The kits can include other materials, for example, instructions, reagents, containers and/or imaging aids (e.g., films, holders, digitizers, etc.).

The following examples are included to more fully illustrate the present invention. Additionally, these examples provide preferred embodiments of the invention and are not meant to limit the scope thereof.

Example 1

Design and Construction of a Three-Dimensional Articular Repair System

Figure 13:
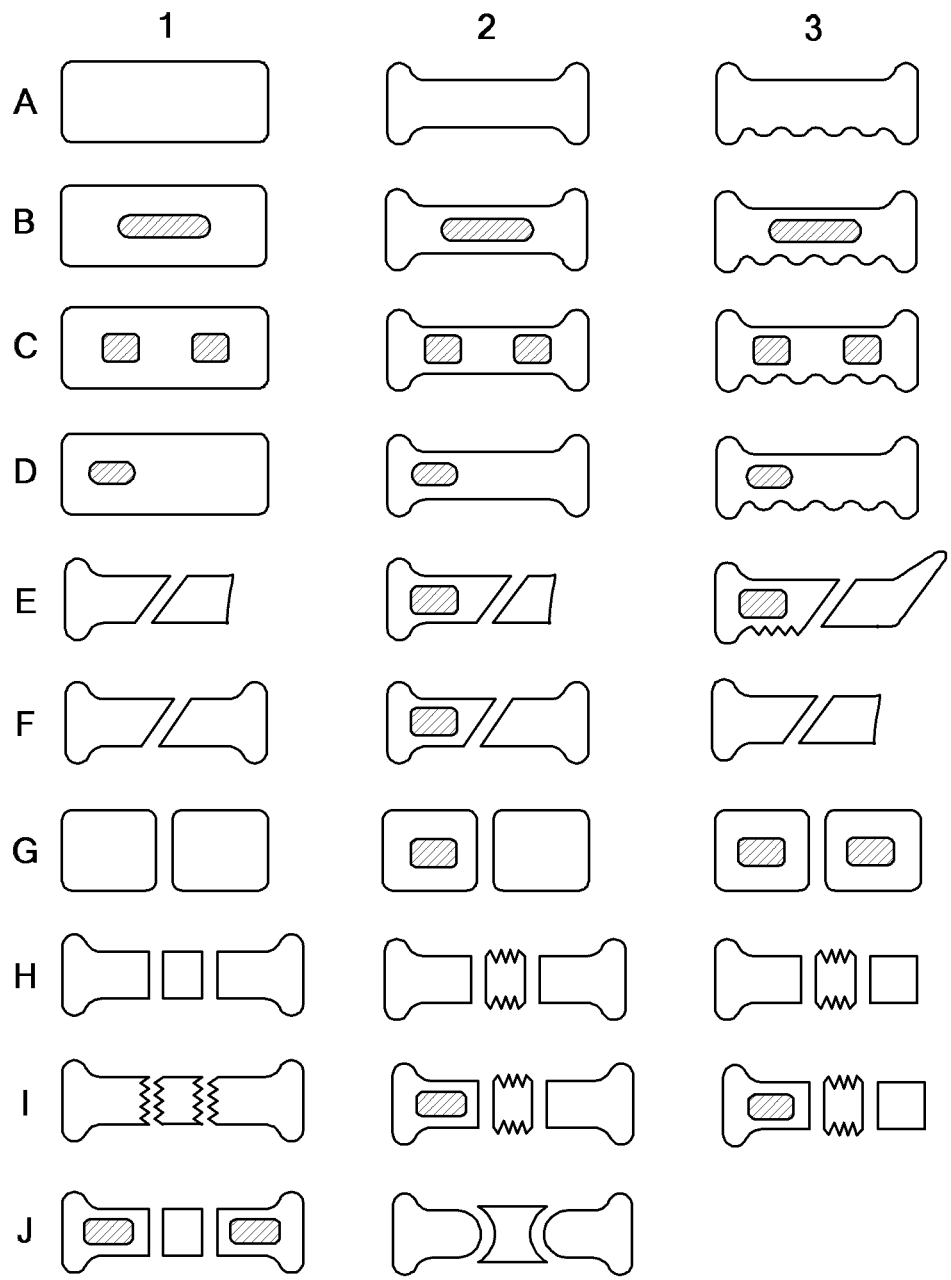
FIGS. 13A-J(1-3) show a variety of cross-sectional views of the inflation devices shown in FIGS. 11 and 12 taken at a position perpendicular to the views shown in FIGS. 11 and 12.

Areas of cartilage are imaged as described herein to detect areas of cartilage loss and/or diseased cartilage. The margins and shape of the cartilage and subchondral bone adjacent to the diseased areas are determined. The thickness of the cartilage is determined. The size of the articular repair system is determined based on the above measurements. (FIGS. 12-14). In particular, the repair system is either selected (based on best fit) from a catalogue of existing, pre-made implants with a range of different sizes and curvatures or custom-designed using CAD/CAM technology. The library of existing shapes is typically on the order of about 30 sizes.

The implant is a chromium cobalt implant (see also FIGS. 12-14 and 17-19). The articular surface is polished and the external dimensions slightly greater than the area of diseased cartilage. The shape is adapted to achieve perfect or near perfect joint congruity utilizing shape information of surrounding cartilage and underlying subchondral bone. Other design features of the implant can include: a slanted (60- to 70-degree angle) interface to adjacent cartilage; a broad-based base component for depth control; a press fit design of base component; a porous coating of base component for ingrowth of bone and rigid stabilization; a dual peg design for large defects implant stabilization, also porous coated (FIG. 12A); a single stabilizer strut with tapered, four fin and step design for small, focal defects, also porous coated (FIG. 12B); and a design applicable to femoral resurfacing (convex external surface) and tibial resurfacing (concave external surface).

Example 2

Minimally Invasive, Arthroscopically Assisted Surgical Technique

The articular repair systems are inserted using arthroscopic assistance. The device does not require the 15 to 30 cm incision utilized in unicompartmental and total knee arthroplasties. The procedure is performed under regional anesthesia, typically epidural anesthesia. The surgeon can apply a tourniquet on the upper thigh of the patient to restrict the blood flow to the knee during the procedure. The leg is prepped and draped in sterile technique. A stylette is used to create two small 2 mm ports at the anteromedial and the anterolateral aspect of the joint using classical arthroscopic technique. The arthroscope is inserted via the lateral port. The arthroscopic instruments are inserted via the medial port. The cartilage defect is visualized using the arthroscope. A cartilage defect locator device is placed inside the diseased cartilage. The probe has a U-shape, with the first arm touching the center of the area of diseased cartilage inside the joint and the second arm of the U remaining outside the joint. The second arm of the U indicates the position of the cartilage relative to the skin. The surgeon marks the position of the cartilage defect on the skin. A 3 cm incision is created over the defect. Tissue retractors are inserted and the defect is visualized.

A translucent Lucite block matching the 3D shape of the adjacent cartilage and the cartilage defect is placed over the cartilage defect (FIG. 13). For larger defects, the Lucite block includes a lateral slot for insertion of a saw. The saw is inserted and a straight cut is made across the articular surface, removing an area slightly larger than the diseased cartilage. The center of the Lucite block contains two drill holes with a 7.2 mm diameter. A 7.1 mm drill with drill guide controlling the depth of tissue penetration is inserted via the drill hole. Holes for the cylindrical pegs of the implant are created. The drill and the Lucite block are subsequently removed.

A plastic model/trial implant of the mini-repair system matching the outer dimensions of the implant is then inserted. The trial implant is utilized to confirm anatomic placement of the actual implant. If indicated, the surgeon can make smaller adjustments at this point to improve the match, e.g. slight expansion of the drill holes or adjustment of the cut plane.

The implant is then inserted with the pegs pointing into the drill holes. Anterior and posterior positions of the implant are color-coded; specifically the anterior peg is marked with a red color and a small letter "A", while the posterior peg has a green color and a small letter "P". Similarly, the medial aspect of the implant is color-coded yellow and marked with a small letter "M" and the lateral aspect of the implant is marked with a small letter "L". The Lucite block is then placed on the external surface of the implant and a plastic hammer is used to gently advance the pegs into the drill holes. The pegs are designed to achieve a press fit.

The same technique can be applied in the tibia. The implant has a concave articular surface matching the 3D shape of the tibial plateau. Immediate stabilization of the device can be achieved by combining it with bone cement if desired.

The foregoing description of embodiments of the present invention has been provided for the purposes of illustration and description. It is not intended to be exhaustive or to limit the invention to the precise forms disclosed. Many modifications and variations will be apparent to the practitioner skilled in the art. The embodiments were chosen and described in order to best explain the principles of the invention and its practical application, thereby enabling others skilled in the art to understand the invention and the various embodiments and with various modifications that are suited to the particular use contemplated. It is intended that the scope of the invention be defined by the following claims equivalents thereof.

What is claimed is:

1. A system for use in surgically replacing or resurfacing at least a portion of a hip joint of a patient, comprising:
   a surgical instrument that includes a body having a patient-specific surface and a guide to direct or accommodate a surgical tool;
     wherein at least a portion of the patient-specific surface has a shape that substantially matches a shape of a corresponding surface of the hip joint, wherein the corresponding surface of the hip joint includes an acetabular surface portion selected from the group consisting of an acetabular fossa, an acetabular rim, an acetabular wall, and any combination thereof;

wherein the guide is configured relative to the patient-specific surface to provide a predefined path for the surgical tool when the patient-specific surface is placed against and aligned with the corresponding surface; and wherein the path for the surgical tool is configured to provide a predefined degree of anteversion and/or rotation of at least one acetabular implant when the patient-specific surface is placed against and aligned with the corresponding surface of the hip joint.

2. The system of claim 1, wherein the acetabular surface includes a cartilage surface.

3. The system of claim 1, wherein the acetabular surface includes a normal cartilage surface.

4. The system of claim 1, wherein the acetabular surface includes a diseased cartilage surface.

5. The system of claim 1, wherein the acetabular surface includes a normal cartilage surface and a diseased cartilage surface.

6. The system of claim 1, wherein the acetabular surface includes a subchondral bone surface.

7. The system of claim 1, wherein the acetabular surface includes a cortical bone surface.

8. The system of claim 1, wherein the acetabular surface includes the surface of at least one osteophyte.

9. The system of claim 1, further comprising the acetabular implant.

10. A system comprising a surgical instrument for use in surgically replacing or resurfacing at least a portion of a hip joint of a patient, the surgical instrument comprising:

a body having a patient-specific surface and a guide to direct or accommodate a surgical tool;

wherein at least a portion of the patient-specific surface has a shape that substantially matches a shape of a corresponding surface of the hip joint, wherein the corresponding surface includes a femoral surface portion of the hip joint;

wherein the guide is configured relative to the patient-specific surface to provide a predefined path for the surgical tool when the patient-specific surface is placed against and aligned with the corresponding surface; and wherein the path for the surgical tool is configured to provide a predefined degree of anteversion and/or rotation of at least one femoral implant when the patient-specific surface is placed against and aligned with the corresponding surface.

11. The system of claim 10, further comprising the femoral implant.

12. The system of claim 10, wherein the corresponding surface includes diseased and or normal cartilage.

13. The system of claim 10, wherein the corresponding surface includes subchondral bone.

14. The system of claim 10, wherein the corresponding surface includes cortical bone.

15. The system of claim 10, wherein the corresponding surface includes at least one osteophyte.

16. A system comprising a surgical instrument for use in surgically replacing or resurfacing at least a portion of a hip joint of a patient, the surgical instrument comprising:

a body having a patient-specific surface and a guide to direct or accommodate a surgical tool;

wherein at least a portion of the patient-specific surface has a shape that substantially matches a shape of a corresponding surface of the hip joint, wherein the corresponding surface of the hip joint includes an acetabular surface portion selected from the group consisting of an acetabular fossa an acetabular rim an acetabular wall and any combination thereof;

wherein the guide is configured relative to the patient-specific surface to provide a predefined path for the surgical tool that is aligned through a portion of tissue associated with the hip joint when the patient-specific surface is placed against and aligned with the corresponding surface; and wherein the path for the surgical tool is configured to provide a predefined degree of tilting of at least one acetabular implant when the patient-specific surface is placed against and aligned with the corresponding surface.

17. The system of claim 16, further comprising the acetabular implant.

18. The system of claim 16, wherein the corresponding surface includes diseased and or normal cartilage.

19. The system of claim 16, wherein the corresponding surface includes subchondral bone.

20. The system of claim 16, wherein the corresponding surface includes cortical bone.

21. The system of claim 16, wherein the corresponding surface includes at least one osteophyte.

* * * * *